US007850974B2

(12) United States Patent
Hook et al.

(10) Patent No.: US 7,850,974 B2
(45) Date of Patent: Dec. 14, 2010

(54) BIOINFORMATIC METHOD FOR IDENTIFYING SURFACE-ANCHORED PROTEINS FROM GRAM-POSITIVE BACTERIA AND PROTEINS OBTAINED THEREBY

(75) Inventors: Magnus Hook, Houston, TX (US); Yi Xu, Houston, TX (US); Jouko V. Sillanpaa, Houston, TX (US); Narayana Sthanam, Birmingham, AL (US); Karthe Ponnuraj, Birmingham, AL (US); Joseph M. Patti, Cumming, GA (US); Jeff T. Hutchins, Cumming, GA (US); Andrea Hall, Acworth, GA (US); Maria G. Bowden, Sugarland, TX (US)

(73) Assignees: The Texas A&M University System, College Station, TX (US); Inhibitex, Inc., Alpharetta, GA (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 12/575,909

(22) Filed: Oct. 8, 2009

(65) Prior Publication Data

US 2010/0068220 A1 Mar. 18, 2010

Related U.S. Application Data

(62) Division of application No. 10/661,809, filed on Sep. 15, 2003, now Pat. No. 7,615,616.

(60) Provisional application No. 60/410,303, filed on Sep. 13, 2002.

(51) Int. Cl.
*A61K 39/02* (2006.01)

(52) U.S. Cl. ............... 424/190.1; 424/185.1; 424/234.1

(58) Field of Classification Search ....................... None
See application file for complete search history.

(56) References Cited

U.S. PATENT DOCUMENTS 6,617,156 B1 * 9/2003 Doucette-Stamm et al. ...... 435/320.1

OTHER PUBLICATIONS

Murphy et al. Pediatr. Infect. Dis. J. 1989. 8: S66-S68.*
Yamanaka et al (J. Pediatrics. 1993. 122(2): 212-218).*

* cited by examiner

*Primary Examiner*—Jennifer E Graser
(74) *Attorney, Agent, or Firm*—B. Aaron Schulman; Terry L. Wright; Stites & Harbison PLLC

(57) ABSTRACT

A bioinformatic method for identifying and isolating proteins and peptides with MSCRAMM®-like characteristics from Gram positive bacteria, such as *Enterococcus, Staphylococcus, Streptococcus* and *Bacillus* bacteria, and proteins and peptides obtained thereby are provided which can be utilized in methods to prevent and treat infections caused by Gram-positive bacteria. The method involves identifying from sequence information those proteins with a putative C-terminal LPXTG (SEQ ID NO:1) cell wall sorting signal and other structural similarities to MSCRAMM® proteins having the LPXTG-anchored cell wall proteins. The MSCRAMM® proteins and immunogenic regions therein that are identified and isolated using the present invention may be useful in the diagnosis, treatment or prevention of Gram positive bacterial infections.

4 Claims, 2 Drawing Sheets

Figure 1:
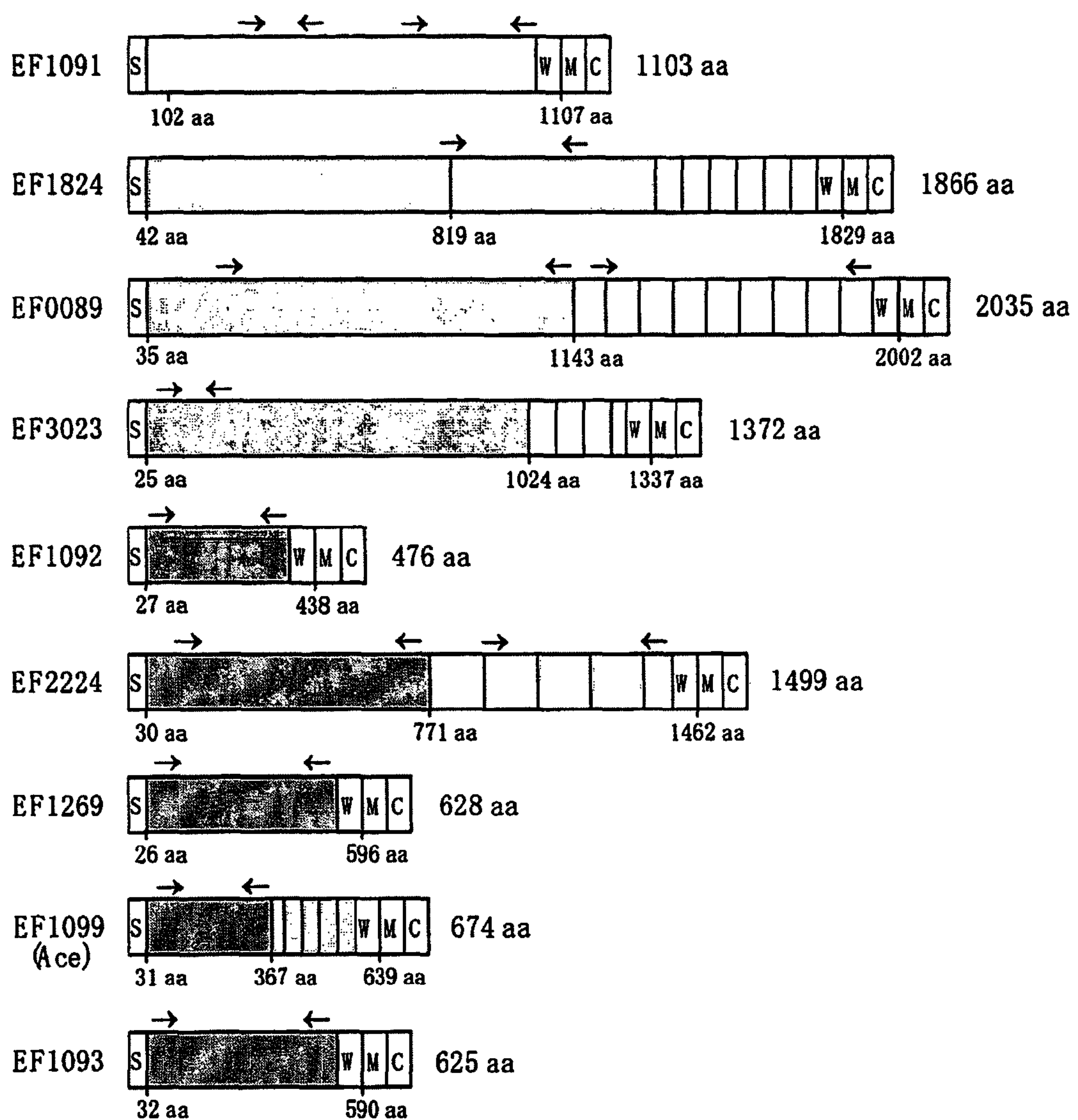

Coomassie-stained SDS-PAGE of the *E. coli*-expressed and purified A domains of *E. faecalis* LPxTG proteins. a, EF1091; b, EF1824; c, EF0089; d, EF3023; e, EF1092; f, EF2224; g, EF1269; h, Ace; I, EF1093.

BIOINFORMATIC METHOD FOR IDENTIFYING SURFACE-ANCHORED PROTEINS FROM GRAM-POSITIVE BACTERIA AND PROTEINS OBTAINED THEREBY

CROSS-REFERENCE TO RELATED APPLICATIONS

The present application is a divisional application of U.S. patent application Ser. No. 10/661,809, filed Sep. 15, 2003 now U.S. Pat. No. 7,615,616, which claims the benefit of U.S. provisional application Ser. No. 60/410,303, filed Sep. 13, 2002.

STATEMENT REGARDING FEDERALLY SPONSORED RESEARCH OR DEVELOPMENT

This Invention was made with Government support under Contracts 7R01-AR44415-04 and 2R01-AI20624-17 awarded by NIH. The government has certain rights in this invention.

FIELD OF THE INVENTION

The present invention relates to the fields of microbiology, molecular biology, and immunology and more particularly relates to surface-anchored proteins known as MSCRAMM®s, and to a bioinformatic method of identifying putative MSCRAMM® proteins, i.e., proteins that can bind to extracellular matrix molecules, from Gram positive bacteria having a recognizable cell wall sorting signal and the genes encoding those proteins through detecting structural features from potential proteins including immunoglobulin (Ig)-like fold regions. In addition, the invention relates to antibodies which recognize such proteins, including polyclonal and monoclonal antibodies as well as host cells transformed with nucleic acids encoding monoclonal antibodies, and the use of such antibodies in the diagnosis, treatment or prevention of Gram positive bacterial infections in humans and animals.

BACKGROUND OF THE INVENTION

There are numerous Gram positive bacteria which have been of interest in the fields of medicine and epidemiology because of their potential to cause a myriad of infectious diseases in humans and animals. One such Gram positive bacterium, *Enterococcus faecalis*, belongs to the commensal flora in mammalian intestines. It has also long been known as a major causative agent of bacterial endocarditis (Murray, 1990). During the last decades, *E. faecalis* has increasingly emerged as an opportunistic nosocomial pathogen, typically causing infections in hospitalized patients receiving antibiotic therapy. Clinical strains of this bacterium frequently harbor a multitude of acquired and intrinsically evolved resistance mechanisms toward the most commonly used antibiotics, which has complicated the treatment of enterococcal infections (Murray, 1990, 1999) (Tailor, 1993) (Huycke, 1998). Many of the antibiotic resistance genes are located in mobile genetic elements, e.g., small plasmids and transposons (Paulsen, 2003) This has raised fears for genetic transfer of resistance determinants from this organism to other bacterial species, e.g., the recently documented transfer of vancomycin resistance to *Staphylococcus aureus* (CDC, 2002). Still other Gram positive bacteria are known which commonly cause infections which are hard to control, including other bacteria from the *Enterococcus* genus, including *Enterococcus faecium*, as well as bacteria from species *Streptococcus*, such as *Streptococcus mutans* and *pneumoniae, Staphylococcus*, such as *Staphylococcus aureus* and *epidermidis*, and *Bacillus*, such as *Bacillus anthracis*.

The ability to adhere to mammalian tissue is a critical step in the colonization and onset of microbial infections. However, in light of the many unknown factors regarding microbial adherence, it remains a challenge to study and utilize information obtained regarding relatively little known adhesion mechanisms of Gram positive bacteria so as to provide a means for developing alternative antibacterial therapies. One such inroad into developing such therapies is the presence of the human extracellular matrix underneath epithelial and endothelial cells which is a complex, dynamic and multifunctional structure consisting mainly of collagens and other glycoproteins. As one of the outermost layers to external environment, it is a major adhesion target and entry point for pathogenic bacteria (Foster and Hook, 1998) (Westerlund and Korhonen, 1993). Numerous bacterial adhesins that specifically bind to ECM components have been characterized at the molecular level. A group of related cell surface proteins from Gram-positive bacteria, collectively designated MSCRAMM® proteins (microbial surface components recognizing adhesive matrix molecules) bind to major components of the ECM, such as collagens, fibronectin, laminin, fibrinogen, keratin, vitronectin and bone sialoprotein (Patti, 1994) (Foster and Hook, 1998) (Tung, 2000) (O'Brien, 2002). MSCRAMM® proteins are mosaic proteins that typically consist of an N-terminal signal sequence for Sec-dependent transport across the cytoplasmic membrane, followed by an N-terminal A domain which exhibits the binding activity in most cases and repetitive B domains that confer fibronectin binding in a group of fibronectin binding MSCRAMM® protein (Joh et al., 1994). Covalent attachment to the bacterial cell wall is mediated through a C-terminally located LPxTG motif preceded by a cell wall spanning domain and followed by a hydrophobic trans-membrane region and, finally, a cytosolic tail composed of a short sequence of positively charged amino acid residues (Schneewind et al., 1995) (Mazmanian et al., 2001).

In any event, it remains a distinct problem in the field of infectious diseases to develop new means of countering a wide range of bacterial infections in an efficient and effective manner without the potential of increasing the development of antibiotic-resistant bacterial strains. Moreover, in light of the potential problems caused by bacterial strains and antibiotic-resistant strains in general, particularly in hospitalized patients, it is increasingly important to develop methods to counteract such infections without utilizing antibiotics or increasing the likelihood that antibiotic-resistant strains will develop. It is thus highly desirable to develop new means for identifying, treating and preventing infectious diseases caused by Gram positive bacteria, and to develop means for identifying and isolating new MSCRAMM® proteins from such bacteria which will allow the generation of antibodies thereto which will lead to new methods for treating and preventing the spread of infections from Gram-positive bacteria.

SUMMARY OF THE INVENTION

Accordingly, it is an object of the present invention to provide a bioinformatic method of identifying and isolating MSCRAMM® proteins from Gram-positive bacteria which can be utilized in methods of treating or preventing infectious diseases arising from Gram-positive bacteria.

It is another object of the present invention to identify and isolate proteins obtained using the bioinformatic method of the present invention, and to identify therein effective antigenic domains such as the A domain, and to utilize these antigenic domains in methods of treating or preventing infectious diseases arising from Gram-positive bacteria.

It is further an object of the present invention to utilize the proteins and antigenic domains isolated and identified using the bioinformatic method of the present invention to generate antibodies which can recognize these proteins and antigenic regions which can thus be useful in diagnosing, treating or preventing diseases and infections caused by Gram positive bacteria It is still further an object of the present invention to provide vaccines, kits and other therapeutic methods which utilize the proteins and antigenic domains identified and isolated using the bioinformatic method of the present invention which can be used as an alternative to conventional antibiotic therapy and can thus provide safe and effective modes of treating or preventing infections caused by Gram-positive bacteria.

These and other objects are provided by virtue of the present invention which utilizes a bioinformatic approach to identify proteins with MSCRAMM®-like characteristics among Gram positive bacteria, such as bacteria from *Enterococcus, Staphylococcus, Streptococcus* and *Bacillus*, among many others, the obtaining of said proteins and peptides therein, which can then be utilized in methods to prevent and treat infections caused by Gram-positive bacteria. In particular, the method involves looking for proteins with a putative C-terminal LPXTG (SEQ ID NO:1) cell wall sorting signal and structural similarities to MSCRAMM® proteins having the LPXTG-anchored cell wall proteins. In particular, the present invention provides a method for identifying and isolating MSCRAMM® proteins, i.e., proteins that can bind to extracellular matrix molecules, such as by locating regions that adopt an immunoglobulin-like fold, and includes the recombinant production of these proteins from nucleic acids identified in the present process which code for those proteins. These Ig fold-containing regions consist of several consecutive and overlapping matches to solved crystal structures (~150-500 aa) of the immunoglobulin superfamily (IgSF), which consist of one to four domains of equal size and Ig-type fold. The homologous Ig-fold regions are indicative of a "beads-in-a-string" arrangement of consecutive modules such like the ones found in fibronectin and other IgSF proteins (Leahy, 1996) (Sharma, 1999) (Hamburger, 1999) (Luo, 2000). For example, a tandem repeat of Ig folded subdomains (N2 and N3) is found in the crystal structure of the fibrinogen-binding domain of ClfA. The full-length A domains of ClfA and the similarly structured ClfB consist of an additional N-terminal subdomain, N1 (Deivanayagam, 2002) (Perkins, 2001). Based on sequence and secondary structure similarities, an analogous subdomain organization is also expected in other MSCRAMM® proteins including FnbpA, FnbpB, Ace and the Sdr proteins. The solved crystal structure of CNA minimum collagen-binding domain is made of a single Ig-type subdomain (N2) (Symersky, 1997) and the C-terminal repeat domains B1 and B2 each consist of a tandem repeat of Ig-folded subdomains (Deivanayagam, 2000). A similar modular structure is expected in the B3 and B4 repeats.

In accordance with the invention, novel MSCRAMM®-like protein surface-anchored proteins which can bind to major extracellular matrix proteins are obtained from Gram-positive bacteria such as those from the genera *Enterococcus, Streptococcus, Staphylococcus* and *Bacillus*, and such proteins are characterized in that they are (i) structurally homologous to the solved Ig-folded crystal structures of ClfA and CNA as well as to the predicted tertiary structures of other MSCRAMM® proteins, (ii) share a similar β-sheet rich secondary structure as is found in Ig-folded proteins and (iii) have a similar organization with a secretion signal, a non-repeated domain followed by repeats as well as a C-terminal cell wall anchor domain. Moreover, the binding of proteins identified by the present method has confirmed that they target and bind to various extracellular matrix (ECM) molecules including proteins and other components. For example, three of the isolated proteins bind to major ECM proteins; two to fibrinogen and at least one to collagen and laminin. The proteins of the present invention have also been shown to be present in most isolates and are expressed in vivo during infection.

Thus, in accordance with the present invention, a method is provided for identifying and isolating a module structure of multiple Ig-folded units which appears to be a general characteristic in the MSCRAMM® protein family. The length of the N-subdomains of MSCRAMM® proteins is typically ~150 aa, and the proteins identified by the present invention including those set forth below may accommodate more than three Ig-folded subdomains in their A domains.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

Figure 2:
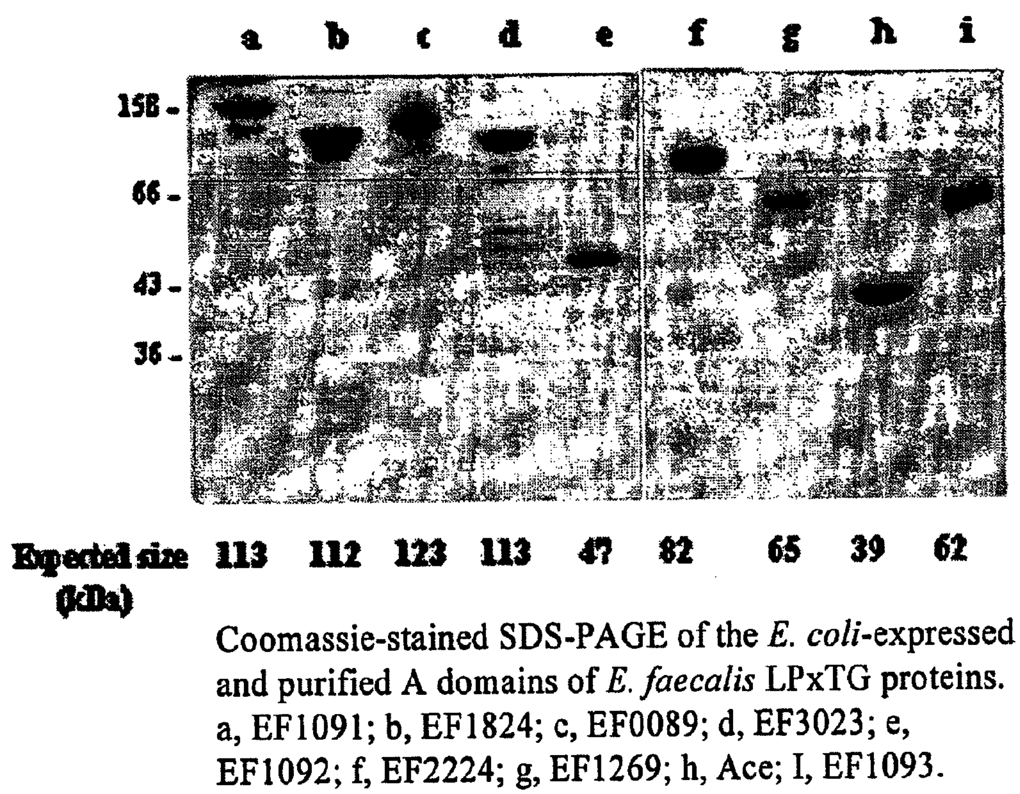

FIG. 1 is a schematic representation of MSCRAMM® proteins identified in accordance with the present invention illustrating the different regions of the proteins and their immunoglobulin-like fold regions FIG. 2 illustrates a Coomassie stained SDS-PAGE of the *E coli*-expressed and purified A domains of the LPXTG-containing proteins of the present invention.

DETAILED DESCRIPTION OF THE PREFERRED EMBODIMENTS

In accordance with the present invention, there is provided a bioinformatic method for identifying and isolating proteins from Gram-positive bacteria, for example bacteria from genera such as *Enterococcus, Staphylococcus, Streptococcus* and *Bacillus*, in particular proteins which have MSCRAMM®-like characteristics, and utilizing the identified and isolated proteins to generate antibodies and diagnose, treat or prevent infections caused by Gram-positive bacteria. In general, the method involves looking for proteins with a putative C-terminal LPXTG (SEQ ID NO:1) cell wall sorting signal and/or other structural similarities to MSCRAMM® proteins (Microbial Surface Components Recognizing Adhesive Matrix Molecules) having LPXTG-containing cell wall-anchored proteins. In the preferred embodiment, the present invention provides a method for identifying and isolating MSCRAMM® proteins, i.e., surface proteins that bind to extracellular matrix molecules, such as proteins, carbohydrates and other components, of host cells, wherein those located proteins contain regions that adopt an immunoglobulin-like fold. These Ig fold-containing regions consist of several consecutive and overlapping matches to solved crystal structures (~150-500 aa) of the immunoglobulin superfamily (IgSF), which consist of one to four domains of equal size and Ig-type fold. The homologous Ig-fold regions are indicative of a "beads-in-a-string" arrangement of consecutive modules such like the ones found in fibronectin and other IgSF proteins (Leahy, 1996) (Sharma, 1999) (Hamburger, 1999) (Luo, 2000). For example, a tandem repeat of Ig folded subdomains (N2 and N3) is found in the crystal structure of the fibrinogen-binding domain of ClfA. The full-length A domains of ClfA and the similarly structured ClfB consist of an additional N-terminal subdomain, N1 (Deivanayagam, 2002) (Perkins, 2001). Based on sequence and secondary structure similarities, an analogous subdomain organization is also expected in other MSCRAMM® proteins including FnbpA, FnbpB, Ace and the Sdr proteins. The solved crystal structure of CNA minimum collagen-binding domain is made of a single Ig-type subdomain (N2) (Symersky, 1997) and the C-terminal repeat domains B1 and B2 each consist of a tandem repeat of Ig-folded subdomains (Deivanayagam, 2000). A similar modular structure is expected in the B3 and B4 repeats.

In accordance with the invention novel MSCRAMM®-like protein surface-anchored proteins are obtained from Gram-positive bacteria such as those from the genera *Enterococcus, Streptococcus, Staphylococcus* and *Bacillus*, and such proteins are characterized in that they are (i) structurally homologous to the solved Ig-folded crystal structures of ClfA and CNA as well as to the predicted tertiary structures of other MSCRAMM® proteins, (ii) share a similar β-sheet rich secondary structure as is found in Ig-folded proteins and (iii) have a similar organization with a secretion signal, a non-repeated domain followed by repeats as well as a C-terminal cell wall anchor domain. Moreover, the binding of proteins identified by the present method has confirmed that they target and bind to various extracellular matrix molecules. For example, three of the isolated proteins bind to major ECM proteins; two to fibrinogen and at least one to collagen and laminin. The proteins of the present invention have also been shown to be present in most isolates and are expressed in vivo during infection.

In accordance with the present invention, a method is provided for identifying and isolating a module structure of multiple Ig-folded units which have the general characteristics of the MSCRAMM® protein family. The length of the N-subdomains of MSCRAMM® proteins is typically ~150 aa, and the proteins identified by the present invention including those set forth below may accommodate more than three Ig-folded subdomains in their A domains. The isolation and use of the MSCRAMM® proteins of the present invention or their A domains in the generation of antibodies that can bind thereto or in methods of diagnosing, treating or preventing disease will be similar to that as described with other MSCRAMM® proteins such as in U.S. Pat. Nos. 6,288,214; 6,177,084; 6,008,241; 6,086,895; 5,980,908; 5,866,541; 5,851,794; 5,840,846; 5,789,549; 5,770,702, 5,652,217; 5,648,240; 5,571,514; 5,440,014; 5,416,021 and 5,320,951; and WO 00/68242; all of said references incorporated herein by reference.

In accordance with the present invention, a series of steps is undertaken in order to identify and isolate the characteristic module structure of one or more surface-anchored MSCRAMM® protein family of Gram positive bacteria, including the step of locating immunoglobulin-like (or Ig-like) folds in the putative LPXTG-containing proteins. This method can be used with any presently known database containing sequence information from Gram positive bacterial species, e.g., amino acid and/or nucleic acid sequences, and involves the steps of locating proteins with the LPXTG (SEQ ID NO:1) motif, and then reviewing and analyzing the sequence information so as to screen for proteins having particular structural similarities to MSCRAMM® as set forth below.

In the general process of the invention, the first part of the process is to search a database containing sequence information on one or more Gram positive bacteria so as to locate those proteins which contain the LPXTG (SEQ ID NO:1) motif contained in cell wall anchored proteins in annotated genomes of Gram-positive bacteria. This is done by initially obtaining the entire genome of amino acids sequences from one or more Gram positive bacteria of interest, such as from any of a number of web sites of sequencing centers, e.g., TIGR, NCBI, etc. In the preferred method, these sequences can be downloaded and stored in electronic memory before carrying out the identifying steps, such as in a local Silicon Graphics machine (SGI) or other suitable computer system. In the preferred method, this stored information is used to prepare a local searchable database, such as by using the program form "atdb" obtained from NCBI, and such a searchable database is installed locally on the SGI.

The LPXTG-motif is identified from the stored sequence information by any of a number of suitable programs. For example, these LPXTG-motif containing proteins can be identified using PHI-blast, which is obtained from NCBI and once again can be installed and stored locally on the SGI or other suitable computer system. The PHI-blast search uses a degenerate LPXTG pattern L-P—X-[TSA]-[GANS] (SEQ ID NO: 25), X being any amino acid. The exact templates for PHI-blast can vary depending on the particular organism, but in any case, the present system includes methods of identifying the LPXTG motif. For each organism, it is preferred to use at least two known cell wall anchored proteins of *S. aureus* with no sequence homology as well as known cell wall anchored proteins from the target organism if available.

Once LPXTG-containing proteins are identified obtained using a suitable system such as PHI-blast, these proteins are further analyzed so as to select for those that contain typical features of LPXTG-motif containing cell wall anchored proteins which have the properties of MSCRAMM®s. In the preferred process, these features will generally include a signal peptide at the N-terminus, the LPXTG-motif being close to the C-terminus, followed by a hydrophobic transmembrane segment, and several positively charged residues at the C-terminus. These are done as described below:

The signal peptides may be identified using any suitable identification method such as that method described in "Identification of prokaryotic and eukaryotic signal peptides and prediction of their cleavage sites". Henrik Nielsen, Jacob Engelbrecht, Søren Brunak and Gunnar von Heijne, *Protein Engineering* 10, 1-6 (1997), incorporated herein by reference. In the present process, a preferred system is to use the SignalP prediction server, but other similar methods for identifying the signal peptide may also be used. Location of LPXTG-motif and the determination of positively charged amino acids residues at the C terminus are accomplished using visual examination of the sequence, although databases may also be used to determine the presence of these features.

In the preferred embodiment, the hydrophobic transmembrane segment after the LPXTG-motif may also be located using a conventional program which can predict the presence of such regions. An example of one such system is the TMHMM server available on the Internet which can be used for the prediction of transmembrane segments. However, a number of other suitable prediction servers are available either on the Internet or in stored computer programs, including the TMpred, the DAS system, and the HMMTOP.

By following the procedures set forth above, putative LPXTG-containing sequences that contain the above features can be selected as highly likely to be MSCRAMM® proteins, i.e., to have the ability to bind extracellular matrix components. Following these initial steps, it is contemplated that the LPXTG-containing proteins identified in this matter will turn out be MSCRAMM® proteins at least about 90% of the time, as confirmed by expressing the putative protein or its A domain and determining if that protein or it's a domain binds to extracellular matrix components. This can be done by simple binding assays which are routine in the art and which would be well within the abilities of one skilled in the art.

Additionally, the LPXTG-containing sequences as initially located, or as further selected using the signal peptide/C terminal/transmembrane identifying characteristics as described above, can be further analyzed as indicated below to confirm the presence of immunoglobulin-like folds characteristic of MSCRAMM® proteins from Gram positive bacteria.

Similarly, in such a method, LPXTG-containing cell wall proteins may also be located using an annotated genomic nucleotide database such as the one located at the TIGR website (comprehensive microbial resource). With these databases, the term "LPXTG" or "cell wall" may be used to search for such proteins that are annotated as cell wall anchored proteins in the genome of interest.

Finally, LPXTG-motif containing cell wall anchored proteins may also be identified in un-annotated nucleotide genomes of Gram-positive bacteria. In this case, genome sequences are obtained from the web sites of sequencing centers, and the sequences may be stored as appropriate in computer memory such as a local Silicon Graphics machine (SGI). Gene prediction may be carried out using the program such as Glimmer 2.0 from TIGR, and this can be facilitated by UNIX C shell scripts which may be modified as desired to suit particular organisms or features. In the preferred process, the predicted genes are translated into amino acid sequences using a suitable translation program, preferably one that is capable of translating large batches of sequences. Finally, the translated amino acid sequences are formatted into a searchable database locally as described above, and subject to further analysis as described below.

In the preferred process of the present invention, steps are carried out by which the Immunoglobulin-like (Ig-like) fold in putative LPXTG-motif containing cell wall anchored proteins can be predicted and identified. In accordance with the invention, the amino acid sequences of putative LPXTG-motif containing cell wall anchored proteins are then analyzed to determine the presence of Ig-like folds which are characteristic of MSCRAMM® proteins. This can be done in a number of ways, such as by processing the putative MSCRAMM® using fold-recognition software, such as available using the web server 3D-PSSM. Additional methods of fold prediction are discussed in Kelley L A, MacCallum R M & Sternberg M J E. Enhanced Genome Annotation using Structural Profiles in the Program 3D-PSSM. J Mol. Biol. 2000 Jun. 2; 299(2):499-520, incorporated herein by reference. Using this method, the output of 3D-PSSM gives a probability E value indicating the likelihood of the submitted sequence adopting a similar 3D structure as the known and published MSCRAMM®s. In accordance with the invention, proteins that have an E value <0.25 to a published Ig-like fold structure, are considered to contain the predicted Ig-like folds, and such proteins are identified as useful MSCRAMM® proteins in accordance with the invention, i.e., proteins that recognize adhesin molecules on the extracellular matrix of host cells.

The present invention has thus been carried out so as to identify and produce proteins and A domains therefrom which have MSCRAMM®-like characteristics from such Gram positive bacteria, such as *Enterococcus, Streptococcus, Staphylococcus* and *Bacillus*. In the preferred process, proteins identified as set forth above or their antigenic A domains may be expressed, purified and characterized as set forth herein.

In accordance with the present invention, a bioinformatic approach was thus used to identify proteins with MSCRAMM®-like characteristics among Gram positive bacteria, and those predicted proteins have been shown to have MSCRAMM-like characteristics. In one such case using *Enterococcus faecalis*, forty-two proteins with a putative C-terminal LPxTG cell wall sorting signal were identified in the *E. faecalis* genome. In accordance with the present method, these proteins were analyzed to determine the presence of Ig-like folds in the manner set forth above. Based on the present method, nine proteins were found to contain regions that adopt an immunoglobulin-like fold. The Ig fold-containing regions for these nine proteins are shown in FIG. 1 and consist of several consecutive and overlapping matches to solved crystal structures (~150-500 aa) of the immunoglobulin superfamily (IgSF), which consist of one to four domains of equal size and Ig-type fold. The homologous Ig-fold regions cover most of the enterococcal proteins and may indicate a similar "beads-in-a-string" arrangement of consecutive modules that are found in fibronectin and other IgSF proteins.

Further expression, purification and analysis of the A domains of these proteins was carried out. As shown in FIG. 2, the A regions of eight proteins expressed as N-terminal His6-tag fusion proteins migrated as expected in SDS-PAGE gels, while EF1091 showed a band approx. 160 kDa in size; a larger-size molecule than the expected 113 kDa. Some degradation was observed in proteins EF1091, EF1824, EF0089 and EF3023, possibly due to their relatively large sizes. They were nevertheless estimated to be >95% pure. The putative glucosyl hydrolase domain of EF1824 (amino acids 42-819), which was cloned and expressed separately from the rest of the protein, (FIG. 1) was found in the insoluble fraction of *E. coli* cytoplasm. Hence, purification by metal affinity chromatography under native, non-denaturing conditions employed for the other expressed proteins was not feasible. The purified proteins were further characterized with Maldi-TOF mass spectrometry. All nine proteins, including EF1091 with aberrant migration in SDS-PAGE, gave peaks that were in good agreement with the molecular weights calculated from amino acid sequences (Table 1), and thus indicated that full-size proteins had been produced with no post-translational processing.

TABLE 1

| Molecular size analysis | | |
|---|---|---|
| | Molecular mass (Da) | |
| Protein | Sequence prediction | Mass spectrometry |
| EF1091 | 113,021 | 113,025 |
| EF1824 | 111,893 | 111,901 |
| EF0089 | 122,853 | 122,857 |
| EF3023 | 113,338 | 113,323 |
| EF1092 | 47,291 | 47,295 |
| EF2224 | 82,194 | 82,199 |
| EF1269 | 64,776 | 64,776 |

TABLE 1-continued

| Molecular size analysis | | |
|---|---|---|
| | Molecular mass (Da) | |
| Protein | Sequence prediction | Mass spectrometry |
| EF1099 | 39,281 | 39,293 |
| EF1093 | 62,363 | 62,366 |

Secondary structure predictions and CD-measurements (Table 2) support finding of Ig-folded module-structures in the enterococcal proteins. Both methods show a similar high proportion of β-sheet (~50%) and coil and a minor quantity of α-helix, an identical situation as seen in MSCRAMM® proteins and in IgSF in general. The higher amount of α-helix in EF1824 and EF3023 probably reflects their relatively short predicted regions with Ig-folds and suggests the remainder of the proteins is structurally more distant to MSCRAMM® proteins.

TABLE 2

| Summary of secondary structure components | | | |
|---|---|---|---|
| Protein | α-Helix | β-Sheet | Other |
| Sequence prediction | | | |
| EF1091 | 0.10 ± 0.05 | 0.33 ± 0.08 | 0.53 ± 0.06 |
| EF1824 | 0.45 ± 0.04 | 0.16 ± 0.04 | 0.39 ± 0.08 |
| EF0089 | 0.07 ± 0.07 | 0.44 ± 0.14 | 0.49 ± 0.08 |
| EF3023 | 0.24 ± 0.09 | 0.29 ± 0.10 | 0.47 ± 0.12 |
| EF1092 | 0.15 ± 0.05 | 0.36 ± 0.06 | 0.49 ± 0.10 |
| EF2224 | 0.15 ± 0.10 | 0.32 ± 0.05 | 0.54 ± 0.10 |
| EF1269 | 0.09 ± 0.10 | 0.42 ± 0.12 | 0.49 ± 0.10 |
| EF1099 | 0.04 ± 0.07 | 0.47 ± 0.07 | 0.49 ± 0.07 |
| EF1093 | 0.09 ± 0.06 | 0.41 ± 0.11 | 0.51 ± 0.11 |
| CD measurement | | | |
| EF1091 | 0.14 ± 0.05 | 0.41 ± 0.11 | 0.45 ± 0.10 |
| EF1824 | 0.29 ± 0.04 | 0.29 ± 0.17 | 0.44 ± 0.17 |
| EF0089 | 0.08 ± 0.04 | 0.49 ± 0.13 | 0.43 ± 0.12 |
| EF3023 | 0.33 ± 0.05 | 0.16 ± 0.05 | 0.51 ± 0.03 |
| EF1092 | 0.05 ± 0.04 | 0.50 ± 0.12 | 0.45 ± 0.14 |
| EF2224 | 0.16 ± 0.03 | 0.36 ± 0.10 | 0.48 ± 0.09 |
| EF1269 | 0.03 ± 0.04 | 0.55 ± 0.14 | 0.42 ± 0.12 |
| EF1099 | 0.07 ± 0.03 | 0.49 ± 0.13 | 0.44 ± 0.14 |
| EF1093 | 0.06 ± 0.05 | 0.57 ± 0.18 | 0.37 ± 0.17 |

In addition to EF1099 (Ace), the primary sequence of EF1269 is clearly related to the MSCRAMM® protein family. Similarly to Ace, it has homologous N2 and N3 subdomains including the conserved TYTDYVD-motif and a connecting tyrosine residue between the two subdomains. The absence of N1 further resembles Ace. However, the rest of their sequences share little homology. Although the A domain of EF1269 is made of similar N2 and N3 subdomains as the fibrinogen-binding ClfA, ClfB, SdrG, and to a lesser extent, FnbpA and FnbpB, it failed to bind fibrinogen. In this respect, EF1269 resembles SdrD and SdrE, which contain N2 and N3 subdomains, but for which the ligand is yet to be found. This is strengthened by our finding that the highest similarity of the EF1269 N2 and N3 domains is to the corresponding region in SdrE (identity 26%). Further, two putative repeats (95 and 109 aa) with lower conservation (identity 20%), which make up the rest of the C-terminal EF1269 sequence, show relatedness to the B repeats of SdrE (25% identity over 375 to 531 aa of EF1269). Proteins EF1091, EF0089, EF1092, EF2224 and EF1093 are not simply orthologs of previously described MSCRAMM® proteins, since they lack high sequence identity to streptococcal and staphylococcal adhesins. Yet, they share similar structural organization and an abundance of β-sheet rich secondary structures with similar predicted folding as MSCRAMM® proteins. The two remaining proteins, EF1824 and EF3023, have large regions related to known enzymes, glucosyl hydrolases and hyaluronan lyases, respectively, which sets these regions apart from MSCRAMM® proteins. Hyaluronidase activity could be significant for bacterial entry and spreading in hyaluronan-containing tissues during infection and/or potentially contribute to bacterial nutrition during commensal life in the human intestine. The large putative catalytic domains of EF1824 and EF3023 agree well with the above-discussed structural unrelatedness in these regions to MSCRAMM® proteins.

When screening binding to major ECM proteins, we found ligands for five of the MSCRAMM® proteins EF0089, EF1091, EF1092, EF1093, and EF2224. The presence of more than one fibrinogen-binding MSCRAMM® proteins in *E. faecalis* is consistent to findings in the related *S. aureus* in which four fibrinogen-binding MSCRAMM® proteins, ClfA, ClfB, FnbpA and FnbpB, have been described (McDevitt et al., 1994) (Ni Eidhin et al., 1998) (Wann et al., 2000) (Davis et al., 2001; Hartford et al., 2001). EF0089 and EF2224 have strong structural resemblance to MSCRAMM® proteins throughout their lengths: similar primary organization and homologous β-sheet rich secondary structure expected to form modular Ig-folded subdomains. Relatively low sequence identity to known fibrinogen binding adhesins may mean novel adaptations for ligand binding. Our initial results suggest EF2224 binds to the α- and β-chains of fibrinogen and thus resembles ClfB (Ni Eidhin et al., 1998). Mammalian tissue surfaces express a multitude of possible ligands for bacterial adherence. Here, we assessed binding to type I, III and IV collagens, laminin, fibronectin, fibrinogen and vitronectin.

In accordance with the invention, a PCR process may be used to amplify A domains from proteins identified and isolated using the present invention. Using PCR oligonucleotides such as those in Table 3, below, the A domains from EF0089, EF1091, EF1092, EF1093, EF1099, EF1269, EF1824, EF2224, and EF3023 were amplified from *E. faecalis* V583 or *E. faecalis* EF1 (EF1099) genomic DNA and subcloned into the *E. coli* expression vector PQE-30 (Qiagen). One liter culture of *E. coli* M15(pREP4) cultures harboring appropriate pQE-30 based constructs were grown to $OD_{600}$=0.6 with an initial 2% inoculation from overnight cultures. After 2-3 h induction with 0.4 mM isopropyl-beta-d-thiogalactoside (IPTG), cells were collected with centrifugation, resuspended in 10 mM Tris-Cl, 100 mM NaCl, pH 7.9 and stored at −80 C.

To lyse the cells and release the expressed protein, cells were passed twice through French Press with a gauge pressure setting at 1200 PSI to give an estimated internal cell pressure of 20,000 PSI. The lysate was centrifuged at $RCF_{max}$ of 165,000×g and the supernatant was filtered through a 0.45 □m filter. The volume was adjusted to 15 ml with 10 mM Tris-Cl, 100 mM NaCl, pH 7.9 and 0.2 M imidazole in the same buffer was added to increase the imidazole concentration to 6.5 mM in order to minimize non-specific binding. The sample was loaded to a nickel affinity chromatography column (HiTrap chelating, Pharmacia) connected to an FPLC system (Pharmacia) and previously equilibrated with 10 mM Tris-Cl, 100 mM NaCl, pH 7.9. Bound protein was eluted with a linear gradient of 0-100 mM imidazole in 10 mM Tris-Cl, 100 mM NaCl, pH 7.9 over 100-200 ml. Protein-containing fractions were analyzed in SDS-PAGE (FIG. 2)

and dialyzed against 25 mM Tris-Cl, 1 mM EDTA, pH 6.5-9 (depending on pI of protein purified) before applying the samples to an ion-exchange column (HiTrap Q, Pharmacia) for further purification. Bound protein was eluted with a linear gradient of 0-0.5 M NaCl in 25 mM Tris-Cl, 1 mM EDTA, pH 6.5-9 over 100 ml. Finally, protein samples were dialyzed extensively against PBS and stored at +4° C.

Alternatively EF1091, EF1092, and EF1093 were expressed in shake flasks or in bioreactors, the cells were harvested by centrifugation and the cell paste frozen at −80° C. Cells were lysed in 1×PBS (10 mL of buffer/1 g of cell paste) using 2 passes through a microfluidizer at 10,000 psi.

This may be due to different expression levels in physiological conditions or to highly immunogenic surface epitopes and, hence, a strong immune response. Interestingly, the three proteins (EF1091, EF1092 and EF1093) with the highest titers are organized as a putative operon in the *E. faecalis* genome. The operon is preceded by two promoter consensus regions and a ribosome binding site and thus, these proteins are likely co-transcribed. The next gene downstream, EF1094, codes for a putative LPxTG transpeptidase sortase and EF1099 (Ace) is closely linked. It remains to be seen what role this cluster of MCSRAMM®-like proteins and a putative sortase may have in the infection process.

TABLE 3

Synthetic oligonucleotides used in this study (SEQ ID NOS: 26-43)

| Oligonucleotide | | Location (aa) | Cloning site | Oligonucleotide |
|---|---|---|---|---|
| EF1091A | Fw | 102 | SphI | 5'-CC**GCATGC**CAAGAGCAAACAGCAAAAGAAG-3' |
| | Rev | 1107 | SalI | 5'-CC**GTCGAC***TTA*AGTACCAGAAGTGGTGGTTTTC-3' |
| EF1824AI | Fw | 42 | SphI | 5'-CC**GCATGC**CAAGAGCAAACAGCAAAAGAAG-3' |
| | Rev | 819 | SalI | 5'-GG**GTCGAC***TTA*TTGTTTCAAGGTTACTTCTGTC |
| EF1824AII | Fw | 819 | BamHI | 5'-CC**GGATCC**GCAGCTAATAAAGAAGAATTTTTAG |
| | Rev | 1829 | SalI | 5'-CC**GTCGAC***TTA*AGTACCAGAAGTGGTGGTTTTC-3' |
| EF0089A | Fw | 35 | SacI | 5'-CC**GAGCTC**GAAGAGGTTAACAGCGATGG-3' |
| | Rev | 1143 | PstI | 5'-CC**CTGCAG***TTA*CCCACCAAATGTGATAACCC-3' |
| EF3023A | Fw | 25 | BamHI | 5'-CC**GGATCC**GAAGAAATAACTGATTTATTTTTAC-3' |
| | Rev | 1024 | SacI | 5'-CC**GAGCTC***TTA*TTGTTCCTGAATTAATTTTTCTAAC-3' |
| EF1092A | Fw | 27 | SphI | 5'-CC**GCATGC**TCGCAAGCAAGCGTTCAAG-3' |
| | Rev | 438 | PstI | 5'-CC**CTGCAG***TTA*GAAGCCTGACTCTTTTACTTTT-3' |
| EF2224A | Fw | 30 | BamHI | 5'-CC**GGATCC**CAAGAAGTAACAAGTGATGCTG-3' |
| | Rev | 771 | SacI | 5'-CC**GAGCTC***TTA*AGTTACTTGTTCGTCCGCAAT-3' |
| EF1269A | Fw | 26 | BamHI | 5'-CC**GGATCC**GAAACAGGATATGCGCAAAC-3' |
| | Rev | 596 | SacI | 5'-CC**GAGCTC***TTA*TTCCTTATTACGAATCGCCTG-3' |
| EF1093A | Fw | 32 | BamHI | 5'-GCG**GGATCC**GAAGAAAATGGGGAGAGCGC-3' |
| | Rev | 590 | SacI | 5'-GCG**GAGCTC***TTA*GGTACCTTTGTGTTTGTTTGG-3' |

5' overhang cloning site in each oligonucleotide sequence is marked in bold, stop codon in italic
Fw, oligonucleotide primer in forward direction; Rev, in reverse direction Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 500 mM imidazole (Buffer B). Protein containing fractions were dialyzed in 1×PBS.

The nine enterococcal genes encoding the MSCRAMM® are ubiquitous among *E. faecalis* strains as summarized in Table 3. Seven of the nine genes were 100% preserved in all strains. The two genes, EF1824 and EF3023, with predicted encoded protein catalytic domains and relatively low proportion of MSCRAMM®-like protein characteristics, were present in 16/30 and 23/30 strains, respectively. Nine enterococcal proteins encoded by their respective gene showed elevated titers in infected individuals suggesting expression in vivo during an *E. faecalis* infection. Although these proteins have a high distribution in strains, there were clear differences in induced antigenic responses; proteins EF1091, EF1092, EF1093 and EF2224 exhibited the highest titers.

The presence of several MSCRAMM®-like proteins in *E. faecalis* including two that bind fibrinogen and the previously described collagen and laminin binding Ace, suggests that *E. faecalis* resembles *S. aureus* and other Gram-positive cocci by having an armory of ECM-binding adhesins. Since the introduction of antibiotic therapy, *E. faecalis* has shown an increasing tendency to emerge as an opportunistic pathogen capable of crossing the thin line from a harmless commensal to being able to invade host tissues and cause infections. A repertoire of adhesins may enhance its adaptability for colonizing and spreading in various human tissue types of susceptible human hosts.

Accordingly, the present invention allows for the identification and ultimate production of novel MSCRAMM®-like protein surface-anchored proteins from Gram positive bacteria which (i) are structurally homologous to the solved Ig-folded crystal structures of ClfA and CNA as well as to the predicted tertiary structures of other MSCRAMM® proteins, (ii) can share a similar β-sheet rich secondary structure as is found in Ig-folded proteins and (iii) have a similar organization with a secretion signal, a non-repeated domain followed by repeats as well as a C-terminal cell wall anchor domain. Further, these proteins may bind to major ECM proteins such as fibrinogen, collagen and laminin, and due to the similarities in proteins from different Gram positive bacterial species, these proteins may provide antibodies which are cross-reactive and can bind to similar proteins found in different Gram positive bacterial species. Such antibodies, as described further below, may thus be useful in diagnosing or fighting a variety of different infections at the same time.

In addition to proteins identified and isolated using the present method, particular, the present invention contemplates the generation of antibodies from the MSCRAMM®-like proteins obtained using the present method, or from antigenic regions such as the A domains from these proteins. By "antibody" is meant any intact antibody molecule or fragments thereof that recognize antigen (e.g. Fab or F(ab')2 fragments) and can be of polyclonal or monoclonal type, and the antibodies in accordance with the invention will be capable of recognizing the MSCRAMM® proteins of the invention and/or the specific antigenic epitopes from said proteins including their A domains. These antibodies will thus be effective in methods of diagnosing, monitoring, treating or preventing infection from Gram positive bacteria. By "epitope" is meant any antigenic determinant responsible for immunochemical binding with an antibody molecule. Epitopes usually reside within chemically active surface groupings of protein molecules (including amino acids and often also sugar side-chains) and have specific three-dimensional structural characteristics and specific charge characteristics. With reference to the proteins of the invention, or epitopes and peptides as described herein, it is understood that such terms also include those proteins and peptides which differ from a naturally occurring or recombinant protein by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end.

Accordingly, in accordance with the present invention, isolated and/or purified antibodies can be generated from the Gram-positive MSCRAMM® proteins of the present invention, or from particular epitopes such as those epitopic peptide sequences from the A domains from those proteins as described herein. These antibodies may be monoclonal or polyclonal and may be generated using any suitable method to raise such antibodies such as would be well known in this art. The antibodies in accordance with the invention will be particularly useful in inhibiting the binding of Gram positive bacteria to extracellular matrix components of the host cells and in diagnosing, treating or preventing infections of Gram positive bacteria.

For example, with regard to polyclonal antibodies, these may be generated using a number of suitable methods generally involving the injection of the isolated and/or purified or recombinantly produced proteins (or their immunogenic active peptides or epitopes) into a suitable host in order to generate the polyclonal antibodies which can then be recovered from the host. For example, in accordance with the invention, an isolated and purified MSCRAMM® protein or its A domain may be injected into rabbits in order to generate polyclonal antisera recognizing this protein.

In addition, monoclonal antibodies in accordance with the invention may be generated using a suitable hybridoma as would be readily understood by those of ordinary skill in the art. In the preferred process, a protein in accordance with the invention is first identified and isolated using the bioinformatic method as described above. Next, the protein is isolated and/or purified in any of a number of suitable ways commonly known in the art, or after the protein is sequenced, the protein used in the monoclonal process may be produced by recombinant means as would be commonly used in the art and then purified for use. In one suitable purification process, the cell wall proteins of the invention are isolated and examined using polyacrylamide gel electrophoresis (PAGE) and Western-blot techniques, and other conventional techniques including those discussed herein. In one suitable process, monoclonal antibodies were generated from proteins isolated and purified as described above by mixing the protein with an adjuvant, and injecting the mixture into BALB/c mice.

Immunization protocols consisted of a first injection (using complete Freund's adjuvant), two subsequent booster injections (with incomplete Freund's adjuvant) at three-week intervals, and one final booster injection without adjuvant three days prior to fusion (all injections were subcutaneous). For hybridoma production, mice were sacrificed and their spleen removed aseptically. Antibody secreting cells isolated and mixed with myeloma cells (NS1) using drop-wise addition of polyethylene glycol. After the fusion, cells were diluted in selective medium (vitamin-supplemented DMEM/HAT) and plated at low densities in multiwell tissue culture dishes. Tissue supernatants from the resulting fusion were screened by both ELISA (using the total 2-ME extract to coat the wells of a microtiter plate) and immunoblot techniques. Cells from these positive wells were grown and single cell cloned by limiting dilution, and supernatants subjected to one more round of screening by both ELISA and immunoblot. Positive clones were identified, and monoclonal antibodies collected as hybridoma supernatants.

In accordance with the invention, antibodies are thus produced which are capable of recognizing and binding proteins obtained using the bioinformatic method of the present invention and/or its epitopes and active regions such as the A domain, and such antibodies can be utilized in many diagnostic and therapeutic applications such as the ones described in more detail below.

Vaccines, Humanized Antibodies and Adjuvants

The isolated antibodies of the present invention, or the isolated proteins or epitopes as described above, may also be utilized in the development of vaccines for active and passive immunization against bacterial infections, as described further below. In the case of active vaccines, said vaccines are prepared by providing an immunogenic amount of the proteins of the invention or their active regions or epitopes as set forth above, and the active vaccine in accordance with the invention will thus comprise an immunogenic amount of the protein or peptide and will be administered to a human or animal in need of such a vaccine. The vaccine may also comprise a suitable, pharmaceutically acceptable vehicle, excipient or carrier which will be those known and commonly used in the vaccine arts. As referred to above, an "immunogenic amount" of the antigen to be used in accordance with the invention is intended to mean a nontoxic but sufficient amount of the agent, such that an immunogenic response will be elicited in the host so that the desired prophylactic or therapeutic effect is produced. Accordingly, the exact amount of the antigen that is required will vary from subject to subject, depending on the species, age, and general condition of the subject, the severity of the condition being treated, the particular carrier or adjuvant being used and its mode of administration, and the like. Similarly, the "immunogenic amount" of any such antigenic vaccine composition will vary based on the particular circumstances, and an appropriate immunogenic amount may be determined in each case of application by one of ordinary skill in the art using only routine experimentation. The dose should be adjusted to suit the individual to whom the composition is administered and will vary with age, weight and metabolism of the individual.

Further, when administered as pharmaceutical composition to a patient or used to coat medical devices or polymeric biomaterials in vitro and in vivo, the antibodies of the present invention may also be useful because these antibodies may be able to interfere with the ability of Gram positive bacteria to adhere to host cells and limit the extent and spread of the infection.

In addition, the antibody may be modified as necessary so that, in certain instances, it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522-525 (1986) or Tempest et al. *Biotechnology* 9:266-273 (1991) or "veneered" by changing the surface exposed murine framework residues in the immunoglobulin variable regions to mimic a homologous human framework counterpart as described, e.g., by Padlan, Molecular 1 mm. 28:489-498 (1991), these references incorporated herein by reference. Even further, under certain circumstances, it may be desirable to combine the monoclonal antibodies of the present invention with a suitable antibiotic when administered so as to further enhance the ability of the present compositions to fight or prevent infections.

In a preferred embodiment, the antibodies may also be used as a passive vaccine which will be useful in providing suitable antibodies to treat or prevent a Gram-positive bacterial infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable vehicle, carrier or excipient to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a bacterial infection, and one would readily recognize that this amount will vary greatly depending on the nature of the infection and the condition of a patient. An "effective amount" of antibody or pharmaceutical agent to be used in accordance with the invention is intended to mean a nontoxic but sufficient amount of the agent, such that the desired prophylactic or therapeutic effect is produced. Accordingly, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

In addition, the antibody compositions of the present invention and the vaccines as described above may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

Pharmaceutical Compositions

As would be recognized by one skilled in the art, the identified and isolated proteins or the invention, and the antibodies thereto capable of recognizing and binding to said proteins may also be formed into suitable pharmaceutical compositions for administration to a human or animal patient in order to treat or prevent a Gram-positive bacterial infection, such as those caused by *Enterococcus, Streptococcus, Staphylococcus*, etc. Pharmaceutical compositions containing the proteins or antibodies of the present invention as defined and described above may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition may be formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of compositions, and other information concerning compositions, methods and applications with regard to other microbial surface proteins and peptides of the present invention and antibodies thereto, will be found in other patent references relating to MSCRAMM®s, including, for example, in U.S. Pat. No. 6,288,214 (Hook et al.), incorporated herein by reference.

The compositions which are generated in accordance with the present invention may also be administered with a suitable adjuvant in an amount effective to enhance the immunogenic response in a patient. For example, suitable adjuvants may include alum (aluminum phosphate or aluminum hydroxide), which is used widely in humans, and other adjuvants such as saponin and its purified component Quil A, Freund's complete adjuvant, RIBI adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410-415 (1991) and incorporated by reference herein, encapsulation of the conjugate within a proteoliposome as described by Miller et al., *J. Exp. Med.* 176:1739-1744 (1992) and incorporated by reference herein, and encapsulation of the protein in lipid vesicles such as Novasome™ lipid vesicles (Micro Vescular Systems, Inc., Nashua, N.H.) may also be useful.

In any event, the compositions of the present invention will thus be useful for interfering with, modulating, or inhibiting binding interactions by Gram positive bacteria. Accordingly, the present invention will have particular applicability in developing compositions and methods of preventing or treating Gram positive bacterial infections, and in inhibiting binding and spreading of bacteria to host cells.

Methods:

Detecting and Diagnosing Infections

In accordance with the present invention, methods are provided for identifying and diagnosing infection from Gram positive bacteria through the use of the proteins, epitopes and peptides obtained by the bioinformatic method of the invention as described above and antibodies that recognize such proteins, epitopes and/or peptides. In accordance with the present invention, the antibodies of the invention as set forth above may be used in kits to diagnose such infections, and such kits may be of the type generally known in the art and commonly used to detect an antigen or microorganism of interest which will bind to the antibodies of the invention. These diagnostic kits will generally include the antibodies of the invention along with suitable means for detecting binding by that antibody such as would be readily understood by one skilled in this art. For example, the means for detecting binding of the antibody may comprise a detectable label that is linked to said antibody. These kits can then be used in diagnostic methods to detect the presence of a Gram positive bacterial infection wherein one obtains a sample suspected of being infected by one or more Gram positive bacteria, such as a sample taken from an individual, for example, from one's blood, saliva, urine, cerebrospinal fluid, genitourinary tract, tissues, bone, muscle, cartilage, or skin, and introduces to the sample one or more of the antibodies as set forth herein. After introduction of the antibodies, it is then determined through conventional means whether there has been binding by the antigens or microorganisms in the sample, such as through suitable labeling, or assays wherein the antibodies are bound to solid supports, and this binding is reflective of the presence of the target antigens or microorganisms in the sample.

Methods for Monitoring Levels of Antibodies or Antigens

In accordance with the present invention, it is also contemplated that another use of the invention may be in monitoring the level of Gram positive bacterial antigens, or antibodies recognizing said antigens in a human or animal patients suspected of containing said antigens or antibodies. In the preferred process, this may be carried out by first obtaining a biological sample from the human or animal patient, and this would include any suitable sample routinely monitored for infection, such as for example, from one's blood, serum, saliva, tissues, bone, muscle, cartilage, or skin. Next, one would introduce into the sample either (1) when monitoring levels of one's antibodies to Gram positive bacteria, a determinable level of a protein or its A domain to which such antibodies will bind; or (2), when monitoring levels of bacterial infestation is desired, introducing into said sample a measurable level of an antibody to a protein as set forth above. The next step in the process is, after allowing sufficient time and conditions so that the antigens and antibodies in the sample can achieve binding, then determining the level of antigen-antibody binding which will be reflective of the amount or level of the Gram positive bacteria, or antibodies thereto, which are located in the sample. In the desired process, levels may be monitored at regular time periods (e.g., hourly, daily, etc.) so as to track the progression/remission of a Gram positive bacterial infection such as during the period of hospitalization or treatment.

Assays for Detecting and Diagnosing Infections

In accordance with the present invention, the detection of Gram positive bacteria present in a biological fluid (e.g. blood, serum, plasma, saliva, urine, cerebrospinal fluid, genitourinary tract) or other biological material (e.g., tissues, bone, muscle, cartilage, or skin) can constitute a method for the diagnosis of acute or chronic infections caused by Gram positive bacteria. Because the antibodies as set forth above can recognize the epitopes found in several Gram positive bacteria, these antibodies can be used in assays to allow the diagnosis of a wide variety of Gram positive bacteria and disease conditions. Either monoclonal antibodies or polyclonal antibodies could be used in the assay, and in the case of the monoclonals such as those referred to above. The detected antigens identified by use of the present assays can be detected by a number of conventional means, including Western immunoblot and other similar tests.

With regard to the assays of the present invention, these assays may use the antibodies of the invention in labeled form, and all well-known methods of labeling antibodies are contemplated, including without limitation enzymatic conjugates, direct labeling with dye, radioisotopes, fluorescence, or particulate labels, such as liposome, latex, polystyrene, and colloid metals or nonmetals. Multiple antibody assay systems, such as antigen capture sandwich assays, are also within the scope of this invention. Further, competitive immunoassays involving labeled protein or assays using the labeled protein to detect serum antibodies are also contemplated forms of the diagnostic assays of the present invention. Beyond diagnostic assays which occur in solution, assays which involve immobilized antibody or protein are also considered within the scope of the invention. (See, for example, Miles et al., Lancet 2:492, 1968; Berry et al., J. Virol. Met. 34:91-100, 1991; Engvall et al., G. Immunochemistry, 8:871, 1971, Tom, Liposomes and Immunology, Elsevier/North Holland, New York, N.Y., 1980; Gribnau et al., J. of Chromatogr. 376:175-89, 1986 and all references cited therein). Examples of the types of labels which can be used in the present invention include, but are not limited to, enzymes, radioisotopes, fluorescent compounds, chemiluminescent compounds, bioluminescent compounds, particulates, and metal chelates. Those of ordinary skill in the art will know of other suitable labels for binding to the monoclonal or polyclonal antibody (or to an antigen) or will be able to ascertain the same by the use of routine experimentation. Furthermore, the binding of these labels to the monoclonal or polyclonal antibody (or antigen) can be accomplished using standard techniques commonly known to those of ordinary skill in the art.

One of the ways in which an assay reagent (generally, a monoclonal antibody, polyclonal antibody or antigen) of the present invention can be detectably labeled is by linking the monoclonal antibody, polyclonal antibody, or antigen to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label the reagents of the present invention include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of the detectably labeled reagent of the present invention can also be detected by labeling the reagent with a radioactive isotope which can then be determined by such means as the use of a gamma counter or a scintillation counter. Isotopes which are particularly useful for the purpose of the present invention are .sup.3H, .sup.125 I, .sup.32 P, .sup.35 S, .sup.14 C, .sup.51 Cr, .sup.36 Cl, .sup.57 Co, .sup.58 Co, .sup.59 Fe and .sup.75 Se. It is also possible to detect the binding of the detectably labeled reagent of the present invention by labeling the monoclonal or polyclonal antibody with a fluorescent compound. When the fluorescently labeled reagent is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, o-phthaldehyde and fluorescamine. The reagents of the present invention also can be detectably labeled by coupling it to a chemiluminescent compound. The presence of the chemiluminescent-tagged reagent is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the reagent of the present invention. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

Another technique which may also result in greater sensitivity when used in conjunction with the present invention consists of coupling the monoclonal or polyclonal antibody of the present invention to low molecular weight haptens. The haptens can then be specifically detected by means of a second reaction. For example, it is common to use such haptens as biotin (reacting with avidin) or dinitrophenol, pyridoxal and fluorescamine (reacting with specific antihapten antibodies) in this manner. Any biological sample containing the detectable yet unknown amount of a Gram positive antigen can be used in the assay. Normally, the sample is preferably a liquid, such as, for example, urine, saliva, cerebrospinal fluid, blood, serum and the like, or a solid or semi-solid, such as, for example, tissue, feces and the like.

The diagnostic assay of the present invention includes kit forms of such an assay. This kit would include antibodies as described above (raised against whole proteins or active immunoreactive fragments such as the A domain or immunogenic analogs thereof) which can be optionally immobilized, as well as any necessary reagents and equipment to prepare the biological sample for and to conduct analysis, e.g. preservatives, reaction media such as nontoxic buffers, microtiter plates, micropipettes, etc. The reagent (Abs and/or antigens) can be lyophilized or cryopreserved. As described above, depending on the assay format, the antibodies can be labeled, or the kit can further comprise labeled proteins, fragments or analogs thereof containing the relevant epitopes so as to enable the detection of antibodies to Gram positive bacteria in biological fluids and tissues. By analog is meant a protein or peptide which may differs from its naturally occurring or recombinant counterpart by the substitution, deletion and/or addition of one or more amino acids but which retains the ability to be recognized by an antibody raised against the entire protein. An example is a carrier/antigen fusion polypeptide of the whole antigen or an immunoreactive fragment thereof, where the antigen or fragment can be embedded within the carrier polypeptide or linked to the carrier polypeptide at either end. Accordingly, antibodies in accordance with the invention may also recognize such analogs. The types of immunoassays which can be incorporated in kit form are many. Typical examples of some of the immunoassays which can utilize the antibodies of the invention are radioimmunoassays (RIA) and immunometric, or sandwich, immunoassays.

By "immunometric assay" or "sandwich immunoassay", in meant to include simultaneous sandwich, forward sandwich and reverse sandwich immunoassays. These terms are well understood by those skilled in the art. Those of skill will also appreciate that the monoclonal antibodies, polyclonal antibodies and/or antigens of the present invention will be useful in other variations and forms of immunoassays which are presently known or which may be developed in the future. These are intended to be included within the scope of the present invention. In a forward sandwich immunoassay, a sample is first incubated with a solid phase immunoadsorbent containing monoclonal or polyclonal antibody(ies) against the antigen. Incubation is continued for a period of time sufficient to allow the antigen in the sample to bind to the immobilized antibody in the solid phase. After the first incubation, the solid phase immunoadsorbent is separated from the incubation mixture and washed to remove excess antigen and other interfering substances, such as non-specific binding proteins, which also may be present in the sample. Solid phase immunoadsorbent containing antigen bound to the immobilized antibody is subsequently incubated for a second time with soluble labeled antibody or antibodies. After the second incubation, another wash is performed to remove unbound labeled antibody(ies) from the solid phase immunoadsorbent and removing non-specifically bound labeled antibody(ies). Labeled antibody(ies) bound to the solid phase immunoadsorbent is then detected and the amount of labeled antibody detected serves as a direct measure of the amount of antigen present in the original sample.

Alternatively, labeled antibody which is not associated with the immunoadsorbent complex can also be detected, in which case the measure is in inverse proportion to the amount of antigen present in the sample. Forward sandwich assays are described, for example, in U.S. Pat. Nos. 3,867,517; 4,012,294 and 4,376,110, incorporated herein by reference.

In carrying out forward immunometric assays, the process may comprise, in more detail: (a) first forming a mixture of the sample with the solid phase bound antibody(ies) and incubating the mixture for a time and under conditions sufficient to allow antigen in the sample to bind to the solid phase bound antibody(ies), (b) adding to the mixture after said incubation of step (a) the detectably labeled antibody or antibodies and incubating the new resulting mixture for a time and under conditions sufficient to allow the labeled antibody to bind to the antigen-antibody complex on the solid phase immunoadsorbent; (c) separating the solid phase immunoadsorbent from the mixture after the incubation in step (b); and (d) detecting either the labeled antibody or antibodies bound to the antigen-antibody complex on the solid phase immunoadsorbent or detecting the antibody not associated therewith.

In a reverse sandwich assay, the sample is initially incubated with labeled antibody(ies), after which the solid phase immunoadsorbent containing multiple immobilized antibodies is added thereto, and a second incubation is carried out. The initial washing step of a forward sandwich assay is not required, although a wash is performed after the second incubation. Reverse sandwich assays have been described, for example, in U.S. Pat. Nos. 4,098,876 and 4,376,110. In carrying out reverse immunometric assays, the process may comprise, in more detail; (a) first forming a mixture of the sample with the soluble detectably labeled antibody for a time and under conditions sufficient to allow antigen in the sample to bind to the labeled antibody; (b) adding to the mixture after the incubation of step (a) the solid phase bound antibodies and incubating the new resulting mixture for a time and under conditions sufficient to allow antigen bound to the labeled antibody to bind to the solid phase antibodies; (c) separating the solid phase immunoadsorbent from the incubating mixture after the incubation in step (b); and (d) detecting either the labeled antibody bound to the solid phase immunoadsorbent or detecting the labeled antibody not associated therewith.

In a simultaneous sandwich assay, the sample, the immunoadsorbent having multiple immobilized antibodies thereon and labeled soluble antibody or antibodies are incubated simultaneously in one incubation step. The simultaneous assay requires only a single incubation and does not include washing steps. The use of a simultaneous assay is by far the preferred one. This type of assay brings about ease of handling, homogeneity, reproducibility, and linearity of the assays and high precision. The sample containing antigen, solid phase immunoadsorbent with immobilized antibodies and labeled soluble antibody or antibodies is incubated under conditions and for a period of time sufficient to allow antigen to bind to the immobilized antibodies and to the soluble antibody(ies). In general, it is desirable to provide incubation conditions sufficient to bind as much antigen as possible, since this maximizes the binding of labeled antibody to the solid phase, thereby increasing the signal. Typical conditions of time and temperature are two hours at 45 degrees C., or twelve hours at 37 degrees C. Antigen typically binds to labeled antibody more rapidly than to immobilized antibody, since the former is in solution whereas the latter is bound to the solid phase support. Because of this, labeled antibody may be employed in a lower concentration than immobilized antibody, and it is also preferable to employ a high specific activity for labeled antibody. For example, labeled antibody might be employed at a concentration of about 1-50 ng per assay, whereas immobilized antibody might have a concentration of 10-500 ng per assay per antibody. The labeled antibody might have a specific activity with, for instance, one radioiodine per molecule, or as high as two or more radioiodines per molecule of antibody.

Of course, the specific concentrations of labeled and immobilized antibodies, the temperature and time of incubation as well as other assay conditions can be varied, depending on various factors including the concentration of antigen in the sample, the nature of the sample and the like. Those skilled in the art will be able to determine operative and optimal assay conditions for each determination by employing routine experimentation.

In carrying out the simultaneous immunometric assay on a sample containing a multivalent antigen, the process may comprise, in more detail: (a) simultaneously forming a mixture comprising the sample, together with the solid phase bound antibody and the soluble labeled antibody or antibodies; (b) incubating the mixture formed in step (a) for a time and under conditions sufficient to allow antigen in the sample to bind to both immobilized and labeled antibodies; (c) separating the solid phase immunoadsorbent from the incubation mixture after the incubation; and (d) detecting either labeled antibody bound to the solid phase immunoadsorbent or detecting labeled antibody not associated therewith. Other such steps as washing, stirring, shaking filtering and the like may of course be added to the assays, as is the custom or necessity for any particular situation.

There are many solid phase immunoadsorbents which have been employed and which can be used in the present invention. Well-known immunoadsorbents include nitrocellulose, glass, polystyrene, polypropylene, dextran, nylon and other materials; tubes, beads, and microtiter plates formed from or coated with such materials, and the like. The immobilized antibodies can be either covalently or physically bound to the solid phase immunoadsorbent, by techniques such as covalent bonding via an amide or ester linkage, or by absorption. Those skilled in the art will know many other suitable solid phase immunoadsorbents and methods for immobilizing antibodies thereon, or will be able to ascertain such, using no more than routine experimentation.

Kits

As indicated above, in accordance with the present invention, the antibodies of the invention as set forth above may be used in kits to diagnose a Gram positive infection. Such diagnostic kits are well known in the art and will generally be prepared so as to be suitable for determining the presence of epitopes or proteins that will bind to the antibodies of the invention. These diagnostic kits will generally include the antibodies of the invention along with suitable means for detecting binding by that antibody such as would be readily understood by one skilled in this art. For example, the means for detecting binding of the antibody may comprise a detectable label that is linked to said antibody. These kits can then be used in diagnostic methods to detect the presence of a bacterial infection wherein one obtains a biological sample suspected of having such an infection, such as a sample taken from an individual, for example, from one's blood, saliva, urine, cerebrospinal fluid, genitourinary tract, tissues, bone, muscle, cartilage, or skin, introduces to the sample one or more of the antibodies as set forth herein, and then determines if the antibodies bind to the sample which would indicated the presence of such microorganisms in the sample.

In addition, as set forth above, these kits can also be useful in methods of monitoring the level of antibodies or bacterial antigens in the serum of a human or animal patient. If monitoring the level of antigen is desired, the kit will include an antibody in accordance with the present invention as described above along with a means of determining the level of binding to that antibody. When it is desired to measure the level of antibodies to Gram positive bacteria in a sample, the kit will preferably include an isolated protein or epitope (e.g., the A domain) such as described above, along with means for detecting binding of those antigens to antibodies present in the sample.

Treating or Protecting Against Infections

In accordance with the present invention, methods are provided for preventing or treating an infection caused by Gram positive bacteria which comprise administering an effective amount of the antibodies as described above to a human or animal patient in need of such treatment in amounts effective to treat or prevent the infection. Accordingly, in accordance with the invention, administration of an effective amount of the antibodies of the present invention in any of the conventional ways described above (e.g., topical, parenteral, intramuscular, etc.), and will thus provide an extremely useful method of treating or preventing bacterial infections in human or animal patients. As indicated above, by effective amount is meant that level of use, such as of an antibody titer, that will be sufficient to either prevent adherence of the bacteria, or to inhibit binding and colonization of such organisms to host cells and thus be useful in the treatment or prevention such infections. In addition, these antibodies also exhibit protective effects by a number of other mechanisms, including direct killing of the infectious microorganisms, increased opsonization, inhibition of morphological transition, etc., and thus an effective amount of antibodies will also include that amount by which any of the means to achieve a protective effect is obtained. As would be recognized by one of ordinary skill in this art, the level of antibody titer needed to be effective in treating or preventing infections will vary depending on the nature and condition of the patient, and/or the severity of the pre-existing infection.

Eliciting an Immune Response

In accordance with the present invention, a method is provided for eliciting an immunogenic reaction in a human or animal comprising administering to the human or animal an immunologically effective amount of a protein isolated using the bioinformatic method as described above, or a recombinantly produced version of such a protein, or an immunogenic fragment, region or epitope as described above so as to elicit an immunogenic response. As indicated above, an "immunogenic amount" of the antigen to be used in accordance with the invention to obtain an immunogenic reaction is intended to mean a nontoxic but sufficient amount of the agent, such that an immunogenic response will be elicited in the host so that the desired prophylactic or therapeutic effect is produced. Accordingly, the exact amount of the isolated protein that is required to elicit such a response will vary from subject to subject, depending on the species, age, and general condition of the subject, the severity of the condition being treated, the particular carrier or adjuvant being used and its mode of administration, and the like. The invention also contemplates methods of generating antibodies which recognize the proteins and epitopes as described above, and suitable methods of generating monoclonal and polyclonal antibodies are described in more detail above.

Coating Devices

In accordance with the invention, the antibodies and compositions as described above may also be utilized to treat or protect against outbreaks of bacterial infections on certain medical devices and other implanted materials such as prosthetic devices. Medical devices or polymeric biomaterials that may be advantageously coated with the antibodies and/or compositions described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or composition as defined above to a surface of the device, preferably an outer surface that would be exposed to an infection such as those caused by Gram positive bacteria. The surface of the device need not be entirely covered by the protein, antibody or active fragment.

As indicated above, the antibodies of the present invention, or active portions or fragments thereof, may also be useful for interfering with the physical interaction between bacteria responsible for infection and a mammalian host, and may also be useful in interfering with the ability of the bacteria to adhere to extracellular matrix proteins such as fibrinogen, collagen, laminin, etc. Accordingly, the antibodies of the invention may be useful both in treating patients and in preventing or reducing bacterial infections, or for reducing or eliminating infection and infestation of such organisms indwelling medical devices and prosthetics to make them safer for use.

In short, the antibodies of the present invention as described above can be extremely useful in detecting, treating or preventing infections by Gram positive bacteria in human and animal patients, or in preventing or reducing infection of medical devices and prosthesis that can be caused by such organisms. In particular, the present invention will be of importance in the treatment or prevention of such infections in highly susceptible groups such as premature newborns, AIDS and debilitated cancer patients, and are particularly frequent and severe after bone marrow transplantation.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Examples

Example 1

Method to Identify MSCRAMM® Proteins from Gram Positive Bacteria and Expression and Purification of their a Domains A. Searching for LPXTG-Motif Containing Cell Wall Anchored Proteins in Annotate Genomes of Gram-Positive Bacteria.

1. Obtain the amino acid sequences of the entire genome of interest from web sites of sequencing centers. These sequences are stored in a local Silicon Graphics machine (SGI).

2. A local searchable database is established using the program format db obtained from NCBI and installed locally on the SGI.

3. LPXTG-motif containing proteins are identified using PHI-blast, which is obtained from NCBI and installed locally on the SGI. The PHI-blast search uses a degenerate LPXTG pattern L-P—X-[TSA]-[GANS], X being any amino acid. The templates for PHI-blast vary depend on the particular organism. For each organism, two known cell wall anchored proteins of *S. aureus* with no sequence homology were used as well as known cell wall anchored proteins from that particular organism if available.

4. The LPXTG-containing proteins obtained from PHI-blast were analyzed to select for those that contain typical features of LPXTG-motif containing cell wall anchored proteins: a signal peptide at the N-terminus, the LPXTG-motif being close to the C-terminus followed by a hydrophobic transmembrane segment, and several positively charged residues at the C-terminus. These are done as described below:

Signal peptide: we use the SignalP prediction server. The method has been described in "Identification of prokaryotic and eukaryotic signal peptides and prediction of their cleavage sites". Henrik Nielsen, Jacob Engelbrecht, Søren Brunak and Gunnar von Heijne, *Protein Engineering* 10, 1-6 (1997).

Location of LPXTG-motif: visual examination of the sequence.

A hydrophobic transmembrane segment after the LPXTG-motif: we use the TMHMM server for the prediction of transmembrane segments. Several other prediction web servers can also be used, among which are TMpred, DAS, and HMMTOP.

Positively charged residues at C-terminus: visual examination.

5. Sequences that contain the above features are putative LPXTG-motif containing cell wall anchored proteins.

6. The term "LPXTG" or "cell wall" are used to search for proteins that are annotated as cell wall anchored proteins in the genome of interest at TIGR website (comprehensive microbial resource, http://www.tigr.org/tigr-scripts/CMR2/CMRHomePage.spl).

B. Searching for LPXTG-Motif Containing Cell Wall Anchored Proteins in Un-Annotated Genomes of Gram-Positive Bacteria.

1. Obtain genome sequences from the web sites of sequencing centers. These sequences are stored in a local Silicon Graphics machine (SGI).

2. Gene prediction using the program Glimmer 2.0 from TIGR. This is facilitated by UNIX C shell scripts written in house.

3. The predicted genes are translated into amino acid sequences using a translation program written in house. This program is capable of translating large batch of sequences.

4. The translated amino acid sequences are formatted into a searchable database locally as in Section A.2. Subsequent analysis is as described in Section A.3-5.

C. Prediction of Immunoglobulin-Like (Ig-Like) Fold in Putative LPXTG-Motif Containing Cell Wall Anchored Proteins.

The amino acid sequences of putative LPXTG-motif containing cell wall anchored proteins are submitted to a Fold recognition web server 3D-PSSM. The method of prediction is described in Kelley L A, MacCallum R M & Sternberg M J E. Enhanced Genome Annotation using Structural Profiles in the Program 3D-PSSM. J Mol Biol. 2000 Jun. 2; 299(2):499-520

The output of 3D-PSSM gives a probability E value indicating the likelihood of the submitted sequence adopting a similar 3D structure as a published structure.

Proteins that have E value <0.25 to a published Ig-like fold structure, are considered containing predicted Ig-like folds. These should be considered MSCRAMM® proteins.

Accordingly, in accordance with the present invention, a bioinformatic approach was used to identify proteins with MSCRAMM®-like characteristics among Gram positive bacteria, particularly *Enterococcus faecalis*. Forty-two proteins with a putative C-terminal LPxTG cell wall sorting signal were identified in the *E. faecalis* genome. We then looked for structural similarities to MSCRAMM® proteins among LPxTG-anchored enterococcal proteins. Nine proteins were predicted to contain regions that adopt an immunoglobulin-like fold. The Ig fold-containing regions in FIG. 1 consist of several consecutive and overlapping matches to solved crystal structures (~150-500 aa) of the immunoglobulin superfamily (IgSF), which consist of one to four domains of equal size and Ig-type fold. The homologous Ig-fold regions cover most of the enterococcal proteins and may indicate a similar "beads-in-a-string" arrangement of consecutive modules that are found in fibronectin and other IgSF proteins (Leahy, 1996) (Sharma, 1999) (Hamburger, 1999) (Luo, 2000). A tandem repeat of Ig folded subdomains (N2 and N3) is found in the crystal structure of the fibrinogen-binding domain of ClfA. The full-length A domains of ClfA and the similarly structured ClfB consist of an additional N-terminal subdomain, N1 (Deivanayagam, 2002) (Perkins,-

2001). Based on sequence and secondary structure similarities, an analogous subdomain organization is also expected in other MSCRAMM® proteins including FnbpA, FnbpB, Ace and the Sdr proteins. The solved crystal structure of CNA minimum collagen-binding domain is made of a single Ig-type subdomain (N2) (Symersky, 1997) and the C-terminal repeat domains B1 and B2 each consist of a tandem repeat of Ig-folded subdomains (Deivanayagam, 2000). A similar modular structure is expected in the B3 and B4 repeats. Thus, a module structure of multiple Ig-folded units seems a general characteristic in the MSCRAMM® protein family. Thelength of the N-subdomains of MSCRAMM® proteins is typically ~150 aa suggesting that the large size of the A domains of EF1091 and EF0089 could accommodate more than three Ig-folded subdomains in their A domains.

Example 3

Expression and Purification of Recombinant Enterococcal MSCRAMM® Protein Fragments To further characterize the utility of this invention, the A-domains of EF1091, EF1092 and EF1093 proteins from *E. faecalis* as well as Efae 2926, Efae 2925 and Efae 2924 proteins from *E. faecium* were cloned, expressed and purified. In addition, EF1824 was cloned in two segments, EF1824AI (aa 43-819) and EF1824AII (aa 820-1829) because of the large size of the protein. EF1824AI was insoluble in *E. coli* cytoplasm and excluded from the assays. Bolded and underlined sequence represents the putative A-domains that were cloned.

EF1824AI: amino acid residues 43-819

(SEQ ID NO: 2)

QEQTAKEDVADSATSVGAIVSIEKAEKNFVITYASGKKAQISILNDHLFRYHLDP
TGKFEEYPTPNDPKHVAKITAKTMADYGTQAFEQTNVTDSGNQFILENNGLKI
MFEKESALMKVLDKKKNQVILEETAPLSFKNDKATQTLKQSSQENYFGGGTQ
NGRFTHKGTAIQIVNTNNWVDGGVASPNPFYWSTAGYGVVRNTWKPGNYDF
GSHDPQKTTTTHEGTDFDAFYFFNDSSAGILKDYYELTGKPALMPEYGFYEAH
LNAYNRDYWVKVAEGTAGAVKFEDGNFYKEYQPGDLGNLNGTLESLNGEKE
NYQFSARAVIDRYKKNDMPLGWFLPNDGYGAGYGQTDSLDGDVQNLKEFTEY
AQANGVEVGLWTQSNLHPADPKNPKKGERDIAKEVSVAGVKALKTDVAWVG
YGYSFGLNGVEDAANVFVKETDGAVRPMIVSLDGWAGTQRHAGIWTGDQTG
GQWEYIRFHIPTYIGTSLSGQPNVGSDMDGIFGGKNKEINIRDFQWKTFTPVQL
NMDGWGSNPKTPFAFDQEATDLNRAYLKLKSMMMPYNYSIAKESVDGLPMV
RAMALEFPNEGTAYTKDSQYQYMWGPNLLVAPIYNGNQDEAGNSIRDGIYLPD
EKQVWVDLFTGEKYQGGRVLNGVKTPLWKVPVFVKDGSIIPMTNPNNNPKEI
QRDQRSFLIYPNGTTSFNMYEDDGISTSYEAGQSATTKINSQGPKSNEKGDLT
VTIEPTKGSYKDFVDERSTTLDLLASEAPESVTAMVGGTEVTLKQ

EF1824AI: amino acid residues 820-1829

(SEQ ID NO: 3)

AANKEEFLAGTNLYYFDKEFQVNQYLSEASGEKLNQSALSVKLAKQSVTAKDVQITVK
GFINKGTVDGGNTTVDDQLTIPANVAINEEKTTPSSLTLQWDQVTEATSYEVERDGTVF
GNIQTNTATFDGFSFLSEHTFRVRAVGKNGVSEWSEPIKGKTQDDPYKETINQVKATS
NLPEQPGAELKKLTDKDLSTGWHTNWSTGIANPSDGNFLSLKFDLGAEYQMDKIEYL
PRDNAGNGNILQLQYRTSKDGANWTEFSEPINWKQDALTKTIETKDQAYRFVEMKVL
KSVGNFGSGREMLFYKQPGTEGILHGDITNDGTIDENDAMSYRNYTGLESVDSDFNGY
VEKGDLNKNGVIDAYDISYVLRQLDGGIEIPDVEEIAGGLSLAVVNENGKDTYLPGDTLT
FILKGQDLKNINALSTKMSFDSSKFELVGQPATTNNTQQMENYSKYRKHSNDVENLYL
VLSNQGNKQLLNGSMDLVTFKVKVKETTRVKRATTVEQPLQFDMSQGLLVGQGFQQ
ATLSDFSVTVKPTELVDKELLQALITLNQARVEKEYTPETWAIFKPILDEAVAVLANEQA
TQTDVSAAAENLEKAASQLEKMPDVANKADLEKAIQEGLAKKPSDGQEFTEETKKVL
EESLAAAQKVFAQEKVTQEEIDQATKTLREAIAQLKEQPVAVDKETLKEQIAQARGRK
PEEGYQFTKETEKQLQEAIQAAEAIVAKETATKEEVSEALNALETAMAQLKEVPLVNK
DQLQEVVKRAQQVTPSEGHQFTASSLQELQKALLAAKNTLKNPAANQKMIDEAVAEL
TSAIDGLQEEVLVTDKKALEAMIAKAKAIKPSAGKEFTSESKARLTEAIDQAEGILADKN
ARQEQIDIAEKNVKTALDSLEEQVLQTDKTKLKELLQKAETLKPKAGKQFTKASQEAL
AEAIKQAKALVEDPNATQEAVDKCLSILSQAIEAMAEEPISSNSTGNNGNHSTVSGTGG
VTSQGKGTATGGTTTKTTTSGT

EF0089A: amino acid residues 36-1143

(SEQ ID NO: 4)

EEVNSDGQLTLGEVKQTSQQEMTLALQGKAQPVTQEVVVHYSANVSIKAAHWAAPN
NTRKIQVDDQKKQIQIELNQQALADTLVLTLNPTATEDVTFSYGQQQRALTLKTGTDPT
ESTAITSSPAASANEGSTEEASTNSSVPRSSEETVASTTKAIESKTTESTTVKPRVAGPT
DISDYFTGDETTIIDNFEDPIYLNPDGTPATPPYKEDVTIHWNFNWSIPEDVREQMKAGD
YFEFQLPGNLKPNKPGSGDLVDAEGNVYGTYTISEDGTVRFTFNERITSESDIHGDFSL
DTHLNDSDGRGPGDWVIDIPTQEDLPPVVIPIVPDTEQQIDKQGHFDRTPNPSAITWTV
DINQAMKDQTNPTVTETWPTGNTFKSVKVYELVMNLDGTIKEVGRELSPDEYTVDKNG
NVTIKGDTNKAYRLEYQTTIDEAVIPDGGGDVPFKNHATLTSDNNPNGLDAEATVTATY
GKMLDKRNIDYDEANQEFTWEINYNYGEQTIPKDQAVITDTMGDNLTFEPDSLHLYSVT
FDDKGNEVVGAELVEGKDYKVVINGDGSFAIDFLHDVTGAVKIDYKTKVDGIVEGDVAV
NNRVDVGTGQHSEDDGTASQQNIIKNTGAVDYQNSTIGWTLAVNQNNYLMENAVITDT
YEPVPGLTMVPNSLVVKDTTTGAQLTLGKDFMVEITRNADGETGFKVSFIGAYAKTSD
AFHITYTTFFDVTELDANNPALDHYRNTAAIDWTDEAGNNHHSEDSKPFKPLPAFDLNA
QKSGVYNAVTKEITWTIAVNLSNNRLVDAFLTDPILTNQTYLAGSLKVYEGNTKPDGSV
EKVKPTQPLTDITMEEPSEKNQNTWRVDFPNDSRTYVIEFKTSVDEKVIEGSASYDNTA
SYTNQGSSRDVTGKVSIQHGGESVKKGGEYHKDDPDHVYWHVMINGAQSVLDDVVIT

-continued

**DTPSPNQVLDPESLVIYGTNVTEDGTITPDKSVILEEGKDYTLEVTTDNETGQQKIVVKM
AHIEAPYYMEYRSLVTSSAAGSTDTVSNQVSITGNGSEVVHGDDNGDVVVDIDHSGGH
ATGTKGKIQLKKTAMDETTILAGAHFQIWDQAKTQVLREGTVDATGVITFGG**

EF3023A: amino acid residues 26-1024

(SEQ ID NO: 5)

**EEITDLFLQKEVTYSGVEGGKIGENWKYPQFVGEKAVDGDETTRWSADKQDEQWLIV
DLGEVKNIGELVLQLHAESPVYEILVSTDGESYQSIFKEENGKGGQPTKKYIDGNNVQA
RFVKYQQMKMWQHTNKQFYSSSIISFEAYEKKRLPEAIKLLTENLTISEKRKQQLAFEV
SPAGVDITEDQIEWSSSDPTIVTVDQTGNLTAVKSGEAKVTVKIKGTEISDTIPVTVVAEN
KQYAEMRAKWKMRLLGTTQYDNDADVQQYRAQIATESLALWQTLNQAADREYLWER
KPSDTVSADYTTQFTNIKKLALGYYEPSSELFEKPEVYDAIVKGIEFMIDTKKYNGTYYT
GNWWDWQIGSAQPLTDTLILLHDDLLNTDAEKLNKFTAPLMLYAKDPNIQWPIYRATG
ANLTDISITVLGTGLLLEDNQRLVQVQEAVPSVLKSVSSGDGLYPDGSLIQHGYFPYNG
SYGNELLKGFGRIQTILQGSDWEMNDPNISNLFNVVDKGYLQLMVNGKMPSMVSGRS
ISRAPETNPFTTEFESGKETIANLTLIAKFAPENLRNDIYTSIQTWLQQSGSYYHFFKKP
RDFEALIDLKNVVNSASPAQATPMQSLNVYGSMDRVLQKNNEYAVGISMYSQRVGNY
EFGNTENKKGWHTADGMLYLYNQDFAQFDEGYWATIDPYRLPGTTVDTRELANGAYT
GKRSPQSWVGGSNNGQVASIGMFLDKSNEGMNLVAKKSWFLLDGQIINLGSGITGTT
DASIETILDNRMIHPQEVKLNQGSDKDNSWISLSAANPLNNIGYVFPNSMNTLDVQIEE
RSGRYGDINEYFVNDKTYTNTFAKISKNYGKTVENGTYEYLTVVGKTNEEIAALSKNKG
YTVLENTANLQAIEAGNYVMMNTWNNDQEIAGLYAYDPMSVISEKIDNGVYRLTLANPL
QNNASVSIEFDKGILEVVAADPEISVDQNIITLNSAGLNGSSRSIIVKTTPEVTKEALEKLI
QEQ**

EF2224A: amino acid residues 31-771

(SEQ ID NO: 6)

**QEVTSDAEKTVEKDGLKVIGKIEDTSSQEDIKTVTYEVTNTRDVPIKDLILKQKNTNDSPI
KFVLDTLSEERGPTSLEEQAKVETNEKDQTTDIKLLNLQPNSTRKITINGQITTKASNKL
LVSVLIEDNEKGTLVIDLPSKDILADKESVSKEKQETSETKVENQANETASSTNEMTATT
SNETKPEAGKAIESIQETALTQATESPEQPPLKAQPTGPLVPPTPGRGFNTPIYQSVHK
GELFSTGNTNLKIANENTAAAQTFLNTRGASSGYAINNFPLEFADVDNDPNTYNSSRAY
IDLNGAKEIAWAGLFWSASRYKGPAYGTNLSDEEISAPVQFTTPNGTVQRVSPQRYHR
IDQDATNPGQRFGYNNTGFSNYADVTSILQGDKSATGSYTLADIPMTSSLNGQYQYYN
FSGWSLFVVTKDQASKSRAFSIYYGARGNAAGTNNEFTMSNFLTAKQGNLDPIVTWFT
VQGDKYWTGDNAQIKNSAGTWVNISNTLNPVNNAMNATVTDNDEHMVDKYPGKFAP
DHPNFLDIDIDRMAIPEGVLNAGQNQINFRTTSSGDDYSTNAIGFAVNAETPEFEIKKEIV
EPKETYKVGETITYRVSLKNTKADSEAINSVSKDALDGRLNYLPGSLKIISGPNSGEKTD
ASGDDQAEYDETNKQIIVRVGNGATATQGGSYKADTAETIYEFKARINERAKANELVPN
SATVEAVDILTSAKVNETSNIVEAKIADEQVT**

EF1269A: amino acid residues 27-596

(SEQ ID NO: 7)

**ETGYAQTEPTSTSETNQISATPNVVPRKQVGNIVTAIQLTDKEGNPLGTINQYTDIYLRIE
FNLPDNTVNSGDTSVITLPEELRLEKNMTFNVVDDTGTVVAIAQTDVANKTVTLTYTDY
VENHANISGSLYFTSLIDFENVENESKIPIYVTVEGEKIFAGDLDYQGEGDDVNEKFSKY
SWFIEDDPTEIYNVLRINPTGQTYTDLEVEDVLKTESLSYMKDTMKIERGQWTLDGNAI
WQFTPEEDITDQLAVQYGPDDRNFSVHFGNIGTNEYRITYKTKIDHLPEKGETFTNYAK
LTENQTVVEEVEVSRVSQTGGGEANGEQYVVEIHKEDEAGQRLAGAEFELIRNSTNQT
VAKITTDQNGTAIVKGLLKDNYTLVETKAPTGYQLSQNKIPITPEDFGKNLVALKTVVNH
KISYQPVAASFLAGKVLLGKPLKDAEFQFELLDEKGTVLETVSNDTLGKIQFSPLTFET
PGNYQYTIREVNTQQTGVSYDTHNLQVQVTVEALLGNLVATTQYDGGQVFTNHYTPE
KPIESTTPPTSGTTDTTTNSTTETTSITIEKQAIRNKE**

EF1091: Nucleotide Sequence (SEQ ID NO: 8)

```
   0 ATGATAACAG ATGAGAATGA TAAAACGAAT ATTAATATCG AGTTAAATCT
  50 TCTCAACCAA ACAGAGGAGC CATTACAACG AGAAATTCAA TTGAAAAATG
 100 CACAGTTCAT GGATACTGCT GTAATTGAAA AAGACGGATA TTCTTACCAA
 150 GTGACTAATG GTACGCTTTA TCTGACTTTG GACGCACAAG TAAAAAAGCC
 200 GGTACAGCTT TCGTTAGCTG TTGAGCAAAG TTCGCTTCAA ACAGCTCAGC
 250 CACCTAAGTT ATTGTATGAA AACAACGAAT ATGATGTTTC AGTTACTTCT
 300 GAAAAAATAA CAGTAGAGGA TTCTGCTAAA GAATCAACTG AACCAGAAAA
 350 AATAACTGTA CCAGAAAATA CGAAAGAAAC TAACAAAAAT GATTCGGCTC
 400 CAGAAAAAAC AGAACAGCCG ACCGCAACAG AAGAGGTAAC CAATCCATTT
 450 GCAGAAGCAA GAATGGCGCC AGCTACTTTG AGAGCGAATC TGGCACTGCC
 500 TTTAATTGCA CCACAATACA CGACGGATAA TTCTGGGACT TATCCGACAG
 550 CTAATTGGCA GCCCACAGGC AATCAAAATG TGTTAAACCA TCAAGGGAAT
 600 AAAGACGGTA GTGCACAATG GGACGGCCAA ACGAGTTGGA ATGGGGACCC
 650 TACTAATCGC ACAAATTCTT ATATTGAGTA TGGCGGTACA GGAGACCAAG
 700 CCGATTATGC CATCCGAAAA TATGCTAGAG AAACAACAAC ACCAGGGCTT
 750 TTTGATGTAT ATCTTAATGT GCGTGGGAAT GTTCAGAAAG AAATCACGCC
 800 ATTGGATTTG GTCTTAGTCG TTGACTGGTC CGGTAGTATG AATGAAAACA
 850 ATCGGATTGG TGAAGTTCAA AAAGGAGTGA ACCGTTTTGT TGATACATTG
 900 GCAGATAGCG GTATTACCAA TAACATCAAC ATGGGCTATG TTGGCTACTC
 950 AAGTGACGGT TATAATAACA ACGCCATTCA AATGGGGCCG TTTGATACAG
1000 TCAAAAATCC AATTAAAAAT ATTACGCCAA GTAGCACTAG AGGAGGAACT
1050 TTCACTCAAA AAGCATTAAG AGATGCTGGT GATATGTTAG CAACGCCAAA
1100 TGGACATAAG AAAGTCATTG TACTTTTAAC GGATGGCGTC CCAACCTTCT
1150 CTTATAAAGT GAGTCGAGTT CAAACAGAGG CGGATGGTCG CTTTTACGGG
```

-continued

```
1200 ACACAATTTA CGAATCGACA AGATCAACCA GGTAGCACTT CTTATATCTC
1250 TGGTAGCTAT AATGCGCCAG ATCAAAACAA TATCAATAAA CGGATTAACA
1300 GTACGTTTAT CGCCACGATA GGTGAGGCAA TGGTCTTAAA ACAACGTGGG
1350 ATTGAAATAC ATGGATTGGG CATTCAATTG CAAAGCGATC CACGAGCTAA
1400 TTTATCTAAA CAACAAGTTG AAGATAAAAT GCGTGAGATG GTGTCAGCCG
1450 ATGAAAATGG AGACCTTTAT TATGAATCCG CGGATTATGC ACCAGACATT
1500 TCTGATTATT TAGCGAAAAA AGCCGTTCAG ATTTCAGGAA CGGTTGTAAA
1550 CGGAAAAGTA GTTGATCCAA TTGCTGAACC TTTTAAATAC GAGCCAAATA
1600 CATTATCAAT GAAAAGTGTG GGTCCTGTTC AGGTTCAAAC ATTACCAGAA
1650 GTGTCGCTAA CAGGCGCTAC AATTAATAGT AATGAGATTT ATTTGGGTAA
1700 AGGGCAAGAA ATTCAAATTC ATTATCAAGT ACGTATTCAA ACAGAGTCAG
1750 AAAACTTCAA ACCTGATTTT TGGTATCAAA TGAATGGTCG GACAACGTTT
1800 CAGCCATTAG CCACGGCCCC TGAAAAAGTT GATTTTGGGG TTCCTTCGGG
1850 AAAAGCACCT GGCGTGAAGT TAAACGTGAA AAAAATCTGG GAAGAGTATG
1900 ATCAAGACCC GACAAGTCGG CCAGATAATG TGATTTATGA AATTAGTAGA
1950 AAGCAAGTAA CTGACACAGC CAACTGGCAA ACTGGGTATA TTAAATTATC
2000 AAAACCAGAA AATGATACCA GCAATAGTTG GGAGCGCAAA AATGTAACCC
2050 AACTTTCCAA AACCGCGGAT GAAAGCTATC AAGAAGTTCT TGGGCTTCCC
2100 CAATACAACA ATCAAGGACA AGCTTTCAAT TATCAAACAA CCCGTGAATT
2150 AGCAGTTCCT GGTTACAGTC AAGAAAAAAT CGACGATACT ACTTGGAAAA
2200 ACACGAAGCA GTTCAAGCCA TTAGATTTAA AAGTAATCAA AAATTCTTCC
2250 TCAGGTGAGA AAAACTTAGT GGGAGCCGTC TTTGAATTGA GTGGTAAAAA
2300 TGTTCAAACA ACATTAGTGG ACAATAAAGA TGGTAGCTAT TCCTTGCCAA
2350 AAGATGTGCG CCTACAAAAA GGGGAACGCT ATACATTAAC TGAAGTAAAA
2400 GCACCTGCAG GACATGAGTT AGGCAAGAAA ACGACTTGGC AAATTGAGGT
2450 GAGTGAGCAA GGCAAAGTAA GCATCGATGG ACAAGAAGTG ACCACCACAA
2500 ATCAAGTTAT TCCATTGGAA ATTGAAAATA AATTTTCTTC TTTGCCAATC
2550 AGAATTAGAA AATACACCAT GCAAAATGGC AAACAAGTGA ACTTAGCAGA
2600 GGCGACTTTT GCGTTGCAAA GAAAAAATGC TCAAGGAAGT TACCAAACTG
2650 TGGCAACTCA AAAAACAGAT ACTACAGGAT TGAGCTATTT TAAAATTAGT
2700 GAACCTGGTG AGTATCGAAT GGTGGAACAA TCAGGACCAT TAGGCTACGA
2750 CACTCTTGCT GGAAATTATG AATTTACTGT TGATAAATAT GGGAAAATTC
2800 ACTATGCAGG CAAAAATATT GAAGAAAATG CGCCAGAATG GACACTGACA
2850 CATCAAAATA ATTTGAAACC TTTTGACTTA ACAGTTAATA AAAAAGCCGA
2900 TAATCAGACG CCACTTAAAG GAGCGAAATT CCGTTTAACA GGACCAGATA
2950 CGGATATTGA ATTACCAAAA GATGGCAAAG AAACGGATAC TTTTGTTTTT
3000 GAAAACTTAA AACCAGGGAA ATATGTTCTA ACAGAAACCT TTACGCCAGA
3050 AGGATATCAG GGGTTAAAAG AACCAATCGA ATTAATAATT CGTGAAGATG
3100 GTTCAGTCAC GATAGATGGG GAAAAAGTAG CAGATGTTTT AATTTCTGGA
3150 GAGAAGAATA ATCAAATTAC TTTAGACGTT ACGAACCAAG CAAAGGTTCC
3200 TTTACCTGAA ACTGGTGGCA TAGGACGCTT GTGGTTTTAC TTGATAGCGA
3250 TTAGTACATT CGTGATAGCG GGTGTTTATC TCTTTATTAG ACGACCAGAA
3300 GGGAGTGTG
```

EF1091 amino acid residues 63-1067

(SEQ ID NO: 9)

```
   0 MITDENDKTN INIELNLLNQ TEQPLQREIQ LKNAOFMDTA VIEKDGYSYQ
  50 VTNGTLYLTL DAQVKKPVQL SLAVEQSSLQ TAQPPKLLYE NNEYDVSVTS
 100 EKITVEDSAK ESTEPEKITV PENTKETNKN DSAPEKTEQP TATEEVTNPF
 150 AEARMAPATL RANLALPLIA PQYTTDNSGT YPTANWQPTG NQNVLNHQGN
 200 KDGSAQWDGQ TSWNGDPTNR TNSYIEYGGT GDQADYAIRK YARETTTPGL
 250 FDVYLNVRGN VQKEITPLDL VLVVDWSGSM NENNRIGEVQ KGVNRFVDTL
 300 ADSGITNNIN MGYVGYSSDG YNNNAIQMGP FDTVKNPIKN ITPSSTRGGT
 350 FTQKALRDAG DMLATPNGHK KVIVLLTDGV PTFSYKVSRV QTEADGRFYG
 400 TQFTNRQDQP GSTSYISGSY NAPDQNNINK RINSTFIATI GEAMVLKQRG
 450 IEIHGLGIQL QSDPRANLSK QQVEDKMREM VSADENGDLY YESADYAPDI
 500 SDYLAKKAVQ ISGTVVNGKV VDPIAEPFKY EPNTLSMKSV GPVQVQTLPE
 550 VSLTGATINS NEIYLGKGQE IQIHYQVRIQ TESENFKPDF WYQMNGRTTF
 600 QPLATAPEKV DFGVPSGKAP GVKLNVKKIW EEYDQDPTSR PDNVIYEISR
 650 KQVTDTANWQ TGYIKLSKPE NDTSNSWERK NVTQLSKTAD ESYQEVLGLP
 700 QYNNQGQAFN YQTTRELAVP GYSQEKIDOT TWKNTKQFKP LDLKVIKNSS
 750 SGEKNLVGAV FELSGKNVQT TLVDNKDGSY SLPKDVRLQK GERYTLTEVK
 800 APAGHELGKK TTWQIEVSEQ GKVSIDGQEV TTTNQVIPLE IENKFSSLPI
 850 RIRKYTMQNG KQVNLAEATF ALQRKNAQGS YQTVATQKTD TTGLSYFKIS
 900 EPGEYRMVEQ SGPLGYDTLA GNYEFTVDKY GKIHYAGKNI EENAPEWTLT
 950 HQNNLKPFDL TVNKKADNQT PLKGAKFRLT GPDTDIELPK DGKETDTFVF
1000 ENLKPGKYVL TETFTPEGYQ GLKEPIELII REDGSVTIDG EKVADVLISG
1050 EKNNQITLDV TNQAKVPLPE TGGIGRLWFY LIAISTFVIA GVYLFIRRPE
1100 GSV
```

EF1092: Nucleotide Sequence (SEQ ID NO: 10)

```
   0 ATGAAAAACG CACGTTGGTT AAGTATTTGC GTCATGCTAC TCGCTCTTTT
  50 CGGGTTTTCA CAGCAAGCAT TAGCAGAGGC ATCGCAAGCA AGCGTTCAAG
 100 TTACGTTGCA CAAATTATTG TTCCCTGATG GTCAATTACC AGAACAGCAG
 150 CAAAACACAG GGGAAGAGGG AACGCTGCTT CAAAATTATC GGGGCTTAAA
 200 TGACGTCACT TATCAAGTCT ATGATGTGAC GGATCCGTTT TATCAGCTTC
 250 GTTCTGAAGG AAAAACGGTC CAAGAGGCAC AGCGTCAATT AGCAGAAACC
 300 GGTGCAACAA ATAGAAAACC GATCGCAGAA GATAAAACAC AGACAATAAA
 350 TGGAGAAGAT GGAGTGGTTT CTTTTTCATT AGCTAGCAAA GATTCGCAGC
```

-continued

400 AACGAGATAA AGCCTATTTA TTTGTTGAAG CGGAAGCACC AGAAGTGGTA
450 AAGGAAAAAG CTAGCAACCT AGTAGTGATT TTGCCTGTTC AAGATCCACA
500 AGGGCAATCG TTAACGCATA TTCATTTATA TCCAAAAAAT GAAGAAAATG
550 CCTATGACTT ACCACCACTT GAAAAAACGG TACTCGATAA GCAACAAGGC
600 TTTAATCAAG GAGAGCACAT TAACTATCAG TTAACGACTC AGATTCCAGC
650 GAATATTTTA GGATATCAGG AATTCCGTTT GTCAGATAAG GCGGATACAA
700 CGTTGACACT TTTACCAGAA TCAATTGAGG TAAAAGTGGC TGGAAAAACA
750 GTTACTACAG GTTACACACT GACGACGCAA AAGCATGGAT TTACGCTTGA
800 TTTTTCAATT AAAGACTTAC AAAACTTTGC AAATCAAACA ATGACTGTGT
850 CGTATCAAAT GCGTTTAGAA AAGACCGCTG AACCTGACAC TGCGATTAAC
900 AACGAAGGAC AATTAGTCAC GGACAAACAT ACCTTGACTA AAAGAGCCAC
950 AGTTCGTACA GGCGGCAAGT CTTTTGTCAA AGTTGATAGT GAAAATGCGA
1000 AAATCACCTT GCCAGAGGCT GTTTTTATCG TCAAAAATCA AGCGGGGGAA
1050 TACCTCAATG AAACAGCAAA CGGGTATCGT TGGCAAAAAG AAAAAGCATT
1100 AGCTAAAAAA TTCACGTCTA ATCAAGCCGG TGAATTTTCA GTTAAAGGCT
1150 TAAAAGATGG CCAGTACTTC TTGGAAGAAA TCTCTGCACC AAAAGGTTAT
1200 CTTCTGAATC AAACAGAAAT TCCTTTTACG GTGGGAAAAA ATTCTTATGC
1250 AACGAACGGA CAACGAACAG CACCGTTACA TGTAATCAAT AAAAAAGTAA
1300 AAGAGTCAGG CTTCTTACCA AAAACAAATG AAGAACGTTC TATTTGGTTG
1350 ACGATTGCAG GCCTGCTAAT CATTGGGATG GTAGTCATTT GGCTATTTTA
1400 TCAAAAACAA AAAAGAGGAG AGAGAAAA

EF1092 amino acid residues 28-438

(SEQ ID NO: 11)

0 MKNARWLSIC VMLLALFGFS QQALAFASQA SVQVTLHKLL FPDGQLPEQQ
50 QNTGEEGTLL QNYRGLNDVT YQVYDVTDPF YQLRSEGKTV QEAQRQLAET
100 GATNRKPIAE DKTQTINGED GVVSFSLASK DSQQRDKAYL FVEAEAPEVV
150 KEKASNLVVI LPVQDPQGQS LTHIHLYPKN EENAYDLPPL EKTVLDKQQG
200 FNQGEHINYQ LTTQIPANIL GYQEFRLSDK ADTTLTLLPE SIEVKVAGKT
250 VTTGYTLTTQ KHGFTLDFSI KDLQNFANQT MTVSYQMRLE KTAEPDTAIN
300 NEGQLVTDKH TLTKRATVRT GGKSFVKVDS ENAKITLPEA VFIVKNQAGE
350 YLNETANGYR WQKEKALAKK FTSNQAGEFS VKGLKDGQYF LEEISAPKGY
400 LLNQTEIPFT VGKNSYATNG QRTAPLHVIN KKVKESGFLP KTNEERSIWL
450 TIAGLLIIGM VVIWLFYOKO KRGERK

EF1093 (V583): Nucleotide Sequence (SEQ ID NO: 12)

0 ATGAAGCAAT TAAAAAAAGT TTGGTACACC GTTAGTACCT TGTTACTAAT
50 TTTGCCACTT TTCACAAGTG TATTAGGGAC AACAACTGCA TTTGCAGAAG
100 AAAATGGGGA GAGCGCACAG CTCGTGATTC ACAAAAAGAA AATGACGGAT
150 TTACCAGATC CGCTTATTCA AAATAGCGGG AAAGAAATGA GCGAGTTTGA
200 TAAATATCAA GGACTGGCAG ATGTGACGTT TAGTATTTAT AACGTGACGA
250 ACGAATTTTA CGAGCAACGA GCGGCAGGCG CAAGCGTTGA TGCAGCTAAA
300 CAAGCTGTCC AAAGTTTAAC TCCTGGGAAA CCTGTTGCTC AAGGAACCAC
350 CGATGCAAAT GGGAATGTCA CTGTTCAGTT ACCTAAAAAA CAAAATGGTA
400 AAGATGCAGT GTATACCATT AAAGAAGAAC CAAAAGAGGG TGTAGTTGCT
450 GCTACGAATA TGGTGGTGGC GTTCCCAGTT TACGAAATGA TCAAGCAAAC
500 AGATGGTTCC TATAAAATATG GAACAGAAGA ATTAGCGGTT GTTCATATTT
550 ATCCTAAAAA TGTGGTAGCC AATGATGGTA GTTTACATGT GAAAAAAGTA
600 GGAACTGCTG AAAATGAAGG ATTAAATGGC GCAGAATTTG TTATTTCTAA
650 AAGCGAAGGC TCACCAGGCA CAGTAAAATA TATCCAAGGA GTCAAAGATG
700 GATTATATAC ATGGACAACG GATAAAGAAC AAGCAAAACG CTTTATTACT
750 GGGAAAAGTT ATGAAATTGG CGAAAATGAT TTCACAGAAG CAGAGAATGG
800 AACGGGAGAA TTAACAGTTA AAAATCTTGA GGTTGGTTCG TATATTTTAG
850 AAGAAGTAAA AGCTCCAAAT AATGCAGAAT TAATTGAAAA TCAAACAAAA
900 ACACCATTTA CAATTGAAGC AAACAATCAA ACACCTGTTG AAAAAACAGT
950 CAAAAATGAT ACCTCTAAAG TTGATAAAAC AACACCAAGC TTAGATGGTA
1000 AAGATGTGGC AATTGGCGAA AAAATTAAAT ATCAAATTTC TGTAAATATT
1050 CCATTGGGGA TTGCAGACAA AGAAGGCGAC GCTAATAAAT ACGTCAAATT
1100 CAATTTAGTT GATAAACATG ATGCAGCCTT AACTTTTGAT AACGTGACTT
1150 CTGGAGAGTA TGCTTATGCG TTATATGATG GGGATACAGT GATTGCTCCT
1200 GAAAATTATC AAGTGACTGA ACAAGCAAAT GGCTTCACTG TCGCCGTTAA
1250 TCCAGCGTAT ATTCCTACGC TAACACCAGG CGGCACACTA AAATTCGTTT
1300 ACTTTATGCA TTTAAATGAA AAAGCAGATC CTACGAAAGG CTTTAAAAAT
1350 GAGGCGAATG TTGATAACGG TCATACCGAC GACCAAACAC CACCAACTGT
1400 TGAAGTTGTG ACAGGTGGGA AACGTTTCAT TAAAGTCGAT GGCGATGTGA
1450 CAGCGACACA AGCCTTGGCG GGAGCTTCCT TTGTCGTCCG TGATCAAAAC
1500 AGCGACACAG CAAATTATTT GAAAATCGAT GAAACAACGA AAGCAGCAAC
1550 TTGGGTGAAA ACAAAAGCTG AAGCAACTAC TTTTACAACA ACGGCTGATG
1600 GATTAGTTGA TATCACAGGG CTTAAATACG GTACCTATTA TTTAGAAGAA
1650 ACTGTAGCTC CTGATGATTA TGTCTTGTTA ACAAATCGGA TTGAATTTGT
1700 GGTCAATGAA CAATCATATG GCACAACAGA AAACCTAGTT TCACCAGAAA
1750 AAGTACCAAA CAAACACAAA GGTACCTTAC CTTCAACAGG TGGCAAAGGA

-continued

```
1800 ATCTACGTTT ACTTAGGAAG TGGCGCAGTC TTGCTACTTA TTGCAGGAGT
1850 CTACTTTGCT AGACGTAGAA AAGAAAATGC T
```

EF1093 amino acid residues 33-592

(SEQ ID NO: 13)

```
   0 MKQLKKVWYT VSTLLLILPL FTSVLGTTTA FAEENGESAQ LVIHKKKMTD
  50 LPDPLIQNSG KEMSEFDKYQ GLADVTFSIY NVTNEFYEQR AAGASVDAAK
 100 QAVQSLTPGK PVAQGTTDAN GNVTVQLPKK QNGKDAVYTI KEEPKEGVVA
 150 ATNMVVAFPV YEMIKQTDGS YKYGTEELAV VHIYPKNVVA NDGSLHVKKV
 200 GTAENEGLNG AEFVISKSEG SPGTVKYIQG VKDGLYTWTT DKEQAKRFIT
 250 GKSYEIGEND FTEAENGTGE LTVKNLEVGS YILEEVKAPN NAELIENQTK
 300 TPFTIEANNQ TPVEKTVKND TSKVDKTTPS LDGKDVAIGE KIKYQISVNI
 350 PLGIADKEGD ANKYVKFNLV DKHDAALTFD NVTSGEYAYA LYDGDTVIAP
 400 ENYQVTEQAN GFTVAVNPAY IPTLTPGGTL KFVYFMHLNE KADPTKGFKN
 450 EANVDNGHTD DQTPPTVEVV TGGKRFIKVD GDVTATQALA GASFVVRDQN
 500 SDTANYLKID ETTKAATWVK TKAEATTFTT TADGLVDITG LKYGTYYLEE
 550 TVAPDDYVLL TNRIEFVVNE QSYGTTENLV SPEKVPNKHK GTLPSTGGKG
 600 IYVYLGSGAV LLLIAGVYFA RRRKENA
```

Efae2926: Nucleotide Sequence (SEQ ID NO: 14)

```
   0 ATGACGACCA CAGGGAAGAA ACTGAAAGTT ATTTTCATGC TGATAATATT
  50 GAGTTTATCA AACTTTGTGC CATTATCTGC AATAGCAGAC ACTACAGATG
 100 ATCCAACAGT TTTAGAAACA ATTTCAGCTG AAGTCATTTC GGATCAGTCT
 150 GGAAAAAAAG CACTGAACAT CAAGCTAAAT GCGAATAACA CCAGTGCTGA
 200 AAAGATAGAA AAAGAAATTG GTCTAGTCGA AAATTACTTA AGTGATGTGG
 250 AAAGAAAAGA AGGAGATGGC TATGCTTATC AGGTAAATAG CGGGAAAATT
 300 ACGTTGGAAA TCTCATCAAA CACTAAACAA ACTATCGATC TGAGTTTTCC
 350 AATCGATCCA GCACTTTACC ACAGCCAGGC AAACAAGCTG ATCGTCGATA
 400 ATAAAGAATA TGACATTATT GATGAGACAG AAAATAAGAA AGATACAGAT
 450 GTGTCAGTAC CAAAGCCAGA CGAAATAGAA GAAGAATCAT CAAAAGAAAA
 500 CGAAAATTCT GTCAGCCCAT TTACATTGCC TACATTATCC TTGCCAGCTG
 550 TGAGTGTGCC ATCTAATCAA ACGATTCCTA CAGAATATAC AACAGATGAT
 600 CAGGGCACTT ATCCTAAAGC CAGTTGGCAA CCTACAGGAA ATACAAATGT
 650 TCTTGATCAT CAAGGCAATA AAAACGGAAC AAATCAATGG GATGGTATAA
 700 ATTCTTGGAA TGGAGATCCT AATGATCGGA CCCATTCGTA TATCGAATAT
 750 GGAGGAACCG GTAATCAAGC AGACTATGCG ATACGAAAGT ATGCAAAGGA
 800 AACAAGTACA CCCGGATTGT TTGATGTTTA TTTGAATGCT CGTGGAAATG
 850 TACAAAAAGA TATCACGCCT CTTGATCTCG TATTGGTCGT AGACTGGTCA
 900 GGAAGTATGA ACGACAATAA TCGGATCGGT GAAGTAAAGA TTGGTGTCGA
 950 TCGTTTTGTC GATACTTTAG CAGATAGCGG TATCACAGAC AAAATCAATA
1000 TGGGATATGT CGGCTACTCA AGCGAAGGAT ATAGCTACAG TAACGGTGCA
1050 GTACAGATGG GTTCATTTGA TTCAGTGAAA AATCAAGTAA AATCCATTAC
1100 ACCTTCACGG ACAAATGGTG GTACTTTTAC ACAAAAAGCA CTAAGAGATG
1150 CAGGAAGCAT GCTATCCGTT CCAAATGGAC ATAAAAAAGT GATCGTTTTG
1200 CTGACGGATG GTGTACCAAC ATTTTCCTAT AAAGTACAGC GGGTACACGC
1250 ACAATCAAGC AGCAATTATT ACGGAACTCA GTTTTCTAAT ACGCAAGATC
1300 GGCCGGGAAA TACTTCTCTA ATCTCAAGAA TCTATGATGC ACCTGACCAA
1350 AACAATCTAT CCAGAAGAAT CGACAGTACG TTTATCGCAA CCATCGGAGA
1400 AGCGATGGCA CTCAAAGAAC GAGGAATCGA AATACATGGT CTTGGCATCC
1450 AACTTCAAAG CGATCCGGCA GCTGGTCTCT CAAAAGCAGA AGTAGAGTCT
1500 CGTATGCGAC AAATGGTTTC ATCAGATGAA AAAGGCGATC TTTACTATGA
1550 ATCAGCTGAT CATGCAACAG ATATCTCTGA ATACCTAGCC AAAAAAGCTG
1600 TACAGATCTC AGCAACTGTA AGCAATGGAC AAATAAATGA TCCAATCGCA
1650 GAACCATTCA TTTATCAGCC TGGTACACTT TCAGTCAAGA GTGTGGGGAC
1700 AAGTCCTACA ACGGTCACTC CATCTATTTC CATAGAAGGA AATACCATCA
1750 AGAGCAATCA GATCTATTTA GGAAAAGACC AAGAAATCCA AATCCATTAC
1800 CAAGTGAGAA TCCAAACAGA AAATGAGGAC TTCCATCCAA ATTTCTGGTA
1850 TCAAATGAAC GGCAGGACAA CTTTCCAGCC AAACATTGAT ACCAATGAAT
1900 TAGCTGAATT CGGTATACCA TCTGCTAAAG CTCCCGGAGT CAGTCTTCAC
1950 ATCAAAAAGT TATGGGAAGA ATTTGACAAC AATCTAGCTG ATCGTCCAGA
2000 TCAAGTTACT TTTGAGATTC AACGGGAACA TACGACAAAT GCTGCAGCTT
2050 GGAAAAACGG ATATATTCGA ATCATTAAAC CAGCTAAAGA TACAACAAAT
2100 ACGTGGGAAC GTGCAGACAT TGACAAATTA TCTGCAAATA GCGGAGAAAG
2150 TTATCAAGAG ATATTATCAC TACCTCAATA CAATAATCAA GGTCAAGCAT
2200 TCAGTTACCA AACAATCAAA GAATTACCTG TACCAGGATA CGATTCTCAA
2250 CAAATAGATG CAATGACATG GAAAAATACT AAACAATTCA CACCGTTAAA
2300 CTTGAAAATA ACGAAAAATT CCTCTACAGG TGAAAAGGAT CTTATTGGCG
2350 CTGTTTTCAA ATTAACAGGA GATTCTATTG ATACTTTACT AACAGATCAT
2400 GGCGACGGAA CCTATTCTCT TCCAGAAAAT GTCAAATTGC AAAAAGAAAT
2450 GACCTATACG CTGACAGAAA CAAAAGCTCC AGAAGGGCAT GGATTAAGCA
2500 AAAAGACTAC TTGGGAAATC AAGATCGCTT CTGATGGTAC GGTAACCATT
2550 GATGGAAAAA CAGTCACTAC TTCCGATGAT ACGATCCAGT TGACTATTGA
2600 AAATCCTTTT GTTGAAGTTC CTGTAGCAGT ACGTAAGTAT GCGATGCAAG
2650 GGACGGACAA AGAGATAAAT CTTAAAGGAG CAGCATTTTC CCTACAGAAA
2700 AAAGAAGCAA ATGGTACTTA TCAGCCAATT GACAGCCAAA CAACGAATGA
2750 AAAAGGTCTT GCCAGTTTTG ATTCACTCAC ACCTGGTAAA TATCGAGTCG
2800 TTGAAACAGC TGGTCCTGCC GGATATGATA CTTCGCCGGG AAATTATGAA
2850 TTCCAAATCG ATAAATATGG AAAAATCATT TACACGGGAA AAAATACCGA
2900 GATGACAAAT AATGTATGGA CGCTCACTCA TCAAAATCGA CTAAAAGCGT
```

-continued

2950 TTGATCTAAC GGTACACAAA AAAGAAGACA ACGGACAGAC ATTAAAAGGA
3000 GCAAAATTCA GACTGCAGGG ACCAGAAATG GACTTAGAAT CGCCAAAAGA
3050 TGGACAAGAA ACAGATACCT TTCTATTCGA AAATTTAAAA CCTGGAACTT
3100 ATACGCTGAC CGAAACTTTT ACACCAGAAG GATACCAAGG TCTAAAAGAG
3150 CCAGTTACTA TAGTTATACA CGAAGATGGG TCAATTCAAG TGGATGGACA
3200 AGATCATGAA TCTGTTCTGT CACCAGGAGC CAAAAACAAC CAGATTTCTT
3250 TAGACATCAC GAATCAGGCA AAAGTACCAT TACCTGAAAC GGGAGGAATT
3300 GGCCGTTTAG GAATCTATCT AGTAGGGATG ATTGGTTGTG CGTTTTCTAT
3350 TTGGTATCTT TTTTTGAAAA AAGAAAGAGG GGGCAGC

Efae2926: amino acid residues 53-734

(SEQ ID NO: 15)

0 MTTTGKKLKV IFMLIILSLS NFVPLSAIAD TTDDPTVLET ISAEVISDQS
50 GKKALNIKLN ANNTSAEKIE KEIGLVENYL SDVERKEGDG YAYQVNSGKI
100 TLEISSNTKQ TIDLSFPIDP ALYHSQANKL IVDNKEYDII DETENKKDTD
150 VSVPKPDEIE EESSKENENS VSPFTLPTLS LPAVSVPSNQ TIPTEYTTDD
200 QGTYPKASWQ PTGNTNVLDH QGNKNGTNQW DGINSWNGDP NDRTHSYIEY
250 GGTGNQADYA IRKYAKETST PGLFDVYLNA RGNVQKDITP LDLVLVVDWS
300 GSMNDNNRIG EVKIGVDRFV DTLADSGITD KINMGYVGYS SEGYSYSNGA
350 VQMGSFDSVK NQVKSITPSR TNGGTFTQKA LRDAGSMLSV PNGHKKVIVL
400 LTDGVPTFSY KVQRVHAQSS SNYYGTQFSN TQDRPGNTSL ISRIYDAPDQ
450 NNLSRRIDST FIATIGEAMA LKERGIEIHG LGIQLQSDPA AGLSKAEVES
500 RMRQMVSSDE KGDLYYESAD HATDISEYLA KKAVQISATV SNGQINDPIA
550 EPFIYQPGTL SVKSVGTSPT TVTPSISIEG NTIKSNQIYL GKDQEIQIHY
600 QVRIQTENED FHPNFWYQMN GRTTFQPNID TNELAEFGIP SAKAPGVSLH
650 IKKLWEEFDN NLADRPDQVT FEIQREHTTN AAAWKNGYIR IIKPAKDTTN
700 TWERADIDKL SANSGESYQE ILSLPQYNNQ GQAFSYOTIK ELPVPGYDSQ
750 QIDAMTWKNT KQFTPLNLKI TKNSSTGEKD LIGAVFKLTG DSIDTLLTDH
800 GDGTYSLPEN VKLQKEMTYT LTETKAPEGH GLSKKTTWEI KIASDGTVTI
850 DGKTVTTSDD TIQLTIENPF VEVPVAVRKY AMQGTDKEIN LKGAAFSLQK
900 KEANOTYQPI DSQTTNEKGL ASFDSLTPGK YRVVETAGPA GYDTSPGNYE
950 FQIDKYGKII YTGKNTEMTN NVWTLTHQNR LKAFDLTVHK KEDNGQTLKG
1000 AKERLQGPEM DLESPKDGQE TDTFLFENLK PGTYTLTETF TPEGYQGLKE
1050 PVTIVIHEDG SIQVDGQDHE SVLSPGAKNN QISLDITNQA KVPLPETGGI
1100 GRLGIYLVGM IGCAFSIWYL FLKKERGGS

Efae2925: Nucleotide Sequence (SEQ ID NO: 16)

0 ATGAAAAAAC TTGGTTGGCT TAGTATGTGT CTCTTCTTGT TACTATTTAA
50 ACCAGCTTTT ACTCAGGTAG CAACAGAAAC AGAAACAGAA ATGGTTCAGA
100 TTACTTTACA CAAATTGCTT TTCCCAAACG GGCAACTGCC GAAAAATCAT
150 CCAAATGACG GACAAGAAAA AGCTTTATTA CAAACGTATC GAGGATTAAA
200 TGGTGTCACA TTCCAAGTTT ATGATGTCAC AGATTCTTTT TACCATCTAC
250 GGGAAAAGGG CAAAACGGTA GAAGAAGCAC AAGCAGAGAT CGCAAAAAAC
300 GGTGCGTCTT CCGGTATGTT TACCGCAGAA GCAACAACTA CAACTCTTAA
350 CAACGAAGAT GGTATCGCTT CTTTTTCTCT GGCCGCTAAA GATCAAGAAA
400 AAAGAGATAA AGCGTATCTT TTCATTGAAT CCAAAGTACC AGAAGTCGTC
450 AAAGAAAAGG CAGAGAATAT GGTAGTTGTT CTTCCTGTAC ATGGACAAAA
500 CAATCAAAAA CTTTCAACTA TCCATTTGTA TCCTAAAAAT GAAGAAAACG
550 ACTACCCTGA TCCACCTTTT GAGAAGGTAT TAGAAGAGCC TAGAAATGAT
600 TTTACGATTG GTGAAAAAAT CACTTATTCC TTGCATACGA CAATTCCTGT
650 AAATATCCTT GACTATCAAA AGTTCGAATT GTCAGATAGT GCGGATGAAG
700 CATTAACGTT TTTACCTAAT AGTTTAACGA TTTCATCGAA TGGAGAAAAG
750 CTGACAGAAG GCTTTGTCAT ACACAAGAAA CCTCACGGAT TTGATGTTTT
800 ATTTTCGATC CCTTCGTTGG AAAAATATGC TGGAAAAAAA CTGACCATTT
850 CTTATCAGAT GCAGCTAAGC AGTACAGCAC AGGCGAACAA GGAAATCAAC
900 AACAACGGAA CACTGGATTT TGGTTTTGGT GTCAGTACAA AGAAAGTCTC
950 TGTATATACA GGGAGTAAGC AATTTGTCAA AATCGAGACA AATAAACCAG
1000 ATAAACGATT AGCTGGCGCA GTATTCCTTA TTAAAAACAA AGCAGGAAAT
1050 TACCTCCAGC AAACAGCCAA CGGATACAAG TGGACAAAGA ACGAATCAGA
1100 TGCGCTTCAC CTGATTTCCG ATAAAAATGG CGCTTTTTCA ATTTCCGGGT
1150 TGAAAACAGG AAGTTATCGA TTAAAAGAGA TCGAAGCACC TTCTGGTTAT
1200 ATTTTAAGTG AAACAGAAAT TCCGTTTACC ATTTCAACTT TTCTTTCTGA
1250 GGATAAAGAG GCGGACAGTA TATTGAAAGT AGTCAATAAA AAAGAAAATA
1300 GCCGTCCATT TCTTCCAAAA ACAAACGAAA CGAAAAATAC ACTTTTAGGC
1350 GTTGTTGGTA TGGTATTCGC AAGCTTTGCA ATCTGGTTGT TTATCAAAAA
1400 AAGAACAGGA GTGAAAAAAT GA

Efae 2925: amino acid residues 30-429

(SEQ ID NO: 17)

0 MKKLGWLSMC LFLLLFKPAF TQVATETETE MVQITLHKLL FPNGQLPKNH
50 PNDGQEKALL QTYRGLNGVT FQVYDVTDSF YHLREKGKTV EEAQAEIAKN
100 GASSGMFTAE ATTTTLNNED GIASFSLAAK DQEKRDKAYL FIESKVPEVV
150 KEKAENMVVV LPVHGQNNQK LSTIHLYPKN EENDYPDPPF EKVLEEPRND
200 FTIGEKITYS LHTTIPVNIL DYQKFELSDS ADEALTFLPN SLTISSNGEK
250 LTEGFVIHKK PHGFDVLFSI PSLEKYAGKK LTISYQMQLS STAQANKEIN
300 NNGTLDFGFG VSTKKVSVYT GSKQFVKIET NKPDKRLAGA VFLIKNKAGN

-continued

```
350 YLQQTANGYK WTKNESDALH LISDKNGAFS ISGLKTGSYR LKEIEAPSGY
400 ILSETEIPFT ISTFLSEDKE ADSILKVVNKENSRPFLPK TNETKNTLLG
450 VVGMVFASFA IWLFIKKRTG VKK
```

Efae 2924: Nucleotide sequence (SEQ ID NO: 18)

```
   0 ATGAAAAATC ATAAAAAAAT AAACGTTATG TTAGGAGTCC TTTTCCTTAT
  50 TTTACCATTA CTCACAAACA GCTTCGGCGC AAAAAAAGTG TTTGCAGAGG
 100 AGACAGCAGC TCAAGTCATC CTTCATAAAA AGAAAATGAC TGATTTACCC
 150 GATCCTTTAA TCCAAAACAG CGGGAAAGAA ATGAGCGAAT TCGATCAATA
 200 CCAAGGATTA GCCGATATTT CATTTTCAGT TTATAACGTC ACTCAAGAAT
 250 TTTATGCGCA ACGAGATAAA GGAGCGTCCG TGGATGCAGC AAAACAAGCA
 300 GTCCAGTCTT TGACTCCTGG TACACCAGTT GCTTCAGGAA CGACAGATGC
 350 TGATGGAAAT GTCACTTTAT CTTTACCTAA AAAACAAAAT GGGAAAGATG
 400 CAGTCTACAC GATCAAAGAA GAACCAAAAG ACGGAGTGTC AGCTGCCGCA
 450 AACATGGTTT TAGCTTTCCC TGTATATGAG ATGATCAAAC AAGCAGATGG
 500 CTCTTATAAA TACGGGACAG AAGAACTAGA TACTATCCAT CTCTACCCTA
 550 AAAATACAGT CGGTAATGAT GGAACGTTGA AAGTTACAAA AATCGGTACT
 600 GCCGAAAACG AAGCACTAAA TGGAGCAGAA TTTATTATTT CTAAAGAAGA
 650 AGGAACACCA AGCGTCAAAA AATACATCCA AAGTGTCACA GATGGATTGT
 700 ACACTTGGAC AACTGATCAA ACCAAAGCCA AACATTTCAT TACTGGTCAT
 750 TCTTATGACA TCGGCAACAA TGACTTTGCC GAGGCATCTA TTGAAAAAGG
 800 CCAGTTGATC GTTAATCATT TAGAAGTTGG AAAATATAAT TTAGAAGAAG
 850 TAAAAGCTCC TGATAATGCG GAAATGATTG AAAAGCAAAC AATCACGCCT
 900 TTTGAGATCC TGGCAAATAG CCAAACACCA GTAGAAAAGA CCATCAAAAA
 950 TGATACGTCT AAAGTTGATA AAACAACACC TCAATTGAAT GGAAAAGATG
1000 TCGCAATCGG TGAAAAAATT CAATATGAGA TTTCTGTCAA TATCCCATTA
1050 GGTATCGCTG ATAAAGAAGG AACGCAAAAC AAGTACACAA CATTCAAACT
1100 TATCGATACT CATGACGCTG CTTTAACATT TGATAATGAT TCTTCAGGAA
1150 CGTATGCTTA TGCCTTATAT GATGGAAATA AAGAAATCGA CCCAGTAAAT
1200 TATTCTGTCA CTGAGCAAAC AGACGGATTC ACGGTTTCAG TTGATCCGAA
1250 TTATATTCCT TCATTAACTC CTGGCGGTAC ATTGAAATTC GTTTACTATA
1300 TGCATTTGAA CGAAAAAGCA GATCCAACCA AAGGATTTTC TAACCAAGCA
1350 AATGTCGATA ACGGGCATAC AAATGATCAA ACACCACCGT CAGTCGATGT
1400 CGTTACTGGG GGCAAACGAT TTGTTAAAGT AGATGGTGAC GTTACATCAG
1450 ACCAAACACT TGCTGGAGCA GAATTCGTCG TTCGTGATCA AGATAGTGAC
1500 ACAGCGAAAT ATTTATCGAT CGACCCATCC ACAAAAGCCG TCAGCTGGGT
1550 ATCGGCGAAA GAATCAGCAA CGGTTTTTAC AACCACAAGT AACGGTTTAA
1600 TCGATGTGAC AGGTCTAAAA TATGGCACGT ACTATCTGGA AGAAACGAAA
1650 GCGCCAGAAA AATATGTTCC ATTAACAAAC CGTGTAGCAT TTACTATCGA
1700 TGAACAATCT TATGTAACAG CAGGACAGTT GATTTCTCCT GAAAAAATAC
1750 CAAATAAACA CAAAGGTACA CTTCCTTCAA CAGGCGGTAA GGGAATCTAT
1800 GTGTATATCG GTGCAGGAGT AGTCCTTCTA CTGATTGCTG GACTGTACTT
1850 TGCTAGACGC AAGCACAGTC AGATTTAG
```

Efae 2924: amino acid residues 55-588

(SEQ ID NO: 19)

```
  0 MKNHKKINVM LGVLFLILPL LTNSFGAKKV FAEETAAQVI LHKKKMTDLP
 50 DPLIQNSGKE MSEFDQYQGL ADISFSVYNV TQEFYAQRDK GASVDAAKQA
100 VQSLTPGTPV ASGTTDADGN VTLSLPKKQN GKDAVYTIKE EPKDGVSAAA
150 NMVLAFPVYE MIKQADGSYK YGTEELDTIH LYPKNTVGND GTLKVTKIGT
200 AENEALNGAE FIISKEEGTP SVKKYIQSVT DGLYTWTTDQ TKAKHFITGH
250 SYDIGNNDFA EASIEKGQLI VNHLEVGKYN LEEVKAPDNA EMIEKQTITP
300 FEILANSQTP VEKTIKNDTS KVDKTTPQLN GKDVAIGEKI QYEISVNIPL
350 GIADKEGTQN KYTTFKLIDT HDAALTFDND SSGTYAYALY DGNKEIDPVN
400 YSVTEQTDGF TVSVDPNYIP SLTPGGTLKF VYYMHLNEKA DPTKGFSNQA
450 NVDNGHTNDQ TPPSVDVVTG GKRFVKVDGD VTSDQTLAGA EFVVRDQDSD
500 TAKYLSIDPS TKAVSWVSAK ESATVFTTTS NGLIDVTGLK YGTYYLEETK
550 APEKYVPLTN RVAFTIDEQS YVTAGQLISP EKIPNKHKGT LPSTGGKGIY
600 VYIGAGVVLL LIAGLYFARR KHSQI
```

Protein Expression and Purification

Using PCR (the oligonucleotides used in the PCR reaction are shown in Table 3), the A domains from EF0089, EF1091, EF1092, EF1093, EF1099, EF1269, EF1824, EF2224, and EF3023 were amplified from *E. faecalis* V583 or *E. faecalis* EF1 (EF1099) genomic DNA and subcloned into the *E. coli* expression vector PQE-30 (Qiagen). One liter culture of *E. coli* M15(pREP4) cultures harboring appropriate pQE-30 based constructs were grown to $OD_{600}$=0.6 with an initial 2% inoculation from overnight cultures. After 2-3 h induction with 0.4 mM isopropyl-beta-d-thiogalactoside (IPTG), cells were collected with centrifugation, resuspended in 10 mM Tris-Cl, 100 mM NaCl, pH 7.9 and stored at −80 C.

To lyse the cells and release the expressed protein, cells were passed twice through French Press with a gauge pressure setting at 1200 PSI to give an estimated internal cell pressure of 20,000 PSI. The lysate was centrifuged at $RCF_{max}$ of 165,000×g and the supernatant was filtered through a 0.45 m filter. The volume was adjusted to 15 ml with 10 mM Tris-Cl, 100 mM NaCl, pH 7.9 and 0.2 M imidazole in the same buffer was added to increase the imidazole concentration to 6.5 mM in order to minimize non-specific binding. The sample was loaded to a nickel affinity chromatography column (HiTrap chelating, Pharmacia) connected to an FPLC system (Pharmacia) and previously equilibrated with 10 mM Tris-Cl, 100 mM NaCl, pH 7.9. Bound protein was eluted with a linear gradient of 0-100 mM imidazole in 10 mM Tris-Cl, 100 mM NaCl, pH 7.9 over 100-200 ml. Protein-containing fractions were analyzed in SDS-PAGE (FIG. 2) and dialyzed against 25 mM Tris-Cl, 1 mM EDTA, pH 6.5-9

(depending on pI of protein purified) before applying the samples to an ion-exchange column (HiTrap Q, Pharmacia) for further purification. Bound protein was eluted with a linear gradient of 0-0.5 M NaCl in 25 mM Tris-Cl, 1 mM EDTA, pH 6.5-9 over 100 ml. Finally, protein samples were dialyzed extensively against PBS and stored at +4° C.

Alternatively EF1091, EF1092, and EF1093 were expressed in shake flasks or in bioreactors, the cells were harvested by centrifugation and the cell paste frozen at −80° C. Cells were lysed in 1×PBS (10 mL of buffer/1 g of cell paste) using 2 passes through a microfluidizer at 10,000 psi. Lysed cells were spun down at 17,000 rpm for 30 minutes to remove cell debris. Supernatant was passed over a 5-mL HiTrap Chelating (Pharmacia) column charged with 0.1M $NiCl_2$. After loading, the column was washed with 5 column volumes of 10 mM Tris, pH 8.0, 100 mM NaCl (Buffer A). Protein was eluted using a 0-100% gradient of 10 mM Tris, pH 8.0, 100 mM NaCl, 500 mM imidazole (Buffer B). Protein containing fractions were dialyzed in 1×PBS.

Example 3

MSCRAMM® Genes Common to *E. faecalis* and *E. faecium* PCR Analysis

Primers for flanking regions of sequences above were used to amplify 1 μg genomic DNA from each *E. faecalis* strain. PCR products from 5 *E. faecalis* strains in Table 1 were sequenced and compared to the TIGR database sequence. Primers used to amplify the enterococcal MSCRAMM® A-domain gene products are shown below.

| Protein | 5' Primer | 3' Primer |
|---|---|---|
| ACE40 | **GAATTGAGCAAAAGTTCAATCG** (SEQ ID NO: 44) | GTCTGTCTTTTCACTTGTTTCTGTTG (SEQ ID NO: 51) |
| EF1091 | **CAAGTAAAAAAGCCGGTACAGC** (SEQ ID NO: 45) | AAAGGAACCTTTGCTTGGTTC SEQ ID NO: 52) |
| EF1092 | TCGCAAGCAAGCGTTCAAG (SEQ ID NO: 46) | AAGCCTGAGTCTTTTACTTTTTTATTG SEQ ID NO: 53) |
| EF1093 | GAGAGCGCACAGCTCGTG (SEQ ID NO: 47) | GGTACCTTTGTGTTTGTTTGGTAC SEQ ID NO: 54) |
| Efae2924 | CGGGATCCCAAAACAGCGGGAAAGAAATGAGCGA (SEQ ID NO: 48) | CCCAAGCTTTCATGTACCTTTGTGTTTATTTGG (SEQ ID NO: 55) |
| Efae2925 | CGGGATCCGAAATGGTTCAGATTACTTTACAC (SEQ ID NO: 49) | TCTGCAGTTCAATTGACTACTTTCAATATACTGTC (SEQ ID NO: 56) |
| Efae2926 | CGGGATCCAAAGCACTGAACATCAAGCTAAATGCG (SEQ ID NO: 50) | CCCAAGCTTTCAGAATGCTTGACCTTGATTATTGTA (SEQ ID NO: 57) |

Homology Among Enterococcal MSCRAMM® Proteins

A blastp search was performed using the AA sequence listed above with the NCBI search engine. The accession number is given for each putative homologue found. Both percent identity and similarity refer to the percentage of AA that match the query sequence exactly while similarity includes conservative AA changes in the matching calculation.

TABLE 4

Comparison of *E. faecium* homologues of *E. faecalis* MSCRAMM ® protein

| *E. faecalis* Protein | *E. faecium* Protein Homologue Name | Accession Number | % Identity | % Similarity |
|---|---|---|---|---|
| EF1091 | Efae2926 | 00038011 | 60 | 75 |
| EF1092 | Efae2925 | 00038010 | 48 | 63 |
| EF1093 | Efae2924 | 00038009 | 74 | 83 |

The "A" domain amino acid sequence from each *E. faecalis* MSCRAMM® protein was used as a query in a blastp search. Results shown were scored by NCBI computers. Identity is calculated as exact matches between the subject and query sequences while similarity also includes conservative changes in sequence at the same position.

Example 4

Additional Gram Positive Amino Acid Sequences Predicted to Be MSCRAMM® Proteins List of LPXTG-motif containing cell wall anchored proteins that contain predicted immunoglobulin-like fold. The sequencing center for each genome is indicated in the parenthesis. All the sequence except for those of CNA from *S. aureus* and *Staphylococcus epidermidis* can be obtained from TIGR website, comprehensive microbial resource section. The *S. epidermidis* RP64A genome is not annotated. However, the nucleotide coordinates of the genes encoding the listed *S. epidermidis* proteins can be obtained through TIGR website.

*Streptococcus pneumoniae* TIGR4 (TIGR)
SP0368
SP0462
SP0463
SP0464

*Enterococcus faecalis* V583 (TIGR)
EF2224
EF1099
EF1092
EF3023
EF1269
EF0089
EF1824
EF1091
EF1093
EF1075
EF1074
EF1651

*Streptococcus mutans* UA159 (University of Oklahoma)
SMU.610
SMU.987
SMU.63c

*Staphylococcus aureus* N315 (Juntendo University, Japan)
SA2447
SA2290
SA2291
SA2423
SA0742
SA0519
SA0520
SA0521

-continued

*Bacillus anthracis* Ames (TIGR)
BA0871
BA5258

*Staphylococcus epidermidis* strain RP62A (TIGR)
>SERP_GSE_14_6.AA 2402 residues (SEQ ID NO: 20)

```
mknkqgflpnllnkygirklsagtaslligatlvfgingqvkaaetdniv
sqngdnktndsessdkelvkseddktsststdtnlesefdqnnnpssiee
stnrndedtlnqrtstetekdthvksadtqttnettnknddnattnhtes
isdestyqsddskttqhdnsntnqdtqstlnptskessnkdeatsptpke
stsiektnlsndanhqttdevnhsdsdnmtnstpndteneldttqltshd
espspqsdnftgftnlmatplnlrndnprinllaatedtkpktykkpnns
eysyllndlgydattvkensdlrhagisqsqdntgsviklnltkwlslqs
dfvnggkvnisfaqsdfytqiesitlndvkmdttnngqnwsapingstvr
sgligsvtnhdivitlknsqtlsslgysnnkpvylthtwttndgaiaees
iqvasitptldskapntiqksdftagrmtnkikydssqnsiksvhtfkpn
enflqtdyravlyikeqvnkelipyidpnsvklyvsdpdgnpisqdryvn
gsidndglfdsskineisiknnntsgqlsnartsldrnvffgtlgqsrsy
tisyklkdgytlesvaskvsaretfdswmevdyldsydsgapnkrllgsy
assyidmidrippvapkansittedtsikgtaevdtninltfndgrtlng
kvdsngnfsiaipsyyvltgketikitsidkgdnvspaitisvidktppa
vkaisnktqkvnteiepikieatdnsgqavtnkveglpagmtfdeatnti
sgtpsevgsyditvtttdengnsetttftidvedttkptvesvadqtqev
nteiepikieatdnsgravtnkvdglpdgvtfdeatntisgtpsevgsyd
itvtttdesgnvtetiftidvedttkptvesiagqtqevnteiepikiea
kdnsgqtvtnkvdglpdgvtfdeatntisgtpsevgsydvtvtttdesgn
setttftievkdttkptvesvadqtqevnteiepikieardnsgqavtnk
vdglpdgvtfdeatntisgtpsevgsyditvtttdesgnvtettftieve
dttkptvenvadqtqevnteitpitiesednsgqtvtnkvdglpdgvtfd
ettntisgtpskvgsyditvtttdesgnatettftievedttkptvenva
gqtqeinteiepikieatdnsgqavtnkveglpagvtfdeatntisgtps
evgsytvtvttmdesgnatettftidvedttkptvesvadqtqevnteit
pitiesednsdqavtnkvdglpdgvtfdeatntisgtpsevgsytvtvtt
tdesgnatettftidvedttkptvksvsdqtqevnteitpikieatdnsg
qtvtnkvdglpdgitfdeatntisgtpsevgsyditvtttdesgnatett
ftinvedttkptvediadqtqevnteiepikieatdnggqavtnkvdglp
dgvtfdeatntisgtpsevgsydiivtttdengnsetttftidvedttkp
tvesvvdqtqevnteitpikieatdnsgqavankvdglpngvtfdettnt
isgtpsevgsydiivtttdesgnvtetiftidvedttkptvesiagqtqe
vnteiepikieatdnsgqavtnkvdglpngvtfdeatntisgtpsevgiy
tvtvtttdesgnatettftidvedttkptvesvadqtqevnteitpitie
sednsgqavtnkveglpagmtfdettntisgtpsevgsytvtvtttdesg
netettftidvedttkptvesianqtqevnteitpikieatdnsgqavtn
kvdglpngvtfdettntisgtpsevgsydikvtttdesgnatettftinv
edttkptvesvadqtqeinteiepikieardnsgqavtnkvdglpdgvtf
deatntisgtpsevgsyditvtttdesgnatettftidvedttkptvedi
tdqtqeintemtpikieatdnsgqavtnkveglpdgvtfdeatntisgtp
sevgkylitittidkdgntatttltinvidtttpeqptinkvtenstevn
grgepgtvvevtfpdgnkvegkvdsdgnyhiqipsettlkggqplqviai
dkagnkseatttnvidttapeqptinkvtenstevsgrgepgtvvevtfp
dgnkvegkvdsdgnyhiqipsderfkvgqqlivkvvdeegnvsepsitmv
qkedknseklstvtgtvtknnskslkhkaseqqsyhnksekiknvnkptk
ivekdmstydysryskdisnknnksatfeqqnvsdinnnqysrnkvnqpv
kksrkneinkdlpqtgeenfnkstlfgtlvaslgalllffkrrkkdende
ke
```

>SERP_GSE_2_50.AA 892 residues (SEQ ID NO: 21)

```
lfglghneakaeentvqdvkdsnmddelsdsndqssneekndvinnsqsi
ntdddnqikkeetnsndaienrskditqsttnvdeneatflqktpqdntq
lkeevvkepssvessnssmdtaqqpshttinseasiqtsdneensrvsdf
anskiiesntesnkeentieqpnkvredsitsqpssyknidekisnqdel
lnlpineyenkvrplsttsaqpsskrvtvnqlaaeqgsnvnhlikvtdqs
itegyddsdgiikahdaenliydvtfevddkvksgdtmtvnidkntvpsd
ltdsfaipkikdnsgeiiatgtydntnkqitytftdyvdkyenikahlkl
tsyidkskvpnnntkldveyktalssvnktitveyqkpnenrtanlqsmf
tnidtknhtveqtiyinplrysaketnvnisgngdegstiiddstiikvy
kvgdnqnlpdsnriydyseyedvtnddyaqlgnnndvninfgnidspyii
kviskydpnkddyttiqqtvtmqttineytgefrtasydntiafstssgq
gqgdlppektykigdyvwedvdkdgiqntndnekplsnvlvtltypdgts
ksvrtdeegkyqfdglkngltykitfetpegytptlkhsgtnpaldsegn
svwvtingqddmtidsgfyqtpkyslgnyvwydtnkdgiqgddekgisgv
kvtlkdengniistttdengkyqfdnlnsgnyivhfdkpsgmtqtttds
gdddeqdadgeevhvtitdhddfsidngyydddsdsdsdsdsddsdsd
sdsdsdsdsdsdsdsdsdsdsdsdsdsdsdsdsdsdsdsgldnssdkntk
dklpdtganedhdskgtllgalfaglgalllgkrrknrknkn
```

>SERP_GSE_9_28.AA 1973 residues (SEQ ID NO: 22)

```
mkenkrknnldknntrfsirkyqgygatsvaiigfiiiscfseakadsdk
heikshqqsmtnhlttlpsdnqentsnnefnnrnhdishlslnksiqmde
lkklikqykainlndkteesiklfqsdlvqaeslinnpqsqqhvdafyhk
flnsagklrkketvsikhersesntyrlgdevrsqtfshirhkrnavsfr
nadqsnlstdplkaneinpeiqngnfsqvsggplptsskrltvvtnvdnw
hsystdpnpeypmfytttavnypnfmsngnapygvilgrttdgwnrnvid
skvagiyqdidvvpgselnvnfistspvfsdgaagaklkisnveqnrvlf
dsrlngmgpyptgklsamvnipndinrvrisflpvsstgrvsvqrssreh
gfgdnssyyhggsvsdvrinsgsyvvskvtqreyttrpnssndtfarati
nlsvenkghnqskdtyyevilpqnsrlistrggsgnynnatnklsirldn
lnpgdrrdisytvdfessspklinlnahllyktnatfrgndgqrtgdniv
dlqsiallmnkdvletelneidkfirdlneadftidswsalqekmteggn
ilneqqnqvalenqasqetinnvtqsleilknnlkyktpsqpiiksnnqi
pnitispadkadkltityqntdnesasiignklnnqwslnnnipgieidm
qtglvtidykavypesvvgandktgnsdasaesritmprkeatplspive
aneervnvviapngeatqiaikyrtpdgqeatlvaskngsswtlnkqidy
vnieensgkvtigyqavqpeseviatetkgnsdesaesrvtmprkeatph
spiveaneehvnvtiapngeatqiaikyrtpdgqettliaskngsswtln
kqidyvnieensgkvtigyqavqleseviatetkgnsdasaesritmlrk
eatphspiveaneehvnvtiapngeatqiaikyrtpdgqeatlvasknes
swtlnkqidhvnidensgkvtigyqavqpeseiiatetkgnsdasaesri
tmprkeatpipptleasvqeasvtvtpnenatkvfikyldindeistiia
skinqqwtlnkdnfgikinpltgkviisyvavqpesdviaiesqgnsdls
eesriimptkeeppeppilesdsieakvnifpndeatrivimytslegqe
atlvaskness wtlnkqidhvnidensgkvtigyqavqpeseviatetkg
nsdasaesrvtmprkeatphspivetneervnvviapngeatqiaikyrt
pdgqettliaskngsswtlnkqidhvnidensgkvtigyqavqpeseiia
tetkgnsdasaesritmprkeaiphspiveaneehvnvtiapngettqia
vkyrtpdgqeatliaskness wtlnkqidhvnidensgkvtigyqavqpe
seviatetkgnsdasaesritmpvkektpappisiinesnasveiipqvn
vtqlslqyidakgqqqnliatlnqnqwtlnknvshitvdkntgkvlinyq
avypeseviareskgnsdssnvsmvimprktatpkppiikvdemnaslai
ipyknntainihyidkkgiksmvtaiknndqwqldekikyvkidaktgtv
iinyqivqenseiiataingnsdkseevkvlmpikeftplaplletnykk
atvsilpqsnatkldfkyrdkkgdskiiivkrfkniwkaneqisgvtinp
efgqvvinyqavypesdilaaqyvgnsdasewakvkmpkkelaphspsli
ydnrnnkiliapnsnatemelsyvdknnqslkvkalkinnrwkfdssvsn
isinpntgkivlqpqflltnskiivfakkgnsdasisvslrvpavkkiel
epmfnvpvlvslnkkriqfddcsgvknclnkqisktqlpdtgysdkasks
nilsvlllgfgflsysrkrkekq
```

>lcl|SEPN_5_124.AA 10203 residues (SEQ ID NO: 23)

```
MKSKPKLNGRNIGSFLLSKCMSYSLSKLSTLKTYNFQITSNNKEKTSRIG
VAIALNNRDKLQKFSIRKYAIGTFSTVIAT
LVFMGINTNHASADELNQNQKLIKQLNQTDDDDSNTHSQEIENNKQNSSG
KTESLRSSTSQNQANARLSDQFKDTNETSQ
QLPTNVSDDSINQSHSEANMNNEPLKVDNSTMQAHSKIVSDSDGNASENK
HHKLTENVLAESRASKNDKEKENLQEKDKS
QQVHPPLDKNALQAFFDASYHNYRMIDRDRADATEYQKVKSTFDYVNDLL
GNNQNIPSEQLVSAYQQLEKALELARTLPQ
QSTTEKRGRRSTRSVVENRSSRSDYLDARTEYYVSKDDDDSGFPPGTFFH
ASNRRWPYNLPRSRNILRASDVQGNAYITT
KRLKDGYQWDILFNSNHKGHEYMYYWFGLPSDQTPTGPVTFTIINRDGSS
TSTGGVGFGSGAPLPQFWRSAGAINSSVAN
DFKHGSATNYAFYDGVNNFSDFARGGELYFDREGATQTNKYYGDENFALL
NSEKPDQIRGLDTIYSFKGSGDVSYRISFK
TQGAPTARLYYAAGARSGEYKQATNYNQLYVEPYKNYRNRVQSNVQVKNR
TLHLKRTIRQFDPTLQRTTDVPILDSDGSG
SIDSVYDPLSYVKNVTGTVLGIYPSYLPYNQERWQGANAMNAYQIEELFS
QENLQNAARSGRPIQFLVGFDVEDSHHNPE
TLLPVNLYVKPELKHTIELYHDNEKQNRKEFSVSKRAGHGVFQIMSGTLH
NTVGSGILPYQQEIRIKLTSNEPIKDSEWS
ITGYPNTLTLQNAVGRTNNATEKNLALVGHIDPGNYFITVKFGDKVEQFE
IRSKPTPPRIITTANELRGNSNHKPEIRVT
DIPNDTTAKIKLVMGGTDGDHDPEINPYTVPENYTVVAEAYHDNDPSKNG
VLTFRSSDYLKDLPLSGELKAIVYYNQYVQ
SNFSNSVPFSSDTTPPTINEPAGLVHKYYRGDHVEITLPVTDNTGGSGLR
DVNVNLPQGWTKTFTINPNNNTEGTLKLIG
NIPSNEAYNTTYHFNITATDNSGNTTNPAKTFILNVGKLADDLNPVGLSR
DQLQLVTDPSSLSNSEREEVKRKISEANAN
IRSYLLQNNPILAGVNGDVTFYYRDGSVDVIDAENVITYEPERKSIFSEN
GNTNKKEAVITIARGQNYTIGPNLRKYFSL
SNGSDLPNRDFTSISAIGSLPSSSEISRLNVGNYNYRVNAKNAYHKTQQE
LNLKLKIVEVNAPTGNNRVYRVSTYNLTND
EINKIKQAFKAANSGLNLNDNDITVSNNFDHRNVSSVTVTIRKGDLIKEF
SSNLNNMNFLRWVNIRDDYTISWTSSKIQG
```

-continued

RNTDGGLEWSPDHKSLIYKYDATLGRQINTNDVLTLLQATAKNSNLRSNI
NSNEKQLAERGSNGYSKSIIRDDGEKSYLL
NSNPIQVLDLVEPDNGYGGRQVSHSNVIYNEKNSSIVNGQVPEANGASAF
NIDKVVKANAANNGIMGVIYKAQLYLAPYS
PKGYIEKLGQNLSNTNNVINVYFVPSDKVNPSITVGNYDHHTVYSGETFK
NTINVNDNYGLNTVASTSDSAITMTRNNNE
LVGQAPNVTNSTNKIVKVKATDKSGNESIVSFTVNIKPLNEKYRITTSSS
NQTPVRISNIQNNANLSIEDQNQVKSSLSM
TKILGTRNYVNESNNDVRSQVVSKVNRSGNNATVNVTTTFSDGTTNTITV
PVKHVLLEVVPTTRTTVRGQQFPTGKGTSP
NDFFSLRTGGPVDARIVWVNNQGPDINSNQIGRDLTLHAEIFFDGETTPI
RKDTTYKLSQSIPKQIYETTINGRFNSSGD
AYPGNFVQAVNQYWPEHMDFRWAQGSGTPSSRNAGSFTKTVTVVYQNGQT
ENVNVLFKVKPNKPVIDSNSVISKGQLNGQ
QILVRNVPQNAQVTLYQSNGTVIPNTNTTIDSNGIATVTIQGTLPTGNIT
AKTSMTNNVTYTKQNSSGIASNTTEDISVF
SENSDQVNVTAGMQAKNDGIKIIKGTNYNFNDFNSFISNIPAHSTLTWNE
EPNSWKNNIGTTTKTVTVTLPNHQGTRTVD
IPITIYPTVTAKNPVRDQKGRNLTNGTDVYNYIIFENNNRLGGTASWKDN
RQPDKNIAGVQNLIALVNYPGISTPLEVPV
KVWVYNFDFTQPIYKIQVGDTFPKGTWAGYYKHLENGEGLPIDGWKFYWN
QQSTGTTSDQWQSLAYTRTPFVKTGTYDVV
NPSNWGVWQTSQSAKFIVTNAKPNQPTITQSKTGDVTVTPGAVRNILISG
TNDYIQASADKIVINKNGNKLTTFVKNNDG
RWTVETGSPDINGIGPTNNGTAISLSRLAVRPGDSIEAIATEGSGETIST
SATSEIYIVKAPQPEQVATHTYDNGTFDIL
PDNSRNSLNPTERVEINYTEKLNGNETQKSFTITKNNNGKWTINNKPNYV
EFNQDNGKVVFSANTIKPNSQITITPKAGQ
GNTENTNPTVIQAPAQHTLTINEIVKEQGQNVTNDDINNAVQVPNKNRVA
IKQGNALPTNLAGGSTSHIPVVIYYSDGSS
EEATETVRTKVNKTELINARRRLDEEISKENKTPSSIRNFDQAMNRAQSQ
INTAKSDADQVIGTEFATPQQVNSALSKVQ
AAQNKINEAKALLQNKADNSQLVRAKEQLQQSIQPAASTDGMTQDSTRNY
KNKRQAAEQAIQHANSVINNGDATSQQIND
AKNTVEQAQRDYVEAKNLRADKSQLQSAYDTLNRDVLTNDKKPASVRRYN
EAISNIRKELDTAKADASSTLRNTNPSVE
QVRDALNKINTVQPKVNQAIALLQPKENNSELVQAKKRLQDAVNDIPQTQ
GMTQQTINNYNDKQREAERALTSAQRVIDN
GDATTQEITSEKSKVEQAMQALTNAKSNLRADKNELQTAYNKLIENVSTN
GKKPASIRQYETAKARIQNQINDAKNEAER
ILGNDNPQVSQVTQALNKIKAIQPKLTEAINMLQNKENNTELVNAKNRLE
NAVNDTDPTHGMTQETINNYNAKKREAQNE
IQKANMIINNGDATAQDISSEKSKVEQVLQALQNAKNDLRADKRELQTAY
NKLIQNVNTNGKKPSSIQNYKSARRNIENQ
YNTAKNEAHNVLENTNPTVNAVEDALRKINAIQPEVTKAINILQDKEDNS
ELVRAKEKLDQAINSQPSLNGMTQESINNY
TTKRREAQNIASSADTIINNGDASIEQITENKIRVEEATNALNEAKQHLT
ADTTSLKTEVRKLSRRGDTNNKKPSSVSAY
NNTIHSLQSEITQTENRANTIINKPIRSVEEVNNALHEVNQLNQRLTDTI
NLLQPLANKESLKEARNRLESKINETVQTD
GMTQQSVENYKQAKIKAQNESSIAQTLINNGDASDQEVSTEIEKLNQKLS
ELTNSINHLTVNKEPLETAKNQLQANIDQK
PSTDGMTQQSVQSYERKLQEAKDKINSINNVLANNPDVNAIRTNKVETEQ
INNELTQAKQGLTVDKQPLINAKTALQQSL
DNQPSTTGMTEATIQNYNAKRQKAEQVIQNANKIIENAQPSVQQVSDEKS
KVEQALSELNNAKSALRADKQELQQAYNQL
IQPTDLNNKKPASITAYNQRYQQFSNELNSTKTNTDRILKEQNPSVADVN
NALNKVREVQQKLNEARALLQNKEDNSALV
RAKEQLQQAVDQVPSTEGMTQQTKDDYNSKQQAAQQEISKAQQVIDNGDA
TTQQISNAKTNVERALEALNNAKTGLRADK
EELQNAYNQLTQNIDTSGKTPASIRKYNEAKSRIQTQIDSAKNEANSILT
NDNPQVSQVTAALNKIKAVQPELDKAIAML
KNKENNNALVQAKQQLQQIVNEVDPTQGMTTDTANNYKSKKREAEDEIQK
AQQIINNGDATEQQITNETNRVNQAINAIN
KAKNDLRADKSQLENAYNQLIQNVDTNGKKPASIQQYQAARQAIETQYNN
AKSEAHQILENSNPSVNEVAQALQKVEAVQ
LKVNDAIHILQNKENNSALVTAKNQLQQSVNDQPLTTGMTQDSINNYEAK
RNEAQSAIRNAEAVINNGDATAKQISDEKS
KVEQALAHLNDAKQQLTADTTELQTAVQQLNRRGDTNNKKPRSINAYNKA
IQSLETQITSAKDNANAVIQKPIRTVQEVN
NALQQVNQLNQQLTEAINQLQPLSNNDALKAARLNLENKINQTVQTDGMT
QQSIEAYQNAKRVAQNESNTALALINNGDA
DEQQITTETDRVNQQTTNLTQAINGLTVNKEPLETAKTALQNNIDQVPST
DGMTQQSVANYNQKLQIAKNEINTINNVLA
NNPDVNAIKTNKAEAERISNDLTQAKNNLQVDTQPLEKIKRQLQDEIDQG
TNTDGMTQDSVDNYNDSLSAAIIEKGKVNK
LLKRNPTVEQVKESVANAQQVIQDLQNARTSLVPDKTQLQEAKNRLENSI
NQQTDTDGMTQDSLNNYNDKLAKARQNLEK
ISKVLGGQPTVAEIRQNTDEANAHKQALDTARSQLTLNREPYINHINNES
HLNNAQKDNFKAQVNSAPNHNTLETIKNKA

-continued

DTLNQSMTALSESIADYENQKQQENYLDASNNKRQDYDNAVNAAKGILNQ
TQSPTMSADVIDQKAEDVKRTKTALDGNQR
LEVAKQQALNHLNTLNDLNDAQRQTLTDTINHSPNINSVNQAKEKANTVN
TAMTQLKQTIANYDDELHDGNYINADKDKK
DAYNNAVNNAKQLINQSDANQAQLDPAEINKVTQRVNTTKNDLNGNDKLA
EAKRDANTTIDGLTYLNEAQRNKAKENVGK
ASTKTNITSQLQDYNQLNIAMQALRNSVNDVNNVKANSNYINEDNGPKEA
YNQAVTHAQTLINAQSNPEMSRDVVNQKTQ
AVNTAHQNLHGQQKLEQAQSSANTEIGNLPNLTNTQKAKEKELVNSKQTR
TEVQEQLNQAKSLDSSMGTLKSLVAKQPTV
QKTSVYINEDQPEQSAYNDSITMGQTIINKTADPVLDKTLVDNAISNIST
KENALHGEQKLTTAKTEAINALNTLADLNT
PQKEAIKTAINTAHTRTDVTAEQSKANQINSAMHTLRQNISDNESVTNES
NYINAEPEKQHAFTEALNNAKEIVNEQQAT
LDANSINQKAQAILTTKNALDGEEQLRRAKENADQEINTLNQLTDAQRNS
EKGLVNSSQTRTEVASQLAKAKELNKVMEQ
LNHLINGKNQMINSSKFINEDANQQQAYSNAIASAEALKNKSQNPELDKV
TIEQAINNINSAINNLNGEAKLTKAKEDAV
ASINNLSGLTNEQKPKENQAVNGAQTRDQVANKLRDAEALDQSMQTLRDL
VNNQNAIHSTSNYFNEDSTQKNTYDNAIDN
GSTYITGQHNPELNKSTIDQTISRINTAKNDLHGVEKLQRDKGTANQEIG
QLGYLNDPQKSGEESLVNGSNTRSEVEEHL
NEAKSLNNAMKQLRDKVAEKTNVKQSSDYINDSTEHQRGYDQALQEAENI
INEIGNPTLNKSEIEQKLQQLTDAQNALQG
SHLLEEAKNNAITGINKLTALNDAQRQKAIENVQAQQTIPAVNQQLTLDR
EINTAMQALRDKVGQQNNVHQQSNYFNEDE
QPKHNYDNSVQAGQTIIDKLQDPIMNKNEIEQAINQINTTQTALSGENKL
HTDQESTNRQIEGLSSLNTAQINAEKDLVN
QAKTRTDVAQKLAAAKEINSAMSNLRDGIQNKEDIKRSSAYINADPTKVT
AYDQALQNAENIINATPNVELNKATIEQAL
SRVQQAQQDLDGVQQLANAKQQATQTVNGLNSLNDGQKRELNLLINSANT
RTKVQEELNKATELNHAMEALRNSVQNVDQ
VKQSSNYVNEDQPEQHNYDNAVNEAQATINNNAQPVLDKLAIERLTQTVN
TTKDALHGAQKLTQDQQAAETGIRGLTSLN
EPQKNAEVAKVTAATTRDEVRNIRQEATTLDTAMLGLRKSIKDKNDTKNS
SKYINEDHDQQQAYDNAVNNAQQVIDETQA
TLSSDTINQLANAVTQAKSNLHGDTKLQHDKDSAKQTIAQLQNLNSAQKH
MEDSLIDNESTRTQVQHDLTEAQALDGLMG
ALKESIKDYTNIVSNGNYINAEPSKKQAYDAAVQNAQNIINGTNQPTINK
GNVTTATQTVKNTKDALDGDHRLEEAKNNA
NQTIRNLSNLNNAQKDAEKNLVNSASTLEQVQQNLQTAQQLDNAMGELRQ
SIAKKDQVKADSKYLNEDPQIKQNYDDAVQ
RVETIINETQNPELLKANIDQATQSVQNAEQALHGAEKLNQDKQTSSTEL
DGLTDLTDAQREKLREQINTSNSRDDIKQK
IEQAKALNDAMKKLKEQVAQKDGVHANSDYTNEDSAQKDAYNNALKQAED
INNSSNPNLNAQDITNALNNIKQAQDNLH
GAQKLQQDKNTTNQAIGNLNHLNQPQKDALIQAINGATSRDQVAEKLKEA
EALDEAMKQLEDQVNQDDQISNSSPFINED
SDKQKTYNDKIQAAKEIINQTSNPTLDKQKIADTLQNIKDAVNNLHGDQK
LAQSKQDANNQLNHLDDLTEEQKNHFKPLI
NNADTRDEVNKQLEIAKQLNGDMSTLHKVINDKDQIQHLSNYINADNDKK
QNYDNAIKEAEDLIHNHPDTLDHKALQDLL
NKIDQAHNELNGESRFKQALDNALNDIDSLNSLNVPQRQTVKDNINHVTT
LESLAQELQKAKELNDAMKAMRDSIMNQEQ
IRKNSNYTNEDLAQQNAYNHAVDKINNIIGEDNATMDPQIIKQATQDINT
AINGLNGDQKLQDAKTDAKQQITNFTGLTE
PQKQALENIINQQTSRANVAKQLSHAKFLNGKMEELKVAVAKASLVRQNS
NYINEDVSEKEAYEQAIAKGQEIINSENNP
TISSTDINRTIQEINDAEQNLHGDNKLRQAQEIAKNEIQNLDGLNSAQIT
KLIQDIGRTTTKPAVTQKLEEAKAINQAMQ
QLKQSIADKDATLNSSNYLNEDSEKKLAYDNAVSQAEQLINQLNDPTMDI
SNIQAITQKVIQAKDSLHGANKLAQNQADS
NLIINQSTNLNDKQKQALNDLINHAQTKQQVAEIIAQANKLNNEMGTLKT
LVEEQSNVHQQSKYINEDPQVQNIYNDSIQ
KGREILNGTTDDVLNNNKIADAIQNIHLTKNDLHGDQKLQKAQQDATNEL
NYLTNLNNSQRQSEHDEINSAPSRTEVSND
LNHAKALNEAMRQLENEVALENSVKKLSDFINEDEAAQNEYSNALQKAKD
IINGVPSSTLDKATIEDALLELQNARESLH
GEQKLQEAKNQAVAEIDNLQALNPGQVLAEKTLVNQASTKPEVQEALQKA
KELNEAMKALKTEINKKEQIKADSRYVNAD
SGLQANYNSALNYGSQIIATTQPPELNKDVINRATQTIKTAENNLNGQSK
LAEAKSDGNQSIEHLQGLTQSQKDKQHDLI
NQAQTKQQVDDIVNNSKQLDNSMNQLQQIVNNDNTVKQNSDFINEDSSQQ
DAYNHAIQAAKDLITAHPTIMDKNQIDQAI
ENIKQALNDLHGSNKLSEDKKEASEQLQNLNSLTNGQKDTILNHIFSAPT
RSQVGEKIASAKQLNNTMKALRDSIADNNE
ILQSSKYFNEDSEQQNAYNQAVNKAKNINDQPTPVMANDEIQSVLNEVKQ
TKDNLHGDQKLANDKTDAQATLNALNYLN
QAQRGNLETKVQNSNSRPEVQKVVQLANQLNDAMKKLDDALTGNDAIKQT
SNYINEDTSQQVNFDEYTDRGKNIVAEQTN

-continued

```
PNMSPTNINTIADKITEAKNDLHGVQKLKQAQQQSINTINQMTGLNQAQK
EQLNQEIQQTQTRSEVHQVINKAQALNDSM
NTLRQSITDEHEVKQTSNYINETVGNQTAYNNAVDRVKQIINQTSNPTMN
PLEVERATSNVKISKDALHGERELNDNKNS
KTFAVNHLDNLNQAQKEALTHEIEQATIVSQVNNIYNKAKALNNDMKKLK
DIVAQQDNVRQSNNYINEDSTPQNMYNDTI
NHAQSIIDQVANPTMSHDEIENAINNIKHAINALDGEHKLQQAKENANLL
INSLNDLNAPQRDAINRLVNEAQTREKVAE
QLQSAQALNDAMKHLRNSIQNQSSVRQESKYINASDAKKEQYNHAVREVE
NINEQHPTLDKEIIKQLTDGVNQANNDLN
GVELLDADKQNAHQSIPTLMHLNQAQQNALNEKINNAVTRTEVAAIIGQA
KLLDHAMENLEESIKDKEQVKQSSNYINED
SDVQETYDNAVDHVTEILNQTVNPTLSIEDIEHAINEVNQAKKQLRGKQK
LYQTIDLADKELSKLDDLTSQQSSSISNQI
YTAKTRTEVAQAIEKAKSLNHAMKALNKVYKNADKVLDSSRFINEDQPEK
KAYQQAINHVDSIIHRQTNPEMDPTVINSI
THELETAQNNLHGDQKLAHAQQDAANVINGLIHLNVAQREVMINTNTNAT
TREKVAKNLDNAQALDKAMETLQQVVAHKN
NILNDSKYLNEDSKYQQQYDRVIADAEQLLNQTTNPTLEPYKVDIVKDNV
LANEKILFGAEKLSYDKSNANDEIKHMNYL
NNAQKQSIKDMISHAALRTEVKQLLQQAKILDEAMKSLEDKTQVVITDTT
LPNYTEASEDKKEKVDQTVSHAQAIIDKIN
GSNVSLDQVRQALEQLTQASENLDGDQRVEEAKVHANQTIDQLTHLNSLQ
QQTAKESVKNATKLEEATVSNNAQALNKV
MGKLEQFINHADSVENSDNYRQADDDKIIAYDEALEHGQDIQKTNATQNE
TKQALQQLIYAETSLNGFERLNHARPRALE
YIKSLEKINNAQKSALEDKVTQSHDLLELEHIVNEGTNLNDIMGELANAI
VNNYAPTKASINYINADNLRKDNFTQAINN
ARDALNKTQGQNLDFNAIDTFKDDIFKTKDALNGIERLTAAKSKAEKLID
SLKFINKAQETHANDEIINTNSIAQLSRIV
NQAFDLNDAMKSLRDELNNQAFPVQASSNYINSDEDLKQQFDHALSNARK
VLAVLAKENGKNLDEKQIQGLKQVIEDTKDALN
GIQRLSKAKAKAIQYVQSLSYINDAQRHIAENNIHNSDDLSSLANTLSKA
SDLDNAMKDLRDTIESNSTSVPNSVNYINA
DKNLQIEFDEALQQASATSSKTSENPATIEEVLGLSQAIYDTKNALNGEQ
RLATEKSKDLKLIKGLKDLNKAQLEDVTNK
VNSANTLTELSQLTQSTLELNDKMKLLRDKLKTLVNPVKASLNYRNADYN
LKRQFNKALKEAKGVLNKNSGTNVNINDIQ
HLLTQIDNAKDQLNGERRLKEHQQKSEVFIIKELDILNNAQKAAIINQIR
ASKDIKIINQIVDNAIELNDAMQGLKEHVA
QLTATTKDNIEYLNADEDHKLQYDYAINLANNVLDKENGTNKDANIIIGM
IQNMDDARALLNGIERLKDAQTKAHNDIKD
TLKRQLDEIEHANATSNSKAQAKQMVNEEARKALSNINDATSNDLVNQAK
DEGQSAIEHIHADELPKAKLDANQMIDQKV
EDINHLISQNPNLSNEEKNKLISQINKLVNGIKNEIQQAINKQQIENATT
KLDEVIETTKKLIIAKAEAKQMIKELSQKK
RDAINNNTDLTPSQKAHALADIDKTEKDALQHIENSNSIDDINNNKEHAF
NTLAHIIIWDTDQQPLVFELPELSLQNALV
TSEVVVHRDETISLESIIGAMTLTDELKVNIVSLPNTDKVADHLTAKVKV
ILADGSYVTVNVPVKVVEKELQIAKKDAIK
TIDVLVKQKIKDIDSNNELTSTQREDAKAEIERLKKQAIDKVNHSKSIKD
IETVKRTDFEEIDQFDPKRFTLNKAKKDII
TDVNTQIQNGFKEIETIKGLTSNEKTQFDKQLTALQKEFLEKVEHAHNLV
ELNQLQQEFNNRYKHILNQAHLLGEKHIAE
HKLGYVVVNKTQQILNNQSASYFIKQWALDRIKQIQLETMNSIRGAHTVQ
DVHKALLQGIEQILKVNVSIINQSFNDSLH
NFNYLHSKFDARLREKDVANHIVQTETFKEVLKGTGVEPGKINKETQQPK
LHKNDNDSLFKHLVDNFGKTVGVITLTGLL
SSFWLVLAKRRKKEEEEKQSIKNHHKDIRLSDTDKIDPIVITKRKIDKEE
QIQNDDKHSIPVAKHKKSKEKQLSEEDIHS
IPVVKRKQNSDNKDTKQKKVTSKKKKTPQSTKKVVKTKKRSKK
```

```
>lcl|SEPN_8_63.AA 1973 residues
                                        (SEQ ID NO: 24)
MKENKRKNNLDKNNTRFSIRKYQGYGATSVAIIGFIIISCFSEAKADSDK
HEIKSHQQSMTNHLTTLPSDNQENTSNNEF
NNRNHDISHLSLNKSIQMDELKKLIKQYKAINLNDKTEESIKLFQSDLVQ
AESLINNPQSQQHVDAFYHKFLNSAGKLRK
KETVSIKHERSESNTYRLGDEVRSQTFSHIRHKRNAVSFRNADQSNLSTD
PLKANEINPEIQNGNFSQVSGGPLPTSSKR
LTVVTNVDNWHSYSTDPNPEYPMFYTTTAVNYPNFMSNGNAPYGVILGRT
TDGWNRNVIDSKVAGIYQDIDVVPGSELNV
NFISTSPVFSDGAAGAKLKISNVEQNRVLFDSRLNGMGPYPTGKLSAMVN
IPNDINRVRISFLPVSSTGRVSVQRSSREH
GFGDNSSYYHGGSVSDVRINSGSYVVSKVTQREYTTRPNSSNDTFARATI
NLSVENKGHNQSKDTYYEVILPQNSRLIST
RGGSGNYNNATNKLSIRLDNLNPGDRRDISYTVDFESSSPKLINLNAHLL
YKTNATFRGNDGQRTGDNIVDLQSIALLMN
KDVLETELNEIDKFIRDLNEADFTIDSWSALQEKMTEGGNILNEQQNQVA
LENQASQETINNVTQSLEILKNNLKYKTPS
```

-continued

```
QPIIKSNNQIPNITISPADKADKLTITYQNTDNESASIIGNKLNNQWSLN
NNIPGIEIDMQTGLVTIDYKAVYPESVVGA
NDKTGNSDASAESRITMPRKEATPLSPIVEANEERVNVVIAPNGEATQIA
IKYRTPDGQEATLVASKNGSSWTLNKQIDY
VNIEENSGKVTIGYQAVQPESEVIATETKGNSDESAESRVTMPRKEATPH
SPIVEANEEHVNVTIAPNGEATQIAIKYRT
PDGQETTLIASKNGSSWTLNKQIDYVNIEENSGKVTIGYQAVQLESEVIA
TETKGNSDASAESRITMLRKEATPHSPIVE
ANEEHVNVTIAPNGEATQIAIKYRTPDGQEATLVASKNESSWTLNKQIDH
VNIDENSGKVTIGYQAVQPESEIIATETKG
NSDASAESRITMPRKEATPIPPTLEASVQEASVTVTPNENATKVFIKYLD
INDEISTIIASKINQQWTLNKDNFGIKINP
LTGKVIISYVAVQPESDVIAIESQGNSDLSEESRIIMPTKEEPPEPPILE
SDSIEAKVNIFPNDEATRIVIMYTSLEGQE
ATLVASKNESSWTLNKQIDHVNIDENSGKVTIGYQAVQPESEVIATETKG
NSDASAESRVTMPRKEATPHSPIVETNEER
VNVVIAPNGEATQIAIKYRTPDGQETTLIASKNGSSWTLNKQIDHVNIDE
NSGKVTIGYQAVQPESEIIATETKGNSDAS
AESRITMPRKEAIPHSPIVEANEEHVNVTIAPNGETTQIAVKYRTPDGQE
ATLIASKNESSWTLNKQIDHVNIDENSGKV
TIGYQAVQPESEVIATETKGNSDASAESRITMPVKEKTPAPPSIINESNA
SVEIIPQVNVTQLSLQYIDAKGQQQNLIA
TLNQNQWTLNKNVSHITVDKNTGKVLINYQAVYPESEVIARESKGNSDSS
NVSMVIMPRKTATPKPPIIKVDEMNASLAI
IPYKNNTAINIHYIDKKGIKSMVTAIKNNDQWQLDEKIKYVKIDAKTGTV
IINYQIVQENSEIIATAINGNSDKSEEVKV
LMPIKEFTPLAPLLETNYKKATVSILPQSNATKLDFKYRDKKGDSKIIIV
KRFKNIWKANEQISGVTINPEFGQVVINYQ
AVYPESDILAAQYVGNSDASEWAKVKMPKKELAPHSPSLIYDNRNNKILI
APNSNATEMELSYVDKNNQSLKVKALKINN
RWKFDSSVSNISINPNTGKIVLQPQFLLTNSKIIVFAKKGNSDASISVSL
RVPAVKKIELEPMENVPVLVSLNKKRIQFD
DCSGVKNCLNKQISKTQLPDTGYSDKASKSNILSVLLLGFGFLSYSRKRK
EKQ
```

Example 5

Immunization Strategies for Antibody Production Using Three Representative Enterococcal MSCRAMM® Proteins Purified EF1091, EF1092, and EF1093 proteins were used to generate a panel of murine antibodies. Briefly, a group of Balb/C mice received a series of subcutaneous immunizations of 1-10 mg of protein in solution or mixed with adjuvant as described below in Table 5:

TABLE 5

| Immunization Scheme Conventional | | | | |
|---|---|---|---|---|
| Injection | Day | Amount (μg) | Route | Adjuvant |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice serum was collected and titered in ELISA assays against MSCRAMM® proteins ACE, EF1091, EF1092 and EF1093 (Table 6).

Serum ELISA

Immulon 2-HB high protein binding 96 well plates were coated with 100 ng/well of the purified A-domains of EF1091, EF1092 or EF1093 and incubated overnight at 2-8° C. Plates were washed four times (350 μl/well) with PBS/0.5% Tween 20 using the Skatron Skanwasher plate washer and then blocked with 1% bovine serum albumin (BSA) solution, 200 μl/well for 1-2 hour at room temperature. Following incubation, the plates were washed as before and 100 it of 1×PBS, 0.05% Tween 20, 0.1% BSA buffer was added to each well of rows B-H of the 96-well plate. The negative control serum (preimmune Balb/C serum) and hyperimmune samples were then diluted 1:100 in 1×PBS, 0.05% Tween 20, 0.1% BSA buffer. 200 it of negative control serum was added in duplicate to wells A1 and A2 of the 96-well plate and 200 μl of each diluted hyperimmune test serum were added in duplicate to wells A3 to A12. Two-fold serial dilutions were performed down the plate ending with Row H with the remaining 100 μl being discarded. The plates were incubated for 1 hour at room temperature. The plates were again washed as before followed by the addition of 1:5000 dilution of a secondary antibody solution, Goat anti-mouse IgG (whole molecule)-AP conjugate (Sigma Cat. A-5153), to each well (100 μl/well) and incubated for 1 hour at room temperature. Following incubation, the plates were washed 4 times (350 μl/well) with PBS/0.5% Tween 20. The developing solution, 1 mg/ml 4-nitrophenyl phosphate (pNPP) in 1M Diethanolamine, pH9.8, 0.5 mM $MgCl_2$, was added to each well (100 μl/well) and the plates incubated at 37° C. for 30 minutes. After incubation, the absorbance ($A405_{nm}$) of each well was measured using the Spectra MAX 190 plate reader (Molecular Devices Corp., Sunnyvale, Calif.). The data was analyzed using SOFTmax Pro v.3.1.2. software (Molecular Devices Corp.) The dilution of the hyperimmune sera where the absorbance was 2-fold above the negative control serum absorbance was used as the titre for that hyperimmune serum sample.

TABLE 6

| Antibody Titer at Sacrifice | |
|---|---|
| Antigen | Polyclonal Antibody Titre |
| EF1091 | >12,800 |
| EF1092 | >12,800 |
| EF1093 | >12,800 |

Example 6

Antibody Reactivity Against *E. faecalis* MSCRAMM® Proteins

Antisera derived from Balb/c mice (as described in Example 3) was used to identify EF1091, EF1092 or EF1093 natively expressed on the surface of *E. faecalis* strains.

Flow Cytometry Analysis—Whole Cell Staining

Bacterial samples (Table 7) were collected, washed and incubated with polyclonal antisera or pre-immune sera (control) at a dilution of 1:2000 after blocking with rabbit IgG (50 mg/ml). Following incubation with sera, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured.

TABLE 7

| Whole Cell Staining of *E. faecalis* and *E. faecium* | | | |
|---|---|---|---|
| | EF1091 | EF1092 | EF1093 |
| *E. faecalis* | | | |
| ATCC700802 | -- | -- | Not done (NA) |
| 687097 | -- | -- | ND |
| V583 | -- | -- | ND |
| CG110 | -- | -- | ND |
| OG1RF | + | + | + |
| TX2708 | -- | -- | ND |
| TX0020 | ND | ND | ND |
| TX0045 | -- | -- | ND |
| TX0002 | -- | -- | ND |
| TX0039 | -- | -- | ND |
| TX0052 | ND | ND | ND |
| TX0012 | -- | -- | ND |
| TX0017 | ND | ND | ND |
| TX0008 | ND | ND | ND |
| TX0024 | ND | ND | ND |
| *E. faecium* | | | |
| 935/01 | -- | -- | ND |
| TX0016 | ND | ND | ND |
| TX0054 | +/- | +/- | ND |
| TX0074 | + | + | ND |
| TX0078 | -- | -- | ND |
| TX0080 | +/- | +/- | ND |
| TX0081 | +/- | +/- | ND |
| TX2535 | ND | ND | ND |
| TX2555 | +/- | + | + |
| TX0110 | -- | -- | -- |
| TX0111 | ND | ND | ND |

Polyclonal antisera raised in mice against EF1091, EF1092 and EF1093 were shown to recognize the native protein expressed on the surface of *E. faecalis* strains as well as *E. faecium* strains in flow cytometry studies (Table 7).

Example 7

Immunization Strategies for Monoclonal Antibody Production

With the goal of generating and characterizing monoclonal antibodies (mAbs), strategies were formulated to generate mAbs against EF1091, EF 1092 and EF 1093 that were of high affinity, able to interrupt or restrict the binding of extracellular matrix proteins (ECM) and demonstrate therapeutic efficacy in vivo. *E. coli* expressed and purified EF1091, EF1092, and EF1093 proteins were used to generate a panel of murine monoclonal antibodies. Briefly, a group of Balb/C or SJL mice received a series of subcutaneous immunizations of 1-10 □g of protein in solution or mixed with adjuvant as described below in Table 8:

TABLE 8

| Immunization Schemes | | | | |
|---|---|---|---|---|
| | Day | Amount (μg) | Route | Adjuvant |
| RIMMS Injection | | | | |
| #1 | 0 | 5 | Subcutaneous | FCA/RIBI |
| #2 | 2 | 1 | Subcutaneous | FCA/RIBI |
| #3 | 4 | 1 | Subcutaneous | FCA/RIBI |
| #4 | 7 | 1 | Subcutaneous | FCA/RIBI |
| #5 | 9 | 1 | Subcutaneous | FCA/RIBI |

TABLE 8-continued

| Immunization Schemes | | | | |
|---|---|---|---|---|
| | Day | Amount (μg) | Route | Adjuvant |
| Conventional Injection | | | | |
| Primary | 0 | 5 | Subcutaneous | FCA |
| Boost #1 | 14 | 1 | Intraperitoneal | RIBI |
| Boost #2 | 28 | 1 | Intraperitoneal | RIBI |
| Boost #3 | 42 | 1 | Intraperitoneal | RIBI |

At the time of sacrifice (RIMMS) or seven days after a boost (conventional) serum was collected and titered in ELISA assays against in immunizing MSCRAMM or on whole cells (*E. faecalis* and/or *E. faecium*). Three days after the final boost, the spleens or lymph nodes were removed, teased into a single cell suspension and the lymphocytes harvested. The lymphocytes were then fused to a P3X63Ag8.653 myeloma cell line (ATCC #CRL-1580). Cell fusion, subsequent plating and feeding were performed according to the Production of Monoclonal Antibodies protocol from *Current Protocols in Immunology* (Chapter 2, Unit 2.).

Example 8

Screening and Selection of Anti-EF1091 Monoclonal Antibodies

Any clones that were generated from the EF1091 fusion were then screened for specific anti-EF1091 antibody production using a standard ELISA assay. Positive clones were expanded and tested further for activity in a whole bacterial cell binding assay by flow cytometry and EF1091 binding by Biacore analysis (Table 9).

ELISA Analysis

Immulon 2-HB high-binding 96-well microtiter plates (Dynex) were coated with 1 μg/well of rEF1091 in 1×PBS, pH 7.4 and incubated for 2 hours at room temperature. All washing steps in ELISAs were performed three times with 1×PBS, 0.05% Tween-20 wash buffer. Plates were washed and blocked with a 1% BSA solution at room temperature for 1 hour before hybridoma supernatant samples were added to wells. Plates were incubated with samples and relevant controls such as media alone for one hour at room temperature, washed, and goat anti-mouse IgG-AP (Sigma) diluted 1:5000 in 1×PBS, 0.05% Tween-20, 0.1% BSA was used as a secondary reagent. Plates were developed by addition of 1 mg/ml solution of 4-nitrophenyl phosphate (pNPP) (Sigma), followed by incubation at 37° C. for 30 minutes. Absorbance was read at 405 nm using a SpectraMax 190 Plate Reader (Molecular Devices Corp.). Antibody supernatants that had an $OD_{405}$≧3 times above background (media alone, ~0.10 D) were considered positive.

Biacore Analysis

Throughout the analysis, the flow rate remained constant at 10 ml/min. Prior to the EF1091 injection, test antibody was adsorbed to the chip via RAM-Fc binding. At time 0, EF1091 at a concentration of 30 mg/ml was injected over the chip for 3 min followed by 2 minutes of dissociation. This phase of the analysis measured the relative association and disassociation kinetics of the mAb/EF1091 interaction.

Flow Cytometric Analysis

Bacterial samples were collected, washed and incubated with mAb or PBS alone (control) at a concentration of 2 mg/ml after blocking with rabbit IgG (50 mg/ml). Following incubation with antibody, bacterial cells were incubated with Goat-$F_{(ab')2}$-Anti-Mouse-$F_{(ab')2}$-FITC which served as the detection antibody. After antibody labeling, bacterial cells were aspirated through the FACScaliber flow cytometer to analyze fluorescence emission (excitation: 488, emission: 570). For each bacterial strain, 10,000 events were collected and measured.

TABLE 9

| Representative Examples of Hybridoma Supernatants | | | | |
|---|---|---|---|---|
| Fusion-Clone | Immunization Antigen | ELISA Data (EF1091) | Biacore Analysis | Flow Cytometric *E. faecalis* Staining |
| 85-8 | EF 1091 | 0.70 | + | + |
| 85-25 | EF 1091 | 0.75 | + | + |
| 85-58 | EF 1091 | 0.76 | + | −− |
| 85-78 | EF 1091 | 0.83 | + | + |
| 85-81 | EF 1091 | 0.84 | + | + |
| 85-162 | EF 1091 | 0.78 | + | + |
| 85-310 | EF 1091 | 0.30 | −− | −− |
| 85-341 | EF 1091 | 0.31 | −− | −− |
| 85-359 | EF 1091 | 0.48 | −− | −− |
| 85-374 | EF 1091 | 0.39 | −− | −− |
| 85-380 | EF 1091 | 0.32 | −− | −− |
| 85-399 | EF 1091 | 0.98 | + | −− |
| 85-473 | EF 1091 | 0.55 | + | −− |
| 85-511 | EF 1091 | 0.85 | + | −− |
| 85-581 | EF 1091 | 0.88 | + | + |
| 85-586 | EF 1091 | 0.88 | + | + |
| 85-641 | EF 1091 | 0.45 | + | + |
| 85-661 | EF 1091 | 0.32 | −− | −− |
| 85-712 | EF 1091 | 0.30 | −− | −− |

Example 9

Binding of Enterococcal MSCRAMM® Proteins to Extracellular Matrix (ECM) Proteins Understanding the potential extracellular matrix proteins that these MSCRAMMs expressed from *Enterococcus* bind to is of great biological importance with therapeutic implications.

ELISA based Extracellular Matrix Ligand Screening

To determine the binding activity of the recombinant proteins EF1091, EF1092 and EF1093 (Table 10) with extracellular matrix molecules, duplicate wells of a 96-well Costar micro-titer plate (Corning) were coated overnight at 4° C. with 2 μg of either human collagen type I, III, IV, V or VI (Rockland Immunochemicals), fibrinogen, fibronectin, plasminogen, vitronectin (Sigma) or elastin (CalBiochem) in 1004 of 1×PBS, pH 7.4 (Gibco). Wells were washed 4 times with 1×PBS, pH 7.4 containing 0.05% Tween 20 (1×PBST). Wells were then blocked with a 1% (w/v) solution of BSA in 1×PBS, pH 7.4 for 1 hour followed by 4 washes with 1×PBST. Next, 5 μg of recombinant protein in 1004 of 1×PBST containing 0.1% BSA (1×PBST-BSA) was added to each well. After incubation with the protein for 1 hour at room temperature, wells were washed 4 times with 1×PBS-T and 100 □L of mouse polyclonal antisera raised against the respective recombinant protein was added to each well at a dilution of 1:2000 in 1×PBST-BSA. Following the 1 hour incubation at room temperature with antisera, the wells were washed 4 times with 1×PBST. Finally, goat anti-mouse IgG-alkaline phsophatase conjugate (Sigma) was diluted 1:2000 with 1×PBST-BSA and 100 µl was added to each well. This incubation proceeded for 1 hour at room temperature and the wells were then washed 4 times with 1×PBST. The alkaline phosphatase was developed by adding 100 µl of a 1 mg/mL pNP solution (Sigma 104 tablets) to each well and incubating for 30 minutes at room temperature. Development was stopped by addition of 504 of 2M NaOH to each well. The absorbance at 405 nm ($A_{405}$) was measured using a SpectraMax 190 (Molecular Devices). Reactivity was noted as positive if the signal was 2.5× greater than background.

Alternatively, EF0089 and EF2224 binding to components of the ECM (Table 10) was tested by immobilizing 1 µg of each ECM protein (human laminin, fibronectin, fibrinogen, type I, III and IV collagens) in 100 µl PBS, or 3% acetic acid in the case of collagens, on microplate wells (96-well, 4HBX, Thermo Labsystems, Franklin, Ma) overnight at 4° C. Plates were washed once with PBS and blocked with 1% BSA in PBS for 1 h. Fifty µl of 5 and 10 µM concentrations of purified His-tag proteins in the blocking buffer were added and incubated at ambient temperature for 2 h. Plates were washed three times with 0.05% Tween20 in PBS and incubated 2 h with 1:3000 dilution of His6-tag monoclonal antibody (Amersham Biosciences Corp., Piscataway, N.J.) in blocking buffer. After three washes, 1:3000 dilution of alkaline phosphatase-conjugated anti-mouse antibody in blocking buffer was added to the wells and incubated 2 h. Finally, signal was detected with nitrobluetetrazolium (NBT) and 5-bromo-4-chloro-3-indolyl-phosphate (BCIP) in 0.1 M $NaHCO_3$, 1 mM $MgCl_2$, pH 9.8. Absorbance at 405 nm was measured with an ELISA reader

TABLE 10

| MSCRAMM ® Protein Recognition of ECM Proteins | | | | | |
|---|---|---|---|---|---|
| ECM Proteins | EF0089 | EF2224 | EF 1091 | EF 1092 | EF 1093 |
| Fibrinogen | + | + | -- | -- | + |
| Fibronectin | -- | -- | -- | -- | -- |
| Collagen I | -- | -- | -- | -- | -- |
| Collagen III | -- | -- | -- | -- | -- |
| Collagen IV | -- | -- | -- | -- | -- |
| Collagen V | Not determined (ND) | ND | -- | -- | -- |

TABLE 10-continued

| MSCRAMM ® Protein Recognition of ECM Proteins | | | | | |
|---|---|---|---|---|---|
| ECM Proteins | EF0089 | EF2224 | EF 1091 | EF 1092 | EF 1093 |
| Collagen VI | -- | -- | -- | + | -- |
| Vitronectin | -- | -- | -- | -- | -- |
| Elastin | ND | ND-- | -- | -- | -- |
| Plasminogen | ND | ND | + | + | + |

Example 10

Serum From Patients Infected With *E. faecalis* Contain Elevated Levels of Antibodies Against MSCRAMM® Proteins The presence of antibodies against enterococcal proteins in human sera collected from hospitalized patients with and without a previous *E. faecalis* infection was tested by an ELISA assay described in (Arduino et al., 1994) (Nallapareddy et al., 2000b) with some modifications (Table 11). Briefly, 20 ng of each purified enterococcal protein in 100 µl PBS was coated on microplates (96 well, 4HBX, Thermo Labsystems, Franklin, Ma) overnight at 4 □C. The plates were blocked with 1% BSA, 0.01% Tween20 in PBS at ambient temperature for 1 h and 100 µl of the sera in blocking buffer were added. Each serum was tested in triplicate with serial dilutions from 1:100 to 1:6400. Plates were incubated for 2 h at ambient temperature and washed three times with 0.01% Tween20 in PBS. 100 µl of 1:3000 dilution of horseradish peroxidase-conjugated anti human IgG was added and incubated 2 h. After three washes, signal was detected with 3,3',5,5'-tetramethylbenzidine (TMB) in the presence of $H_2O_2$ in 0.1 M citrate-acetate buffer, pH 6.0 at ambient temperature for 15 min. The reaction was stopped with 2 M $H_2SO_4$ and absorbance at 450 nm was recorded. Titers were determined after subtracting $A_{450nm}$ values from appropriate controls. To determine a cut-off level for serum titers, four additional control sera from healthy individuals without a prior *E. faecalis* infection were assayed. The sum of average $A_{450nm}$ values and two times the standard deviations for each dilution of the control sera were set as cut-off levels for positive titers.

TABLE 11

| | Infection | | | | | | | | No infection | |
|---|---|---|---|---|---|---|---|---|---|---|
| ≧1:6400 | ••••••• | • | •• | • | •••• | •••• | | •••••••• | | |
| 1:3200 | | • | | • | | | • | | | |
| 1:1600 | | | | | | | | | | |
| 1:800 | | | | | | | | | | |
| 1:400 | | | | | | | • | | | |
| 1:200 | | | •• | • | • | ••• | | • | | • |
| ≦1:100 | •• | ••••••• | ••••• | •••••• | •••• | •• | ••••••• | | ••••••••• | ••••••••• |
| | EF1091 | EF1824 | EF0089 | EF3023 | EF1092 | EF2224 | EF1269 | EF1093 | EF1091 | EF1824 |

| | No infection | | | | | |
|---|---|---|---|---|---|---|
| ≧1:6400 | | | | | | • |
| 1:3200 | | | | | | |
| 1:1600 | | | | | | |
| 1:800 | | | | | | |
| 1:400 | | | | | | |
| 1:200 | • | • | • | • | | |
| ≦1:100 | ••••••••• | ••••••••• | ••••••••• | ••••••••• | •••••••••• | ••••••••• |
| | EF0089 | EF3023 | EF1092 | EF2224 | EF1269 | EF1093 |

The following references referred to in the above description are incorporated as is set forth in their entirety herein:

CDC. 2002. Vancomycin-resistant *Staphylococcus aureus*—Pennsylvania, 2002. *Morb. Mortal. Wkly.* 51:902.

Deivanayagam, C. C., R. L. Rich, M. Carson, R. T. Owens, S. Danthuluri, T. Bice, M. Hook, and S. V. Narayana. 2000. Novel fold and assembly of the repetitive B region of the *Staphylococcus aureus* collagen-binding surface protein. *Structure Fold Des* 8:67-78.

Deivanayagam, C. C., E. R. Wann, W. Chen, M. Carson, K. R. Rajashankar, M. Hook, and S. V. Narayana. 2002. A novel variant of the immunoglobulin fold in surface adhesins of *Staphylococcus aureus*: crystal structure of the fibrinogen-binding MSCRAMM, clumping factor A. *Embo J* 21:6660-72.

Hamburger, Z. A., M. S. Brown, R. R. Isberg, and P. J. Bjorkman. 1999. Crystal structure of invasin: a bacterial integrin-binding protein. *Science* 286:291-5.

Huycke, M. M., D. F. Sahm, and M. S. Gilmore. 1998. Multiple-drug resistant enterococci: the nature of the problem and an agenda for the future. *Emerg Infect Dis* 4:239-49.

Leahy, D. J., I. Aukhil, and H. P. Erickson. 1996. 2.0 A crystal structure of a four-domain segment of human fibronectin encompassing the RGD loop and synergy region. *Cell* 84:155-64.

Luo, Y., E. A. Frey, R. A. Pfuetzner, A. L. Creagh, D. G. Knoechel, C. A. Haynes, B. B. Finlay, and N. C. Strynadka. 2000. Crystal structure of enteropathogenic *Escherichia coli* intimin-receptor complex. *Nature* 405:1073-7.

O'Brien, L. M., E. J. Walsh, R. C. Massey, S. J. Peacock, and T. J. Foster. 2002. *Staphylococcus aureus* clumping factor B (ClfB) promotes adherence to human type I cytokeratin 10: implications for nasal colonization. *Cell Microbiol* 4:759-70.

Patti, J. M., and M. Hook. 1994. Microbial adhesins recognizing extracellular matrix macromolecules. *Curr. Biol.* 6:752-758.

Paulsen, I. T., L. Banerjei, G. S. Myers, K. E. Nelson, R. Seshadri, T. D. Read, D. E. Fouts, J. A. Eisen, S. R. Gill, J. F. Heidelberg, H. Tettelin, R. J. Dodson, L. Umayam, L. Brinkac, M. Beanan, S. Daugherty, R. T. DeBoy, S. Durkin, J. Kolonay, R. Madupu, W. Nelson, J. Vamathevan, B. Tran, J. Upton, T. Hansen, J. Shetty, H. Khouri, T. Utterback, D. Radune, K. A. Ketchum, B. A. Dougherty, and C. M. Fraser. 2003. Role of mobile DNA in the evolution of vancomycin-resistant *Enterococcus faecalis*. *Science* 299: 2071-4.

Perkins, S., E. J. Walsh, C. C. Deivanayagam, S. V. Narayana, T. J. Foster, and M. Hook. 2001. Structural organization of the fibrinogen-binding region of the clumping factor B MSCRAMM of *Staphylococcus aureus*. *J Biol Chem* 276: 44721-8.

Sharma, A., J. A. Askari, M. J. Humphries, E. Y. Jones, and D. I. Stuart. 1999. Crystal structure of a heparin- and integrin-binding segment of human fibronectin. *Embo J* 18:1468-79.

Symersky, J., J. M. Patti, M. Carson, K. House-Pompeo, M. Teale, D. Moore, L. Jin, A. Schneider, L. J. DeLucas, M. Hook, and S. V. Narayana. 1997. Structure of the collagen-binding domain from a *Staphylococcus aureus* adhesin. *Nat Struct Biol* 4:833-8.

Tailor, S. A., E. M. Bailey, and M. J. Rybak. 1993. *Enterococcus*, an emerging pathogen. *Ann Pharmacother* 27:1231-42.

Tung, H., B. Guss, U. Hellman, L. Persson, K. Rubin, and C. Ryden. 2000. A bone sialoprotein-binding protein from *Staphylococcus aureus*: a member of the staphylococcal Sdr family. Biochem J 345 Pt 3:611-9.

Arduino, R. C., Murray, B. E., and Rakita, R. M. (1994) Roles of antibodies and complement in phagocytic killing of enterococci. *Infection and Immunity* 62: 987-993.

Davis, S. L., Gurusiddappa, S., McCrea, K. W., Perkins, S., and Hook, M. (2001) SdrG, a fibrinogen-binding bacterial adhesin of the microbial surface components recognizing adhesive matrix molecules subfamily from *Staphylococcus epidermidis*, targets the thrombin cleavage site in the Bbeta chain. *J Biol Chem* 276: 27799-27805.

Deivanayagam, C. C., Perkins, S., Danthuluri, S., Owens, R. T., Bice, T., Nanavathy, T., Foster, T. J., Hook, M., and Narayana, S. V. (1999) Crystallization of ClfA and ClfB fragments: the fibrinogen-binding surface proteins of *Staphylococcus aureus*. *Acta Crystallogr D Biol Crystallogr* 55 (Pt 2): 554-556.

Deivanayagam, C. C., Wann, E. R., Chen, W., Carson, M., Rajashankar, K. R., Hook, M., and Narayana, S. V. (2002) A novel variant of the immunoglobulin fold in surface adhesins of *Staphylococcus aureus*: crystal structure of the fibrinogen-binding MSCRAMM, clumping factor A. *Embo J* 21: 6660-6672.

Foster, T. J., and Hook, M. (1998) Surface protein adhesins of *Staphylococcus aureus*. *Trends Microbiol.* 6: 484-488.

Hartford, O., O'Brien, L., Schofield, K., Wells, J., and Foster, T. J. (2001) The Fbe (SdrG) protein of *Staphylococcus epidermidis* HB promotes bacterial adherence to fibrinogen. *Microbiology* 147: 2545-2552.

Joh, H. J., House-Pompeo, K., Patti, J. M., Gurusiddappa, S., and Hook, M. (1994) Fibronectin receptors from Gram-positive bacteria: comparison of active sites. *Biochemistry* 33: 6086-6092.

Lee, J. O., Rieu, P., Arnaout, M. A., and Liddington, R. (1995) Crystal structure of the A-domain from the a subunit of integrin CR3 (CDIIb/CD18). *Cell* 180: 631-638.

Mazmanian, S. K., Ton-That, H., and Schneewind, O. (2001) Sortase-catalyzed anchoring of surface proteins to the cell wall of *Staphylococcus aureus*. *Molecular Microbiology* 40: 1049-1057.

McDevitt, D., Francois, P., Vaudaux, P., and Foster, T. J. (1994) Molecular characterization of the clumping factor (fibrinogen receptor) of *Staphylococcus aureus*. *Mol Microbiol* 11: 237-248.

Murray, B. E. (1990) The life and times of the *enterococcus*. *Clin. Microbiol. Rev* 3: 46-65.

Murray, B. E., and Weinstock, G. M. (1999) Enterococci: new aspects of an old organism. *Proc. Assoc. Am. Physicians* 111: 328-334.

Nallapareddy, S. R., Qin, X., Weinstock, G. M., Hook, M., and Murray, B. E. (2000a) *Enterococcus faecalis* adhesin, ace, mediates attachment to extracellular matrix proteins collagen type IV and laminin as well as collagen type I. *Infect Immun* 68: 5218-5224.

Nallapareddy, S. R., Singh, K. V., Duh, R. W., Weinstock, G. M., and Murray, B. E. (2000b) Diversity of ace, a gene encoding a microbial surface component recognizing adhesive matrix molecules, from different strains of *Enterococcus faecalis* and evidence for production of ace during human infections. *Infect Immun* 68: 5210-5217.

Ni Eidhin, D., Perkins, S., Francois, P., Vaudaux, P., Hook, M., and Foster, T. J. (1998) Clumping factor B (ClfB), a new surface-located fibrinogen-binding adhesin of *Staphylococcus aureus*. *Mol Microbiol* 30: 245-257.

Pace, C. N., Vajdos, F., Fee, L., Grimsley, G., and Gray, T. (1995) How to measure and predict the molar absorption coefficient of a protein. *Protein Science* 4: 2411-2423.

Perkins, S., Walsh, E. J., Deivanayagam, C. C., Narayana, S. V., Foster, T. J., and Hook, M. (2001) Structural organization of the fibrinogen-binding region of the clumping factor B MSCRAMM of *Staphylococcus aureus. J Biol Chem* 276: 44721-44728.

Ponnuraj, K., Xu, Y., Moore, D., Deivanayagam, C. C., Boque, L., Hook, M., and Narayana, S. V. (2002) Crystallization and preliminary X-ray crystallographic analysis of Ace: a collagen-binding MSCRAMM from *Enterococcus faecalis. Biochim Biophys Acta* 1596: 173-176.

Rich, R. L., Kreikemeyer, B., Owens, R. T., LaBrenz, S., Narayana, S. V., Weinstock, G. M., Murray, B. E., and Hook, M. (1999) Ace is a collagen-binding MSCRAMM from *Enterococcus faecalis. J Biol Chem* 274: 26939-26945.

Sahm, D. F., Kissinger, J., Gilmore, M. S., Murray, P. R., Mulder, R., Solliday, J., and Clarke, B. (1989) In vitro susceptibility studies of vancomycin-resistant *Enterococcus faecalis. Antimicrob. Agents Chemother.* 33: 1588-1591.

Schneewind, O., Fowler, A., and Faull, K. F. (1995) Structure of the cell wall anchor of surface proteins in *Staphylococcus aureus. Science* 268: 103-106.

Symersky, J., Patti, J. M., Carson, M., House-Pompeo, K., Teale, M., Moore, D., Jin, L., Schneider, A., DeLucas, L. J., Hook, M., and Narayana, S. V. (1997) Structure of the collagen-binding domain from a *Staphylococcus aureus* adhesin. *Nature Structural Biology* 4: 833-838.

Wann, E. R., Gurusiddappa, S., and Hook, M. (2000) The fibronectin-binding MSCRAMM FnbpA of *Staphylococcus aureus* is a bifunctional protein that also binds to fibrinogen. *J Biol Chem* 275: 13863-13871.

Westerlund, B., and Korhonen, T. K. (1993) Bacterial proteins binding to the mammalian extracellular matrix. *Mol. Microbiol.* 9: 687-694.

---

What is claimed is:

1. A method of raising an immune response in a human or animal patient comprising administering to the human or animal patient an effective amount of an isolated protein comprising the amino acid sequence of SEQ ID NO: 9.

2. A method of eliciting an immune response in a human or animal comprising administering to said human or animal an immunologically effective amount of an isolated protein comprising the amino acid sequence of SEQ ID NO: 9.

3. A method of raising an immune response in a human or animal patient comprising administering to the human or animal patient an effective amount of an isolated peptide comprising the amino acid sequence of amino acids 63-1067 of SEQ ID NO: 9.

4. A method of eliciting an immune response in a human or animal comprising administering to said human or animal an immunologically effective amount of an isolated peptide comprising the amino acid sequence of amino acids 63-1067 of SEQ ID NO: 9.

* * * * *

SEQUENCE LISTING

```
<160> NUMBER OF SEQ ID NOS: 57

<210> SEQ ID NO 1
<211> LENGTH: 5
<212> TYPE: PRT
<213> ORGANISM: Staphylococcus epidermidis
<220> FEATURE:
<221> NAME/KEY: MISC_FEATURE
<222> LOCATION: (3)..(3)
<223> OTHER INFORMATION: X = any amino acid

<400> SEQUENCE: 1

Leu Pro Xaa Thr Gly
1               5


<210> SEQ ID NO 2
<211> LENGTH: 777
<212> TYPE: PRT
<213> ORGANISM: Staphylococcus epidermidis

<400> SEQUENCE: 2

Gln Glu Gln Thr Ala Lys Glu Asp Val Ala Asp Ser Ala Thr Ser Val
1               5                   10                  15

Gly Ala Ile Val Ser Ile Glu Lys Ala Glu Lys Asn Phe Val Ile Thr
            20                  25                  30

Tyr Ala Ser Gly Lys Lys Ala Gln Ile Ser Ile Leu Asn Asp His Leu
        35                  40                  45

Phe Arg Tyr His Leu Asp Pro Thr Gly Lys Phe Glu Glu Tyr Pro Thr
    50                  55                  60

Pro Asn Asp Pro Lys His Val Ala Lys Ile Thr Ala Lys Thr Met Ala
65                  70                  75                  80

Asp Tyr Gly Thr Gln Ala Phe Glu Gln Thr Asn Val Thr Asp Ser Gly
                85                  90                  95

Asn Gln Phe Ile Leu Glu Asn Asn Gly Leu Lys Ile Met Phe Glu Lys
            100                 105                 110

Glu Ser Ala Leu Met Lys Val Leu Asp Lys Lys Lys Asn Gln Val Ile
        115                 120                 125

Leu Glu Glu Thr Ala Pro Leu Ser Phe Lys Asn Asp Lys Ala Thr Gln
    130                 135                 140

Thr Leu Lys Gln Ser Ser Gln Glu Asn Tyr Phe Gly Gly Gly Thr Gln
```

-continued

```
145                 150                 155                 160

Asn Gly Arg Phe Thr His Lys Gly Thr Ala Ile Gln Ile Val Asn Thr
                165                 170                 175

Asn Asn Trp Val Asp Gly Gly Val Ala Ser Pro Asn Pro Phe Tyr Trp
            180                 185                 190

Ser Thr Ala Gly Tyr Gly Val Val Arg Asn Thr Trp Lys Pro Gly Asn
        195                 200                 205

Tyr Asp Phe Gly Ser His Asp Pro Gln Lys Thr Thr Thr Thr His Glu
    210                 215                 220

Gly Thr Asp Phe Asp Ala Phe Tyr Phe Phe Asn Asp Ser Ser Ala Gly
225                 230                 235                 240

Ile Leu Lys Asp Tyr Tyr Glu Leu Thr Gly Lys Pro Ala Leu Met Pro
                245                 250                 255

Glu Tyr Gly Phe Tyr Glu Ala His Leu Asn Ala Tyr Asn Arg Asp Tyr
            260                 265                 270

Trp Val Lys Val Ala Glu Gly Thr Ala Gly Ala Val Lys Phe Glu Asp
        275                 280                 285

Gly Asn Phe Tyr Lys Glu Tyr Gln Pro Gly Asp Leu Gly Asn Leu Asn
    290                 295                 300

Gly Thr Leu Glu Ser Leu Asn Gly Glu Lys Glu Asn Tyr Gln Phe Ser
305                 310                 315                 320

Ala Arg Ala Val Ile Asp Arg Tyr Lys Lys Asn Asp Met Pro Leu Gly
                325                 330                 335

Trp Phe Leu Pro Asn Asp Gly Tyr Gly Ala Gly Tyr Gly Gln Thr Asp
            340                 345                 350

Ser Leu Asp Gly Asp Val Gln Asn Leu Lys Glu Phe Thr Glu Tyr Ala
        355                 360                 365

Gln Ala Asn Gly Val Glu Val Gly Leu Trp Thr Gln Ser Asn Leu His
    370                 375                 380

Pro Ala Asp Pro Lys Asn Pro Lys Lys Gly Glu Arg Asp Ile Ala Lys
385                 390                 395                 400

Glu Val Ser Val Ala Gly Val Lys Ala Leu Lys Thr Asp Val Ala Trp
                405                 410                 415

Val Gly Tyr Gly Tyr Ser Phe Gly Leu Asn Gly Val Glu Asp Ala Ala
            420                 425                 430

Asn Val Phe Val Lys Glu Thr Asp Gly Ala Val Arg Pro Met Ile Val
        435                 440                 445

Ser Leu Asp Gly Trp Ala Gly Thr Gln Arg His Ala Gly Ile Trp Thr
    450                 455                 460

Gly Asp Gln Thr Gly Gly Gln Trp Glu Tyr Ile Arg Phe His Ile Pro
465                 470                 475                 480

Thr Tyr Ile Gly Thr Ser Leu Ser Gly Gln Pro Asn Val Gly Ser Asp
                485                 490                 495

Met Asp Gly Ile Phe Gly Gly Lys Asn Lys Glu Ile Asn Ile Arg Asp
            500                 505                 510

Phe Gln Trp Lys Thr Phe Thr Pro Val Gln Leu Asn Met Asp Gly Trp
        515                 520                 525

Gly Ser Asn Pro Lys Thr Pro Phe Ala Phe Asp Gln Glu Ala Thr Asp
    530                 535                 540

Leu Asn Arg Ala Tyr Leu Lys Leu Lys Ser Met Met Met Pro Tyr Asn
545                 550                 555                 560

Tyr Ser Ile Ala Lys Glu Ser Val Asp Gly Leu Pro Met Val Arg Ala
                565                 570                 575
```

```
Met Ala Leu Glu Phe Pro Asn Glu Gly Thr Ala Tyr Thr Lys Asp Ser
            580                 585                 590

Gln Tyr Gln Tyr Met Trp Gly Pro Asn Leu Leu Val Ala Pro Ile Tyr
        595                 600                 605

Asn Gly Asn Gln Asp Glu Ala Gly Asn Ser Ile Arg Asp Gly Ile Tyr
    610                 615                 620

Leu Pro Asp Glu Lys Gln Val Trp Val Asp Leu Phe Thr Gly Glu Lys
625                 630                 635                 640

Tyr Gln Gly Gly Arg Val Leu Asn Gly Val Lys Thr Pro Leu Trp Lys
                645                 650                 655

Val Pro Val Phe Val Lys Asp Gly Ser Ile Ile Pro Met Thr Asn Pro
            660                 665                 670

Asn Asn Asn Pro Lys Glu Ile Gln Arg Asp Gln Arg Ser Phe Leu Ile
        675                 680                 685

Tyr Pro Asn Gly Thr Thr Ser Phe Asn Met Tyr Glu Asp Asp Gly Ile
    690                 695                 700

Ser Thr Ser Tyr Glu Ala Gly Gln Ser Ala Thr Thr Lys Ile Asn Ser
705                 710                 715                 720

Gln Gly Pro Lys Ser Asn Glu Lys Gly Asp Leu Thr Val Thr Ile Glu
                725                 730                 735

Pro Thr Lys Gly Ser Tyr Lys Asp Phe Val Asp Glu Arg Ser Thr Thr
            740                 745                 750

Leu Asp Leu Leu Ala Ser Glu Ala Pro Glu Ser Val Thr Ala Met Val
        755                 760                 765

Gly Gly Thr Glu Val Thr Leu Lys Gln
    770                 775


<210> SEQ ID NO 3
<211> LENGTH: 1010
<212> TYPE: PRT
<213> ORGANISM: Staphylococcus epidermidis

<400> SEQUENCE: 3

Ala Ala Asn Lys Glu Glu Phe Leu Ala Gly Thr Asn Leu Tyr Tyr Phe
1               5                   10                  15

Asp Lys Glu Phe Gln Val Asn Gln Tyr Leu Ser Glu Ala Ser Gly Glu
            20                  25                  30

Lys Leu Asn Gln Ser Ala Leu Ser Val Lys Leu Ala Lys Gln Ser Val
        35                  40                  45

Thr Ala Lys Asp Val Gln Ile Thr Val Lys Gly Phe Ile Asn Lys Gly
    50                  55                  60

Thr Val Asp Gly Gly Asn Thr Thr Val Asp Asp Gln Leu Thr Ile Pro
65                  70                  75                  80

Ala Asn Val Ala Ile Asn Glu Glu Lys Thr Thr Pro Ser Ser Leu Thr
                85                  90                  95

Leu Gln Trp Asp Gln Val Thr Glu Ala Thr Ser Tyr Glu Val Glu Arg
            100                 105                 110

Asp Gly Thr Val Phe Gly Asn Ile Gln Thr Asn Thr Ala Thr Phe Asp
        115                 120                 125

Gly Phe Ser Phe Leu Ser Glu His Thr Phe Arg Val Arg Ala Val Gly
    130                 135                 140

Lys Asn Gly Val Ser Glu Trp Ser Glu Pro Ile Lys Gly Lys Thr Gln
145                 150                 155                 160

Asp Asp Pro Tyr Lys Glu Thr Ile Asn Gln Val Lys Ala Thr Ser Asn
```

-continued

```
                165                 170                 175

Leu Pro Glu Gln Pro Gly Ala Glu Leu Lys Lys Leu Thr Asp Lys Asp
            180                 185                 190

Leu Ser Thr Gly Trp His Thr Asn Trp Ser Thr Gly Ile Ala Asn Pro
        195                 200                 205

Ser Asp Gly Asn Phe Leu Ser Leu Lys Phe Asp Leu Gly Ala Glu Tyr
    210                 215                 220

Gln Met Asp Lys Ile Glu Tyr Leu Pro Arg Asp Asn Ala Gly Asn Gly
225                 230                 235                 240

Asn Ile Leu Gln Leu Gln Tyr Arg Thr Ser Lys Asp Gly Ala Asn Trp
                245                 250                 255

Thr Glu Phe Ser Glu Pro Ile Asn Trp Lys Gln Asp Ala Leu Thr Lys
            260                 265                 270

Thr Ile Glu Thr Lys Asp Gln Ala Tyr Arg Phe Val Glu Met Lys Val
        275                 280                 285

Leu Lys Ser Val Gly Asn Phe Gly Ser Gly Arg Glu Met Leu Phe Tyr
    290                 295                 300

Lys Gln Pro Gly Thr Glu Gly Ile Leu His Gly Asp Ile Thr Asn Asp
305                 310                 315                 320

Gly Thr Ile Asp Glu Asn Asp Ala Met Ser Tyr Arg Asn Tyr Thr Gly
                325                 330                 335

Leu Glu Ser Val Asp Ser Asp Phe Asn Gly Tyr Val Glu Lys Gly Asp
            340                 345                 350

Leu Asn Lys Asn Gly Val Ile Asp Ala Tyr Asp Ile Ser Tyr Val Leu
        355                 360                 365

Arg Gln Leu Asp Gly Gly Ile Glu Ile Pro Asp Val Glu Glu Ile Ala
    370                 375                 380

Gly Gly Leu Ser Leu Ala Val Val Asn Glu Asn Gly Lys Asp Thr Tyr
385                 390                 395                 400

Leu Pro Gly Asp Thr Leu Thr Phe Ile Leu Lys Gly Gln Asp Leu Lys
                405                 410                 415

Asn Ile Asn Ala Leu Ser Thr Lys Met Ser Phe Asp Ser Ser Lys Phe
            420                 425                 430

Glu Leu Val Gly Gln Pro Ala Thr Thr Asn Asn Thr Gln Gln Met Glu
        435                 440                 445

Asn Tyr Ser Lys Tyr Arg Lys His Ser Asn Asp Val Glu Asn Leu Tyr
    450                 455                 460

Leu Val Leu Ser Asn Gln Gly Asn Lys Gln Leu Leu Asn Gly Ser Met
465                 470                 475                 480

Asp Leu Val Thr Phe Lys Val Lys Val Lys Glu Thr Thr Arg Val Lys
                485                 490                 495

Arg Ala Thr Thr Val Glu Gln Pro Leu Gln Phe Asp Met Ser Gln Gly
            500                 505                 510

Leu Leu Val Gly Gln Gly Phe Gln Gln Ala Thr Leu Ser Asp Phe Ser
        515                 520                 525

Val Thr Val Lys Pro Thr Glu Leu Val Asp Lys Glu Leu Leu Gln Ala
    530                 535                 540

Leu Ile Thr Leu Asn Gln Ala Arg Val Glu Lys Glu Tyr Thr Pro Glu
545                 550                 555                 560

Thr Trp Ala Ile Phe Lys Pro Ile Leu Asp Glu Ala Val Ala Val Leu
                565                 570                 575

Ala Asn Glu Gln Ala Thr Gln Thr Asp Val Ser Ala Ala Ala Glu Asn
            580                 585                 590
```

-continued

```
Leu Glu Lys Ala Ala Ser Gln Leu Glu Lys Met Pro Asp Val Ala Asn
        595                 600                 605

Lys Ala Asp Leu Glu Lys Ala Ile Gln Glu Gly Leu Ala Lys Lys Pro
    610                 615                 620

Ser Asp Gly Gln Glu Phe Thr Glu Glu Thr Lys Lys Val Leu Glu Glu
625                 630                 635                 640

Ser Leu Ala Ala Ala Gln Lys Val Phe Ala Gln Glu Lys Val Thr Gln
                645                 650                 655

Glu Glu Ile Asp Gln Ala Thr Lys Thr Leu Arg Glu Ala Ile Ala Gln
            660                 665                 670

Leu Lys Glu Gln Pro Val Ala Val Asp Lys Glu Thr Leu Lys Glu Gln
        675                 680                 685

Ile Ala Gln Ala Arg Gly Arg Lys Pro Glu Glu Gly Tyr Gln Phe Thr
    690                 695                 700

Lys Glu Thr Glu Lys Gln Leu Gln Glu Ala Ile Gln Ala Ala Glu Ala
705                 710                 715                 720

Ile Val Ala Lys Glu Thr Ala Thr Lys Glu Glu Val Ser Glu Ala Leu
                725                 730                 735

Asn Ala Leu Glu Thr Ala Met Ala Gln Leu Lys Glu Val Pro Leu Val
            740                 745                 750

Asn Lys Asp Gln Leu Gln Glu Val Val Lys Arg Ala Gln Gln Val Thr
        755                 760                 765

Pro Ser Glu Gly His Gln Phe Thr Ala Ser Ser Leu Gln Glu Leu Gln
    770                 775                 780

Lys Ala Leu Leu Ala Ala Lys Asn Thr Leu Lys Asn Pro Ala Ala Asn
785                 790                 795                 800

Gln Lys Met Ile Asp Glu Ala Val Ala Glu Leu Thr Ser Ala Ile Asp
                805                 810                 815

Gly Leu Gln Glu Glu Val Leu Val Thr Asp Lys Lys Ala Leu Glu Ala
            820                 825                 830

Met Ile Ala Lys Ala Lys Ala Ile Lys Pro Ser Ala Gly Lys Glu Phe
        835                 840                 845

Thr Ser Glu Ser Lys Ala Arg Leu Thr Glu Ala Ile Asp Gln Ala Glu
    850                 855                 860

Gly Ile Leu Ala Asp Lys Asn Ala Arg Gln Glu Gln Ile Asp Ile Ala
865                 870                 875                 880

Glu Lys Asn Val Lys Thr Ala Leu Asp Ser Leu Glu Glu Gln Val Leu
                885                 890                 895

Gln Thr Asp Lys Thr Lys Leu Lys Glu Leu Leu Gln Lys Ala Glu Thr
            900                 905                 910

Leu Lys Pro Lys Ala Gly Lys Gln Phe Thr Lys Ala Ser Gln Glu Ala
        915                 920                 925

Leu Ala Glu Ala Ile Lys Gln Ala Lys Ala Leu Val Glu Asp Pro Asn
    930                 935                 940

Ala Thr Gln Glu Ala Val Asp Lys Cys Leu Ser Ile Leu Ser Gln Ala
945                 950                 955                 960

Ile Glu Ala Met Ala Glu Glu Pro Ile Ser Ser Asn Ser Thr Gly Asn
                965                 970                 975

Asn Gly Asn His Ser Thr Val Ser Gly Thr Gly Gly Val Thr Ser Gln
            980                 985                 990

Gly Lys Gly Thr Ala Thr Gly Gly  Thr Thr Thr Lys Thr  Thr Thr Ser
        995                 1000                1005
```

```
Gly Thr
    1010


<210> SEQ ID NO 4
<211> LENGTH: 1108
<212> TYPE: PRT
<213> ORGANISM: Staphylococcus epidermidis

<400> SEQUENCE: 4

Glu Glu Val Asn Ser Asp Gly Gln Leu Thr Leu Gly Glu Val Lys Gln
1               5                   10                  15

Thr Ser Gln Gln Glu Met Thr Leu Ala Leu Gln Gly Lys Ala Gln Pro
            20                  25                  30

Val Thr Gln Glu Val Val Val His Tyr Ser Ala Asn Val Ser Ile Lys
        35                  40                  45

Ala Ala His Trp Ala Ala Pro Asn Asn Thr Arg Lys Ile Gln Val Asp
    50                  55                  60

Asp Gln Lys Lys Gln Ile Gln Ile Glu Leu Asn Gln Gln Ala Leu Ala
65                  70                  75                  80

Asp Thr Leu Val Leu Thr Leu Asn Pro Thr Ala Thr Glu Asp Val Thr
                85                  90                  95

Phe Ser Tyr Gly Gln Gln Gln Arg Ala Leu Thr Leu Lys Thr Gly Thr
            100                 105                 110

Asp Pro Thr Glu Ser Thr Ala Ile Thr Ser Ser Pro Ala Ala Ser Ala
        115                 120                 125

Asn Glu Gly Ser Thr Glu Glu Ala Ser Thr Asn Ser Ser Val Pro Arg
    130                 135                 140

Ser Ser Glu Glu Thr Val Ala Ser Thr Thr Lys Ala Ile Glu Ser Lys
145                 150                 155                 160

Thr Thr Glu Ser Thr Thr Val Lys Pro Arg Val Ala Gly Pro Thr Asp
                165                 170                 175

Ile Ser Asp Tyr Phe Thr Gly Asp Glu Thr Thr Ile Ile Asp Asn Phe
            180                 185                 190

Glu Asp Pro Ile Tyr Leu Asn Pro Asp Gly Thr Pro Ala Thr Pro Pro
        195                 200                 205

Tyr Lys Glu Asp Val Thr Ile His Trp Asn Phe Asn Trp Ser Ile Pro
    210                 215                 220

Glu Asp Val Arg Glu Gln Met Lys Ala Gly Asp Tyr Phe Glu Phe Gln
225                 230                 235                 240

Leu Pro Gly Asn Leu Lys Pro Asn Lys Pro Gly Ser Gly Asp Leu Val
                245                 250                 255

Asp Ala Glu Gly Asn Val Tyr Gly Thr Tyr Thr Ile Ser Glu Asp Gly
            260                 265                 270

Thr Val Arg Phe Thr Phe Asn Glu Arg Ile Thr Ser Glu Ser Asp Ile
        275                 280                 285

His Gly Asp Phe Ser Leu Asp Thr His Leu Asn Asp Ser Asp Gly Arg
    290                 295                 300

Gly Pro Gly Asp Trp Val Ile Asp Ile Pro Thr Gln Glu Asp Leu Pro
305                 310                 315                 320

Pro Val Val Ile Pro Ile Val Pro Asp Thr Glu Gln Gln Ile Asp Lys
                325                 330                 335

Gln Gly His Phe Asp Arg Thr Pro Asn Pro Ser Ala Ile Thr Trp Thr
            340                 345                 350

Val Asp Ile Asn Gln Ala Met Lys Asp Gln Thr Asn Pro Thr Val Thr
        355                 360                 365
```

```
Glu Thr Trp Pro Thr Gly Asn Thr Phe Lys Ser Val Lys Val Tyr Glu
    370                 375                 380

Leu Val Met Asn Leu Asp Gly Thr Ile Lys Glu Val Gly Arg Glu Leu
385                 390                 395                 400

Ser Pro Asp Glu Tyr Thr Val Asp Lys Asn Gly Asn Val Thr Ile Lys
                405                 410                 415

Gly Asp Thr Asn Lys Ala Tyr Arg Leu Glu Tyr Gln Thr Thr Ile Asp
            420                 425                 430

Glu Ala Val Ile Pro Asp Gly Gly Gly Asp Val Pro Phe Lys Asn His
        435                 440                 445

Ala Thr Leu Thr Ser Asp Asn Asn Pro Asn Gly Leu Asp Ala Glu Ala
    450                 455                 460

Thr Val Thr Ala Thr Tyr Gly Lys Met Leu Asp Lys Arg Asn Ile Asp
465                 470                 475                 480

Tyr Asp Glu Ala Asn Gln Glu Phe Thr Trp Glu Ile Asn Tyr Asn Tyr
                485                 490                 495

Gly Glu Gln Thr Ile Pro Lys Asp Gln Ala Val Ile Thr Asp Thr Met
            500                 505                 510

Gly Asp Asn Leu Thr Phe Glu Pro Asp Ser Leu His Leu Tyr Ser Val
        515                 520                 525

Thr Phe Asp Asp Lys Gly Asn Glu Val Val Gly Ala Glu Leu Val Glu
    530                 535                 540

Gly Lys Asp Tyr Lys Val Val Ile Asn Gly Asp Gly Ser Phe Ala Ile
545                 550                 555                 560

Asp Phe Leu His Asp Val Thr Gly Ala Val Lys Ile Asp Tyr Lys Thr
                565                 570                 575

Lys Val Asp Gly Ile Val Glu Gly Asp Val Ala Val Asn Asn Arg Val
            580                 585                 590

Asp Val Gly Thr Gly Gln His Ser Glu Asp Asp Gly Thr Ala Ser Gln
        595                 600                 605

Gln Asn Ile Ile Lys Asn Thr Gly Ala Val Asp Tyr Gln Asn Ser Thr
    610                 615                 620

Ile Gly Trp Thr Leu Ala Val Asn Gln Asn Asn Tyr Leu Met Glu Asn
625                 630                 635                 640

Ala Val Ile Thr Asp Thr Tyr Glu Pro Val Pro Gly Leu Thr Met Val
                645                 650                 655

Pro Asn Ser Leu Val Val Lys Asp Thr Thr Thr Gly Ala Gln Leu Thr
            660                 665                 670

Leu Gly Lys Asp Phe Met Val Glu Ile Thr Arg Asn Ala Asp Gly Glu
        675                 680                 685

Thr Gly Phe Lys Val Ser Phe Ile Gly Ala Tyr Ala Lys Thr Ser Asp
    690                 695                 700

Ala Phe His Ile Thr Tyr Thr Thr Phe Phe Asp Val Thr Glu Leu Asp
705                 710                 715                 720

Ala Asn Asn Pro Ala Leu Asp His Tyr Arg Asn Thr Ala Ala Ile Asp
                725                 730                 735

Trp Thr Asp Glu Ala Gly Asn Asn His His Ser Glu Asp Ser Lys Pro
            740                 745                 750

Phe Lys Pro Leu Pro Ala Phe Asp Leu Asn Ala Gln Lys Ser Gly Val
        755                 760                 765

Tyr Asn Ala Val Thr Lys Glu Ile Thr Trp Thr Ile Ala Val Asn Leu
    770                 775                 780
```

-continued

```
Ser Asn Asn Arg Leu Val Asp Ala Phe Leu Thr Asp Pro Ile Leu Thr
785                 790                 795                 800

Asn Gln Thr Tyr Leu Ala Gly Ser Leu Lys Val Tyr Glu Gly Asn Thr
                805                 810                 815

Lys Pro Asp Gly Ser Val Glu Lys Val Lys Pro Thr Gln Pro Leu Thr
            820                 825                 830

Asp Ile Thr Met Glu Glu Pro Ser Glu Lys Asn Gln Asn Thr Trp Arg
        835                 840                 845

Val Asp Phe Pro Asn Asp Ser Arg Thr Tyr Val Ile Glu Phe Lys Thr
    850                 855                 860

Ser Val Asp Glu Lys Val Ile Glu Gly Ser Ala Ser Tyr Asp Asn Thr
865                 870                 875                 880

Ala Ser Tyr Thr Asn Gln Gly Ser Ser Arg Asp Val Thr Gly Lys Val
                885                 890                 895

Ser Ile Gln His Gly Gly Glu Ser Val Lys Lys Gly Gly Glu Tyr His
            900                 905                 910

Lys Asp Asp Pro Asp His Val Tyr Trp His Val Met Ile Asn Gly Ala
        915                 920                 925

Gln Ser Val Leu Asp Asp Val Val Ile Thr Asp Thr Pro Ser Pro Asn
    930                 935                 940

Gln Val Leu Asp Pro Glu Ser Leu Val Ile Tyr Gly Thr Asn Val Thr
945                 950                 955                 960

Glu Asp Gly Thr Ile Thr Pro Asp Lys Ser Val Ile Leu Glu Glu Gly
                965                 970                 975

Lys Asp Tyr Thr Leu Glu Val Thr Thr Asp Asn Glu Thr Gly Gln Gln
            980                 985                 990

Lys Ile Val Val Lys Met Ala His  Ile Glu Ala Pro Tyr  Tyr Met Glu
        995                 1000                1005

Tyr Arg  Ser Leu Val Thr Ser  Ser Ala Ala Gly Ser  Thr Asp Thr
    1010                1015                1020

Val Ser  Asn Gln Val Ser Ile  Thr Gly Asn Gly Ser  Glu Val Val
    1025                1030                1035

His Gly  Asp Asp Asn Gly Asp  Val Val Val Asp Ile  Asp His Ser
    1040                1045                1050

Gly Gly  His Ala Thr Gly Thr  Lys Gly Lys Ile Gln  Leu Lys Lys
    1055                1060                1065

Thr Ala  Met Asp Glu Thr Thr  Ile Leu Ala Gly Ala  His Phe Gln
    1070                1075                1080

Ile Trp  Asp Gln Ala Lys Thr  Gln Val Leu Arg Glu  Gly Thr Val
    1085                1090                1095

Asp Ala  Thr Gly Val Ile Thr  Phe Gly Gly
    1100                1105


<210> SEQ ID NO 5
<211> LENGTH: 999
<212> TYPE: PRT
<213> ORGANISM: Staphylococcus epidermidis

<400> SEQUENCE: 5

Glu Glu Ile Thr Asp Leu Phe Leu Gln Lys Glu Val Thr Tyr Ser Gly
1               5                   10                  15

Val Glu Gly Gly Lys Ile Gly Glu Asn Trp Lys Tyr Pro Gln Phe Val
            20                  25                  30

Gly Glu Lys Ala Val Asp Gly Asp Glu Thr Thr Arg Trp Ser Ala Asp
        35                  40                  45
```

-continued

```
Lys Gln Asp Glu Gln Trp Leu Ile Val Asp Leu Gly Glu Val Lys Asn
    50                  55                  60

Ile Gly Glu Leu Val Leu Gln Leu His Ala Glu Ser Pro Val Tyr Glu
65                  70                  75                  80

Ile Leu Val Ser Thr Asp Gly Glu Ser Tyr Gln Ser Ile Phe Lys Glu
                85                  90                  95

Glu Asn Gly Lys Gly Gly Gln Pro Thr Lys Lys Tyr Ile Asp Gly Asn
            100                 105                 110

Asn Val Gln Ala Arg Phe Val Lys Tyr Gln Gln Met Lys Met Trp Gln
        115                 120                 125

His Thr Asn Lys Gln Phe Tyr Ser Ser Ser Ile Ile Ser Phe Glu Ala
    130                 135                 140

Tyr Glu Lys Lys Arg Leu Pro Glu Ala Ile Lys Leu Leu Thr Glu Asn
145                 150                 155                 160

Leu Thr Ile Ser Glu Lys Arg Lys Gln Gln Leu Ala Phe Glu Val Ser
                165                 170                 175

Pro Ala Gly Val Asp Ile Thr Glu Asp Gln Ile Glu Trp Ser Ser Ser
            180                 185                 190

Asp Pro Thr Ile Val Thr Val Asp Gln Thr Gly Asn Leu Thr Ala Val
        195                 200                 205

Lys Ser Gly Glu Ala Lys Val Thr Val Lys Ile Lys Gly Thr Glu Ile
    210                 215                 220

Ser Asp Thr Ile Pro Val Thr Val Val Ala Glu Asn Lys Gln Tyr Ala
225                 230                 235                 240

Glu Met Arg Ala Lys Trp Lys Met Arg Leu Leu Gly Thr Thr Gln Tyr
                245                 250                 255

Asp Asn Asp Ala Asp Val Gln Gln Tyr Arg Ala Gln Ile Ala Thr Glu
            260                 265                 270

Ser Leu Ala Leu Trp Gln Thr Leu Asn Gln Ala Ala Asp Arg Glu Tyr
        275                 280                 285

Leu Trp Glu Arg Lys Pro Ser Asp Thr Val Ser Ala Asp Tyr Thr Thr
    290                 295                 300

Gln Phe Thr Asn Ile Lys Lys Leu Ala Leu Gly Tyr Tyr Glu Pro Ser
305                 310                 315                 320

Ser Glu Leu Phe Glu Lys Pro Glu Val Tyr Asp Ala Ile Val Lys Gly
                325                 330                 335

Ile Glu Phe Met Ile Asp Thr Lys Lys Tyr Asn Gly Thr Tyr Tyr Thr
            340                 345                 350

Gly Asn Trp Trp Asp Trp Gln Ile Gly Ser Ala Gln Pro Leu Thr Asp
        355                 360                 365

Thr Leu Ile Leu Leu His Asp Asp Leu Leu Asn Thr Asp Ala Glu Lys
    370                 375                 380

Leu Asn Lys Phe Thr Ala Pro Leu Met Leu Tyr Ala Lys Asp Pro Asn
385                 390                 395                 400

Ile Gln Trp Pro Ile Tyr Arg Ala Thr Gly Ala Asn Leu Thr Asp Ile
                405                 410                 415

Ser Ile Thr Val Leu Gly Thr Gly Leu Leu Glu Asp Asn Gln Arg
            420                 425                 430

Leu Val Gln Val Gln Glu Ala Val Pro Ser Val Leu Lys Ser Val Ser
        435                 440                 445

Ser Gly Asp Gly Leu Tyr Pro Asp Gly Ser Leu Ile Gln His Gly Tyr
    450                 455                 460
```

-continued

```
Phe Pro Tyr Asn Gly Ser Tyr Gly Asn Glu Leu Leu Lys Gly Phe Gly
465                 470                 475                 480

Arg Ile Gln Thr Ile Leu Gln Gly Ser Asp Trp Glu Met Asn Asp Pro
                485                 490                 495

Asn Ile Ser Asn Leu Phe Asn Val Val Asp Lys Gly Tyr Leu Gln Leu
            500                 505                 510

Met Val Asn Gly Lys Met Pro Ser Met Val Ser Gly Arg Ser Ile Ser
        515                 520                 525

Arg Ala Pro Glu Thr Asn Pro Phe Thr Thr Glu Phe Glu Ser Gly Lys
    530                 535                 540

Glu Thr Ile Ala Asn Leu Thr Leu Ile Ala Lys Phe Ala Pro Glu Asn
545                 550                 555                 560

Leu Arg Asn Asp Ile Tyr Thr Ser Ile Gln Thr Trp Leu Gln Gln Ser
                565                 570                 575

Gly Ser Tyr Tyr His Phe Phe Lys Lys Pro Arg Asp Phe Glu Ala Leu
            580                 585                 590

Ile Asp Leu Lys Asn Val Val Asn Ser Ala Ser Pro Ala Gln Ala Thr
        595                 600                 605

Pro Met Gln Ser Leu Asn Val Tyr Gly Ser Met Asp Arg Val Leu Gln
    610                 615                 620

Lys Asn Asn Glu Tyr Ala Val Gly Ile Ser Met Tyr Ser Gln Arg Val
625                 630                 635                 640

Gly Asn Tyr Glu Phe Gly Asn Thr Glu Asn Lys Lys Gly Trp His Thr
                645                 650                 655

Ala Asp Gly Met Leu Tyr Leu Tyr Asn Gln Asp Phe Ala Gln Phe Asp
            660                 665                 670

Glu Gly Tyr Trp Ala Thr Ile Asp Pro Tyr Arg Leu Pro Gly Thr Thr
        675                 680                 685

Val Asp Thr Arg Glu Leu Ala Asn Gly Ala Tyr Thr Gly Lys Arg Ser
    690                 695                 700

Pro Gln Ser Trp Val Gly Gly Ser Asn Asn Gly Gln Val Ala Ser Ile
705                 710                 715                 720

Gly Met Phe Leu Asp Lys Ser Asn Glu Gly Met Asn Leu Val Ala Lys
                725                 730                 735

Lys Ser Trp Phe Leu Leu Asp Gly Gln Ile Ile Asn Leu Gly Ser Gly
            740                 745                 750

Ile Thr Gly Thr Thr Asp Ala Ser Ile Glu Thr Ile Leu Asp Asn Arg
        755                 760                 765

Met Ile His Pro Gln Glu Val Lys Leu Asn Gln Gly Ser Asp Lys Asp
    770                 775                 780

Asn Ser Trp Ile Ser Leu Ser Ala Ala Asn Pro Leu Asn Asn Ile Gly
785                 790                 795                 800

Tyr Val Phe Pro Asn Ser Met Asn Thr Leu Asp Val Gln Ile Glu Glu
                805                 810                 815

Arg Ser Gly Arg Tyr Gly Asp Ile Asn Glu Tyr Phe Val Asn Asp Lys
            820                 825                 830

Thr Tyr Thr Asn Thr Phe Ala Lys Ile Ser Lys Asn Tyr Gly Lys Thr
        835                 840                 845

Val Glu Asn Gly Thr Tyr Glu Tyr Leu Thr Val Val Gly Lys Thr Asn
    850                 855                 860

Glu Glu Ile Ala Ala Leu Ser Lys Asn Lys Gly Tyr Thr Val Leu Glu
865                 870                 875                 880

Asn Thr Ala Asn Leu Gln Ala Ile Glu Ala Gly Asn Tyr Val Met Met
```

```
                885                 890                 895

Asn Thr Trp Asn Asn Asp Gln Glu Ile Ala Gly Leu Tyr Ala Tyr Asp
            900                 905                 910

Pro Met Ser Val Ile Ser Glu Lys Ile Asp Asn Gly Val Tyr Arg Leu
        915                 920                 925

Thr Leu Ala Asn Pro Leu Gln Asn Asn Ala Ser Val Ser Ile Glu Phe
    930                 935                 940

Asp Lys Gly Ile Leu Glu Val Val Ala Ala Asp Pro Glu Ile Ser Val
945                 950                 955                 960

Asp Gln Asn Ile Ile Thr Leu Asn Ser Ala Gly Leu Asn Gly Ser Ser
                965                 970                 975

Arg Ser Ile Ile Val Lys Thr Thr Pro Glu Val Thr Lys Glu Ala Leu
            980                 985                 990

Glu Lys Leu Ile Gln Glu Gln
        995


<210> SEQ ID NO 6
<211> LENGTH: 741
<212> TYPE: PRT
<213> ORGANISM: Staphylococcus epidermidis

<400> SEQUENCE: 6

Gln Glu Val Thr Ser Asp Ala Glu Lys Thr Val Glu Lys Asp Gly Leu
1               5                   10                  15

Lys Val Ile Gly Lys Ile Glu Asp Thr Ser Ser Gln Glu Asp Ile Lys
            20                  25                  30

Thr Val Thr Tyr Glu Val Thr Asn Thr Arg Asp Val Pro Ile Lys Asp
        35                  40                  45

Leu Ile Leu Lys Gln Lys Asn Thr Asn Asp Ser Pro Ile Lys Phe Val
    50                  55                  60

Leu Asp Thr Leu Ser Glu Glu Arg Gly Pro Thr Ser Leu Glu Glu Gln
65                  70                  75                  80

Ala Lys Val Glu Thr Asn Glu Lys Asp Gln Thr Thr Asp Ile Lys Leu
                85                  90                  95

Leu Asn Leu Gln Pro Asn Ser Thr Arg Lys Ile Thr Ile Asn Gly Gln
            100                 105                 110

Ile Thr Thr Lys Ala Ser Asn Lys Leu Leu Val Ser Val Leu Ile Glu
        115                 120                 125

Asp Asn Glu Lys Gly Thr Leu Val Ile Asp Leu Pro Ser Lys Asp Ile
    130                 135                 140

Leu Ala Asp Lys Glu Ser Val Ser Lys Glu Lys Gln Glu Thr Ser Glu
145                 150                 155                 160

Thr Lys Val Glu Asn Gln Ala Asn Glu Thr Ala Ser Ser Thr Asn Glu
                165                 170                 175

Met Thr Ala Thr Thr Ser Asn Glu Thr Lys Pro Glu Ala Gly Lys Ala
            180                 185                 190

Ile Glu Ser Ile Gln Glu Thr Ala Leu Thr Gln Ala Thr Glu Ser Pro
        195                 200                 205

Glu Gln Pro Pro Leu Lys Ala Gln Pro Thr Gly Pro Leu Val Pro Pro
    210                 215                 220

Thr Pro Gly Arg Gly Phe Asn Thr Pro Ile Tyr Gln Ser Val His Lys
225                 230                 235                 240

Gly Glu Leu Phe Ser Thr Gly Asn Thr Asn Leu Lys Ile Ala Asn Glu
                245                 250                 255
```

-continued

```
Asn Thr Ala Ala Ala Gln Thr Phe Leu Asn Thr Arg Gly Ala Ser Ser
            260                 265                 270

Gly Tyr Ala Ile Asn Asn Phe Pro Leu Glu Phe Ala Asp Val Asp Asn
        275                 280                 285

Asp Pro Asn Thr Tyr Asn Ser Ser Arg Ala Tyr Ile Asp Leu Asn Gly
    290                 295                 300

Ala Lys Glu Ile Ala Trp Ala Gly Leu Phe Trp Ser Ala Ser Arg Tyr
305                 310                 315                 320

Lys Gly Pro Ala Tyr Gly Thr Asn Leu Ser Asp Glu Glu Ile Ser Ala
                325                 330                 335

Pro Val Gln Phe Thr Thr Pro Asn Gly Thr Val Gln Arg Val Ser Pro
            340                 345                 350

Gln Arg Tyr His Arg Ile Asp Gln Asp Ala Thr Asn Pro Gly Gln Arg
        355                 360                 365

Phe Gly Tyr Asn Asn Thr Gly Phe Ser Asn Tyr Ala Asp Val Thr Ser
    370                 375                 380

Ile Leu Gln Gly Asp Lys Ser Ala Thr Gly Ser Tyr Thr Leu Ala Asp
385                 390                 395                 400

Ile Pro Met Thr Ser Ser Leu Asn Gly Gln Tyr Gln Tyr Tyr Asn Phe
                405                 410                 415

Ser Gly Trp Ser Leu Phe Val Val Thr Lys Asp Gln Ala Ser Lys Ser
            420                 425                 430

Arg Ala Phe Ser Ile Tyr Tyr Gly Ala Arg Gly Asn Ala Ala Gly Thr
        435                 440                 445

Asn Asn Glu Phe Thr Met Ser Asn Phe Leu Thr Ala Lys Gln Gly Asn
    450                 455                 460

Leu Asp Pro Ile Val Thr Trp Phe Thr Val Gln Gly Asp Lys Tyr Trp
465                 470                 475                 480

Thr Gly Asp Asn Ala Gln Ile Lys Asn Ser Ala Gly Thr Trp Val Asn
                485                 490                 495

Ile Ser Asn Thr Leu Asn Pro Val Asn Asn Ala Met Asn Ala Thr Val
            500                 505                 510

Thr Asp Asn Asp Glu His Met Val Asp Lys Tyr Pro Gly Lys Phe Ala
        515                 520                 525

Pro Asp His Pro Asn Phe Leu Asp Ile Asp Ile Asp Arg Met Ala Ile
    530                 535                 540

Pro Glu Gly Val Leu Asn Ala Gly Gln Asn Gln Ile Asn Phe Arg Thr
545                 550                 555                 560

Thr Ser Ser Gly Asp Asp Tyr Ser Thr Asn Ala Ile Gly Phe Ala Val
                565                 570                 575

Asn Ala Glu Thr Pro Glu Phe Glu Ile Lys Lys Glu Ile Val Glu Pro
            580                 585                 590

Lys Glu Thr Tyr Lys Val Gly Glu Thr Ile Thr Tyr Arg Val Ser Leu
        595                 600                 605

Lys Asn Thr Lys Ala Asp Ser Glu Ala Ile Asn Ser Val Ser Lys Asp
    610                 615                 620

Ala Leu Asp Gly Arg Leu Asn Tyr Leu Pro Gly Ser Leu Lys Ile Ile
625                 630                 635                 640

Ser Gly Pro Asn Ser Gly Glu Lys Thr Asp Ala Ser Gly Asp Asp Gln
                645                 650                 655

Ala Glu Tyr Asp Glu Thr Asn Lys Gln Ile Ile Val Arg Val Gly Asn
            660                 665                 670

Gly Ala Thr Ala Thr Gln Gly Gly Ser Tyr Lys Ala Asp Thr Ala Glu
```

```
        675                 680                 685

Thr Ile Tyr Glu Phe Lys Ala Arg Ile Asn Glu Arg Ala Lys Ala Asn
    690                 695                 700

Glu Leu Val Pro Asn Ser Ala Thr Val Glu Ala Val Asp Ile Leu Thr
705                 710                 715                 720

Ser Ala Lys Val Asn Glu Thr Ser Asn Ile Val Glu Ala Lys Ile Ala
                725                 730                 735

Asp Glu Gln Val Thr
            740


<210> SEQ ID NO 7
<211> LENGTH: 570
<212> TYPE: PRT
<213> ORGANISM: Staphylococcus epidermidis

<400> SEQUENCE: 7

Glu Thr Gly Tyr Ala Gln Thr Glu Pro Thr Ser Thr Ser Glu Thr Asn
1               5                   10                  15

Gln Ile Ser Ala Thr Pro Asn Val Val Pro Arg Lys Gln Val Gly Asn
            20                  25                  30

Ile Val Thr Ala Ile Gln Leu Thr Asp Lys Glu Gly Asn Pro Leu Gly
        35                  40                  45

Thr Ile Asn Gln Tyr Thr Asp Ile Tyr Leu Arg Ile Glu Phe Asn Leu
    50                  55                  60

Pro Asp Asn Thr Val Asn Ser Gly Asp Thr Ser Val Ile Thr Leu Pro
65                  70                  75                  80

Glu Glu Leu Arg Leu Glu Lys Asn Met Thr Phe Asn Val Val Asp Asp
                85                  90                  95

Thr Gly Thr Val Val Ala Ile Ala Gln Thr Asp Val Ala Asn Lys Thr
            100                 105                 110

Val Thr Leu Thr Tyr Thr Asp Tyr Val Glu Asn His Ala Asn Ile Ser
        115                 120                 125

Gly Ser Leu Tyr Phe Thr Ser Leu Ile Asp Phe Glu Asn Val Glu Asn
    130                 135                 140

Glu Ser Lys Ile Pro Ile Tyr Val Thr Val Glu Gly Glu Lys Ile Phe
145                 150                 155                 160

Ala Gly Asp Leu Asp Tyr Gln Gly Glu Gly Asp Asp Val Asn Glu Lys
                165                 170                 175

Phe Ser Lys Tyr Ser Trp Phe Ile Glu Asp Asp Pro Thr Glu Ile Tyr
            180                 185                 190

Asn Val Leu Arg Ile Asn Pro Thr Gly Gln Thr Tyr Thr Asp Leu Glu
        195                 200                 205

Val Glu Asp Val Leu Lys Thr Glu Ser Leu Ser Tyr Met Lys Asp Thr
    210                 215                 220

Met Lys Ile Glu Arg Gly Gln Trp Thr Leu Asp Gly Asn Ala Ile Trp
225                 230                 235                 240

Gln Phe Thr Pro Glu Glu Asp Ile Thr Asp Gln Leu Ala Val Gln Tyr
                245                 250                 255

Gly Pro Asp Asp Arg Asn Phe Ser Val His Phe Gly Asn Ile Gly Thr
            260                 265                 270

Asn Glu Tyr Arg Ile Thr Tyr Lys Thr Lys Ile Asp His Leu Pro Glu
        275                 280                 285

Lys Gly Glu Thr Phe Thr Asn Tyr Ala Lys Leu Thr Glu Asn Gln Thr
    290                 295                 300
```

-continued

```
Val Val Glu Glu Val Glu Val Ser Arg Val Ser Gln Thr Gly Gly Gly
305                 310                 315                 320

Glu Ala Asn Gly Glu Gln Tyr Val Val Glu Ile His Lys Glu Asp Glu
                325                 330                 335

Ala Gly Gln Arg Leu Ala Gly Ala Glu Phe Glu Leu Ile Arg Asn Ser
            340                 345                 350

Thr Asn Gln Thr Val Ala Lys Ile Thr Thr Asp Gln Asn Gly Thr Ala
        355                 360                 365

Ile Val Lys Gly Leu Leu Lys Asp Asn Tyr Thr Leu Val Glu Thr Lys
    370                 375                 380

Ala Pro Thr Gly Tyr Gln Leu Ser Gln Asn Lys Ile Pro Ile Thr Pro
385                 390                 395                 400

Glu Asp Phe Gly Lys Asn Leu Val Ala Leu Lys Thr Val Val Asn His
                405                 410                 415

Lys Ile Ser Tyr Gln Pro Val Ala Ala Ser Phe Leu Ala Gly Lys Val
            420                 425                 430

Leu Leu Gly Lys Pro Leu Lys Asp Ala Glu Phe Gln Phe Glu Leu Leu
        435                 440                 445

Asp Glu Lys Gly Thr Val Leu Glu Thr Val Ser Asn Asp Thr Leu Gly
    450                 455                 460

Lys Ile Gln Phe Ser Pro Leu Thr Phe Glu Thr Pro Gly Asn Tyr Gln
465                 470                 475                 480

Tyr Thr Ile Arg Glu Val Asn Thr Gln Gln Thr Gly Val Ser Tyr Asp
                485                 490                 495

Thr His Asn Leu Gln Val Gln Val Thr Val Glu Ala Leu Leu Gly Asn
            500                 505                 510

Leu Val Ala Thr Thr Gln Tyr Asp Gly Gly Gln Val Phe Thr Asn His
        515                 520                 525

Tyr Thr Pro Glu Lys Pro Ile Glu Ser Thr Thr Pro Pro Thr Ser Gly
    530                 535                 540

Thr Thr Asp Thr Thr Thr Asn Ser Thr Thr Glu Thr Thr Ser Ile Thr
545                 550                 555                 560

Ile Glu Lys Gln Ala Ile Arg Asn Lys Glu
                565                 570
```

<210> SEQ ID NO 8
<211> LENGTH: 3309
<212> TYPE: DNA
<213> ORGANISM: Staphylococcus epidermidis

<400> SEQUENCE: 8

```
atgataacag atgagaatga taaaacgaat attaatatcg agttaaatct tctcaaccaa     60

acagagcagc cattacaacg agaaattcaa ttgaaaaatg cacagttcat ggatactgct    120

gtaattgaaa aagacggata ttcttaccaa gtgactaatg gtacgcttta tctgactttg    180

gacgcacaag taaaaaagcc ggtacagctt tcgttagctg ttgagcaaag ttcgcttcaa    240

acagctcagc cacctaagtt attgtatgaa aacaacgaat atgatgtttc agttacttct    300

gaaaaaataa cagtagagga ttctgctaaa gaatcaactg aaccagaaaa aataactgta    360

ccagaaaata cgaaagaaac taacaaaaat gattcggctc cagaaaaaac agaacagccg    420

accgcaacag aagaggtaac caatccattt gcagaagcaa gaatggcgcc agctactttg    480

agagcgaatc tggcactgcc tttaattgca ccacaataca cgacggataa ttctgggact    540

tatccgacag ctaattggca gcccacaggc aatcaaaatg tgttaaacca tcaagggaat    600
```

-continued

```
aaagacggta gtgcacaatg ggacggccaa acgagttgga atggggaccc tactaatcgc    660
acaaattctt atattgagta tggcggtaca ggagaccaag ccgattatgc catccgaaaa    720
tatgctagag aaacaacaac accagggctt tttgatgtat atcttaatgt gcgtgggaat    780
gttcagaaag aaatcacgcc attggatttg gtcttagtcg ttgactggtc cggtagtatg    840
aatgaaaaca atcggattgg tgaagttcaa aaaggagtga accgttttgt tgatacattg    900
gcagatagcg gtattaccaa taacatcaac atgggctatg ttggctactc aagtgacggt    960
tataataaca acgccattca aatggggccg tttgatacag tcaaaaaatcc aattaaaaat  1020
attacgccaa gtagcactag aggaggaact ttcactcaaa aagcattaag agatgctggt   1080
gatatgttag caacgccaaa tggacataag aaagtcattg tacttttaac ggatggcgtc   1140
ccaaccttct cttataaagt gagtcgagtt caaacagagg cggatggtcg cttttacggg   1200
acacaattta cgaatcgaca agatcaacca ggtagcactt cttatatctc tggtagctat   1260
aatgcgccag atcaaaacaa tatcaataaa cggattaaca gtacgtttat cgccacgata   1320
ggtgaggcaa tggtcttaaa acaacgtggg attgaaatac atggattggg cattcaattg   1380
caaagcgatc cacgagctaa tttatctaaa caacaagttg aagataaaat gcgtgagatg   1440
gtgtcagccg atgaaaatgg agacctttat tatgaatccg cggattatgc accagacatt   1500
tctgattatt tagcgaaaaa agccgttcag atttcaggaa cggttgtaaa cggaaaagta   1560
gttgatccaa ttgctgaacc ttttaaatac gagccaaata cattatcaat gaaaagtgtg   1620
ggtcctgttc aggttcaaac attaccagaa gtgtcgctaa caggcgctac aattaatagt   1680
aatgagattt atttgggtaa agggcaagaa attcaaattc attatcaagt acgtattcaa   1740
acagagtcag aaaacttcaa acctgatttt tggtatcaaa tgaatggtcg gacaacgttt   1800
cagccattag ccacggcccc tgaaaaagtt gattttgggg ttccttcggg aaaagcacct   1860
ggcgtgaagt taaacgtgaa aaaaatctgg gaagagtatg atcaagaccc gacaagtcgg   1920
ccagataatg tgatttatga aattagtaga aagcaagtaa ctgacacagc caactggcaa   1980
actgggtata ttaaattatc aaaaccagaa aatgatacca gcaatagttg ggagcgcaaa   2040
aatgtaaccc aactttccaa aaccgcggat gaaagctatc aagaagttct tgggcttccc   2100
caatacaaca atcaaggaca agctttcaat tatcaaacaa cccgtgaatt agcagttcct   2160
ggttacagtc aagaaaaaat cgacgatact acttggaaaa acacgaagca gttcaagcca   2220
ttagatttaa aagtaatcaa aaattcttcc tcaggtgaga aaaacttagt gggagccgtc   2280
tttgaattga gtggtaaaaa tgttcaaaca acattagtgg acaataaaga tggtagctat   2340
tccttgccaa aagatgtgcg cctacaaaaa ggggaacgct atacattaac tgaagtaaaa   2400
gcacctgcag gacatgagtt aggcaagaaa acgacttggc aaattgaggt gagtgagcaa   2460
ggcaaagtaa gcatcgatgg acaagaagtg accaccacaa atcaagttat tccattggaa   2520
attgaaaata aattttcttc tttgccaatc agaattagaa aatacaccat gcaaaatggc   2580
aaacaagtga acttagcaga ggcgactttt gcgttgcaaa gaaaaaatgc tcaaggaagt   2640
taccaaactg tggcaactca aaaaacagat actacaggat tgagctattt taaaattagt   2700
gaacctggtg agtatcgaat ggtggaacaa tcaggaccat taggctacga cactcttgct   2760
ggaaattatg aatttactgt tgataaatat gggaaaattc actatgcagg caaaaatatt   2820
gaagaaaatg cgccagaatg gacactgaca catcaaaata atttgaaacc ttttgactta   2880
acagttaata aaaaagccga taatcagacg ccacttaaag gagcgaaatt ccgtttaaca   2940
ggaccagata cggatattga attaccaaaa gatggcaaag aaacggatac ttttgttttt   3000
```

gaaaacttaa aaccagggaa atatgttcta acagaaacct ttacgccaga aggatatcag 3060
gggttaaaag aaccaatcga attaataatt cgtgaagatg gttcagtcac gatagatggg 3120
gaaaaagtag cagatgtttt aatttctgga gagaagaata atcaaattac tttagacgtt 3180
acgaaccaag caaaggttcc tttacctgaa actggtggca taggacgctt gtggttttac 3240
ttgatagcga ttagtacatt cgtgatagcg ggtgtttatc tctttattag acgaccagaa 3300
gggagtgtg 3309

<210> SEQ ID NO 9
<211> LENGTH: 1103
<212> TYPE: PRT
<213> ORGANISM: Staphylococcus epidermidis

<400> SEQUENCE: 9

Met Ile Thr Asp Glu Asn Asp Lys Thr Asn Ile Asn Ile Glu Leu Asn
1 5 10 15

Leu Leu Asn Gln Thr Glu Gln Pro Leu Gln Arg Glu Ile Gln Leu Lys
20 25 30

Asn Ala Gln Phe Met Asp Thr Ala Val Ile Glu Lys Asp Gly Tyr Ser
35 40 45

Tyr Gln Val Thr Asn Gly Thr Leu Tyr Leu Thr Leu Asp Ala Gln Val
50 55 60

Lys Lys Pro Val Gln Leu Ser Leu Ala Val Glu Gln Ser Ser Leu Gln
65 70 75 80

Thr Ala Gln Pro Pro Lys Leu Leu Tyr Glu Asn Asn Glu Tyr Asp Val
85 90 95

Ser Val Thr Ser Glu Lys Ile Thr Val Glu Asp Ser Ala Lys Glu Ser
100 105 110

Thr Glu Pro Glu Lys Ile Thr Val Pro Glu Asn Thr Lys Glu Thr Asn
115 120 125

Lys Asn Asp Ser Ala Pro Glu Lys Thr Glu Gln Pro Thr Ala Thr Glu
130 135 140

Glu Val Thr Asn Pro Phe Ala Glu Ala Arg Met Ala Pro Ala Thr Leu
145 150 155 160

Arg Ala Asn Leu Ala Leu Pro Leu Ile Ala Pro Gln Tyr Thr Thr Asp
165 170 175

Asn Ser Gly Thr Tyr Pro Thr Ala Asn Trp Gln Pro Thr Gly Asn Gln
180 185 190

Asn Val Leu Asn His Gln Gly Asn Lys Asp Gly Ser Ala Gln Trp Asp
195 200 205

Gly Gln Thr Ser Trp Asn Gly Asp Pro Thr Asn Arg Thr Asn Ser Tyr
210 215 220

Ile Glu Tyr Gly Gly Thr Gly Asp Gln Ala Asp Tyr Ala Ile Arg Lys
225 230 235 240

Tyr Ala Arg Glu Thr Thr Thr Pro Gly Leu Phe Asp Val Tyr Leu Asn
245 250 255

Val Arg Gly Asn Val Gln Lys Glu Ile Thr Pro Leu Asp Leu Val Leu
260 265 270

Val Val Asp Trp Ser Gly Ser Met Asn Glu Asn Asn Arg Ile Gly Glu
275 280 285

Val Gln Lys Gly Val Asn Arg Phe Val Asp Thr Leu Ala Asp Ser Gly
290 295 300

Ile Thr Asn Asn Ile Asn Met Gly Tyr Val Gly Tyr Ser Ser Asp Gly

-continued

```
305                 310                 315                 320

Tyr Asn Asn Asn Ala Ile Gln Met Gly Pro Phe Asp Thr Val Lys Asn
                325                 330                 335

Pro Ile Lys Asn Ile Thr Pro Ser Ser Thr Arg Gly Gly Thr Phe Thr
            340                 345                 350

Gln Lys Ala Leu Arg Asp Ala Gly Asp Met Leu Ala Thr Pro Asn Gly
        355                 360                 365

His Lys Lys Val Ile Val Leu Leu Thr Asp Gly Val Pro Thr Phe Ser
    370                 375                 380

Tyr Lys Val Ser Arg Val Gln Thr Glu Ala Asp Gly Arg Phe Tyr Gly
385                 390                 395                 400

Thr Gln Phe Thr Asn Arg Gln Asp Gln Pro Gly Ser Thr Ser Tyr Ile
                405                 410                 415

Ser Gly Ser Tyr Asn Ala Pro Asp Gln Asn Asn Ile Asn Lys Arg Ile
            420                 425                 430

Asn Ser Thr Phe Ile Ala Thr Ile Gly Glu Ala Met Val Leu Lys Gln
        435                 440                 445

Arg Gly Ile Glu Ile His Gly Leu Gly Ile Gln Leu Gln Ser Asp Pro
    450                 455                 460

Arg Ala Asn Leu Ser Lys Gln Gln Val Glu Asp Lys Met Arg Glu Met
465                 470                 475                 480

Val Ser Ala Asp Glu Asn Gly Asp Leu Tyr Tyr Glu Ser Ala Asp Tyr
                485                 490                 495

Ala Pro Asp Ile Ser Asp Tyr Leu Ala Lys Lys Ala Val Gln Ile Ser
            500                 505                 510

Gly Thr Val Val Asn Gly Lys Val Val Asp Pro Ile Ala Glu Pro Phe
        515                 520                 525

Lys Tyr Glu Pro Asn Thr Leu Ser Met Lys Ser Val Gly Pro Val Gln
    530                 535                 540

Val Gln Thr Leu Pro Glu Val Ser Leu Thr Gly Ala Thr Ile Asn Ser
545                 550                 555                 560

Asn Glu Ile Tyr Leu Gly Lys Gly Gln Glu Ile Gln Ile His Tyr Gln
                565                 570                 575

Val Arg Ile Gln Thr Glu Ser Glu Asn Phe Lys Pro Asp Phe Trp Tyr
            580                 585                 590

Gln Met Asn Gly Arg Thr Thr Phe Gln Pro Leu Ala Thr Ala Pro Glu
        595                 600                 605

Lys Val Asp Phe Gly Val Pro Ser Gly Lys Ala Pro Gly Val Lys Leu
    610                 615                 620

Asn Val Lys Lys Ile Trp Glu Glu Tyr Asp Gln Asp Pro Thr Ser Arg
625                 630                 635                 640

Pro Asp Asn Val Ile Tyr Glu Ile Ser Arg Lys Gln Val Thr Asp Thr
                645                 650                 655

Ala Asn Trp Gln Thr Gly Tyr Ile Lys Leu Ser Lys Pro Glu Asn Asp
            660                 665                 670

Thr Ser Asn Ser Trp Glu Arg Lys Asn Val Thr Gln Leu Ser Lys Thr
        675                 680                 685

Ala Asp Glu Ser Tyr Gln Glu Val Leu Gly Leu Pro Gln Tyr Asn Asn
    690                 695                 700

Gln Gly Gln Ala Phe Asn Tyr Gln Thr Thr Arg Glu Leu Ala Val Pro
705                 710                 715                 720

Gly Tyr Ser Gln Glu Lys Ile Asp Asp Thr Thr Trp Lys Asn Thr Lys
                725                 730                 735
```

```
Gln Phe Lys Pro Leu Asp Leu Lys Val Ile Lys Asn Ser Ser Ser Gly
            740                 745                 750

Glu Lys Asn Leu Val Gly Ala Val Phe Glu Leu Ser Gly Lys Asn Val
        755                 760                 765

Gln Thr Thr Leu Val Asp Asn Lys Asp Gly Ser Tyr Ser Leu Pro Lys
    770                 775                 780

Asp Val Arg Leu Gln Lys Gly Glu Arg Tyr Thr Leu Thr Glu Val Lys
785                 790                 795                 800

Ala Pro Ala Gly His Glu Leu Gly Lys Lys Thr Thr Trp Gln Ile Glu
                805                 810                 815

Val Ser Glu Gln Gly Lys Val Ser Ile Asp Gly Gln Glu Val Thr Thr
            820                 825                 830

Thr Asn Gln Val Ile Pro Leu Glu Ile Glu Asn Lys Phe Ser Ser Leu
        835                 840                 845

Pro Ile Arg Ile Arg Lys Tyr Thr Met Gln Asn Gly Lys Gln Val Asn
    850                 855                 860

Leu Ala Glu Ala Thr Phe Ala Leu Gln Arg Lys Asn Ala Gln Gly Ser
865                 870                 875                 880

Tyr Gln Thr Val Ala Thr Gln Lys Thr Asp Thr Thr Gly Leu Ser Tyr
                885                 890                 895

Phe Lys Ile Ser Glu Pro Gly Glu Tyr Arg Met Val Glu Gln Ser Gly
            900                 905                 910

Pro Leu Gly Tyr Asp Thr Leu Ala Gly Asn Tyr Glu Phe Thr Val Asp
        915                 920                 925

Lys Tyr Gly Lys Ile His Tyr Ala Gly Lys Asn Ile Glu Glu Asn Ala
    930                 935                 940

Pro Glu Trp Thr Leu Thr His Gln Asn Asn Leu Lys Pro Phe Asp Leu
945                 950                 955                 960

Thr Val Asn Lys Lys Ala Asp Asn Gln Thr Pro Leu Lys Gly Ala Lys
                965                 970                 975

Phe Arg Leu Thr Gly Pro Asp Thr Asp Ile Glu Leu Pro Lys Asp Gly
            980                 985                 990

Lys Glu Thr Asp Thr Phe Val Phe  Glu Asn Leu Lys Pro  Gly Lys Tyr
        995                 1000                1005

Val Leu  Thr Glu Thr Phe Thr  Pro Glu Gly Tyr Gln  Gly Leu Lys
    1010                 1015                 1020

Glu Pro  Ile Glu Leu Ile Ile  Arg Glu Asp Gly Ser  Val Thr Ile
    1025                 1030                 1035

Asp Gly  Glu Lys Val Ala Asp  Val Leu Ile Ser Gly  Glu Lys Asn
    1040                 1045                 1050

Asn Gln  Ile Thr Leu Asp Val  Thr Asn Gln Ala Lys  Val Pro Leu
    1055                 1060                 1065

Pro Glu  Thr Gly Gly Ile Gly  Arg Leu Trp Phe Tyr  Leu Ile Ala
    1070                 1075                 1080

Ile Ser  Thr Phe Val Ile Ala  Gly Val Tyr Leu Phe  Ile Arg Arg
    1085                 1090                 1095

Pro Glu  Gly Ser Val
    1100
```

<210> SEQ ID NO 10
<211> LENGTH: 1428
<212> TYPE: DNA
<213> ORGANISM: Staphylococcus epidermidis

<400> SEQUENCE: 10

```
atgaaaaacg cacgttggtt aagtatttgc gtcatgctac tcgctctttt cgggttttca     60
cagcaagcat tagcagaggc atcgcaagca agcgttcaag ttacgttgca caaattattg    120
ttccctgatg gtcaattacc agaacagcag caaaacacag ggaagagggg aacgctgctt    180
caaaattatc ggggcttaaa tgacgtcact tatcaagtct atgatgtgac ggatccgttt    240
tatcagcttc gttctgaagg aaaaacggtc caagaggcac agcgtcaatt agcagaaacc    300
ggtgcaacaa atagaaaacc gatcgcagaa gataaaacac agacaataaa tggagaagat    360
ggagtggttt ctttttcatt agctagcaaa gattcgcagc aacgagataa agcctattta    420
tttgttgaag cggaagcacc agaagtggta aaggaaaaag ctagcaacct agtagtgatt    480
ttgcctgttc aagatccaca agggcaatcg ttaacgcata ttcatttata tccaaaaaat    540
gaagaaaatg cctatgactt accaccactt gaaaaaaacgg tactcgataa gcaacaaggc    600
tttaatcaag gagagcacat taactatcag ttaacgactc agattccagc gaatatttta    660
ggatatcagg aattccgttt gtcagataag gcggatacaa cgttgacact tttaccagaa    720
tcaattgagg taaaagtggc tggaaaaaca gttactacag gttacacact gacgacgcaa    780
aagcatggat ttacgcttga tttttcaatt aaagacttac aaaactttgc aaatcaaaca    840
atgactgtgt cgtatcaaat gcgtttagaa aagaccgctg aacctgacac tgcgattaac    900
aacgaaggac aattagtcac ggacaaacat accttgacta aaagagccac agttcgtaca    960
ggcggcaagt cttttgtcaa agttgatagt gaaaatgcga aaatcacctt gccagaggct   1020
gtttttatcg tcaaaaatca agcgggggaa tacctcaatg aaacagcaaa cgggtatcgt   1080
tggcaaaaag aaaaagcatt agctaaaaaa ttcacgtcta atcaagccgg tgaattttca   1140
gttaaaggct taaaagatgg ccagtacttc ttggaagaaa tctctgcacc aaaaggttat   1200
cttctgaatc aaacagaaat tccttttacg gtgggaaaaa attcttatgc aacgaacgga   1260
caacgaacag caccgttaca tgtaatcaat aaaaaagtaa aagagtcagg cttcttacca   1320
aaaacaaatg aagaacgttc tatttggttg acgattgcag gcctgctaat cattgggatg   1380
gtagtcattt ggctatttta tcaaaaacaa aaaagaggag agagaaaa                1428
```

<210> SEQ ID NO 11
<211> LENGTH: 476
<212> TYPE: PRT
<213> ORGANISM: Staphylococcus epidermidis

<400> SEQUENCE: 11

```
Met Lys Asn Ala Arg Trp Leu Ser Ile Cys Val Met Leu Leu Ala Leu
1               5                   10                  15

Phe Gly Phe Ser Gln Gln Ala Leu Ala Glu Ala Ser Gln Ala Ser Val
            20                  25                  30

Gln Val Thr Leu His Lys Leu Leu Phe Pro Asp Gly Gln Leu Pro Glu
        35                  40                  45

Gln Gln Gln Asn Thr Gly Glu Glu Gly Thr Leu Leu Gln Asn Tyr Arg
    50                  55                  60

Gly Leu Asn Asp Val Thr Tyr Gln Val Tyr Asp Val Thr Asp Pro Phe
65                  70                  75                  80

Tyr Gln Leu Arg Ser Glu Gly Lys Thr Val Gln Glu Ala Gln Arg Gln
                85                  90                  95

Leu Ala Glu Thr Gly Ala Thr Asn Arg Lys Pro Ile Ala Glu Asp Lys
            100                 105                 110
```

-continued

```
Thr Gln Thr Ile Asn Gly Glu Asp Gly Val Val Ser Phe Ser Leu Ala
        115                 120                 125

Ser Lys Asp Ser Gln Gln Arg Asp Lys Ala Tyr Leu Phe Val Glu Ala
    130                 135                 140

Glu Ala Pro Glu Val Val Lys Glu Lys Ala Ser Asn Leu Val Val Ile
145                 150                 155                 160

Leu Pro Val Gln Asp Pro Gln Gly Gln Ser Leu Thr His Ile His Leu
                165                 170                 175

Tyr Pro Lys Asn Glu Glu Asn Ala Tyr Asp Leu Pro Pro Leu Glu Lys
            180                 185                 190

Thr Val Leu Asp Lys Gln Gln Gly Phe Asn Gln Gly Glu His Ile Asn
        195                 200                 205

Tyr Gln Leu Thr Thr Gln Ile Pro Ala Asn Ile Leu Gly Tyr Gln Glu
    210                 215                 220

Phe Arg Leu Ser Asp Lys Ala Asp Thr Thr Leu Thr Leu Leu Pro Glu
225                 230                 235                 240

Ser Ile Glu Val Lys Val Ala Gly Lys Thr Val Thr Thr Gly Tyr Thr
                245                 250                 255

Leu Thr Thr Gln Lys His Gly Phe Thr Leu Asp Phe Ser Ile Lys Asp
            260                 265                 270

Leu Gln Asn Phe Ala Asn Gln Thr Met Thr Val Ser Tyr Gln Met Arg
        275                 280                 285

Leu Glu Lys Thr Ala Glu Pro Asp Thr Ala Ile Asn Asn Glu Gly Gln
    290                 295                 300

Leu Val Thr Asp Lys His Thr Leu Thr Lys Arg Ala Thr Val Arg Thr
305                 310                 315                 320

Gly Gly Lys Ser Phe Val Lys Val Asp Ser Glu Asn Ala Lys Ile Thr
                325                 330                 335

Leu Pro Glu Ala Val Phe Ile Val Lys Asn Gln Ala Gly Glu Tyr Leu
            340                 345                 350

Asn Glu Thr Ala Asn Gly Tyr Arg Trp Gln Lys Glu Lys Ala Leu Ala
        355                 360                 365

Lys Lys Phe Thr Ser Asn Gln Ala Gly Glu Phe Ser Val Lys Gly Leu
    370                 375                 380

Lys Asp Gly Gln Tyr Phe Leu Glu Glu Ile Ser Ala Pro Lys Gly Tyr
385                 390                 395                 400

Leu Leu Asn Gln Thr Glu Ile Pro Phe Thr Val Gly Lys Asn Ser Tyr
                405                 410                 415

Ala Thr Asn Gly Gln Arg Thr Ala Pro Leu His Val Ile Asn Lys Lys
            420                 425                 430

Val Lys Glu Ser Gly Phe Leu Pro Lys Thr Asn Glu Glu Arg Ser Ile
        435                 440                 445

Trp Leu Thr Ile Ala Gly Leu Leu Ile Ile Gly Met Val Val Ile Trp
    450                 455                 460

Leu Phe Tyr Gln Lys Gln Lys Arg Gly Glu Arg Lys
465                 470                 475


<210> SEQ ID NO 12
<211> LENGTH: 1881
<212> TYPE: DNA
<213> ORGANISM: Staphylococcus epidermidis

<400> SEQUENCE: 12

atgaagcaat taaaaaaagt ttggtacacc gttagtacct tgttactaat tttgccactt      60
```

-continued

```
ttcacaagtg tattagggac aacaactgca tttgcagaag aaaatgggga gagcgcacag    120

ctcgtgattc acaaaaagaa aatgacggat ttaccagatc cgcttattca aaatagcggg    180

aaagaaatga gcgagtttga taaatatcaa ggactggcag atgtgacgtt tagtatttat    240

aacgtgacga acgaatttta cgagcaacga gcggcaggcg caagcgttga tgcagctaaa    300

caagctgtcc aaagtttaac tcctgggaaa cctgttgctc aaggaaccac cgatgcaaat    360

gggaatgtca ctgttcagtt acctaaaaaa caaaatggta aagatgcagt gtataccatt    420

aaagaagaac caaaagaggg tgtagttgct gctacgaata tggtggtggc gttcccagtt    480

tacgaaatga tcaagcaaac agatggttcc tataaatatg gaacagaaga attagcggtt    540

gttcatattt atcctaaaaa tgtggtagcc aatgatggta gtttacatgt gaaaaaagta    600

ggaactgctg aaaatgaagg attaaatggc gcagaatttg ttatttctaa aagcgaaggc    660

tcaccaggca cagtaaaata tatccaagga gtcaaagatg gattatatac atggacaacg    720

gataaagaac aagcaaaacg ctttattact gggaaaagtt atgaaattgg cgaaaatgat    780

ttcacagaag cagagaatgg aacgggagaa ttaacagtta aaaatcttga ggttggttcg    840

tatattttag aagaagtaaa agctccaaat aatgcagaat taattgaaaa tcaaacaaaa    900

acaccattta caattgaagc aaacaatcaa acacctgttg aaaaaacagt caaaaatgat    960

acctctaaag ttgataaaac aacaccaagc ttagatggta aagatgtggc aattggcgaa   1020

aaaattaaat atcaaatttc tgtaaatatt ccattgggga ttgcagacaa agaaggcgac   1080

gctaataaat acgtcaaatt caatttagtt gataaacatg atgcagcctt aacttttgat   1140

aacgtgactt ctggagagta tgcttatgcg ttatatgatg gggatacagt gattgctcct   1200

gaaaattatc aagtgactga acaagcaaat ggcttcactg tcgccgttaa tccagcgtat   1260

attcctacgc taacaccagg cggcacacta aaattcgttt actttatgca tttaaatgaa   1320

aaagcagatc ctacgaaagg ctttaaaaat gaggcgaatg ttgataacgg tcataccgac   1380

gaccaaacac caccaactgt tgaagttgtg acaggtggga aacgtttcat taaagtcgat   1440

ggcgatgtga cagcgacaca agccttggcg ggagcttcct ttgtcgtccg tgatcaaaac   1500

agcgacacag caaattattt gaaaatcgat gaaacaacga aagcagcaac ttgggtgaaa   1560

acaaaagctg aagcaactac ttttacaaca acggctgatg gattagttga tatcacaggg   1620

cttaaatacg gtacctatta tttagaagaa actgtagctc ctgatgatta tgtcttgtta   1680

acaaatcgga ttgaatttgt ggtcaatgaa caatcatatg gcacaacaga aaacctagtt   1740

tcaccagaaa aagtaccaaa caaacacaaa ggtaccttac cttcaacagg tggcaaagga   1800

atctacgttt acttaggaag tggcgcagtc ttgctactta ttgcaggagt ctactttgct   1860

agacgtagaa aagaaaatgc t                                             1881
```

<210> SEQ ID NO 13
<211> LENGTH: 627
<212> TYPE: PRT
<213> ORGANISM: Staphylococcus epidermidis

<400> SEQUENCE: 13

```
Met Lys Gln Leu Lys Lys Val Trp Tyr Thr Val Ser Thr Leu Leu Leu
1               5                   10                  15

Ile Leu Pro Leu Phe Thr Ser Val Leu Gly Thr Thr Thr Ala Phe Ala
            20                  25                  30

Glu Glu Asn Gly Glu Ser Ala Gln Leu Val Ile His Lys Lys Lys Met
        35                  40                  45
```

-continued

```
Thr Asp Leu Pro Asp Pro Leu Ile Gln Asn Ser Gly Lys Glu Met Ser
    50                  55                  60

Glu Phe Asp Lys Tyr Gln Gly Leu Ala Asp Val Thr Phe Ser Ile Tyr
65                  70                  75                  80

Asn Val Thr Asn Glu Phe Tyr Glu Gln Arg Ala Ala Gly Ala Ser Val
                85                  90                  95

Asp Ala Ala Lys Gln Ala Val Gln Ser Leu Thr Pro Gly Lys Pro Val
            100                 105                 110

Ala Gln Gly Thr Thr Asp Ala Asn Gly Asn Val Thr Val Gln Leu Pro
        115                 120                 125

Lys Lys Gln Asn Gly Lys Asp Ala Val Tyr Thr Ile Lys Glu Glu Pro
    130                 135                 140

Lys Glu Gly Val Val Ala Ala Thr Asn Met Val Val Ala Phe Pro Val
145                 150                 155                 160

Tyr Glu Met Ile Lys Gln Thr Asp Gly Ser Tyr Lys Tyr Gly Thr Glu
                165                 170                 175

Glu Leu Ala Val Val His Ile Tyr Pro Lys Asn Val Val Ala Asn Asp
            180                 185                 190

Gly Ser Leu His Val Lys Lys Val Gly Thr Ala Glu Asn Glu Gly Leu
        195                 200                 205

Asn Gly Ala Glu Phe Val Ile Ser Lys Ser Glu Gly Ser Pro Gly Thr
    210                 215                 220

Val Lys Tyr Ile Gln Gly Val Lys Asp Gly Leu Tyr Thr Trp Thr Thr
225                 230                 235                 240

Asp Lys Glu Gln Ala Lys Arg Phe Ile Thr Gly Lys Ser Tyr Glu Ile
                245                 250                 255

Gly Glu Asn Asp Phe Thr Glu Ala Glu Asn Gly Thr Gly Glu Leu Thr
            260                 265                 270

Val Lys Asn Leu Glu Val Gly Ser Tyr Ile Leu Glu Glu Val Lys Ala
        275                 280                 285

Pro Asn Asn Ala Glu Leu Ile Glu Asn Gln Thr Lys Thr Pro Phe Thr
    290                 295                 300

Ile Glu Ala Asn Asn Gln Thr Pro Val Glu Lys Thr Val Lys Asn Asp
305                 310                 315                 320

Thr Ser Lys Val Asp Lys Thr Thr Pro Ser Leu Asp Gly Lys Asp Val
                325                 330                 335

Ala Ile Gly Glu Lys Ile Lys Tyr Gln Ile Ser Val Asn Ile Pro Leu
            340                 345                 350

Gly Ile Ala Asp Lys Glu Gly Asp Ala Asn Lys Tyr Val Lys Phe Asn
        355                 360                 365

Leu Val Asp Lys His Asp Ala Ala Leu Thr Phe Asp Asn Val Thr Ser
    370                 375                 380

Gly Glu Tyr Ala Tyr Ala Leu Tyr Asp Gly Asp Thr Val Ile Ala Pro
385                 390                 395                 400

Glu Asn Tyr Gln Val Thr Glu Gln Ala Asn Gly Phe Thr Val Ala Val
                405                 410                 415

Asn Pro Ala Tyr Ile Pro Thr Leu Thr Pro Gly Gly Thr Leu Lys Phe
            420                 425                 430

Val Tyr Phe Met His Leu Asn Glu Lys Ala Asp Pro Thr Lys Gly Phe
        435                 440                 445

Lys Asn Glu Ala Asn Val Asp Asn Gly His Thr Asp Asp Gln Thr Pro
    450                 455                 460

Pro Thr Val Glu Val Val Thr Gly Gly Lys Arg Phe Ile Lys Val Asp
```

```
465                 470                 475                 480

Gly Asp Val Thr Ala Thr Gln Ala Leu Ala Gly Ala Ser Phe Val Val
                485                 490                 495

Arg Asp Gln Asn Ser Asp Thr Ala Asn Tyr Leu Lys Ile Asp Glu Thr
            500                 505                 510

Thr Lys Ala Ala Thr Trp Val Lys Thr Lys Ala Glu Ala Thr Thr Phe
        515                 520                 525

Thr Thr Thr Ala Asp Gly Leu Val Asp Ile Thr Gly Leu Lys Tyr Gly
    530                 535                 540

Thr Tyr Tyr Leu Glu Glu Thr Val Ala Pro Asp Asp Tyr Val Leu Leu
545                 550                 555                 560

Thr Asn Arg Ile Glu Phe Val Val Asn Glu Gln Ser Tyr Gly Thr Thr
                565                 570                 575

Glu Asn Leu Val Ser Pro Glu Lys Val Pro Asn Lys His Lys Gly Thr
            580                 585                 590

Leu Pro Ser Thr Gly Gly Lys Gly Ile Tyr Val Tyr Leu Gly Ser Gly
        595                 600                 605

Ala Val Leu Leu Leu Ile Ala Gly Val Tyr Phe Ala Arg Arg Arg Lys
    610                 615                 620

Glu Asn Ala
625
```

<210> SEQ ID NO 14
<211> LENGTH: 3387
<212> TYPE: DNA
<213> ORGANISM: Staphylococcus epidermidis

<400> SEQUENCE: 14

```
atgacgacca cagggaagaa actgaaagtt attttcatgc tgataatatt gagtttatca      60

aactttgtgc cattatctgc aatagcagac actacagatg atccaacagt tttagaaaca     120

atttcagctg aagtcatttc ggatcagtct ggaaaaaaag cactgaacat caagctaaat     180

gcgaataaca ccagtgctga aaagatagaa aaagaaattg gtctagtcga aaattactta     240

agtgatgtgg aaagaaaaga aggagatggc tatgcttatc aggtaaatag cgggaaaatt     300

acgttggaaa tctcatcaaa cactaaacaa actatcgatc tgagttttcc aatcgatcca     360

gcactttacc acagccaggc aaacaagctg atcgtcgata ataaagaata tgacattatt     420

gatgagacag aaaataagaa agatacagat gtgtcagtac caaagccaga cgaaatagaa     480

gaagaatcat caaaagaaaa cgaaaattct gtcagcccat ttacattgcc tacattatcc     540

ttgccagctg tgagtgtgcc atctaatcaa acgattccta cagaatatac aacagatgat     600

cagggcactt atcctaaagc cagttggcaa cctacaggaa atacaaatgt tcttgatcat     660

caaggcaata aaaacggaac aaatcaatgg gatggtataa attcttggaa tggagatcct     720

aatgatcgga cccattcgta tatcgaatat ggaggaaccg gtaatcaagc agactatgcg     780

atacgaaagt atgcaaagga aacaagtaca cccggattgt ttgatgttta tttgaatgct     840

cgtggaaatg tacaaaaaga tatcacgcct cttgatctcg tattggtcgt agactggtca     900

ggaagtatga acgacaataa tcggatcggt gaagtaaaga ttggtgtcga tcgttttgtc     960

gatactttag cagatagcgg tatcacagac aaaatcaata tgggatatgt cggctactca    1020

agcgaaggat atagctacag taacggtgca gtacagatgg gttcatttga ttcagtgaaa    1080

aatcaagtaa aatccattac accttcacgg acaaatggtg gtacttttac acaaaaagca    1140

ctaagagatg caggaagcat gctatccgtt ccaaatggac ataaaaaagt gatcgttttg    1200
```

```
ctgacggatg gtgtaccaac attttcctat aaagtacagc gggtacacgc acaatcaagc   1260

agcaattatt acggaactca gttttctaat acgcaagatc ggccgggaaa tacttctcta   1320

atctcaagaa tctatgatgc acctgaccaa aacaatctat ccagaagaat cgacagtacg   1380

tttatcgcaa ccatcggaga agcgatggca ctcaaagaac gaggaatcga aatacatggt   1440

cttggcatcc aacttcaaag cgatccggca gctggtctct caaaagcaga agtagagtct   1500

cgtatgcgac aaatggtttc atcagatgaa aaaggcgatc tttactatga atcagctgat   1560

catgcaacag atatctctga atacctagcc aaaaaagctg tacagatctc agcaactgta   1620

agcaatggac aaataaatga tccaatcgca gaaccattca tttatcagcc tggtacactt   1680

tcagtcaaga gtgtggggac aagtcctaca acggtcactc catctatttc catagaagga   1740

aataccatca agagcaatca gatctattta ggaaaagacc aagaaatcca aatccattac   1800

caagtgagaa tccaaacaga aaatgaggac ttccatccaa atttctggta tcaaatgaac   1860

ggcaggacaa ctttccagcc aaacattgat accaatgaat tagctgaatt cggtatacca   1920

tctgctaaag ctcccggagt cagtcttcac atcaaaaagt tatgggaaga atttgacaac   1980

aatctagctg atcgtccaga tcaagttact tttgagattc aacgggaaca tacgacaaat   2040

gctgcagctt ggaaaaacgg atatattcga atcattaaac cagctaaaga tacaacaaat   2100

acgtgggaac gtgcagacat tgacaaatta tctgcaaata gcggagaaag ttatcaagag   2160

atattatcac tacctcaata caataatcaa ggtcaagcat tcagttacca aacaatcaaa   2220

gaattacctg taccaggata cgattctcaa caaatagatg caatgacatg gaaaaatact   2280

aaacaattca caccgttaaa cttgaaaata acgaaaaatt cctctacagg tgaaaaggat   2340

cttattggcg ctgttttcaa attaacagga gattctattg atactttact aacagatcat   2400

ggcgacggaa cctattctct tccagaaaat gtcaaattgc aaaaagaaat gacctatacg   2460

ctgacagaaa caaaagctcc agaagggcat ggattaagca aaaagactac ttgggaaatc   2520

aagatcgctt ctgatggtac ggtaaccatt gatggaaaaa cagtcactac ttccgatgat   2580

acgatccagt tgactattga aaatcctttt gttgaagttc ctgtagcagt acgtaagtat   2640

gcgatgcaag ggacggacaa agagataaat cttaaaggag cagcattttc cctacagaaa   2700

aaagaagcaa atggtactta tcagccaatt gacagccaaa caacgaatga aaaaggtctt   2760

gccagttttg attcactcac acctggtaaa tatcgagtcg ttgaaacagc tggtcctgcc   2820

ggatatgata cttcgccggg aaattatgaa ttccaaatcg ataaatatgg aaaaatcatt   2880

tacacgggaa aaaataccga gatgacaaat aatgtatgga cgctcactca tcaaaatcga   2940

ctaaaagcgt ttgatctaac ggtacacaaa aaagaagaca acggacagac attaaaagga   3000

gcaaaattca gactgcaggg accagaaatg gacttagaat cgccaaaaga tggacaagaa   3060

acagatacct ttctattcga aaatttaaaa cctggaactt atacgctgac cgaaactttt   3120

acaccagaag gataccaagg tctaaaagag ccagttacta tagttataca cgaagatggg   3180

tcaattcaag tggatggaca agatcatgaa tctgttctgt caccaggagc caaaaacaac   3240

cagatttctt tagacatcac gaatcaggca aaagtaccat tacctgaaac gggaggaatt   3300

ggccgtttag gaatctatct agtagggatg attggttgtg cgttttctat ttggtatctt   3360

tttttgaaaa aagaaagagg gggcagc                                       3387
```

<210> SEQ ID NO 15
<211> LENGTH: 1129
<212> TYPE: PRT

<213> ORGANISM: Staphylococcus epidermidis

<400> SEQUENCE: 15

```
Met Thr Thr Thr Gly Lys Lys Leu Lys Val Ile Phe Met Leu Ile Ile
1               5                   10                  15

Leu Ser Leu Ser Asn Phe Val Pro Leu Ser Ala Ile Ala Asp Thr Thr
            20                  25                  30

Asp Asp Pro Thr Val Leu Glu Thr Ile Ser Ala Glu Val Ile Ser Asp
        35                  40                  45

Gln Ser Gly Lys Lys Ala Leu Asn Ile Lys Leu Asn Ala Asn Asn Thr
    50                  55                  60

Ser Ala Glu Lys Ile Glu Lys Glu Ile Gly Leu Val Glu Asn Tyr Leu
65                  70                  75                  80

Ser Asp Val Glu Arg Lys Glu Gly Asp Gly Tyr Ala Tyr Gln Val Asn
                85                  90                  95

Ser Gly Lys Ile Thr Leu Glu Ile Ser Ser Asn Thr Lys Gln Thr Ile
            100                 105                 110

Asp Leu Ser Phe Pro Ile Asp Pro Ala Leu Tyr His Ser Gln Ala Asn
        115                 120                 125

Lys Leu Ile Val Asp Asn Lys Glu Tyr Asp Ile Ile Asp Glu Thr Glu
    130                 135                 140

Asn Lys Lys Asp Thr Asp Val Ser Val Pro Lys Pro Asp Glu Ile Glu
145                 150                 155                 160

Glu Glu Ser Ser Lys Glu Asn Glu Asn Ser Val Ser Pro Phe Thr Leu
                165                 170                 175

Pro Thr Leu Ser Leu Pro Ala Val Ser Val Pro Ser Asn Gln Thr Ile
            180                 185                 190

Pro Thr Glu Tyr Thr Thr Asp Asp Gln Gly Thr Tyr Pro Lys Ala Ser
        195                 200                 205

Trp Gln Pro Thr Gly Asn Thr Asn Val Leu Asp His Gln Gly Asn Lys
    210                 215                 220

Asn Gly Thr Asn Gln Trp Asp Gly Ile Asn Ser Trp Asn Gly Asp Pro
225                 230                 235                 240

Asn Asp Arg Thr His Ser Tyr Ile Glu Tyr Gly Gly Thr Gly Asn Gln
                245                 250                 255

Ala Asp Tyr Ala Ile Arg Lys Tyr Ala Lys Glu Thr Ser Thr Pro Gly
            260                 265                 270

Leu Phe Asp Val Tyr Leu Asn Ala Arg Gly Asn Val Gln Lys Asp Ile
        275                 280                 285

Thr Pro Leu Asp Leu Val Leu Val Val Asp Trp Ser Gly Ser Met Asn
    290                 295                 300

Asp Asn Asn Arg Ile Gly Glu Val Lys Ile Gly Val Asp Arg Phe Val
305                 310                 315                 320

Asp Thr Leu Ala Asp Ser Gly Ile Thr Asp Lys Ile Asn Met Gly Tyr
                325                 330                 335

Val Gly Tyr Ser Ser Glu Gly Tyr Ser Tyr Ser Asn Gly Ala Val Gln
            340                 345                 350

Met Gly Ser Phe Asp Ser Val Lys Asn Gln Val Lys Ser Ile Thr Pro
        355                 360                 365

Ser Arg Thr Asn Gly Gly Thr Phe Thr Gln Lys Ala Leu Arg Asp Ala
    370                 375                 380

Gly Ser Met Leu Ser Val Pro Asn Gly His Lys Lys Val Ile Val Leu
385                 390                 395                 400
```

-continued

```
Leu Thr Asp Gly Val Pro Thr Phe Ser Tyr Lys Val Gln Arg Val His
                405                 410                 415

Ala Gln Ser Ser Ser Asn Tyr Tyr Gly Thr Gln Phe Ser Asn Thr Gln
            420                 425                 430

Asp Arg Pro Gly Asn Thr Ser Leu Ile Ser Arg Ile Tyr Asp Ala Pro
        435                 440                 445

Asp Gln Asn Asn Leu Ser Arg Arg Ile Asp Ser Thr Phe Ile Ala Thr
    450                 455                 460

Ile Gly Glu Ala Met Ala Leu Lys Glu Arg Gly Ile Glu Ile His Gly
465                 470                 475                 480

Leu Gly Ile Gln Leu Gln Ser Asp Pro Ala Ala Gly Leu Ser Lys Ala
                485                 490                 495

Glu Val Glu Ser Arg Met Arg Gln Met Val Ser Ser Asp Glu Lys Gly
            500                 505                 510

Asp Leu Tyr Tyr Glu Ser Ala Asp His Ala Thr Asp Ile Ser Glu Tyr
        515                 520                 525

Leu Ala Lys Lys Ala Val Gln Ile Ser Ala Thr Val Ser Asn Gly Gln
    530                 535                 540

Ile Asn Asp Pro Ile Ala Glu Pro Phe Ile Tyr Gln Pro Gly Thr Leu
545                 550                 555                 560

Ser Val Lys Ser Val Gly Thr Ser Pro Thr Thr Val Thr Pro Ser Ile
                565                 570                 575

Ser Ile Glu Gly Asn Thr Ile Lys Ser Asn Gln Ile Tyr Leu Gly Lys
            580                 585                 590

Asp Gln Glu Ile Gln Ile His Tyr Gln Val Arg Ile Gln Thr Glu Asn
        595                 600                 605

Glu Asp Phe His Pro Asn Phe Trp Tyr Gln Met Asn Gly Arg Thr Thr
    610                 615                 620

Phe Gln Pro Asn Ile Asp Thr Asn Glu Leu Ala Glu Phe Gly Ile Pro
625                 630                 635                 640

Ser Ala Lys Ala Pro Gly Val Ser Leu His Ile Lys Lys Leu Trp Glu
                645                 650                 655

Glu Phe Asp Asn Asn Leu Ala Asp Arg Pro Asp Gln Val Thr Phe Glu
            660                 665                 670

Ile Gln Arg Glu His Thr Thr Asn Ala Ala Ala Trp Lys Asn Gly Tyr
        675                 680                 685

Ile Arg Ile Ile Lys Pro Ala Lys Asp Thr Thr Asn Thr Trp Glu Arg
    690                 695                 700

Ala Asp Ile Asp Lys Leu Ser Ala Asn Ser Gly Glu Ser Tyr Gln Glu
705                 710                 715                 720

Ile Leu Ser Leu Pro Gln Tyr Asn Asn Gln Gly Gln Ala Phe Ser Tyr
                725                 730                 735

Gln Thr Ile Lys Glu Leu Pro Val Pro Gly Tyr Asp Ser Gln Gln Ile
            740                 745                 750

Asp Ala Met Thr Trp Lys Asn Thr Lys Gln Phe Thr Pro Leu Asn Leu
        755                 760                 765

Lys Ile Thr Lys Asn Ser Ser Thr Gly Glu Lys Asp Leu Ile Gly Ala
    770                 775                 780

Val Phe Lys Leu Thr Gly Asp Ser Ile Asp Thr Leu Leu Thr Asp His
785                 790                 795                 800

Gly Asp Gly Thr Tyr Ser Leu Pro Glu Asn Val Lys Leu Gln Lys Glu
                805                 810                 815

Met Thr Tyr Thr Leu Thr Glu Thr Lys Ala Pro Glu Gly His Gly Leu
```

```
            820                 825                 830

Ser Lys Lys Thr Thr Trp Glu Ile Lys Ile Ala Ser Asp Gly Thr Val
        835                 840                 845

Thr Ile Asp Gly Lys Thr Val Thr Thr Ser Asp Asp Thr Ile Gln Leu
    850                 855                 860

Thr Ile Glu Asn Pro Phe Val Glu Val Pro Val Ala Val Arg Lys Tyr
865                 870                 875                 880

Ala Met Gln Gly Thr Asp Lys Glu Ile Asn Leu Lys Gly Ala Ala Phe
                885                 890                 895

Ser Leu Gln Lys Lys Glu Ala Asn Gly Thr Tyr Gln Pro Ile Asp Ser
            900                 905                 910

Gln Thr Thr Asn Glu Lys Gly Leu Ala Ser Phe Asp Ser Leu Thr Pro
        915                 920                 925

Gly Lys Tyr Arg Val Val Glu Thr Ala Gly Pro Ala Gly Tyr Asp Thr
    930                 935                 940

Ser Pro Gly Asn Tyr Glu Phe Gln Ile Asp Lys Tyr Gly Lys Ile Ile
945                 950                 955                 960

Tyr Thr Gly Lys Asn Thr Glu Met Thr Asn Asn Val Trp Thr Leu Thr
                965                 970                 975

His Gln Asn Arg Leu Lys Ala Phe Asp Leu Thr Val His Lys Lys Glu
            980                 985                 990

Asp Asn Gly Gln Thr Leu Lys Gly  Ala Lys Phe Arg Leu  Gln Gly Pro
        995                 1000                 1005

Glu Met  Asp Leu Glu Ser Pro  Lys Asp Gly Gln Glu  Thr Asp Thr
    1010                 1015                 1020

Phe Leu  Phe Glu Asn Leu Lys  Pro Gly Thr Tyr Thr  Leu Thr Glu
    1025                 1030                 1035

Thr Phe  Thr Pro Glu Gly Tyr  Gln Gly Leu Lys Glu  Pro Val Thr
    1040                 1045                 1050

Ile Val  Ile His Glu Asp Gly  Ser Ile Gln Val Asp  Gly Gln Asp
    1055                 1060                 1065

His Glu  Ser Val Leu Ser Pro  Gly Ala Lys Asn Asn  Gln Ile Ser
    1070                 1075                 1080

Leu Asp  Ile Thr Asn Gln Ala  Lys Val Pro Leu Pro  Glu Thr Gly
    1085                 1090                 1095

Gly Ile  Gly Arg Leu Gly Ile  Tyr Leu Val Gly Met  Ile Gly Cys
    1100                 1105                 1110

Ala Phe  Ser Ile Trp Tyr Leu  Phe Leu Lys Lys Glu  Arg Gly Gly
    1115                 1120                 1125

Ser


<210> SEQ ID NO 16
<211> LENGTH: 1422
<212> TYPE: DNA
<213> ORGANISM: Staphylococcus epidermidis

<400> SEQUENCE: 16

atgaaaaaac ttggttggct tagtatgtgt ctcttcttgt tactatttaa accagctttt      60

actcaggtag caacagaaac agaaacagaa atggttcaga ttactttaca caaattgctt     120

ttcccaaacg ggcaactgcc gaaaaatcat ccaaatgacg gacaagaaaa agctttatta     180

caaacgtatc gaggattaaa tggtgtcaca ttccaagttt atgatgtcac agattctttt     240

taccatctac gggaaaaggg caaaacggta gaagaagcac aagcagagat cgcaaaaaac     300
```

-continued

```
ggtgcgtctt ccggtatgtt taccgcagaa gcaacaacta caactcttaa caacgaagat    360

ggtatcgctt ctttttctct ggccgctaaa gatcaagaaa aaagagataa agcgtatctt    420

ttcattgaat ccaaagtacc agaagtcgtc aaagaaaagg cagagaatat ggtagttgtt    480

cttcctgtac atggacaaaa caatcaaaaa ctttcaacta tccatttgta tcctaaaaat    540

gaagaaaacg actaccctga tccacctttt gagaaggtat tagaagagcc tagaaatgat    600

tttacgattg gtgaaaaaat cacttattcc ttgcatacga caattcctgt aaatatcctt    660

gactatcaaa agttcgaatt gtcagatagt gcggatgaag cattaacgtt tttacctaat    720

agtttaacga tttcatcgaa tggagaaaag ctgacagaag gctttgtcat acacaagaaa    780

cctcacggat ttgatgtttt attttcgatc ccttcgttgg aaaaatatgc tggaaaaaaa    840

ctgaccattt cttatcagat gcagctaagc agtacagcac aggcgaacaa ggaaatcaac    900

aacaacggaa cactggattt tggttttggt gtcagtacaa agaaagtctc tgtatataca    960

gggagtaagc aatttgtcaa aatcgagaca aataaaccag ataaacgatt agctggcgca   1020

gtattcctta ttaaaaacaa agcaggaaat tacctccagc aaacagccaa cggatacaag   1080

tggacaaaga acgaatcaga tgcgcttcac ctgatttccg ataaaaatgg cgctttttca   1140

atttccgggt tgaaaacagg aagttatcga ttaaaagaga tcgaagcacc ttctggttat   1200

attttaagtg aaacagaaat tccgtttacc atttcaactt ttctttctga ggataaagag   1260

gcggacagta tattgaaagt agtcaataaa aaagaaaata gccgtccatt tcttccaaaa   1320

acaaacgaaa cgaaaaatac acttttaggc gttgttggta tggtattcgc aagctttgca   1380

atctggttgt ttatcaaaaa aagaacagga gtgaaaaaat ga                      1422
```

<210> SEQ ID NO 17
<211> LENGTH: 473
<212> TYPE: PRT
<213> ORGANISM: Staphylococcus epidermidis

<400> SEQUENCE: 17

```
Met Lys Lys Leu Gly Trp Leu Ser Met Cys Leu Phe Leu Leu Leu Phe
1               5                   10                  15

Lys Pro Ala Phe Thr Gln Val Ala Thr Glu Thr Glu Thr Glu Met Val
            20                  25                  30

Gln Ile Thr Leu His Lys Leu Leu Phe Pro Asn Gly Gln Leu Pro Lys
        35                  40                  45

Asn His Pro Asn Asp Gly Gln Glu Lys Ala Leu Leu Gln Thr Tyr Arg
    50                  55                  60

Gly Leu Asn Gly Val Thr Phe Gln Val Tyr Asp Val Thr Asp Ser Phe
65                  70                  75                  80

Tyr His Leu Arg Glu Lys Gly Lys Thr Val Glu Glu Ala Gln Ala Glu
                85                  90                  95

Ile Ala Lys Asn Gly Ala Ser Ser Gly Met Phe Thr Ala Glu Ala Thr
            100                 105                 110

Thr Thr Thr Leu Asn Asn Glu Asp Gly Ile Ala Ser Phe Ser Leu Ala
        115                 120                 125

Ala Lys Asp Gln Glu Lys Arg Asp Lys Ala Tyr Leu Phe Ile Glu Ser
    130                 135                 140

Lys Val Pro Glu Val Val Lys Glu Lys Ala Glu Asn Met Val Val Val
145                 150                 155                 160

Leu Pro Val His Gly Gln Asn Asn Gln Lys Leu Ser Thr Ile His Leu
                165                 170                 175
```

-continued

```
Tyr Pro Lys Asn Glu Glu Asn Asp Tyr Pro Asp Pro Pro Phe Glu Lys
            180                 185                 190

Val Leu Glu Glu Pro Arg Asn Asp Phe Thr Ile Gly Glu Lys Ile Thr
        195                 200                 205

Tyr Ser Leu His Thr Thr Ile Pro Val Asn Ile Leu Asp Tyr Gln Lys
    210                 215                 220

Phe Glu Leu Ser Asp Ser Ala Asp Glu Ala Leu Thr Phe Leu Pro Asn
225                 230                 235                 240

Ser Leu Thr Ile Ser Ser Asn Gly Glu Lys Leu Thr Glu Gly Phe Val
                245                 250                 255

Ile His Lys Lys Pro His Gly Phe Asp Val Leu Phe Ser Ile Pro Ser
            260                 265                 270

Leu Glu Lys Tyr Ala Gly Lys Lys Leu Thr Ile Ser Tyr Gln Met Gln
        275                 280                 285

Leu Ser Ser Thr Ala Gln Ala Asn Lys Glu Ile Asn Asn Asn Gly Thr
    290                 295                 300

Leu Asp Phe Gly Phe Gly Val Ser Thr Lys Lys Val Ser Val Tyr Thr
305                 310                 315                 320

Gly Ser Lys Gln Phe Val Lys Ile Glu Thr Asn Lys Pro Asp Lys Arg
                325                 330                 335

Leu Ala Gly Ala Val Phe Leu Ile Lys Asn Lys Ala Gly Asn Tyr Leu
            340                 345                 350

Gln Gln Thr Ala Asn Gly Tyr Lys Trp Thr Lys Asn Glu Ser Asp Ala
        355                 360                 365

Leu His Leu Ile Ser Asp Lys Asn Gly Ala Phe Ser Ile Ser Gly Leu
    370                 375                 380

Lys Thr Gly Ser Tyr Arg Leu Lys Glu Ile Glu Ala Pro Ser Gly Tyr
385                 390                 395                 400

Ile Leu Ser Glu Thr Glu Ile Pro Phe Thr Ile Ser Thr Phe Leu Ser
                405                 410                 415

Glu Asp Lys Glu Ala Asp Ser Ile Leu Lys Val Val Asn Lys Lys Glu
            420                 425                 430

Asn Ser Arg Pro Phe Leu Pro Lys Thr Asn Glu Thr Lys Asn Thr Leu
        435                 440                 445

Leu Gly Val Val Gly Met Val Phe Ala Ser Phe Ala Ile Trp Leu Phe
    450                 455                 460

Ile Lys Lys Arg Thr Gly Val Lys Lys
465                 470
```

<210> SEQ ID NO 18
<211> LENGTH: 1878
<212> TYPE: DNA
<213> ORGANISM: Staphylococcus epidermidis

<400> SEQUENCE: 18

```
atgaaaaatc ataaaaaaat aaacgttatg ttaggagtcc ttttccttat tttaccatta      60

ctcacaaaca gcttcggcgc aaaaaaagtg tttgcagagg agacagcagc tcaagtcatc     120

cttcataaaa agaaaatgac tgatttaccc gatcctttaa tccaaaacag cgggaaagaa     180

atgagcgaat tcgatcaata ccaaggatta gccgatattt cattttcagt ttataacgtc     240

actcaagaat tttatgcgca acgagataaa ggagcgtccg tggatgcagc aaaacaagca     300

gtccagtctt tgactcctgg tacaccagtt gcttcaggaa cgacagatgc tgatggaaat     360

gtcactttat ctttacctaa aaaacaaaat gggaaagatg cagtctacac gatcaaagaa     420
```

-continued

```
gaaccaaaag acggagtgtc agctgccgca aacatggttt tagctttccc tgtatatgag    480

atgatcaaac aagcagatgg ctcttataaa tacgggacag aagaactaga tactatccat    540

ctctacccta aaaatacagt cggtaatgat ggaacgttga aagttacaaa aatcggtact    600

gccgaaaacg aagcactaaa tggagcagaa tttattattt ctaaagaaga aggaacacca    660

agcgtcaaaa aatacatcca aagtgtcaca gatggattgt acacttggac aactgatcaa    720

accaaagcca aacatttcat tactggtcat tcttatgaca tcggcaacaa tgactttgcc    780

gaggcatcta ttgaaaaagg ccagttgatc gttaatcatt tagaagttgg aaaatataat    840

ttagaagaag taaaagctcc tgataatgcg gaaatgattg aaaagcaaac aatcacgcct    900

tttgagatcc tggcaaatag ccaaacacca gtagaaaaga ccatcaaaaa tgatacgtct    960

aaagttgata aaacaacacc tcaattgaat ggaaaagatg tcgcaatcgg tgaaaaaatt   1020

caatatgaga tttctgtcaa tatcccatta ggtatcgctg ataaagaagg aacgcaaaac   1080

aagtacacaa cattcaaact tatcgatact catgacgctg ctttaacatt tgataatgat   1140

tcttcaggaa cgtatgctta tgccttatat gatggaaata aagaaatcga cccagtaaat   1200

tattctgtca ctgagcaaac agacggattc acggtttcag ttgatccgaa ttatattcct   1260

tcattaactc ctggcggtac attgaaattc gtttactata tgcatttgaa cgaaaaagca   1320

gatccaacca aaggattttc taaccaagca aatgtcgata acgggcatac aaatgatcaa   1380

acaccaccgt cagtcgatgt cgttactggg ggcaaacgat ttgttaaagt agatggtgac   1440

gttacatcag accaaacact tgctggagca gaattcgtcg ttcgtgatca agatagtgac   1500

acagcgaaat atttatcgat cgacccatcc acaaaagccg tcagctgggt atcggcgaaa   1560

gaatcagcaa cggtttttac aaccacaagt aacggtttaa tcgatgtgac aggtctaaaa   1620

tatggcacgt actatctgga agaaacgaaa gcgccagaaa aatatgttcc attaacaaac   1680

cgtgtagcat ttactatcga tgaacaatct tatgtaacag caggacagtt gatttctcct   1740

gaaaaaatac caaataaaca caaaggtaca cttccttcaa caggcggtaa gggaatctat   1800

gtgtatatcg gtgcaggagt agtccttcta ctgattgctg gactgtactt tgctagacgc   1860

aagcacagtc agatttag                                                 1878
```

```
<210> SEQ ID NO 19
<211> LENGTH: 625
<212> TYPE: PRT
<213> ORGANISM: Staphylococcus epidermidis

<400> SEQUENCE: 19

Met Lys Asn His Lys Lys Ile Asn Val Met Leu Gly Val Leu Phe Leu
1               5                   10                  15

Ile Leu Pro Leu Leu Thr Asn Ser Phe Gly Ala Lys Lys Val Phe Ala
            20                  25                  30

Glu Glu Thr Ala Ala Gln Val Ile Leu His Lys Lys Lys Met Thr Asp
        35                  40                  45

Leu Pro Asp Pro Leu Ile Gln Asn Ser Gly Lys Glu Met Ser Glu Phe
    50                  55                  60

Asp Gln Tyr Gln Gly Leu Ala Asp Ile Ser Phe Ser Val Tyr Asn Val
65                  70                  75                  80

Thr Gln Glu Phe Tyr Ala Gln Arg Asp Lys Gly Ala Ser Val Asp Ala
                85                  90                  95

Ala Lys Gln Ala Val Gln Ser Leu Thr Pro Gly Thr Pro Val Ala Ser
            100                 105                 110
```

-continued

```
Gly Thr Thr Asp Ala Asp Gly Asn Val Thr Leu Ser Leu Pro Lys Lys
        115                 120                 125

Gln Asn Gly Lys Asp Ala Val Tyr Thr Ile Lys Glu Glu Pro Lys Asp
    130                 135                 140

Gly Val Ser Ala Ala Ala Asn Met Val Leu Ala Phe Pro Val Tyr Glu
145                 150                 155                 160

Met Ile Lys Gln Ala Asp Gly Ser Tyr Lys Tyr Gly Thr Glu Glu Leu
                165                 170                 175

Asp Thr Ile His Leu Tyr Pro Lys Asn Thr Val Gly Asn Asp Gly Thr
            180                 185                 190

Leu Lys Val Thr Lys Ile Gly Thr Ala Glu Asn Glu Ala Leu Asn Gly
        195                 200                 205

Ala Glu Phe Ile Ile Ser Lys Glu Glu Gly Thr Pro Ser Val Lys Lys
    210                 215                 220

Tyr Ile Gln Ser Val Thr Asp Gly Leu Tyr Thr Trp Thr Thr Asp Gln
225                 230                 235                 240

Thr Lys Ala Lys His Phe Ile Thr Gly His Ser Tyr Asp Ile Gly Asn
                245                 250                 255

Asn Asp Phe Ala Glu Ala Ser Ile Glu Lys Gly Gln Leu Ile Val Asn
            260                 265                 270

His Leu Glu Val Gly Lys Tyr Asn Leu Glu Glu Val Lys Ala Pro Asp
        275                 280                 285

Asn Ala Glu Met Ile Glu Lys Gln Thr Ile Thr Pro Phe Glu Ile Leu
    290                 295                 300

Ala Asn Ser Gln Thr Pro Val Glu Lys Thr Ile Lys Asn Asp Thr Ser
305                 310                 315                 320

Lys Val Asp Lys Thr Thr Pro Gln Leu Asn Gly Lys Asp Val Ala Ile
                325                 330                 335

Gly Glu Lys Ile Gln Tyr Glu Ile Ser Val Asn Ile Pro Leu Gly Ile
            340                 345                 350

Ala Asp Lys Glu Gly Thr Gln Asn Lys Tyr Thr Thr Phe Lys Leu Ile
        355                 360                 365

Asp Thr His Asp Ala Ala Leu Thr Phe Asp Asn Asp Ser Ser Gly Thr
    370                 375                 380

Tyr Ala Tyr Ala Leu Tyr Asp Gly Asn Lys Glu Ile Asp Pro Val Asn
385                 390                 395                 400

Tyr Ser Val Thr Glu Gln Thr Asp Gly Phe Thr Val Ser Val Asp Pro
                405                 410                 415

Asn Tyr Ile Pro Ser Leu Thr Pro Gly Gly Thr Leu Lys Phe Val Tyr
            420                 425                 430

Tyr Met His Leu Asn Glu Lys Ala Asp Pro Thr Lys Gly Phe Ser Asn
        435                 440                 445

Gln Ala Asn Val Asp Asn Gly His Thr Asn Asp Gln Thr Pro Pro Ser
    450                 455                 460

Val Asp Val Val Thr Gly Gly Lys Arg Phe Val Lys Val Asp Gly Asp
465                 470                 475                 480

Val Thr Ser Asp Gln Thr Leu Ala Gly Ala Glu Phe Val Val Arg Asp
                485                 490                 495

Gln Asp Ser Asp Thr Ala Lys Tyr Leu Ser Ile Asp Pro Ser Thr Lys
            500                 505                 510

Ala Val Ser Trp Val Ser Ala Lys Glu Ser Ala Thr Val Phe Thr Thr
        515                 520                 525

Thr Ser Asn Gly Leu Ile Asp Val Thr Gly Leu Lys Tyr Gly Thr Tyr
```

```
    530                 535                 540

Tyr Leu Glu Glu Thr Lys Ala Pro Glu Lys Tyr Val Pro Leu Thr Asn
545                 550                 555                 560

Arg Val Ala Phe Thr Ile Asp Glu Gln Ser Tyr Val Thr Ala Gly Gln
                565                 570                 575

Leu Ile Ser Pro Glu Lys Ile Pro Asn Lys His Lys Gly Thr Leu Pro
            580                 585                 590

Ser Thr Gly Gly Lys Gly Ile Tyr Val Tyr Ile Gly Ala Gly Val Val
        595                 600                 605

Leu Leu Leu Ile Ala Gly Leu Tyr Phe Ala Arg Arg Lys His Ser Gln
    610                 615                 620

Ile
625


<210> SEQ ID NO 20
<211> LENGTH: 2402
<212> TYPE: PRT
<213> ORGANISM: Staphylococcus epidermidis

<400> SEQUENCE: 20

Met Lys Asn Lys Gln Gly Phe Leu Pro Asn Leu Leu Asn Lys Tyr Gly
1               5                   10                  15

Ile Arg Lys Leu Ser Ala Gly Thr Ala Ser Leu Leu Ile Gly Ala Thr
            20                  25                  30

Leu Val Phe Gly Ile Asn Gly Gln Val Lys Ala Ala Glu Thr Asp Asn
        35                  40                  45

Ile Val Ser Gln Asn Gly Asp Asn Lys Thr Asn Asp Ser Glu Ser Ser
    50                  55                  60

Asp Lys Glu Leu Val Lys Ser Glu Asp Asp Lys Thr Ser Ser Thr Ser
65                  70                  75                  80

Thr Asp Thr Asn Leu Glu Ser Glu Phe Asp Gln Asn Asn Asn Pro Ser
                85                  90                  95

Ser Ile Glu Glu Ser Thr Asn Arg Asn Asp Glu Asp Thr Leu Asn Gln
            100                 105                 110

Arg Thr Ser Thr Glu Thr Glu Lys Asp Thr His Val Lys Ser Ala Asp
        115                 120                 125

Thr Gln Thr Thr Asn Glu Thr Thr Asn Lys Asn Asp Asp Asn Ala Thr
    130                 135                 140

Thr Asn His Thr Glu Ser Ile Ser Asp Glu Ser Thr Tyr Gln Ser Asp
145                 150                 155                 160

Asp Ser Lys Thr Thr Gln His Asp Asn Ser Asn Thr Asn Gln Asp Thr
                165                 170                 175

Gln Ser Thr Leu Asn Pro Thr Ser Lys Glu Ser Ser Asn Lys Asp Glu
            180                 185                 190

Ala Thr Ser Pro Thr Pro Lys Glu Ser Thr Ser Ile Glu Lys Thr Asn
        195                 200                 205

Leu Ser Asn Asp Ala Asn His Gln Thr Thr Asp Glu Val Asn His Ser
    210                 215                 220

Asp Ser Asp Asn Met Thr Asn Ser Thr Pro Asn Asp Thr Glu Asn Glu
225                 230                 235                 240

Leu Asp Thr Thr Gln Leu Thr Ser His Asp Glu Ser Pro Ser Pro Gln
                245                 250                 255

Ser Asp Asn Phe Thr Gly Phe Thr Asn Leu Met Ala Thr Pro Leu Asn
            260                 265                 270
```

-continued

```
Leu Arg Asn Asp Asn Pro Arg Ile Asn Leu Leu Ala Ala Thr Glu Asp
        275                 280                 285

Thr Lys Pro Lys Thr Tyr Lys Lys Pro Asn Asn Ser Glu Tyr Ser Tyr
    290                 295                 300

Leu Leu Asn Asp Leu Gly Tyr Asp Ala Thr Thr Val Lys Glu Asn Ser
305                 310                 315                 320

Asp Leu Arg His Ala Gly Ile Ser Gln Ser Gln Asp Asn Thr Gly Ser
                325                 330                 335

Val Ile Lys Leu Asn Leu Thr Lys Trp Leu Ser Leu Gln Ser Asp Phe
            340                 345                 350

Val Asn Gly Gly Lys Val Asn Leu Ser Phe Ala Gln Ser Asp Phe Tyr
        355                 360                 365

Thr Gln Ile Glu Ser Ile Thr Leu Asn Asp Val Lys Met Asp Thr Thr
    370                 375                 380

Asn Asn Gly Gln Asn Trp Ser Ala Pro Ile Asn Gly Ser Thr Val Arg
385                 390                 395                 400

Ser Gly Leu Ile Gly Ser Val Thr Asn His Asp Ile Val Ile Thr Leu
                405                 410                 415

Lys Asn Ser Gln Thr Leu Ser Ser Leu Gly Tyr Ser Asn Asn Lys Pro
            420                 425                 430

Val Tyr Leu Thr His Thr Trp Thr Thr Asn Asp Gly Ala Ile Ala Glu
        435                 440                 445

Glu Ser Ile Gln Val Ala Ser Ile Thr Pro Thr Leu Asp Ser Lys Ala
    450                 455                 460

Pro Asn Thr Ile Gln Lys Ser Asp Phe Thr Ala Gly Arg Met Thr Asn
465                 470                 475                 480

Lys Ile Lys Tyr Asp Ser Ser Gln Asn Ser Ile Lys Ser Val His Thr
                485                 490                 495

Phe Lys Pro Asn Glu Asn Phe Leu Gln Thr Asp Tyr Arg Ala Val Leu
            500                 505                 510

Tyr Ile Lys Glu Gln Val Asn Lys Glu Leu Ile Pro Tyr Ile Asp Pro
        515                 520                 525

Asn Ser Val Lys Leu Tyr Val Ser Asp Pro Asp Gly Asn Pro Ile Ser
    530                 535                 540

Gln Asp Arg Tyr Val Asn Gly Ser Ile Asp Asn Asp Gly Leu Phe Asp
545                 550                 555                 560

Ser Ser Lys Ile Asn Glu Ile Ser Ile Lys Asn Asn Asn Thr Ser Gly
                565                 570                 575

Gln Leu Ser Asn Ala Arg Thr Ser Leu Asp Arg Asn Val Phe Phe Gly
            580                 585                 590

Thr Leu Gly Gln Ser Arg Ser Tyr Thr Ile Ser Tyr Lys Leu Lys Asp
        595                 600                 605

Gly Tyr Thr Leu Glu Ser Val Ala Ser Lys Val Ser Ala Arg Glu Thr
    610                 615                 620

Phe Asp Ser Trp Met Glu Val Asp Tyr Leu Asp Ser Tyr Asp Ser Gly
625                 630                 635                 640

Ala Pro Asn Lys Arg Leu Leu Gly Ser Tyr Ala Ser Ser Tyr Ile Asp
                645                 650                 655

Met Ile Asp Arg Ile Pro Pro Val Ala Pro Lys Ala Asn Ser Ile Thr
            660                 665                 670

Thr Glu Asp Thr Ser Ile Lys Gly Thr Ala Glu Val Asp Thr Asn Ile
        675                 680                 685

Asn Leu Thr Phe Asn Asp Gly Arg Thr Leu Asn Gly Lys Val Asp Ser
```

-continued

```
    690                 695                 700

Asn Gly Asn Phe Ser Ile Ala Ile Pro Ser Tyr Tyr Val Leu Thr Gly
705                 710                 715                 720

Lys Glu Thr Ile Lys Ile Thr Ser Ile Asp Lys Gly Asp Asn Val Ser
                725                 730                 735

Pro Ala Ile Thr Ile Ser Val Ile Asp Lys Thr Pro Pro Ala Val Lys
            740                 745                 750

Ala Ile Ser Asn Lys Thr Gln Lys Val Asn Thr Glu Ile Glu Pro Ile
        755                 760                 765

Lys Ile Glu Ala Thr Asp Asn Ser Gly Gln Ala Val Thr Asn Lys Val
    770                 775                 780

Glu Gly Leu Pro Ala Gly Met Thr Phe Asp Glu Ala Thr Asn Thr Ile
785                 790                 795                 800

Ser Gly Thr Pro Ser Glu Val Gly Ser Tyr Asp Ile Thr Val Thr Thr
                805                 810                 815

Thr Asp Glu Asn Gly Asn Ser Glu Thr Thr Thr Phe Thr Ile Asp Val
            820                 825                 830

Glu Asp Thr Thr Lys Pro Thr Val Glu Ser Val Ala Asp Gln Thr Gln
        835                 840                 845

Glu Val Asn Thr Glu Ile Glu Pro Ile Lys Ile Glu Ala Thr Asp Asn
    850                 855                 860

Ser Gly Arg Ala Val Thr Asn Lys Val Asp Gly Leu Pro Asp Gly Val
865                 870                 875                 880

Thr Phe Asp Glu Ala Thr Asn Thr Ile Ser Gly Thr Pro Ser Glu Val
                885                 890                 895

Gly Ser Tyr Asp Ile Thr Val Thr Thr Thr Asp Glu Ser Gly Asn Val
            900                 905                 910

Thr Glu Thr Ile Phe Thr Ile Asp Val Glu Asp Thr Thr Lys Pro Thr
        915                 920                 925

Val Glu Ser Ile Ala Gly Gln Thr Gln Glu Val Asn Thr Glu Ile Glu
    930                 935                 940

Pro Ile Lys Ile Glu Ala Lys Asp Asn Ser Gly Gln Thr Val Thr Asn
945                 950                 955                 960

Lys Val Asp Gly Leu Pro Asp Gly Val Thr Phe Asp Glu Ala Thr Asn
                965                 970                 975

Thr Ile Ser Gly Thr Pro Ser Glu Val Gly Ser Tyr Asp Val Thr Val
            980                 985                 990

Thr Thr Thr Asp Glu Ser Gly Asn  Ser Glu Thr Thr Thr  Phe Thr Ile
        995                 1000                1005

Glu Val  Lys Asp Thr Thr Lys  Pro Thr Val Glu Ser  Val Ala Asp
    1010                1015                1020

Gln Thr  Gln Glu Val Asn Thr  Glu Ile Glu Pro Ile  Lys Ile Glu
    1025                1030                1035

Ala Arg  Asp Asn Ser Gly Gln  Ala Val Thr Asn Lys  Val Asp Gly
    1040                1045                1050

Leu Pro  Asp Gly Val Thr Phe  Asp Glu Ala Thr Asn  Thr Ile Ser
    1055                1060                1065

Gly Thr  Pro Ser Glu Val Gly  Ser Tyr Asp Ile Thr  Val Thr Thr
    1070                1075                1080

Thr Asp  Glu Ser Gly Asn Val  Thr Glu Thr Thr Phe  Thr Ile Glu
    1085                1090                1095

Val Glu  Asp Thr Thr Lys Pro  Thr Val Glu Asn Val  Ala Asp Gln
    1100                1105                1110
```

-continued

```
Thr Gln  Glu Val Asn Thr Glu  Ile Thr Pro Ile Thr  Ile Glu Ser
    1115                 1120                 1125

Glu Asp  Asn Ser Gly Gln Thr  Val Thr Asn Lys Val  Asp Gly Leu
    1130                 1135                 1140

Pro Asp  Gly Val Thr Phe Asp  Glu Thr Thr Asn Thr  Ile Ser Gly
    1145                 1150                 1155

Thr Pro  Ser Lys Val Gly Ser  Tyr Asp Ile Thr Val  Thr Thr Thr
    1160                 1165                 1170

Asp Glu  Ser Gly Asn Ala Thr  Glu Thr Thr Phe Thr  Ile Glu Val
    1175                 1180                 1185

Glu Asp  Thr Thr Lys Pro Thr  Val Glu Asn Val Ala  Gly Gln Thr
    1190                 1195                 1200

Gln Glu  Ile Asn Thr Glu Ile  Glu Pro Ile Lys Ile  Glu Ala Thr
    1205                 1210                 1215

Asp Asn  Ser Gly Gln Ala Val  Thr Asn Lys Val Glu  Gly Leu Pro
    1220                 1225                 1230

Ala Gly  Val Thr Phe Asp Glu  Ala Thr Asn Thr Ile  Ser Gly Thr
    1235                 1240                 1245

Pro Ser  Glu Val Gly Ser Tyr  Thr Val Thr Val Thr  Thr Met Asp
    1250                 1255                 1260

Glu Ser  Gly Asn Ala Thr Glu  Thr Thr Phe Thr Ile  Asp Val Glu
    1265                 1270                 1275

Asp Thr  Thr Lys Pro Thr Val  Glu Ser Val Ala Asp  Gln Thr Gln
    1280                 1285                 1290

Glu Val  Asn Thr Glu Ile Thr  Pro Ile Thr Ile Glu  Ser Glu Asp
    1295                 1300                 1305

Asn Ser  Asp Gln Ala Val Thr  Asn Lys Val Asp Gly  Leu Pro Asp
    1310                 1315                 1320

Gly Val  Thr Phe Asp Glu Ala  Thr Asn Thr Ile Ser  Gly Thr Pro
    1325                 1330                 1335

Ser Glu  Val Gly Ser Tyr Thr  Val Thr Val Thr Thr  Thr Asp Glu
    1340                 1345                 1350

Ser Gly  Asn Ala Thr Glu Thr  Thr Phe Thr Ile Asp  Val Glu Asp
    1355                 1360                 1365

Thr Thr  Lys Pro Thr Val Lys  Ser Val Ser Asp Gln  Thr Gln Glu
    1370                 1375                 1380

Val Asn  Thr Glu Ile Thr Pro  Ile Lys Ile Glu Ala  Thr Asp Asn
    1385                 1390                 1395

Ser Gly  Gln Thr Val Thr Asn  Lys Val Asp Gly Leu  Pro Asp Gly
    1400                 1405                 1410

Ile Thr  Phe Asp Glu Ala Thr  Asn Thr Ile Ser Gly  Thr Pro Ser
    1415                 1420                 1425

Glu Val  Gly Ser Tyr Asp Ile  Thr Val Thr Thr Thr  Asp Glu Ser
    1430                 1435                 1440

Gly Asn  Ala Thr Glu Thr Thr  Phe Thr Ile Asn Val  Glu Asp Thr
    1445                 1450                 1455

Thr Lys  Pro Thr Val Glu Asp  Ile Ala Asp Gln Thr  Gln Glu Val
    1460                 1465                 1470

Asn Thr  Glu Ile Glu Pro Ile  Lys Ile Glu Ala Thr  Asp Asn Gly
    1475                 1480                 1485

Gly Gln  Ala Val Thr Asn Lys  Val Asp Gly Leu Pro  Asp Gly Val
    1490                 1495                 1500
```

-continued

```
Thr Phe  Asp Glu Ala Thr Asn  Thr Ile Ser Gly Thr  Pro Ser Glu
    1505                 1510                 1515

Val Gly  Ser Tyr Asp Ile Ile  Val Thr Thr Thr Asp  Glu Asn Gly
    1520                 1525                 1530

Asn Ser  Glu Thr Thr Thr Phe  Thr Ile Asp Val Glu  Asp Thr Thr
    1535                 1540                 1545

Lys Pro  Thr Val Glu Ser Val  Val Asp Gln Thr Gln  Glu Val Asn
    1550                 1555                 1560

Thr Glu  Ile Thr Pro Ile Lys  Ile Glu Ala Thr Asp  Asn Ser Gly
    1565                 1570                 1575

Gln Ala  Val Ala Asn Lys Val  Asp Gly Leu Pro Asn  Gly Val Thr
    1580                 1585                 1590

Phe Asp  Glu Thr Thr Asn Thr  Ile Ser Gly Thr Pro  Ser Glu Val
    1595                 1600                 1605

Gly Ser  Tyr Asp Ile Ile Val  Thr Thr Thr Asp Glu  Ser Gly Asn
    1610                 1615                 1620

Val Thr  Glu Thr Ile Phe Thr  Ile Asp Val Glu Asp  Thr Thr Lys
    1625                 1630                 1635

Pro Thr  Val Glu Ser Ile Ala  Gly Gln Thr Gln Glu  Val Asn Thr
    1640                 1645                 1650

Glu Ile  Glu Pro Ile Lys Ile  Glu Ala Thr Asp Asn  Ser Gly Gln
    1655                 1660                 1665

Ala Val  Thr Asn Lys Val Asp  Gly Leu Pro Asn Gly  Val Thr Phe
    1670                 1675                 1680

Asp Glu  Ala Thr Asn Thr Ile  Ser Gly Thr Pro Ser  Glu Val Gly
    1685                 1690                 1695

Ile Tyr  Thr Val Thr Val Thr  Thr Thr Asp Glu Ser  Gly Asn Ala
    1700                 1705                 1710

Thr Glu  Thr Thr Phe Thr Ile  Asp Val Glu Asp Thr  Thr Lys Pro
    1715                 1720                 1725

Thr Val  Glu Ser Val Ala Asp  Gln Thr Gln Glu Val  Asn Thr Glu
    1730                 1735                 1740

Ile Thr  Pro Ile Thr Ile Glu  Ser Glu Asp Asn Ser  Gly Gln Ala
    1745                 1750                 1755

Val Thr  Asn Lys Val Glu Gly  Leu Pro Ala Gly Met  Thr Phe Asp
    1760                 1765                 1770

Glu Thr  Thr Asn Thr Ile Ser  Gly Thr Pro Ser Glu  Val Gly Ser
    1775                 1780                 1785

Tyr Thr  Val Thr Val Thr Thr  Thr Asp Glu Ser Gly  Asn Glu Thr
    1790                 1795                 1800

Glu Thr  Thr Phe Thr Ile Asp  Val Glu Asp Thr Thr  Lys Pro Thr
    1805                 1810                 1815

Val Glu  Ser Ile Ala Asn Gln  Thr Gln Glu Val Asn  Thr Glu Ile
    1820                 1825                 1830

Thr Pro  Ile Lys Ile Glu Ala  Thr Asp Asn Ser Gly  Gln Ala Val
    1835                 1840                 1845

Thr Asn  Lys Val Asp Gly Leu  Pro Asn Gly Val Thr  Phe Asp Glu
    1850                 1855                 1860

Thr Thr  Asn Thr Ile Ser Gly  Thr Pro Ser Glu Val  Gly Ser Tyr
    1865                 1870                 1875

Asp Ile  Lys Val Thr Thr Thr  Asp Glu Ser Gly Asn  Ala Thr Glu
    1880                 1885                 1890

Thr Thr  Phe Thr Ile Asn Val  Glu Asp Thr Thr Lys  Pro Thr Val
```

-continued

```
    1895                1900                1905

Glu Ser  Val Ala Asp Gln Thr  Gln Glu Ile Asn Thr  Glu Ile Glu
    1910                1915                1920

Pro Ile  Lys Ile Glu Ala Arg  Asp Asn Ser Gly Gln  Ala Val Thr
    1925                1930                1935

Asn Lys  Val Asp Gly Leu Pro  Asp Gly Val Thr Phe  Asp Glu Ala
    1940                1945                1950

Thr Asn  Thr Ile Ser Gly Thr  Pro Ser Glu Val Gly  Ser Tyr Asp
    1955                1960                1965

Ile Thr  Val Thr Thr Thr Asp  Glu Ser Gly Asn Ala  Thr Glu Thr
    1970                1975                1980

Thr Phe  Thr Ile Asp Val Glu  Asp Thr Thr Lys Pro  Thr Val Glu
    1985                1990                1995

Asp Ile  Thr Asp Gln Thr Gln  Glu Ile Asn Thr Glu  Met Thr Pro
    2000                2005                2010

Ile Lys  Ile Glu Ala Thr Asp  Asn Ser Gly Gln Ala  Val Thr Asn
    2015                2020                2025

Lys Val  Glu Gly Leu Pro Asp  Gly Val Thr Phe Asp  Glu Ala Thr
    2030                2035                2040

Asn Thr  Ile Ser Gly Thr Pro  Ser Glu Val Gly Lys  Tyr Leu Ile
    2045                2050                2055

Thr Ile  Thr Thr Ile Asp Lys  Asp Gly Asn Thr Ala  Thr Thr Thr
    2060                2065                2070

Leu Thr  Ile Asn Val Ile Asp  Thr Thr Thr Pro Glu  Gln Pro Thr
    2075                2080                2085

Ile Asn  Lys Val Thr Glu Asn  Ser Thr Glu Val Asn  Gly Arg Gly
    2090                2095                2100

Glu Pro  Gly Thr Val Val Glu  Val Thr Phe Pro Asp  Gly Asn Lys
    2105                2110                2115

Val Glu  Gly Lys Val Asp Ser  Asp Gly Asn Tyr His  Ile Gln Ile
    2120                2125                2130

Pro Ser  Glu Thr Thr Leu Lys  Gly Gly Gln Pro Leu  Gln Val Ile
    2135                2140                2145

Ala Ile  Asp Lys Ala Gly Asn  Lys Ser Glu Ala Thr  Thr Thr Asn
    2150                2155                2160

Val Ile  Asp Thr Thr Ala Pro  Glu Gln Pro Thr Ile  Asn Lys Val
    2165                2170                2175

Thr Glu  Asn Ser Thr Glu Val  Ser Gly Arg Gly Glu  Pro Gly Thr
    2180                2185                2190

Val Val  Glu Val Thr Phe Pro  Asp Gly Asn Lys Val  Glu Gly Lys
    2195                2200                2205

Val Asp  Ser Asp Gly Asn Tyr  His Ile Gln Ile Pro  Ser Asp Glu
    2210                2215                2220

Arg Phe  Lys Val Gly Gln Gln  Leu Ile Val Lys Val  Val Asp Glu
    2225                2230                2235

Glu Gly  Asn Val Ser Glu Pro  Ser Ile Thr Met Val  Gln Lys Glu
    2240                2245                2250

Asp Lys  Asn Ser Glu Lys Leu  Ser Thr Val Thr Gly  Thr Val Thr
    2255                2260                2265

Lys Asn  Asn Ser Lys Ser Leu  Lys His Lys Ala Ser  Glu Gln Gln
    2270                2275                2280

Ser Tyr  His Asn Lys Ser Glu  Lys Ile Lys Asn Val  Asn Lys Pro
    2285                2290                2295
```

```
Thr Lys  Ile Val Glu Lys Asp  Met Ser Thr Tyr Asp  Tyr Ser Arg
    2300                 2305                 2310

Tyr Ser  Lys Asp Ile Ser Asn  Lys Asn Asn Lys Ser  Ala Thr Phe
    2315                 2320                 2325

Glu Gln  Gln Asn Val Ser Asp  Ile Asn Asn Asn Gln  Tyr Ser Arg
    2330                 2335                 2340

Asn Lys  Val Asn Gln Pro Val  Lys Lys Ser Arg Lys  Asn Glu Ile
    2345                 2350                 2355

Asn Lys  Asp Leu Pro Gln Thr  Gly Glu Glu Asn Phe  Asn Lys Ser
    2360                 2365                 2370

Thr Leu  Phe Gly Thr Leu Val  Ala Ser Leu Gly Ala  Leu Leu Leu
    2375                 2380                 2385

Phe Phe  Lys Arg Arg Lys Lys  Asp Glu Asn Asp Glu  Lys Glu
    2390                 2395                 2400


<210> SEQ ID NO 21
<211> LENGTH: 892
<212> TYPE: PRT
<213> ORGANISM: Staphylococcus epidermidis

<400> SEQUENCE: 21

Leu Phe Gly Leu Gly His Asn Glu Ala Lys Ala Glu Glu Asn Thr Val
1               5                   10                  15

Gln Asp Val Lys Asp Ser Asn Met Asp Asp Glu Leu Ser Asp Ser Asn
            20                  25                  30

Asp Gln Ser Ser Asn Glu Glu Lys Asn Asp Val Ile Asn Asn Ser Gln
        35                  40                  45

Ser Ile Asn Thr Asp Asp Asp Asn Gln Ile Lys Lys Glu Glu Thr Asn
    50                  55                  60

Ser Asn Asp Ala Ile Glu Asn Arg Ser Lys Asp Ile Thr Gln Ser Thr
65                  70                  75                  80

Thr Asn Val Asp Glu Asn Glu Ala Thr Phe Leu Gln Lys Thr Pro Gln
                85                  90                  95

Asp Asn Thr Gln Leu Lys Glu Glu Val Val Lys Glu Pro Ser Ser Val
            100                 105                 110

Glu Ser Ser Asn Ser Ser Met Asp Thr Ala Gln Gln Pro Ser His Thr
        115                 120                 125

Thr Ile Asn Ser Glu Ala Ser Ile Gln Thr Ser Asp Asn Glu Glu Asn
    130                 135                 140

Ser Arg Val Ser Asp Phe Ala Asn Ser Lys Ile Ile Glu Ser Asn Thr
145                 150                 155                 160

Glu Ser Asn Lys Glu Glu Asn Thr Ile Glu Gln Pro Asn Lys Val Arg
                165                 170                 175

Glu Asp Ser Ile Thr Ser Gln Pro Ser Ser Tyr Lys Asn Ile Asp Glu
            180                 185                 190

Lys Ile Ser Asn Gln Asp Glu Leu Leu Asn Leu Pro Ile Asn Glu Tyr
        195                 200                 205

Glu Asn Lys Val Arg Pro Leu Ser Thr Thr Ser Ala Gln Pro Ser Ser
    210                 215                 220

Lys Arg Val Thr Val Asn Gln Leu Ala Ala Glu Gln Gly Ser Asn Val
225                 230                 235                 240

Asn His Leu Ile Lys Val Thr Asp Gln Ser Ile Thr Glu Gly Tyr Asp
                245                 250                 255

Asp Ser Asp Gly Ile Ile Lys Ala His Asp Ala Glu Asn Leu Ile Tyr
```

-continued

```
            260                 265                 270

Asp Val Thr Phe Glu Val Asp Asp Lys Val Lys Ser Gly Asp Thr Met
        275                 280                 285

Thr Val Asn Ile Asp Lys Asn Thr Val Pro Ser Asp Leu Thr Asp Ser
    290                 295                 300

Phe Ala Ile Pro Lys Ile Lys Asp Asn Ser Gly Glu Ile Ile Ala Thr
305                 310                 315                 320

Gly Thr Tyr Asp Asn Thr Asn Lys Gln Ile Thr Tyr Thr Phe Thr Asp
                325                 330                 335

Tyr Val Asp Lys Tyr Glu Asn Ile Lys Ala His Leu Lys Leu Thr Ser
            340                 345                 350

Tyr Ile Asp Lys Ser Lys Val Pro Asn Asn Asn Thr Lys Leu Asp Val
        355                 360                 365

Glu Tyr Lys Thr Ala Leu Ser Ser Val Asn Lys Thr Ile Thr Val Glu
    370                 375                 380

Tyr Gln Lys Pro Asn Glu Asn Arg Thr Ala Asn Leu Gln Ser Met Phe
385                 390                 395                 400

Thr Asn Ile Asp Thr Lys Asn His Thr Val Glu Gln Thr Ile Tyr Ile
                405                 410                 415

Asn Pro Leu Arg Tyr Ser Ala Lys Glu Thr Asn Val Asn Ile Ser Gly
            420                 425                 430

Asn Gly Asp Glu Gly Ser Thr Ile Ile Asp Asp Ser Thr Ile Ile Lys
        435                 440                 445

Val Tyr Lys Val Gly Asp Asn Gln Asn Leu Pro Asp Ser Asn Arg Ile
    450                 455                 460

Tyr Asp Tyr Ser Glu Tyr Glu Asp Val Thr Asn Asp Asp Tyr Ala Gln
465                 470                 475                 480

Leu Gly Asn Asn Asn Asp Val Asn Ile Asn Phe Gly Asn Ile Asp Ser
                485                 490                 495

Pro Tyr Ile Ile Lys Val Ile Ser Lys Tyr Asp Pro Asn Lys Asp Asp
            500                 505                 510

Tyr Thr Thr Ile Gln Gln Thr Val Thr Met Gln Thr Thr Ile Asn Glu
        515                 520                 525

Tyr Thr Gly Glu Phe Arg Thr Ala Ser Tyr Asp Asn Thr Ile Ala Phe
    530                 535                 540

Ser Thr Ser Ser Gly Gln Gly Gln Gly Asp Leu Pro Pro Glu Lys Thr
545                 550                 555                 560

Tyr Lys Ile Gly Asp Tyr Val Trp Glu Asp Val Asp Lys Asp Gly Ile
                565                 570                 575

Gln Asn Thr Asn Asp Asn Glu Lys Pro Leu Ser Asn Val Leu Val Thr
            580                 585                 590

Leu Thr Tyr Pro Asp Gly Thr Ser Lys Ser Val Arg Thr Asp Glu Glu
        595                 600                 605

Gly Lys Tyr Gln Phe Asp Gly Leu Lys Asn Gly Leu Thr Tyr Lys Ile
    610                 615                 620

Thr Phe Glu Thr Pro Glu Gly Tyr Thr Pro Thr Leu Lys His Ser Gly
625                 630                 635                 640

Thr Asn Pro Ala Leu Asp Ser Glu Gly Asn Ser Val Trp Val Thr Ile
                645                 650                 655

Asn Gly Gln Asp Asp Met Thr Ile Asp Ser Gly Phe Tyr Gln Thr Pro
            660                 665                 670

Lys Tyr Ser Leu Gly Asn Tyr Val Trp Tyr Asp Thr Asn Lys Asp Gly
        675                 680                 685
```

```
Ile Gln Gly Asp Asp Glu Lys Gly Ile Ser Gly Val Lys Val Thr Leu
    690                 695                 700

Lys Asp Glu Asn Gly Asn Ile Ile Ser Thr Thr Thr Thr Asp Glu Asn
705                 710                 715                 720

Gly Lys Tyr Gln Phe Asp Asn Leu Asn Ser Gly Asn Tyr Ile Val His
                725                 730                 735

Phe Asp Lys Pro Ser Gly Met Thr Gln Thr Thr Thr Asp Ser Gly Asp
            740                 745                 750

Asp Asp Glu Gln Asp Ala Asp Gly Glu Glu Val His Val Thr Ile Thr
        755                 760                 765

Asp His Asp Asp Phe Ser Ile Asp Asn Gly Tyr Tyr Asp Asp Asp Ser
    770                 775                 780

Asp Ser Asp Ser Asp Ser Asp Ser Asp Ser Asp Asp Ser Asp Ser Asp
785                 790                 795                 800

Ser Asp Ser Asp Ser Asp Ser Asp Ser Asp Ser Asp Ser Asp Ser Asp
                805                 810                 815

Ser Asp Ser Asp Ser Asp Ser Asp Ser Asp Ser Asp Ser Asp Ser Asp
            820                 825                 830

Ser Asp Ser Asp Ser Asp Ser Gly Leu Asp Asn Ser Ser Asp Lys Asn
        835                 840                 845

Thr Lys Asp Lys Leu Pro Asp Thr Gly Ala Asn Glu Asp His Asp Ser
    850                 855                 860

Lys Gly Thr Leu Leu Gly Ala Leu Phe Ala Gly Leu Gly Ala Leu Leu
865                 870                 875                 880

Leu Gly Lys Arg Arg Lys Asn Arg Lys Asn Lys Asn
                885                 890


<210> SEQ ID NO 22
<211> LENGTH: 1973
<212> TYPE: PRT
<213> ORGANISM: Staphylococcus epidermidis

<400> SEQUENCE: 22

Met Lys Glu Asn Lys Arg Lys Asn Asn Leu Asp Lys Asn Asn Thr Arg
1               5                   10                  15

Phe Ser Ile Arg Lys Tyr Gln Gly Tyr Gly Ala Thr Ser Val Ala Ile
            20                  25                  30

Ile Gly Phe Ile Ile Ile Ser Cys Phe Ser Glu Ala Lys Ala Asp Ser
        35                  40                  45

Asp Lys His Glu Ile Lys Ser His Gln Gln Ser Met Thr Asn His Leu
    50                  55                  60

Thr Thr Leu Pro Ser Asp Asn Gln Glu Asn Thr Ser Asn Asn Glu Phe
65                  70                  75                  80

Asn Asn Arg Asn His Asp Ile Ser His Leu Ser Leu Asn Lys Ser Ile
                85                  90                  95

Gln Met Asp Glu Leu Lys Lys Leu Ile Lys Gln Tyr Lys Ala Ile Asn
            100                 105                 110

Leu Asn Asp Lys Thr Glu Glu Ser Ile Lys Leu Phe Gln Ser Asp Leu
        115                 120                 125

Val Gln Ala Glu Ser Leu Ile Asn Asn Pro Gln Ser Gln Gln His Val
    130                 135                 140

Asp Ala Phe Tyr His Lys Phe Leu Asn Ser Ala Gly Lys Leu Arg Lys
145                 150                 155                 160

Lys Glu Thr Val Ser Ile Lys His Glu Arg Ser Glu Ser Asn Thr Tyr
```

-continued

```
                165                 170                 175

Arg Leu Gly Asp Glu Val Arg Ser Gln Thr Phe Ser His Ile Arg His
            180                 185                 190

Lys Arg Asn Ala Val Ser Phe Arg Asn Ala Asp Gln Ser Asn Leu Ser
        195                 200                 205

Thr Asp Pro Leu Lys Ala Asn Glu Ile Asn Pro Glu Ile Gln Asn Gly
    210                 215                 220

Asn Phe Ser Gln Val Ser Gly Gly Pro Leu Pro Thr Ser Ser Lys Arg
225                 230                 235                 240

Leu Thr Val Val Thr Asn Val Asp Asn Trp His Ser Tyr Ser Thr Asp
                245                 250                 255

Pro Asn Pro Glu Tyr Pro Met Phe Tyr Thr Thr Thr Ala Val Asn Tyr
            260                 265                 270

Pro Asn Phe Met Ser Asn Gly Asn Ala Pro Tyr Gly Val Ile Leu Gly
        275                 280                 285

Arg Thr Thr Asp Gly Trp Asn Arg Asn Val Ile Asp Ser Lys Val Ala
    290                 295                 300

Gly Ile Tyr Gln Asp Ile Asp Val Val Pro Gly Ser Glu Leu Asn Val
305                 310                 315                 320

Asn Phe Ile Ser Thr Ser Pro Val Phe Ser Asp Gly Ala Ala Gly Ala
                325                 330                 335

Lys Leu Lys Ile Ser Asn Val Glu Gln Asn Arg Val Leu Phe Asp Ser
            340                 345                 350

Arg Leu Asn Gly Met Gly Pro Tyr Pro Thr Gly Lys Leu Ser Ala Met
        355                 360                 365

Val Asn Ile Pro Asn Asp Ile Asn Arg Val Arg Ile Ser Phe Leu Pro
    370                 375                 380

Val Ser Ser Thr Gly Arg Val Ser Val Gln Arg Ser Ser Arg Glu His
385                 390                 395                 400

Gly Phe Gly Asp Asn Ser Ser Tyr Tyr His Gly Gly Ser Val Ser Asp
                405                 410                 415

Val Arg Ile Asn Ser Gly Ser Tyr Val Val Ser Lys Val Thr Gln Arg
            420                 425                 430

Glu Tyr Thr Thr Arg Pro Asn Ser Ser Asn Asp Thr Phe Ala Arg Ala
        435                 440                 445

Thr Ile Asn Leu Ser Val Glu Asn Lys Gly His Asn Gln Ser Lys Asp
    450                 455                 460

Thr Tyr Tyr Glu Val Ile Leu Pro Gln Asn Ser Arg Leu Ile Ser Thr
465                 470                 475                 480

Arg Gly Gly Ser Gly Asn Tyr Asn Asn Ala Thr Asn Lys Leu Ser Ile
                485                 490                 495

Arg Leu Asp Asn Leu Asn Pro Gly Asp Arg Arg Asp Ile Ser Tyr Thr
            500                 505                 510

Val Asp Phe Glu Ser Ser Ser Pro Lys Leu Ile Asn Leu Asn Ala His
        515                 520                 525

Leu Leu Tyr Lys Thr Asn Ala Thr Phe Arg Gly Asn Asp Gly Gln Arg
    530                 535                 540

Thr Gly Asp Asn Ile Val Asp Leu Gln Ser Ile Ala Leu Leu Met Asn
545                 550                 555                 560

Lys Asp Val Leu Glu Thr Glu Leu Asn Glu Ile Asp Lys Phe Ile Arg
                565                 570                 575

Asp Leu Asn Glu Ala Asp Phe Thr Ile Asp Ser Trp Ser Ala Leu Gln
            580                 585                 590
```

```
Glu Lys Met Thr Glu Gly Gly Asn Ile Leu Asn Glu Gln Gln Asn Gln
        595                 600                 605

Val Ala Leu Glu Asn Gln Ala Ser Gln Glu Thr Ile Asn Asn Val Thr
    610                 615                 620

Gln Ser Leu Glu Ile Leu Lys Asn Asn Leu Lys Tyr Lys Thr Pro Ser
625                 630                 635                 640

Gln Pro Ile Ile Lys Ser Asn Asn Gln Ile Pro Asn Ile Thr Ile Ser
                645                 650                 655

Pro Ala Asp Lys Ala Asp Lys Leu Thr Ile Thr Tyr Gln Asn Thr Asp
            660                 665                 670

Asn Glu Ser Ala Ser Ile Ile Gly Asn Lys Leu Asn Asn Gln Trp Ser
        675                 680                 685

Leu Asn Asn Asn Ile Pro Gly Ile Glu Ile Asp Met Gln Thr Gly Leu
    690                 695                 700

Val Thr Ile Asp Tyr Lys Ala Val Tyr Pro Glu Ser Val Val Gly Ala
705                 710                 715                 720

Asn Asp Lys Thr Gly Asn Ser Asp Ala Ser Ala Glu Ser Arg Ile Thr
                725                 730                 735

Met Pro Arg Lys Glu Ala Thr Pro Leu Ser Pro Ile Val Glu Ala Asn
            740                 745                 750

Glu Glu Arg Val Asn Val Val Ile Ala Pro Asn Gly Glu Ala Thr Gln
        755                 760                 765

Ile Ala Ile Lys Tyr Arg Thr Pro Asp Gly Gln Glu Ala Thr Leu Val
    770                 775                 780

Ala Ser Lys Asn Gly Ser Ser Trp Thr Leu Asn Lys Gln Ile Asp Tyr
785                 790                 795                 800

Val Asn Ile Glu Glu Asn Ser Gly Lys Val Thr Ile Gly Tyr Gln Ala
                805                 810                 815

Val Gln Pro Glu Ser Glu Val Ile Ala Thr Glu Thr Lys Gly Asn Ser
            820                 825                 830

Asp Glu Ser Ala Glu Ser Arg Val Thr Met Pro Arg Lys Glu Ala Thr
        835                 840                 845

Pro His Ser Pro Ile Val Glu Ala Asn Glu Glu His Val Asn Val Thr
    850                 855                 860

Ile Ala Pro Asn Gly Glu Ala Thr Gln Ile Ala Ile Lys Tyr Arg Thr
865                 870                 875                 880

Pro Asp Gly Gln Glu Thr Thr Leu Ile Ala Ser Lys Asn Gly Ser Ser
                885                 890                 895

Trp Thr Leu Asn Lys Gln Ile Asp Tyr Val Asn Ile Glu Glu Asn Ser
            900                 905                 910

Gly Lys Val Thr Ile Gly Tyr Gln Ala Val Gln Leu Glu Ser Glu Val
        915                 920                 925

Ile Ala Thr Glu Thr Lys Gly Asn Ser Asp Ala Ser Ala Glu Ser Arg
    930                 935                 940

Ile Thr Met Leu Arg Lys Glu Ala Thr Pro His Ser Pro Ile Val Glu
945                 950                 955                 960

Ala Asn Glu Glu His Val Asn Val Thr Ile Ala Pro Asn Gly Glu Ala
                965                 970                 975

Thr Gln Ile Ala Ile Lys Tyr Arg Thr Pro Asp Gly Gln Glu Ala Thr
            980                 985                 990

Leu Val Ala Ser Lys Asn Glu Ser  Ser Trp Thr Leu Asn  Lys Gln Ile
        995                 1000                 1005
```

-continued

```
Asp His  Val Asn Ile Asp Glu  Asn Ser Gly Lys Val  Thr Ile Gly
    1010                 1015                 1020

Tyr Gln  Ala Val Gln Pro Glu  Ser Glu Ile Ile Ala  Thr Glu Thr
    1025                 1030                 1035

Lys Gly  Asn Ser Asp Ala Ser  Ala Glu Ser Arg Ile  Thr Met Pro
    1040                 1045                 1050

Arg Lys  Glu Ala Thr Pro Ile  Pro Pro Thr Leu Glu  Ala Ser Val
    1055                 1060                 1065

Gln Glu  Ala Ser Val Thr Val  Thr Pro Asn Glu Asn  Ala Thr Lys
    1070                 1075                 1080

Val Phe  Ile Lys Tyr Leu Asp  Ile Asn Asp Glu Ile  Ser Thr Ile
    1085                 1090                 1095

Ile Ala  Ser Lys Ile Asn Gln  Gln Trp Thr Leu Asn  Lys Asp Asn
    1100                 1105                 1110

Phe Gly  Ile Lys Ile Asn Pro  Leu Thr Gly Lys Val  Ile Ile Ser
    1115                 1120                 1125

Tyr Val  Ala Val Gln Pro Glu  Ser Asp Val Ile Ala  Ile Glu Ser
    1130                 1135                 1140

Gln Gly  Asn Ser Asp Leu Ser  Glu Glu Ser Arg Ile  Ile Met Pro
    1145                 1150                 1155

Thr Lys  Glu Glu Pro Pro Glu  Pro Pro Ile Leu Glu  Ser Asp Ser
    1160                 1165                 1170

Ile Glu  Ala Lys Val Asn Ile  Phe Pro Asn Asp Glu  Ala Thr Arg
    1175                 1180                 1185

Ile Val  Ile Met Tyr Thr Ser  Leu Glu Gly Gln Glu  Ala Thr Leu
    1190                 1195                 1200

Val Ala  Ser Lys Asn Glu Ser  Ser Trp Thr Leu Asn  Lys Gln Ile
    1205                 1210                 1215

Asp His  Val Asn Ile Asp Glu  Asn Ser Gly Lys Val  Thr Ile Gly
    1220                 1225                 1230

Tyr Gln  Ala Val Gln Pro Glu  Ser Glu Val Ile Ala  Thr Glu Thr
    1235                 1240                 1245

Lys Gly  Asn Ser Asp Ala Ser  Ala Glu Ser Arg Val  Thr Met Pro
    1250                 1255                 1260

Arg Lys  Glu Ala Thr Pro His  Ser Pro Ile Val Glu  Thr Asn Glu
    1265                 1270                 1275

Glu Arg  Val Asn Val Val Ile  Ala Pro Asn Gly Glu  Ala Thr Gln
    1280                 1285                 1290

Ile Ala  Ile Lys Tyr Arg Thr  Pro Asp Gly Gln Glu  Thr Thr Leu
    1295                 1300                 1305

Ile Ala  Ser Lys Asn Gly Ser  Ser Trp Thr Leu Asn  Lys Gln Ile
    1310                 1315                 1320

Asp His  Val Asn Ile Asp Glu  Asn Ser Gly Lys Val  Thr Ile Gly
    1325                 1330                 1335

Tyr Gln  Ala Val Gln Pro Glu  Ser Glu Ile Ile Ala  Thr Glu Thr
    1340                 1345                 1350

Lys Gly  Asn Ser Asp Ala Ser  Ala Glu Ser Arg Ile  Thr Met Pro
    1355                 1360                 1365

Arg Lys  Glu Ala Ile Pro His  Ser Pro Ile Val Glu  Ala Asn Glu
    1370                 1375                 1380

Glu His  Val Asn Val Thr Ile  Ala Pro Asn Gly Glu  Thr Thr Gln
    1385                 1390                 1395

Ile Ala  Val Lys Tyr Arg Thr  Pro Asp Gly Gln Glu  Ala Thr Leu
```

-continued

```
    1400                1405                1410

Ile Ala  Ser Lys Asn Glu Ser  Ser Trp Thr Leu Asn  Lys Gln Ile
    1415                1420                1425

Asp His  Val Asn Ile Asp Glu  Asn Ser Gly Lys Val  Thr Ile Gly
    1430                1435                1440

Tyr Gln  Ala Val Gln Pro Glu  Ser Glu Val Ile Ala  Thr Glu Thr
    1445                1450                1455

Lys Gly  Asn Ser Asp Ala Ser  Ala Glu Ser Arg Ile  Thr Met Pro
    1460                1465                1470

Val Lys  Glu Lys Thr Pro Ala  Pro Pro Ile Ser Ile  Ile Asn Glu
    1475                1480                1485

Ser Asn  Ala Ser Val Glu Ile  Ile Pro Gln Val Asn  Val Thr Gln
    1490                1495                1500

Leu Ser  Leu Gln Tyr Ile Asp  Ala Lys Gly Gln Gln  Gln Asn Leu
    1505                1510                1515

Ile Ala  Thr Leu Asn Gln Asn  Gln Trp Thr Leu Asn  Lys Asn Val
    1520                1525                1530

Ser His  Ile Thr Val Asp Lys  Asn Thr Gly Lys Val  Leu Ile Asn
    1535                1540                1545

Tyr Gln  Ala Val Tyr Pro Glu  Ser Glu Val Ile Ala  Arg Glu Ser
    1550                1555                1560

Lys Gly  Asn Ser Asp Ser Ser  Asn Val Ser Met Val  Ile Met Pro
    1565                1570                1575

Arg Lys  Thr Ala Thr Pro Lys  Pro Pro Ile Ile Lys  Val Asp Glu
    1580                1585                1590

Met Asn  Ala Ser Leu Ala Ile  Ile Pro Tyr Lys Asn  Asn Thr Ala
    1595                1600                1605

Ile Asn  Ile His Tyr Ile Asp  Lys Lys Gly Ile Lys  Ser Met Val
    1610                1615                1620

Thr Ala  Ile Lys Asn Asn Asp  Gln Trp Gln Leu Asp  Glu Lys Ile
    1625                1630                1635

Lys Tyr  Val Lys Ile Asp Ala  Lys Thr Gly Thr Val  Ile Ile Asn
    1640                1645                1650

Tyr Gln  Ile Val Gln Glu Asn  Ser Glu Ile Ile Ala  Thr Ala Ile
    1655                1660                1665

Asn Gly  Asn Ser Asp Lys Ser  Glu Glu Val Lys Val  Leu Met Pro
    1670                1675                1680

Ile Lys  Glu Phe Thr Pro Leu  Ala Pro Leu Leu Glu  Thr Asn Tyr
    1685                1690                1695

Lys Lys  Ala Thr Val Ser Ile  Leu Pro Gln Ser Asn  Ala Thr Lys
    1700                1705                1710

Leu Asp  Phe Lys Tyr Arg Asp  Lys Lys Gly Asp Ser  Lys Ile Ile
    1715                1720                1725

Ile Val  Lys Arg Phe Lys Asn  Ile Trp Lys Ala Asn  Glu Gln Ile
    1730                1735                1740

Ser Gly  Val Thr Ile Asn Pro  Glu Phe Gly Gln Val  Val Ile Asn
    1745                1750                1755

Tyr Gln  Ala Val Tyr Pro Glu  Ser Asp Ile Leu Ala  Ala Gln Tyr
    1760                1765                1770

Val Gly  Asn Ser Asp Ala Ser  Glu Trp Ala Lys Val  Lys Met Pro
    1775                1780                1785

Lys Lys  Glu Leu Ala Pro His  Ser Pro Ser Leu Ile  Tyr Asp Asn
    1790                1795                1800
```

-continued

```
Arg Asn  Asn Lys Ile Leu Ile  Ala Pro Asn Ser Asn  Ala Thr Glu
    1805                 1810                 1815

Met Glu  Leu Ser Tyr Val Asp  Lys Asn Asn Gln Ser  Leu Lys Val
    1820                 1825                 1830

Lys Ala  Leu Lys Ile Asn Asn  Arg Trp Lys Phe Asp  Ser Ser Val
    1835                 1840                 1845

Ser Asn  Ile Ser Ile Asn Pro  Asn Thr Gly Lys Ile  Val Leu Gln
    1850                 1855                 1860

Pro Gln  Phe Leu Leu Thr Asn  Ser Lys Ile Ile Val  Phe Ala Lys
    1865                 1870                 1875

Lys Gly  Asn Ser Asp Ala Ser  Ile Ser Val Ser Leu  Arg Val Pro
    1880                 1885                 1890

Ala Val  Lys Lys Ile Glu Leu  Glu Pro Met Phe Asn  Val Pro Val
    1895                 1900                 1905

Leu Val  Ser Leu Asn Lys Lys  Arg Ile Gln Phe Asp  Asp Cys Ser
    1910                 1915                 1920

Gly Val  Lys Asn Cys Leu Asn  Lys Gln Ile Ser Lys  Thr Gln Leu
    1925                 1930                 1935

Pro Asp  Thr Gly Tyr Ser Asp  Lys Ala Ser Lys Ser  Asn Ile Leu
    1940                 1945                 1950

Ser Val  Leu Leu Leu Gly Phe  Gly Phe Leu Ser Tyr  Ser Arg Lys
    1955                 1960                 1965

Arg Lys  Glu Lys Gln
    1970
```

<210> SEQ ID NO 23
<211> LENGTH: 10203
<212> TYPE: PRT
<213> ORGANISM: Staphylococcus epidermidis

<400> SEQUENCE: 23

```
Met Lys Ser Lys Pro Lys Leu Asn Gly Arg Asn Ile Cys Ser Phe Leu
1               5                   10                  15

Leu Ser Lys Cys Met Ser Tyr Ser Leu Ser Lys Leu Ser Thr Leu Lys
            20                  25                  30

Thr Tyr Asn Phe Gln Ile Thr Ser Asn Asn Lys Glu Lys Thr Ser Arg
        35                  40                  45

Ile Gly Val Ala Ile Ala Leu Asn Asn Arg Asp Lys Leu Gln Lys Phe
    50                  55                  60

Ser Ile Arg Lys Tyr Ala Ile Gly Thr Phe Ser Thr Val Ile Ala Thr
65                  70                  75                  80

Leu Val Phe Met Gly Ile Asn Thr Asn His Ala Ser Ala Asp Glu Leu
                85                  90                  95

Asn Gln Asn Gln Lys Leu Ile Lys Gln Leu Asn Gln Thr Asp Asp Asp
            100                 105                 110

Asp Ser Asn Thr His Ser Gln Glu Ile Glu Asn Asn Lys Gln Asn Ser
        115                 120                 125

Ser Gly Lys Thr Glu Ser Leu Arg Ser Ser Thr Ser Gln Asn Gln Ala
    130                 135                 140

Asn Ala Arg Leu Ser Asp Gln Phe Lys Asp Thr Asn Glu Thr Ser Gln
145                 150                 155                 160

Gln Leu Pro Thr Asn Val Ser Asp Asp Ser Ile Asn Gln Ser His Ser
                165                 170                 175

Glu Ala Asn Met Asn Asn Glu Pro Leu Lys Val Asp Asn Ser Thr Met
```

```
            180                 185                 190

Gln Ala His Ser Lys Ile Val Ser Asp Ser Asp Gly Asn Ala Ser Glu
        195                 200                 205

Asn Lys His His Lys Leu Thr Glu Asn Val Leu Ala Glu Ser Arg Ala
    210                 215                 220

Ser Lys Asn Asp Lys Glu Lys Glu Asn Leu Gln Glu Lys Asp Lys Ser
225                 230                 235                 240

Gln Gln Val His Pro Pro Leu Asp Lys Asn Ala Leu Gln Ala Phe Phe
                245                 250                 255

Asp Ala Ser Tyr His Asn Tyr Arg Met Ile Asp Arg Asp Arg Ala Asp
            260                 265                 270

Ala Thr Glu Tyr Gln Lys Val Lys Ser Thr Phe Asp Tyr Val Asn Asp
        275                 280                 285

Leu Leu Gly Asn Asn Gln Asn Ile Pro Ser Glu Gln Leu Val Ser Ala
    290                 295                 300

Tyr Gln Gln Leu Glu Lys Ala Leu Glu Leu Ala Arg Thr Leu Pro Gln
305                 310                 315                 320

Gln Ser Thr Thr Glu Lys Arg Gly Arg Arg Ser Thr Arg Ser Val Val
                325                 330                 335

Glu Asn Arg Ser Ser Arg Ser Asp Tyr Leu Asp Ala Arg Thr Glu Tyr
            340                 345                 350

Tyr Val Ser Lys Asp Asp Asp Asp Ser Gly Phe Pro Pro Gly Thr Phe
        355                 360                 365

Phe His Ala Ser Asn Arg Arg Trp Pro Tyr Asn Leu Pro Arg Ser Arg
    370                 375                 380

Asn Ile Leu Arg Ala Ser Asp Val Gln Gly Asn Ala Tyr Ile Thr Thr
385                 390                 395                 400

Lys Arg Leu Lys Asp Gly Tyr Gln Trp Asp Ile Leu Phe Asn Ser Asn
                405                 410                 415

His Lys Gly His Glu Tyr Met Tyr Tyr Trp Phe Gly Leu Pro Ser Asp
            420                 425                 430

Gln Thr Pro Thr Gly Pro Val Thr Phe Thr Ile Ile Asn Arg Asp Gly
        435                 440                 445

Ser Ser Thr Ser Thr Gly Gly Val Gly Phe Gly Ser Gly Ala Pro Leu
    450                 455                 460

Pro Gln Phe Trp Arg Ser Ala Gly Ala Ile Asn Ser Ser Val Ala Asn
465                 470                 475                 480

Asp Phe Lys His Gly Ser Ala Thr Asn Tyr Ala Phe Tyr Asp Gly Val
                485                 490                 495

Asn Asn Phe Ser Asp Phe Ala Arg Gly Gly Glu Leu Tyr Phe Asp Arg
            500                 505                 510

Glu Gly Ala Thr Gln Thr Asn Lys Tyr Tyr Gly Asp Glu Asn Phe Ala
        515                 520                 525

Leu Leu Asn Ser Glu Lys Pro Asp Gln Ile Arg Gly Leu Asp Thr Ile
    530                 535                 540

Tyr Ser Phe Lys Gly Ser Gly Asp Val Ser Tyr Arg Ile Ser Phe Lys
545                 550                 555                 560

Thr Gln Gly Ala Pro Thr Ala Arg Leu Tyr Tyr Ala Ala Gly Ala Arg
                565                 570                 575

Ser Gly Glu Tyr Lys Gln Ala Thr Asn Tyr Asn Gln Leu Tyr Val Glu
            580                 585                 590

Pro Tyr Lys Asn Tyr Arg Asn Arg Val Gln Ser Asn Val Gln Val Lys
        595                 600                 605
```

-continued

```
Asn Arg Thr Leu His Leu Lys Arg Thr Ile Arg Gln Phe Asp Pro Thr
    610                 615                 620

Leu Gln Arg Thr Thr Asp Val Pro Ile Leu Asp Ser Asp Gly Ser Gly
625                 630                 635                 640

Ser Ile Asp Ser Val Tyr Asp Pro Leu Ser Tyr Val Lys Asn Val Thr
                645                 650                 655

Gly Thr Val Leu Gly Ile Tyr Pro Ser Tyr Leu Pro Tyr Asn Gln Glu
            660                 665                 670

Arg Trp Gln Gly Ala Asn Ala Met Asn Ala Tyr Gln Ile Glu Glu Leu
        675                 680                 685

Phe Ser Gln Glu Asn Leu Gln Asn Ala Ala Arg Ser Gly Arg Pro Ile
    690                 695                 700

Gln Phe Leu Val Gly Phe Asp Val Glu Asp Ser His His Asn Pro Glu
705                 710                 715                 720

Thr Leu Leu Pro Val Asn Leu Tyr Val Lys Pro Glu Leu Lys His Thr
                725                 730                 735

Ile Glu Leu Tyr His Asp Asn Glu Lys Gln Asn Arg Lys Glu Phe Ser
            740                 745                 750

Val Ser Lys Arg Ala Gly His Gly Val Phe Gln Ile Met Ser Gly Thr
        755                 760                 765

Leu His Asn Thr Val Gly Ser Gly Ile Leu Pro Tyr Gln Gln Glu Ile
    770                 775                 780

Arg Ile Lys Leu Thr Ser Asn Glu Pro Ile Lys Asp Ser Glu Trp Ser
785                 790                 795                 800

Ile Thr Gly Tyr Pro Asn Thr Leu Thr Leu Gln Asn Ala Val Gly Arg
                805                 810                 815

Thr Asn Asn Ala Thr Glu Lys Asn Leu Ala Leu Val Gly His Ile Asp
            820                 825                 830

Pro Gly Asn Tyr Phe Ile Thr Val Lys Phe Gly Asp Lys Val Glu Gln
        835                 840                 845

Phe Glu Ile Arg Ser Lys Pro Thr Pro Pro Arg Ile Ile Thr Thr Ala
    850                 855                 860

Asn Glu Leu Arg Gly Asn Ser Asn His Lys Pro Glu Ile Arg Val Thr
865                 870                 875                 880

Asp Ile Pro Asn Asp Thr Thr Ala Lys Ile Lys Leu Val Met Gly Gly
                885                 890                 895

Thr Asp Gly Asp His Asp Pro Glu Ile Asn Pro Tyr Thr Val Pro Glu
            900                 905                 910

Asn Tyr Thr Val Val Ala Glu Ala Tyr His Asp Asn Asp Pro Ser Lys
        915                 920                 925

Asn Gly Val Leu Thr Phe Arg Ser Ser Asp Tyr Leu Lys Asp Leu Pro
    930                 935                 940

Leu Ser Gly Glu Leu Lys Ala Ile Val Tyr Tyr Asn Gln Tyr Val Gln
945                 950                 955                 960

Ser Asn Phe Ser Asn Ser Val Pro Phe Ser Ser Asp Thr Thr Pro Pro
                965                 970                 975

Thr Ile Asn Glu Pro Ala Gly Leu Val His Lys Tyr Tyr Arg Gly Asp
            980                 985                 990

His Val Glu Ile Thr Leu Pro Val  Thr Asp Asn Thr Gly  Gly Ser Gly
        995                 1000                1005

Leu Arg  Asp Val Asn Val Asn  Leu Pro Gln Gly Trp  Thr Lys Thr
    1010                 1015                 1020
```

-continued

```
Phe Thr  Ile Asn Pro Asn Asn  Asn Thr Glu Gly Thr  Leu Lys Leu
    1025                 1030                 1035

Ile Gly  Asn Ile Pro Ser Asn  Glu Ala Tyr Asn Thr  Thr Tyr His
    1040                 1045                 1050

Phe Asn  Ile Thr Ala Thr Asp  Asn Ser Gly Asn Thr  Thr Asn Pro
    1055                 1060                 1065

Ala Lys  Thr Phe Ile Leu Asn  Val Gly Lys Leu Ala  Asp Asp Leu
    1070                 1075                 1080

Asn Pro  Val Gly Leu Ser Arg  Asp Gln Leu Gln Leu  Val Thr Asp
    1085                 1090                 1095

Pro Ser  Ser Leu Ser Asn Ser  Glu Arg Glu Glu Val  Lys Arg Lys
    1100                 1105                 1110

Ile Ser  Glu Ala Asn Ala Asn  Ile Arg Ser Tyr Leu  Leu Gln Asn
    1115                 1120                 1125

Asn Pro  Ile Leu Ala Gly Val  Asn Gly Asp Val Thr  Phe Tyr Tyr
    1130                 1135                 1140

Arg Asp  Gly Ser Val Asp Val  Ile Asp Ala Glu Asn  Val Ile Thr
    1145                 1150                 1155

Tyr Glu  Pro Glu Arg Lys Ser  Ile Phe Ser Glu Asn  Gly Asn Thr
    1160                 1165                 1170

Asn Lys  Lys Glu Ala Val Ile  Thr Ile Ala Arg Gly  Gln Asn Tyr
    1175                 1180                 1185

Thr Ile  Gly Pro Asn Leu Arg  Lys Tyr Phe Ser Leu  Ser Asn Gly
    1190                 1195                 1200

Ser Asp  Leu Pro Asn Arg Asp  Phe Thr Ser Ile Ser  Ala Ile Gly
    1205                 1210                 1215

Ser Leu  Pro Ser Ser Ser Glu  Ile Ser Arg Leu Asn  Val Gly Asn
    1220                 1225                 1230

Tyr Asn  Tyr Arg Val Asn Ala  Lys Asn Ala Tyr His  Lys Thr Gln
    1235                 1240                 1245

Gln Glu  Leu Asn Leu Lys Leu  Lys Ile Val Glu Val  Asn Ala Pro
    1250                 1255                 1260

Thr Gly  Asn Asn Arg Val Tyr  Arg Val Ser Thr Tyr  Asn Leu Thr
    1265                 1270                 1275

Asn Asp  Glu Ile Asn Lys Ile  Lys Gln Ala Phe Lys  Ala Ala Asn
    1280                 1285                 1290

Ser Gly  Leu Asn Leu Asn Asp  Asn Asp Ile Thr Val  Ser Asn Asn
    1295                 1300                 1305

Phe Asp  His Arg Asn Val Ser  Ser Val Thr Val Thr  Ile Arg Lys
    1310                 1315                 1320

Gly Asp  Leu Ile Lys Glu Phe  Ser Ser Asn Leu Asn  Asn Met Asn
    1325                 1330                 1335

Phe Leu  Arg Trp Val Asn Ile  Arg Asp Asp Tyr Thr  Ile Ser Trp
    1340                 1345                 1350

Thr Ser  Ser Lys Ile Gln Gly  Arg Asn Thr Asp Gly  Gly Leu Glu
    1355                 1360                 1365

Trp Ser  Pro Asp His Lys Ser  Leu Ile Tyr Lys Tyr  Asp Ala Thr
    1370                 1375                 1380

Leu Gly  Arg Gln Ile Asn Thr  Asn Asp Val Leu Thr  Leu Leu Gln
    1385                 1390                 1395

Ala Thr  Ala Lys Asn Ser Asn  Leu Arg Ser Asn Ile  Asn Ser Asn
    1400                 1405                 1410

Glu Lys  Gln Leu Ala Glu Arg  Gly Ser Asn Gly Tyr  Ser Lys Ser
```

-continued

```
    1415                1420                1425

Ile Ile  Arg Asp Asp Gly Glu  Lys Ser Tyr Leu Leu  Asn Ser Asn
    1430                1435                1440

Pro Ile  Gln Val Leu Asp Leu  Val Glu Pro Asp Asn  Gly Tyr Gly
    1445                1450                1455

Gly Arg  Gln Val Ser His Ser  Asn Val Ile Tyr Asn  Glu Lys Asn
    1460                1465                1470

Ser Ser  Ile Val Asn Gly Gln  Val Pro Glu Ala Asn  Gly Ala Ser
    1475                1480                1485

Ala Phe  Asn Ile Asp Lys Val  Val Lys Ala Asn Ala  Ala Asn Asn
    1490                1495                1500

Gly Ile  Met Gly Val Ile Tyr  Lys Ala Gln Leu Tyr  Leu Ala Pro
    1505                1510                1515

Tyr Ser  Pro Lys Gly Tyr Ile  Glu Lys Leu Gly Gln  Asn Leu Ser
    1520                1525                1530

Asn Thr  Asn Asn Val Ile Asn  Val Tyr Phe Val Pro  Ser Asp Lys
    1535                1540                1545

Val Asn  Pro Ser Ile Thr Val  Gly Asn Tyr Asp His  His Thr Val
    1550                1555                1560

Tyr Ser  Gly Glu Thr Phe Lys  Asn Thr Ile Asn Val  Asn Asp Asn
    1565                1570                1575

Tyr Gly  Leu Asn Thr Val Ala  Ser Thr Ser Asp Ser  Ala Ile Thr
    1580                1585                1590

Met Thr  Arg Asn Asn Asn Glu  Leu Val Gly Gln Ala  Pro Asn Val
    1595                1600                1605

Thr Asn  Ser Thr Asn Lys Ile  Val Lys Val Lys Ala  Thr Asp Lys
    1610                1615                1620

Ser Gly  Asn Glu Ser Ile Val  Ser Phe Thr Val Asn  Ile Lys Pro
    1625                1630                1635

Leu Asn  Glu Lys Tyr Arg Ile  Thr Thr Ser Ser Ser  Asn Gln Thr
    1640                1645                1650

Pro Val  Arg Ile Ser Asn Ile  Gln Asn Asn Ala Asn  Leu Ser Ile
    1655                1660                1665

Glu Asp  Gln Asn Arg Val Lys  Ser Ser Leu Ser Met  Thr Lys Ile
    1670                1675                1680

Leu Gly  Thr Arg Asn Tyr Val  Asn Glu Ser Asn Asn  Asp Val Arg
    1685                1690                1695

Ser Gln  Val Val Ser Lys Val  Asn Arg Ser Gly Asn  Asn Ala Thr
    1700                1705                1710

Val Asn  Val Thr Thr Thr Phe  Ser Asp Gly Thr Thr  Asn Thr Ile
    1715                1720                1725

Thr Val  Pro Val Lys His Val  Leu Leu Glu Val Val  Pro Thr Thr
    1730                1735                1740

Arg Thr  Thr Val Arg Gly Gln  Gln Phe Pro Thr Gly  Lys Gly Thr
    1745                1750                1755

Ser Pro  Asn Asp Phe Phe Ser  Leu Arg Thr Gly Gly  Pro Val Asp
    1760                1765                1770

Ala Arg  Ile Val Trp Val Asn  Asn Gln Gly Pro Asp  Ile Asn Ser
    1775                1780                1785

Asn Gln  Ile Gly Arg Asp Leu  Thr Leu His Ala Glu  Ile Phe Phe
    1790                1795                1800

Asp Gly  Glu Thr Thr Pro Ile  Arg Lys Asp Thr Thr  Tyr Lys Leu
    1805                1810                1815
```

```
Ser Gln  Ser Ile Pro Lys Gln  Ile Tyr Glu Thr Thr  Ile Asn Gly
    1820                 1825                 1830

Arg Phe  Asn Ser Ser Gly Asp  Ala Tyr Pro Gly Asn  Phe Val Gln
    1835                 1840                 1845

Ala Val  Asn Gln Tyr Trp Pro  Glu His Met Asp Phe  Arg Trp Ala
    1850                 1855                 1860

Gln Gly  Ser Gly Thr Pro Ser  Ser Arg Asn Ala Gly  Ser Phe Thr
    1865                 1870                 1875

Lys Thr  Val Thr Val Val Tyr  Gln Asn Gly Gln Thr  Glu Asn Val
    1880                 1885                 1890

Asn Val  Leu Phe Lys Val Lys  Pro Asn Lys Pro Val  Ile Asp Ser
    1895                 1900                 1905

Asn Ser  Val Ile Ser Lys Gly  Gln Leu Asn Gly Gln  Gln Ile Leu
    1910                 1915                 1920

Val Arg  Asn Val Pro Gln Asn  Ala Gln Val Thr Leu  Tyr Gln Ser
    1925                 1930                 1935

Asn Gly  Thr Val Ile Pro Asn  Thr Asn Thr Thr Ile  Asp Ser Asn
    1940                 1945                 1950

Gly Ile  Ala Thr Val Thr Ile  Gln Gly Thr Leu Pro  Thr Gly Asn
    1955                 1960                 1965

Ile Thr  Ala Lys Thr Ser Met  Thr Asn Asn Val Thr  Tyr Thr Lys
    1970                 1975                 1980

Gln Asn  Ser Ser Gly Ile Ala  Ser Asn Thr Thr Glu  Asp Ile Ser
    1985                 1990                 1995

Val Phe  Ser Glu Asn Ser Asp  Gln Val Asn Val Thr  Ala Gly Met
    2000                 2005                 2010

Gln Ala  Lys Asn Asp Gly Ile  Lys Ile Ile Lys Gly  Thr Asn Tyr
    2015                 2020                 2025

Asn Phe  Asn Asp Phe Asn Ser  Phe Ile Ser Asn Ile  Pro Ala His
    2030                 2035                 2040

Ser Thr  Leu Thr Trp Asn Glu  Glu Pro Asn Ser Trp  Lys Asn Asn
    2045                 2050                 2055

Ile Gly  Thr Thr Thr Lys Thr  Val Thr Val Thr Leu  Pro Asn His
    2060                 2065                 2070

Gln Gly  Thr Arg Thr Val Asp  Ile Pro Ile Thr Ile  Tyr Pro Thr
    2075                 2080                 2085

Val Thr  Ala Lys Asn Pro Val  Arg Asp Gln Lys Gly  Arg Asn Leu
    2090                 2095                 2100

Thr Asn  Gly Thr Asp Val Tyr  Asn Tyr Ile Ile Phe  Glu Asn Asn
    2105                 2110                 2115

Asn Arg  Leu Gly Gly Thr Ala  Ser Trp Lys Asp Asn  Arg Gln Pro
    2120                 2125                 2130

Asp Lys  Asn Ile Ala Gly Val  Gln Asn Leu Ile Ala  Leu Val Asn
    2135                 2140                 2145

Tyr Pro  Gly Ile Ser Thr Pro  Leu Glu Val Pro Val  Lys Val Trp
    2150                 2155                 2160

Val Tyr  Asn Phe Asp Phe Thr  Gln Pro Ile Tyr Lys  Ile Gln Val
    2165                 2170                 2175

Gly Asp  Thr Phe Pro Lys Gly  Thr Trp Ala Gly Tyr  Tyr Lys His
    2180                 2185                 2190

Leu Glu  Asn Gly Glu Gly Leu  Pro Ile Asp Gly Trp  Lys Phe Tyr
    2195                 2200                 2205
```

-continued

```
Trp Asn  Gln Gln Ser Thr Gly  Thr Thr Ser Asp Gln  Trp Gln Ser
    2210                 2215                 2220

Leu Ala  Tyr Thr Arg Thr Pro  Phe Val Lys Thr Gly  Thr Tyr Asp
    2225                 2230                 2235

Val Val  Asn Pro Ser Asn Trp  Gly Val Trp Gln Thr  Ser Gln Ser
    2240                 2245                 2250

Ala Lys  Phe Ile Val Thr Asn  Ala Lys Pro Asn Gln  Pro Thr Ile
    2255                 2260                 2265

Thr Gln  Ser Lys Thr Gly Asp  Val Thr Val Thr Pro  Gly Ala Val
    2270                 2275                 2280

Arg Asn  Ile Leu Ile Ser Gly  Thr Asn Asp Tyr Ile  Gln Ala Ser
    2285                 2290                 2295

Ala Asp  Lys Ile Val Ile Asn  Lys Asn Gly Asn Lys  Leu Thr Thr
    2300                 2305                 2310

Phe Val  Lys Asn Asn Asp Gly  Arg Trp Thr Val Glu  Thr Gly Ser
    2315                 2320                 2325

Pro Asp  Ile Asn Gly Ile Gly  Pro Thr Asn Asn Gly  Thr Ala Ile
    2330                 2335                 2340

Ser Leu  Ser Arg Leu Ala Val  Arg Pro Gly Asp Ser  Ile Glu Ala
    2345                 2350                 2355

Ile Ala  Thr Glu Gly Ser Gly  Glu Thr Ile Ser Thr  Ser Ala Thr
    2360                 2365                 2370

Ser Glu  Ile Tyr Ile Val Lys  Ala Pro Gln Pro Glu  Gln Val Ala
    2375                 2380                 2385

Thr His  Thr Tyr Asp Asn Gly  Thr Phe Asp Ile Leu  Pro Asp Asn
    2390                 2395                 2400

Ser Arg  Asn Ser Leu Asn Pro  Thr Glu Arg Val Glu  Ile Asn Tyr
    2405                 2410                 2415

Thr Glu  Lys Leu Asn Gly Asn  Glu Thr Gln Lys Ser  Phe Thr Ile
    2420                 2425                 2430

Thr Lys  Asn Asn Asn Gly Lys  Trp Thr Ile Asn Asn  Lys Pro Asn
    2435                 2440                 2445

Tyr Val  Glu Phe Asn Gln Asp  Asn Gly Lys Val Val  Phe Ser Ala
    2450                 2455                 2460

Asn Thr  Ile Lys Pro Asn Ser  Gln Ile Thr Ile Thr  Pro Lys Ala
    2465                 2470                 2475

Gly Gln  Gly Asn Thr Glu Asn  Thr Asn Pro Thr Val  Ile Gln Ala
    2480                 2485                 2490

Pro Ala  Gln His Thr Leu Thr  Ile Asn Glu Ile Val  Lys Glu Gln
    2495                 2500                 2505

Gly Gln  Asn Val Thr Asn Asp  Asp Ile Asn Asn Ala  Val Gln Val
    2510                 2515                 2520

Pro Asn  Lys Asn Arg Val Ala  Ile Lys Gln Gly Asn  Ala Leu Pro
    2525                 2530                 2535

Thr Asn  Leu Ala Gly Gly Ser  Thr Ser His Ile Pro  Val Val Ile
    2540                 2545                 2550

Tyr Tyr  Ser Asp Gly Ser Ser  Glu Glu Ala Thr Glu  Thr Val Arg
    2555                 2560                 2565

Thr Lys  Val Asn Lys Thr Glu  Leu Ile Asn Ala Arg  Arg Arg Leu
    2570                 2575                 2580

Asp Glu  Glu Ile Ser Lys Glu  Asn Lys Thr Pro Ser  Ser Ile Arg
    2585                 2590                 2595

Asn Phe  Asp Gln Ala Met Asn  Arg Ala Gln Ser Gln  Ile Asn Thr
```

-continued

```
    2600                2605                2610

Ala Lys  Ser Asp Ala Asp Gln  Val Ile Gly Thr Glu  Phe Ala Thr
    2615                2620                2625

Pro Gln  Gln Val Asn Ser Ala  Leu Ser Lys Val Gln  Ala Ala Gln
    2630                2635                2640

Asn Lys  Ile Asn Glu Ala Lys  Ala Leu Leu Gln Asn  Lys Ala Asp
    2645                2650                2655

Asn Ser  Gln Leu Val Arg Ala  Lys Glu Gln Leu Gln  Gln Ser Ile
    2660                2665                2670

Gln Pro  Ala Ala Ser Thr Asp  Gly Met Thr Gln Asp  Ser Thr Arg
    2675                2680                2685

Asn Tyr  Lys Asn Lys Arg Gln  Ala Ala Glu Gln Ala  Ile Gln His
    2690                2695                2700

Ala Asn  Ser Val Ile Asn Asn  Gly Asp Ala Thr Ser  Gln Gln Ile
    2705                2710                2715

Asn Asp  Ala Lys Asn Thr Val  Glu Gln Ala Gln Arg  Asp Tyr Val
    2720                2725                2730

Glu Ala  Lys Ser Asn Leu Arg  Ala Asp Lys Ser Gln  Leu Gln Ser
    2735                2740                2745

Ala Tyr  Asp Thr Leu Asn Arg  Asp Val Leu Thr Asn  Asp Lys Lys
    2750                2755                2760

Pro Ala  Ser Val Arg Arg Tyr  Asn Glu Ala Ile Ser  Asn Ile Arg
    2765                2770                2775

Lys Glu  Leu Asp Thr Ala Lys  Ala Asp Ala Ser Ser  Thr Leu Arg
    2780                2785                2790

Asn Thr  Asn Pro Ser Val Glu  Gln Val Arg Asp Ala  Leu Asn Lys
    2795                2800                2805

Ile Asn  Thr Val Gln Pro Lys  Val Asn Gln Ala Ile  Ala Leu Leu
    2810                2815                2820

Gln Pro  Lys Glu Asn Asn Ser  Glu Leu Val Gln Ala  Lys Lys Arg
    2825                2830                2835

Leu Gln  Asp Ala Val Asn Asp  Ile Pro Gln Thr Gln  Gly Met Thr
    2840                2845                2850

Gln Gln  Thr Ile Asn Asn Tyr  Asn Asp Lys Gln Arg  Glu Ala Glu
    2855                2860                2865

Arg Ala  Leu Thr Ser Ala Gln  Arg Val Ile Asp Asn  Gly Asp Ala
    2870                2875                2880

Thr Thr  Gln Glu Ile Thr Ser  Glu Lys Ser Lys Val  Glu Gln Ala
    2885                2890                2895

Met Gln  Ala Leu Thr Asn Ala  Lys Ser Asn Leu Arg  Ala Asp Lys
    2900                2905                2910

Asn Glu  Leu Gln Thr Ala Tyr  Asn Lys Leu Ile Glu  Asn Val Ser
    2915                2920                2925

Thr Asn  Gly Lys Lys Pro Ala  Ser Ile Arg Gln Tyr  Glu Thr Ala
    2930                2935                2940

Lys Ala  Arg Ile Gln Asn Gln  Ile Asn Asp Ala Lys  Asn Glu Ala
    2945                2950                2955

Glu Arg  Ile Leu Gly Asn Asp  Asn Pro Gln Val Ser  Gln Val Thr
    2960                2965                2970

Gln Ala  Leu Asn Lys Ile Lys  Ala Ile Gln Pro Lys  Leu Thr Glu
    2975                2980                2985

Ala Ile  Asn Met Leu Gln Asn  Lys Glu Asn Asn Thr  Glu Leu Val
    2990                2995                3000
```

```
Asn Ala  Lys Asn Arg Leu Glu  Asn Ala Val Asn Asp  Thr Asp Pro
    3005                 3010                 3015

Thr His  Gly Met Thr Gln Glu  Thr Ile Asn Asn Tyr  Asn Ala Lys
    3020                 3025                 3030

Lys Arg  Glu Ala Gln Asn Glu  Ile Gln Lys Ala Asn  Met Ile Ile
    3035                 3040                 3045

Asn Asn  Gly Asp Ala Thr Ala  Gln Asp Ile Ser Ser  Glu Lys Ser
    3050                 3055                 3060

Lys Val  Glu Gln Val Leu Gln  Ala Leu Gln Asn Ala  Lys Asn Asp
    3065                 3070                 3075

Leu Arg  Ala Asp Lys Arg Glu  Leu Gln Thr Ala Tyr  Asn Lys Leu
    3080                 3085                 3090

Ile Gln  Asn Val Asn Thr Asn  Gly Lys Lys Pro Ser  Ser Ile Gln
    3095                 3100                 3105

Asn Tyr  Lys Ser Ala Arg Arg  Asn Ile Glu Asn Gln  Tyr Asn Thr
    3110                 3115                 3120

Ala Lys  Asn Glu Ala His Asn  Val Leu Glu Asn Thr  Asn Pro Thr
    3125                 3130                 3135

Val Asn  Ala Val Glu Asp Ala  Leu Arg Lys Ile Asn  Ala Ile Gln
    3140                 3145                 3150

Pro Glu  Val Thr Lys Ala Ile  Asn Ile Leu Gln Asp  Lys Glu Asp
    3155                 3160                 3165

Asn Ser  Glu Leu Val Arg Ala  Lys Glu Lys Leu Asp  Gln Ala Ile
    3170                 3175                 3180

Asn Ser  Gln Pro Ser Leu Asn  Gly Met Thr Gln Glu  Ser Ile Asn
    3185                 3190                 3195

Asn Tyr  Thr Thr Lys Arg Arg  Glu Ala Gln Asn Ile  Ala Ser Ser
    3200                 3205                 3210

Ala Asp  Thr Ile Ile Asn Asn  Gly Asp Ala Ser Ile  Glu Gln Ile
    3215                 3220                 3225

Thr Glu  Asn Lys Ile Arg Val  Glu Glu Ala Thr Asn  Ala Leu Asn
    3230                 3235                 3240

Glu Ala  Lys Gln His Leu Thr  Ala Asp Thr Thr Ser  Leu Lys Thr
    3245                 3250                 3255

Glu Val  Arg Lys Leu Ser Arg  Arg Gly Asp Thr Asn  Asn Lys Lys
    3260                 3265                 3270

Pro Ser  Ser Val Ser Ala Tyr  Asn Asn Thr Ile His  Ser Leu Gln
    3275                 3280                 3285

Ser Glu  Ile Thr Gln Thr Glu  Asn Arg Ala Asn Thr  Ile Ile Asn
    3290                 3295                 3300

Lys Pro  Ile Arg Ser Val Glu  Glu Val Asn Asn Ala  Leu His Glu
    3305                 3310                 3315

Val Asn  Gln Leu Asn Gln Arg  Leu Thr Asp Thr Ile  Asn Leu Leu
    3320                 3325                 3330

Gln Pro  Leu Ala Asn Lys Glu  Ser Leu Lys Glu Ala  Arg Asn Arg
    3335                 3340                 3345

Leu Glu  Ser Lys Ile Asn Glu  Thr Val Gln Thr Asp  Gly Met Thr
    3350                 3355                 3360

Gln Gln  Ser Val Glu Asn Tyr  Lys Gln Ala Lys Ile  Lys Ala Gln
    3365                 3370                 3375

Asn Glu  Ser Ser Ile Ala Gln  Thr Leu Ile Asn Asn  Gly Asp Ala
    3380                 3385                 3390
```

-continued

```
Ser Asp  Gln Glu Val Ser Thr  Glu Ile Glu Lys Leu  Asn Gln Lys
    3395                 3400                 3405

Leu Ser  Glu Leu Thr Asn Ser  Ile Asn His Leu Thr  Val Asn Lys
    3410                 3415                 3420

Glu Pro  Leu Glu Thr Ala Lys  Asn Gln Leu Gln Ala  Asn Ile Asp
    3425                 3430                 3435

Gln Lys  Pro Ser Thr Asp Gly  Met Thr Gln Gln Ser  Val Gln Ser
    3440                 3445                 3450

Tyr Glu  Arg Lys Leu Gln Glu  Ala Lys Asp Lys Ile  Asn Ser Ile
    3455                 3460                 3465

Asn Asn  Val Leu Ala Asn Asn  Pro Asp Val Asn Ala  Ile Arg Thr
    3470                 3475                 3480

Asn Lys  Val Glu Thr Glu Gln  Ile Asn Asn Glu Leu  Thr Gln Ala
    3485                 3490                 3495

Lys Gln  Gly Leu Thr Val Asp  Lys Gln Pro Leu Ile  Asn Ala Lys
    3500                 3505                 3510

Thr Ala  Leu Gln Gln Ser Leu  Asp Asn Gln Pro Ser  Thr Thr Gly
    3515                 3520                 3525

Met Thr  Glu Ala Thr Ile Gln  Asn Tyr Asn Ala Lys  Arg Gln Lys
    3530                 3535                 3540

Ala Glu  Gln Val Ile Gln Asn  Ala Asn Lys Ile Ile  Glu Asn Ala
    3545                 3550                 3555

Gln Pro  Ser Val Gln Gln Val  Ser Asp Glu Lys Ser  Lys Val Glu
    3560                 3565                 3570

Gln Ala  Leu Ser Glu Leu Asn  Asn Ala Lys Ser Ala  Leu Arg Ala
    3575                 3580                 3585

Asp Lys  Gln Glu Leu Gln Gln  Ala Tyr Asn Gln Leu  Ile Gln Pro
    3590                 3595                 3600

Thr Asp  Leu Asn Asn Lys Lys  Pro Ala Ser Ile Thr  Ala Tyr Asn
    3605                 3610                 3615

Gln Arg  Tyr Gln Gln Phe Ser  Asn Glu Leu Asn Ser  Thr Lys Thr
    3620                 3625                 3630

Asn Thr  Asp Arg Ile Leu Lys  Glu Gln Asn Pro Ser  Val Ala Asp
    3635                 3640                 3645

Val Asn  Asn Ala Leu Asn Lys  Val Arg Glu Val Gln  Gln Lys Leu
    3650                 3655                 3660

Asn Glu  Ala Arg Ala Leu Leu  Gln Asn Lys Glu Asp  Asn Ser Ala
    3665                 3670                 3675

Leu Val  Arg Ala Lys Glu Gln  Leu Gln Gln Ala Val  Asp Gln Val
    3680                 3685                 3690

Pro Ser  Thr Glu Gly Met Thr  Gln Gln Thr Lys Asp  Asp Tyr Asn
    3695                 3700                 3705

Ser Lys  Gln Gln Ala Ala Gln  Gln Glu Ile Ser Lys  Ala Gln Gln
    3710                 3715                 3720

Val Ile  Asp Asn Gly Asp Ala  Thr Thr Gln Gln Ile  Ser Asn Ala
    3725                 3730                 3735

Lys Thr  Asn Val Glu Arg Ala  Leu Glu Ala Leu Asn  Asn Ala Lys
    3740                 3745                 3750

Thr Gly  Leu Arg Ala Asp Lys  Glu Glu Leu Gln Asn  Ala Tyr Asn
    3755                 3760                 3765

Gln Leu  Thr Gln Asn Ile Asp  Thr Ser Gly Lys Thr  Pro Ala Ser
    3770                 3775                 3780

Ile Arg  Lys Tyr Asn Glu Ala  Lys Ser Arg Ile Gln  Thr Gln Ile
```

-continued

```
    3785                3790                3795

Asp Ser  Ala Lys Asn Glu Ala  Asn Ser Ile Leu Thr  Asn Asp Asn
    3800                3805                3810

Pro Gln  Val Ser Gln Val Thr  Ala Ala Leu Asn Lys  Ile Lys Ala
    3815                3820                3825

Val Gln  Pro Glu Leu Asp Lys  Ala Ile Ala Met Leu  Lys Asn Lys
    3830                3835                3840

Glu Asn  Asn Asn Ala Leu Val  Gln Ala Lys Gln Gln  Leu Gln Gln
    3845                3850                3855

Ile Val  Asn Glu Val Asp Pro  Thr Gln Gly Met Thr  Thr Asp Thr
    3860                3865                3870

Ala Asn  Asn Tyr Lys Ser Lys  Lys Arg Glu Ala Glu  Asp Glu Ile
    3875                3880                3885

Gln Lys  Ala Gln Gln Ile Ile  Asn Asn Gly Asp Ala  Thr Glu Gln
    3890                3895                3900

Gln Ile  Thr Asn Glu Thr Asn  Arg Val Asn Gln Ala  Ile Asn Ala
    3905                3910                3915

Ile Asn  Lys Ala Lys Asn Asp  Leu Arg Ala Asp Lys  Ser Gln Leu
    3920                3925                3930

Glu Asn  Ala Tyr Asn Gln Leu  Ile Gln Asn Val Asp  Thr Asn Gly
    3935                3940                3945

Lys Lys  Pro Ala Ser Ile Gln  Gln Tyr Gln Ala Ala  Arg Gln Ala
    3950                3955                3960

Ile Glu  Thr Gln Tyr Asn Asn  Ala Lys Ser Glu Ala  His Gln Ile
    3965                3970                3975

Leu Glu  Asn Ser Asn Pro Ser  Val Asn Glu Val Ala  Gln Ala Leu
    3980                3985                3990

Gln Lys  Val Glu Ala Val Gln  Leu Lys Val Asn Asp  Ala Ile His
    3995                4000                4005

Ile Leu  Gln Asn Lys Glu Asn  Asn Ser Ala Leu Val  Thr Ala Lys
    4010                4015                4020

Asn Gln  Leu Gln Gln Ser Val  Asn Asp Gln Pro Leu  Thr Thr Gly
    4025                4030                4035

Met Thr  Gln Asp Ser Ile Asn  Asn Tyr Glu Ala Lys  Arg Asn Glu
    4040                4045                4050

Ala Gln  Ser Ala Ile Arg Asn  Ala Glu Ala Val Ile  Asn Asn Gly
    4055                4060                4065

Asp Ala  Thr Ala Lys Gln Ile  Ser Asp Glu Lys Ser  Lys Val Glu
    4070                4075                4080

Gln Ala  Leu Ala His Leu Asn  Asp Ala Lys Gln Gln  Leu Thr Ala
    4085                4090                4095

Asp Thr  Thr Glu Leu Gln Thr  Ala Val Gln Gln Leu  Asn Arg Arg
    4100                4105                4110

Gly Asp  Thr Asn Asn Lys Lys  Pro Arg Ser Ile Asn  Ala Tyr Asn
    4115                4120                4125

Lys Ala  Ile Gln Ser Leu Glu  Thr Gln Ile Thr Ser  Ala Lys Asp
    4130                4135                4140

Asn Ala  Asn Ala Val Ile Gln  Lys Pro Ile Arg Thr  Val Gln Glu
    4145                4150                4155

Val Asn  Asn Ala Leu Gln Gln  Val Asn Gln Leu Asn  Gln Gln Leu
    4160                4165                4170

Thr Glu  Ala Ile Asn Gln Leu  Gln Pro Leu Ser Asn  Asn Asp Ala
    4175                4180                4185
```

-continued

```
Leu Lys Ala Ala Arg Leu Asn Leu Glu Asn Lys Ile Asn Gln Thr
    4190                4195                4200

Val Gln Thr Asp Gly Met Thr Gln Gln Ser Ile Glu Ala Tyr Gln
    4205                4210                4215

Asn Ala Lys Arg Val Ala Gln Asn Glu Ser Asn Thr Ala Leu Ala
    4220                4225                4230

Leu Ile Asn Asn Gly Asp Ala Asp Glu Gln Gln Ile Thr Thr Glu
    4235                4240                4245

Thr Asp Arg Val Asn Gln Gln Thr Thr Asn Leu Thr Gln Ala Ile
    4250                4255                4260

Asn Gly Leu Thr Val Asn Lys Glu Pro Leu Glu Thr Ala Lys Thr
    4265                4270                4275

Ala Leu Gln Asn Asn Ile Asp Gln Val Pro Ser Thr Asp Gly Met
    4280                4285                4290

Thr Gln Gln Ser Val Ala Asn Tyr Asn Gln Lys Leu Gln Ile Ala
    4295                4300                4305

Lys Asn Glu Ile Asn Thr Ile Asn Asn Val Leu Ala Asn Asn Pro
    4310                4315                4320

Asp Val Asn Ala Ile Lys Thr Asn Lys Ala Glu Ala Glu Arg Ile
    4325                4330                4335

Ser Asn Asp Leu Thr Gln Ala Lys Asn Asn Leu Gln Val Asp Thr
    4340                4345                4350

Gln Pro Leu Glu Lys Ile Lys Arg Gln Leu Gln Asp Glu Ile Asp
    4355                4360                4365

Gln Gly Thr Asn Thr Asp Gly Met Thr Gln Asp Ser Val Asp Asn
    4370                4375                4380

Tyr Asn Asp Ser Leu Ser Ala Ala Ile Ile Glu Lys Gly Lys Val
    4385                4390                4395

Asn Lys Leu Leu Lys Arg Asn Pro Thr Val Glu Gln Val Lys Glu
    4400                4405                4410

Ser Val Ala Asn Ala Gln Gln Val Ile Gln Asp Leu Gln Asn Ala
    4415                4420                4425

Arg Thr Ser Leu Val Pro Asp Lys Thr Gln Leu Gln Glu Ala Lys
    4430                4435                4440

Asn Arg Leu Glu Asn Ser Ile Asn Gln Gln Thr Asp Thr Asp Gly
    4445                4450                4455

Met Thr Gln Asp Ser Leu Asn Asn Tyr Asn Asp Lys Leu Ala Lys
    4460                4465                4470

Ala Arg Gln Asn Leu Glu Lys Ile Ser Lys Val Leu Gly Gly Gln
    4475                4480                4485

Pro Thr Val Ala Glu Ile Arg Gln Asn Thr Asp Glu Ala Asn Ala
    4490                4495                4500

His Lys Gln Ala Leu Asp Thr Ala Arg Ser Gln Leu Thr Leu Asn
    4505                4510                4515

Arg Glu Pro Tyr Ile Asn His Ile Asn Asn Glu Ser His Leu Asn
    4520                4525                4530

Asn Ala Gln Lys Asp Asn Phe Lys Ala Gln Val Asn Ser Ala Pro
    4535                4540                4545

Asn His Asn Thr Leu Glu Thr Ile Lys Asn Lys Ala Asp Thr Leu
    4550                4555                4560

Asn Gln Ser Met Thr Ala Leu Ser Glu Ser Ile Ala Asp Tyr Glu
    4565                4570                4575
```

```
Asn Gln  Lys Gln Gln Glu Asn  Tyr Leu Asp Ala Ser  Asn Asn Lys
    4580                 4585                 4590

Arg Gln  Asp Tyr Asp Asn Ala  Val Asn Ala Ala Lys  Gly Ile Leu
    4595                 4600                 4605

Asn Gln  Thr Gln Ser Pro Thr  Met Ser Ala Asp Val  Ile Asp Gln
    4610                 4615                 4620

Lys Ala  Glu Asp Val Lys Arg  Thr Lys Thr Ala Leu  Asp Gly Asn
    4625                 4630                 4635

Gln Arg  Leu Glu Val Ala Lys  Gln Gln Ala Leu Asn  His Leu Asn
    4640                 4645                 4650

Thr Leu  Asn Asp Leu Asn Asp  Ala Gln Arg Gln Thr  Leu Thr Asp
    4655                 4660                 4665

Thr Ile  Asn His Ser Pro Asn  Ile Asn Ser Val Asn  Gln Ala Lys
    4670                 4675                 4680

Glu Lys  Ala Asn Thr Val Asn  Thr Ala Met Thr Gln  Leu Lys Gln
    4685                 4690                 4695

Thr Ile  Ala Asn Tyr Asp Asp  Glu Leu His Asp Gly  Asn Tyr Ile
    4700                 4705                 4710

Asn Ala  Asp Lys Asp Lys Lys  Asp Ala Tyr Asn Asn  Ala Val Asn
    4715                 4720                 4725

Asn Ala  Lys Gln Leu Ile Asn  Gln Ser Asp Ala Asn  Gln Ala Gln
    4730                 4735                 4740

Leu Asp  Pro Ala Glu Ile Asn  Lys Val Thr Gln Arg  Val Asn Thr
    4745                 4750                 4755

Thr Lys  Asn Asp Leu Asn Gly  Asn Asp Lys Leu Ala  Glu Ala Lys
    4760                 4765                 4770

Arg Asp  Ala Asn Thr Thr Ile  Asp Gly Leu Thr Tyr  Leu Asn Glu
    4775                 4780                 4785

Ala Gln  Arg Asn Lys Ala Lys  Glu Asn Val Gly Lys  Ala Ser Thr
    4790                 4795                 4800

Lys Thr  Asn Ile Thr Ser Gln  Leu Gln Asp Tyr Asn  Gln Leu Asn
    4805                 4810                 4815

Ile Ala  Met Gln Ala Leu Arg  Asn Ser Val Asn Asp  Val Asn Asn
    4820                 4825                 4830

Val Lys  Ala Asn Ser Asn Tyr  Ile Asn Glu Asp Asn  Gly Pro Lys
    4835                 4840                 4845

Glu Ala  Tyr Asn Gln Ala Val  Thr His Ala Gln Thr  Leu Ile Asn
    4850                 4855                 4860

Ala Gln  Ser Asn Pro Glu Met  Ser Arg Asp Val Val  Asn Gln Lys
    4865                 4870                 4875

Thr Gln  Ala Val Asn Thr Ala  His Gln Asn Leu His  Gly Gln Gln
    4880                 4885                 4890

Lys Leu  Glu Gln Ala Gln Ser  Ser Ala Asn Thr Glu  Ile Gly Asn
    4895                 4900                 4905

Leu Pro  Asn Leu Thr Asn Thr  Gln Lys Ala Lys Glu  Lys Glu Leu
    4910                 4915                 4920

Val Asn  Ser Lys Gln Thr Arg  Thr Glu Val Gln Glu  Gln Leu Asn
    4925                 4930                 4935

Gln Ala  Lys Ser Leu Asp Ser  Ser Met Gly Thr Leu  Lys Ser Leu
    4940                 4945                 4950

Val Ala  Lys Gln Pro Thr Val  Gln Lys Thr Ser Val  Tyr Ile Asn
    4955                 4960                 4965

Glu Asp  Gln Pro Glu Gln Ser  Ala Tyr Asn Asp Ser  Ile Thr Met
```

```
    4970                4975                4980

Gly Gln  Thr Ile Ile Asn Lys  Thr Ala Asp Pro Val  Leu Asp Lys
    4985                4990                4995

Thr Leu  Val Asp Asn Ala Ile  Ser Asn Ile Ser Thr  Lys Glu Asn
    5000                5005                5010

Ala Leu  His Gly Glu Gln Lys  Leu Thr Thr Ala Lys  Thr Glu Ala
    5015                5020                5025

Ile Asn  Ala Leu Asn Thr Leu  Ala Asp Leu Asn Thr  Pro Gln Lys
    5030                5035                5040

Glu Ala  Ile Lys Thr Ala Ile  Asn Thr Ala His Thr  Arg Thr Asp
    5045                5050                5055

Val Thr  Ala Glu Gln Ser Lys  Ala Asn Gln Ile Asn  Ser Ala Met
    5060                5065                5070

His Thr  Leu Arg Gln Asn Ile  Ser Asp Asn Glu Ser  Val Thr Asn
    5075                5080                5085

Glu Ser  Asn Tyr Ile Asn Ala  Glu Pro Glu Lys Gln  His Ala Phe
    5090                5095                5100

Thr Glu  Ala Leu Asn Asn Ala  Lys Glu Ile Val Asn  Glu Gln Gln
    5105                5110                5115

Ala Thr  Leu Asp Ala Asn Ser  Ile Asn Gln Lys Ala  Gln Ala Ile
    5120                5125                5130

Leu Thr  Thr Lys Asn Ala Leu  Asp Gly Glu Glu Gln  Leu Arg Arg
    5135                5140                5145

Ala Lys  Glu Asn Ala Asp Gln  Glu Ile Asn Thr Leu  Asn Gln Leu
    5150                5155                5160

Thr Asp  Ala Gln Arg Asn Ser  Glu Lys Gly Leu Val  Asn Ser Ser
    5165                5170                5175

Gln Thr  Arg Thr Glu Val Ala  Ser Gln Leu Ala Lys  Ala Lys Glu
    5180                5185                5190

Leu Asn  Lys Val Met Glu Gln  Leu Asn His Leu Ile  Asn Gly Lys
    5195                5200                5205

Asn Gln  Met Ile Asn Ser Ser  Lys Phe Ile Asn Glu  Asp Ala Asn
    5210                5215                5220

Gln Gln  Gln Ala Tyr Ser Asn  Ala Ile Ala Ser Ala  Glu Ala Leu
    5225                5230                5235

Lys Asn  Lys Ser Gln Asn Pro  Glu Leu Asp Lys Val  Thr Ile Glu
    5240                5245                5250

Gln Ala  Ile Asn Asn Ile Asn  Ser Ala Ile Asn Asn  Leu Asn Gly
    5255                5260                5265

Glu Ala  Lys Leu Thr Lys Ala  Lys Glu Asp Ala Val  Ala Ser Ile
    5270                5275                5280

Asn Asn  Leu Ser Gly Leu Thr  Asn Glu Gln Lys Pro  Lys Glu Asn
    5285                5290                5295

Gln Ala  Val Asn Gly Ala Gln  Thr Arg Asp Gln Val  Ala Asn Lys
    5300                5305                5310

Leu Arg  Asp Ala Glu Ala Leu  Asp Gln Ser Met Gln  Thr Leu Arg
    5315                5320                5325

Asp Leu  Val Asn Asn Gln Asn  Ala Ile His Ser Thr  Ser Asn Tyr
    5330                5335                5340

Phe Asn  Glu Asp Ser Thr Gln  Lys Asn Thr Tyr Asp  Asn Ala Ile
    5345                5350                5355

Asp Asn  Gly Ser Thr Tyr Ile  Thr Gly Gln His Asn  Pro Glu Leu
    5360                5365                5370
```

-continued

Asn Lys Ser Thr Ile Asp Gln Thr Ile Ser Arg Ile Asn Thr Ala
5375 5380 5385

Lys Asn Asp Leu His Gly Val Glu Lys Leu Gln Arg Asp Lys Gly
5390 5395 5400

Thr Ala Asn Gln Glu Ile Gly Gln Leu Gly Tyr Leu Asn Asp Pro
5405 5410 5415

Gln Lys Ser Gly Glu Glu Ser Leu Val Asn Gly Ser Asn Thr Arg
5420 5425 5430

Ser Glu Val Glu Glu His Leu Asn Glu Ala Lys Ser Leu Asn Asn
5435 5440 5445

Ala Met Lys Gln Leu Arg Asp Lys Val Ala Glu Lys Thr Asn Val
5450 5455 5460

Lys Gln Ser Ser Asp Tyr Ile Asn Asp Ser Thr Glu His Gln Arg
5465 5470 5475

Gly Tyr Asp Gln Ala Leu Gln Glu Ala Glu Asn Ile Ile Asn Glu
5480 5485 5490

Ile Gly Asn Pro Thr Leu Asn Lys Ser Glu Ile Glu Gln Lys Leu
5495 5500 5505

Gln Gln Leu Thr Asp Ala Gln Asn Ala Leu Gln Gly Ser His Leu
5510 5515 5520

Leu Glu Glu Ala Lys Asn Asn Ala Ile Thr Gly Ile Asn Lys Leu
5525 5530 5535

Thr Ala Leu Asn Asp Ala Gln Arg Gln Lys Ala Ile Glu Asn Val
5540 5545 5550

Gln Ala Gln Gln Thr Ile Pro Ala Val Asn Gln Gln Leu Thr Leu
5555 5560 5565

Asp Arg Glu Ile Asn Thr Ala Met Gln Ala Leu Arg Asp Lys Val
5570 5575 5580

Gly Gln Gln Asn Asn Val His Gln Gln Ser Asn Tyr Phe Asn Glu
5585 5590 5595

Asp Glu Gln Pro Lys His Asn Tyr Asp Asn Ser Val Gln Ala Gly
5600 5605 5610

Gln Thr Ile Ile Asp Lys Leu Gln Asp Pro Ile Met Asn Lys Asn
5615 5620 5625

Glu Ile Glu Gln Ala Ile Asn Gln Ile Asn Thr Thr Gln Thr Ala
5630 5635 5640

Leu Ser Gly Glu Asn Lys Leu His Thr Asp Gln Glu Ser Thr Asn
5645 5650 5655

Arg Gln Ile Glu Gly Leu Ser Ser Leu Asn Thr Ala Gln Ile Asn
5660 5665 5670

Ala Glu Lys Asp Leu Val Asn Gln Ala Lys Thr Arg Thr Asp Val
5675 5680 5685

Ala Gln Lys Leu Ala Ala Ala Lys Glu Ile Asn Ser Ala Met Ser
5690 5695 5700

Asn Leu Arg Asp Gly Ile Gln Asn Lys Glu Asp Ile Lys Arg Ser
5705 5710 5715

Ser Ala Tyr Ile Asn Ala Asp Pro Thr Lys Val Thr Ala Tyr Asp
5720 5725 5730

Gln Ala Leu Gln Asn Ala Glu Asn Ile Ile Asn Ala Thr Pro Asn
5735 5740 5745

Val Glu Leu Asn Lys Ala Thr Ile Glu Gln Ala Leu Ser Arg Val
5750 5755 5760

-continued

```
Gln Gln  Ala Gln Gln Asp Leu  Asp Gly Val Gln Gln  Leu Ala Asn
    5765                 5770                 5775

Ala Lys  Gln Gln Ala Thr Gln  Thr Val Asn Gly Leu  Asn Ser Leu
    5780                 5785                 5790

Asn Asp  Gly Gln Lys Arg Glu  Leu Asn Leu Leu Ile  Asn Ser Ala
    5795                 5800                 5805

Asn Thr  Arg Thr Lys Val Gln  Glu Glu Leu Asn Lys  Ala Thr Glu
    5810                 5815                 5820

Leu Asn  His Ala Met Glu Ala  Leu Arg Asn Ser Val  Gln Asn Val
    5825                 5830                 5835

Asp Gln  Val Lys Gln Ser Ser  Asn Tyr Val Asn Glu  Asp Gln Pro
    5840                 5845                 5850

Glu Gln  His Asn Tyr Asp Asn  Ala Val Asn Glu Ala  Gln Ala Thr
    5855                 5860                 5865

Ile Asn  Asn Asn Ala Gln Pro  Val Leu Asp Lys Leu  Ala Ile Glu
    5870                 5875                 5880

Arg Leu  Thr Gln Thr Val Asn  Thr Thr Lys Asp Ala  Leu His Gly
    5885                 5890                 5895

Ala Gln  Lys Leu Thr Gln Asp  Gln Gln Ala Ala Glu  Thr Gly Ile
    5900                 5905                 5910

Arg Gly  Leu Thr Ser Leu Asn  Glu Pro Gln Lys Asn  Ala Glu Val
    5915                 5920                 5925

Ala Lys  Val Thr Ala Ala Thr  Thr Arg Asp Glu Val  Arg Asn Ile
    5930                 5935                 5940

Arg Gln  Glu Ala Thr Thr Leu  Asp Thr Ala Met Leu  Gly Leu Arg
    5945                 5950                 5955

Lys Ser  Ile Lys Asp Lys Asn  Asp Thr Lys Asn Ser  Ser Lys Tyr
    5960                 5965                 5970

Ile Asn  Glu Asp His Asp Gln  Gln Gln Ala Tyr Asp  Asn Ala Val
    5975                 5980                 5985

Asn Asn  Ala Gln Gln Val Ile  Asp Glu Thr Gln Ala  Thr Leu Ser
    5990                 5995                 6000

Ser Asp  Thr Ile Asn Gln Leu  Ala Asn Ala Val Thr  Gln Ala Lys
    6005                 6010                 6015

Ser Asn  Leu His Gly Asp Thr  Lys Leu Gln His Asp  Lys Asp Ser
    6020                 6025                 6030

Ala Lys  Gln Thr Ile Ala Gln  Leu Gln Asn Leu Asn  Ser Ala Gln
    6035                 6040                 6045

Lys His  Met Glu Asp Ser Leu  Ile Asp Asn Glu Ser  Thr Arg Thr
    6050                 6055                 6060

Gln Val  Gln His Asp Leu Thr  Glu Ala Gln Ala Leu  Asp Gly Leu
    6065                 6070                 6075

Met Gly  Ala Leu Lys Glu Ser  Ile Lys Asp Tyr Thr  Asn Ile Val
    6080                 6085                 6090

Ser Asn  Gly Asn Tyr Ile Asn  Ala Glu Pro Ser Lys  Lys Gln Ala
    6095                 6100                 6105

Tyr Asp  Ala Ala Val Gln Asn  Ala Gln Asn Ile Ile  Asn Gly Thr
    6110                 6115                 6120

Asn Gln  Pro Thr Ile Asn Lys  Gly Asn Val Thr Thr  Ala Thr Gln
    6125                 6130                 6135

Thr Val  Lys Asn Thr Lys Asp  Ala Leu Asp Gly Asp  His Arg Leu
    6140                 6145                 6150

Glu Glu  Ala Lys Asn Asn Ala  Asn Gln Thr Ile Arg  Asn Leu Ser
```

-continued

```
    6155                6160                6165

Asn Leu  Asn Asn Ala Gln Lys  Asp Ala Glu Lys Asn  Leu Val Asn
    6170                6175                6180

Ser Ala  Ser Thr Leu Glu Gln  Val Gln Gln Asn Leu  Gln Thr Ala
    6185                6190                6195

Gln Gln  Leu Asp Asn Ala Met  Gly Glu Leu Arg Gln  Ser Ile Ala
    6200                6205                6210

Lys Lys  Asp Gln Val Lys Ala  Asp Ser Lys Tyr Leu  Asn Glu Asp
    6215                6220                6225

Pro Gln  Ile Lys Gln Asn Tyr  Asp Asp Ala Val Gln  Arg Val Glu
    6230                6235                6240

Thr Ile  Ile Asn Glu Thr Gln  Asn Pro Glu Leu Leu  Lys Ala Asn
    6245                6250                6255

Ile Asp  Gln Ala Thr Gln Ser  Val Gln Asn Ala Glu  Gln Ala Leu
    6260                6265                6270

His Gly  Ala Glu Lys Leu Asn  Gln Asp Lys Gln Thr  Ser Ser Thr
    6275                6280                6285

Glu Leu  Asp Gly Leu Thr Asp  Leu Thr Asp Ala Gln  Arg Glu Lys
    6290                6295                6300

Leu Arg  Glu Gln Ile Asn Thr  Ser Asn Ser Arg Asp  Asp Ile Lys
    6305                6310                6315

Gln Lys  Ile Glu Gln Ala Lys  Ala Leu Asn Asp Ala  Met Lys Lys
    6320                6325                6330

Leu Lys  Glu Gln Val Ala Gln  Lys Asp Gly Val His  Ala Asn Ser
    6335                6340                6345

Asp Tyr  Thr Asn Glu Asp Ser  Ala Gln Lys Asp Ala  Tyr Asn Asn
    6350                6355                6360

Ala Leu  Lys Gln Ala Glu Asp  Ile Ile Asn Asn Ser  Ser Asn Pro
    6365                6370                6375

Asn Leu  Asn Ala Gln Asp Ile  Thr Asn Ala Leu Asn  Asn Ile Lys
    6380                6385                6390

Gln Ala  Gln Asp Asn Leu His  Gly Ala Gln Lys Leu  Gln Gln Asp
    6395                6400                6405

Lys Asn  Thr Thr Asn Gln Ala  Ile Gly Asn Leu Asn  His Leu Asn
    6410                6415                6420

Gln Pro  Gln Lys Asp Ala Leu  Ile Gln Ala Ile Asn  Gly Ala Thr
    6425                6430                6435

Ser Arg  Asp Gln Val Ala Glu  Lys Leu Lys Glu Ala  Glu Ala Leu
    6440                6445                6450

Asp Glu  Ala Met Lys Gln Leu  Glu Asp Gln Val Asn  Gln Asp Asp
    6455                6460                6465

Gln Ile  Ser Asn Ser Ser Pro  Phe Ile Asn Glu Asp  Ser Asp Lys
    6470                6475                6480

Gln Lys  Thr Tyr Asn Asp Lys  Ile Gln Ala Ala Lys  Glu Ile Ile
    6485                6490                6495

Asn Gln  Thr Ser Asn Pro Thr  Leu Asp Lys Gln Lys  Ile Ala Asp
    6500                6505                6510

Thr Leu  Gln Asn Ile Lys Asp  Ala Val Asn Asn Leu  His Gly Asp
    6515                6520                6525

Gln Lys  Leu Ala Gln Ser Lys  Gln Asp Ala Asn Asn  Gln Leu Asn
    6530                6535                6540

His Leu  Asp Asp Leu Thr Glu  Glu Gln Lys Asn His  Phe Lys Pro
    6545                6550                6555
```

```
Leu Ile  Asn Asn Ala Asp Thr  Arg Asp Glu Val Asn  Lys Gln Leu
    6560                 6565                 6570

Glu Ile  Ala Lys Gln Leu Asn  Gly Asp Met Ser Thr  Leu His Lys
    6575                 6580                 6585

Val Ile  Asn Asp Lys Asp Gln  Ile Gln His Leu Ser  Asn Tyr Ile
    6590                 6595                 6600

Asn Ala  Asp Asn Asp Lys Lys  Gln Asn Tyr Asp Asn  Ala Ile Lys
    6605                 6610                 6615

Glu Ala  Glu Asp Leu Ile His  Asn His Pro Asp Thr  Leu Asp His
    6620                 6625                 6630

Lys Ala  Leu Gln Asp Leu Leu  Asn Lys Ile Asp Gln  Ala His Asn
    6635                 6640                 6645

Glu Leu  Asn Gly Glu Ser Arg  Phe Lys Gln Ala Leu  Asp Asn Ala
    6650                 6655                 6660

Leu Asn  Asp Ile Asp Ser Leu  Asn Ser Leu Asn Val  Pro Gln Arg
    6665                 6670                 6675

Gln Thr  Val Lys Asp Asn Ile  Asn His Val Thr Thr  Leu Glu Ser
    6680                 6685                 6690

Leu Ala  Gln Glu Leu Gln Lys  Ala Lys Glu Leu Asn  Asp Ala Met
    6695                 6700                 6705

Lys Ala  Met Arg Asp Ser Ile  Met Asn Gln Glu Gln  Ile Arg Lys
    6710                 6715                 6720

Asn Ser  Asn Tyr Thr Asn Glu  Asp Leu Ala Gln Gln  Asn Ala Tyr
    6725                 6730                 6735

Asn His  Ala Val Asp Lys Ile  Asn Asn Ile Ile Gly  Glu Asp Asn
    6740                 6745                 6750

Ala Thr  Met Asp Pro Gln Ile  Ile Lys Gln Ala Thr  Gln Asp Ile
    6755                 6760                 6765

Asn Thr  Ala Ile Asn Gly Leu  Asn Gly Asp Gln Lys  Leu Gln Asp
    6770                 6775                 6780

Ala Lys  Thr Asp Ala Lys Gln  Gln Ile Thr Asn Phe  Thr Gly Leu
    6785                 6790                 6795

Thr Glu  Pro Gln Lys Gln Ala  Leu Glu Asn Ile Ile  Asn Gln Gln
    6800                 6805                 6810

Thr Ser  Arg Ala Asn Val Ala  Lys Gln Leu Ser His  Ala Lys Phe
    6815                 6820                 6825

Leu Asn  Gly Lys Met Glu Glu  Leu Lys Val Ala Val  Ala Lys Ala
    6830                 6835                 6840

Ser Leu  Val Arg Gln Asn Ser  Asn Tyr Ile Asn Glu  Asp Val Ser
    6845                 6850                 6855

Glu Lys  Glu Ala Tyr Glu Gln  Ala Ile Ala Lys Gly  Gln Glu Ile
    6860                 6865                 6870

Ile Asn  Ser Glu Asn Asn Pro  Thr Ile Ser Ser Thr  Asp Ile Asn
    6875                 6880                 6885

Arg Thr  Ile Gln Glu Ile Asn  Asp Ala Glu Gln Asn  Leu His Gly
    6890                 6895                 6900

Asp Asn  Lys Leu Arg Gln Ala  Gln Glu Ile Ala Lys  Asn Glu Ile
    6905                 6910                 6915

Gln Asn  Leu Asp Gly Leu Asn  Ser Ala Gln Ile Thr  Lys Leu Ile
    6920                 6925                 6930

Gln Asp  Ile Gly Arg Thr Thr  Thr Lys Pro Ala Val  Thr Gln Lys
    6935                 6940                 6945
```

-continued

```
Leu Glu  Glu Ala Lys Ala Ile  Asn Gln Ala Met Gln  Gln Leu Lys
    6950                 6955                 6960

Gln Ser  Ile Ala Asp Lys Asp  Ala Thr Leu Asn Ser  Ser Asn Tyr
    6965                 6970                 6975

Leu Asn  Glu Asp Ser Glu Lys  Lys Leu Ala Tyr Asp  Asn Ala Val
    6980                 6985                 6990

Ser Gln  Ala Glu Gln Leu Ile  Asn Gln Leu Asn Asp  Pro Thr Met
    6995                 7000                 7005

Asp Ile  Ser Asn Ile Gln Ala  Ile Thr Gln Lys Val  Ile Gln Ala
    7010                 7015                 7020

Lys Asp  Ser Leu His Gly Ala  Asn Lys Leu Ala Gln  Asn Gln Ala
    7025                 7030                 7035

Asp Ser  Asn Leu Ile Ile Asn  Gln Ser Thr Asn Leu  Asn Asp Lys
    7040                 7045                 7050

Gln Lys  Gln Ala Leu Asn Asp  Leu Ile Asn His Ala  Gln Thr Lys
    7055                 7060                 7065

Gln Gln  Val Ala Glu Ile Ile  Ala Gln Ala Asn Lys  Leu Asn Asn
    7070                 7075                 7080

Glu Met  Gly Thr Leu Lys Thr  Leu Val Glu Glu Gln  Ser Asn Val
    7085                 7090                 7095

His Gln  Gln Ser Lys Tyr Ile  Asn Glu Asp Pro Gln  Val Gln Asn
    7100                 7105                 7110

Ile Tyr  Asn Asp Ser Ile Gln  Lys Gly Arg Glu Ile  Leu Asn Gly
    7115                 7120                 7125

Thr Thr  Asp Asp Val Leu Asn  Asn Asn Lys Ile Ala  Asp Ala Ile
    7130                 7135                 7140

Gln Asn  Ile His Leu Thr Lys  Asn Asp Leu His Gly  Asp Gln Lys
    7145                 7150                 7155

Leu Gln  Lys Ala Gln Gln Asp  Ala Thr Asn Glu Leu  Asn Tyr Leu
    7160                 7165                 7170

Thr Asn  Leu Asn Asn Ser Gln  Arg Gln Ser Glu His  Asp Glu Ile
    7175                 7180                 7185

Asn Ser  Ala Pro Ser Arg Thr  Glu Val Ser Asn Asp  Leu Asn His
    7190                 7195                 7200

Ala Lys  Ala Leu Asn Glu Ala  Met Arg Gln Leu Glu  Asn Glu Val
    7205                 7210                 7215

Ala Leu  Glu Asn Ser Val Lys  Lys Leu Ser Asp Phe  Ile Asn Glu
    7220                 7225                 7230

Asp Glu  Ala Ala Gln Asn Glu  Tyr Ser Asn Ala Leu  Gln Lys Ala
    7235                 7240                 7245

Lys Asp  Ile Ile Asn Gly Val  Pro Ser Ser Thr Leu  Asp Lys Ala
    7250                 7255                 7260

Thr Ile  Glu Asp Ala Leu Leu  Glu Leu Gln Asn Ala  Arg Glu Ser
    7265                 7270                 7275

Leu His  Gly Glu Gln Lys Leu  Gln Glu Ala Lys Asn  Gln Ala Val
    7280                 7285                 7290

Ala Glu  Ile Asp Asn Leu Gln  Ala Leu Asn Pro Gly  Gln Val Leu
    7295                 7300                 7305

Ala Glu  Lys Thr Leu Val Asn  Gln Ala Ser Thr Lys  Pro Glu Val
    7310                 7315                 7320

Gln Glu  Ala Leu Gln Lys Ala  Lys Glu Leu Asn Glu  Ala Met Lys
    7325                 7330                 7335

Ala Leu  Lys Thr Glu Ile Asn  Lys Lys Glu Gln Ile  Lys Ala Asp
```

```
    7340                7345                7350

Ser Arg  Tyr Val Asn Ala Asp  Ser Gly Leu Gln Ala  Asn Tyr Asn
    7355                7360                7365

Ser Ala  Leu Asn Tyr Gly Ser  Gln Ile Ile Ala Thr  Thr Gln Pro
    7370                7375                7380

Pro Glu  Leu Asn Lys Asp Val  Ile Asn Arg Ala Thr  Gln Thr Ile
    7385                7390                7395

Lys Thr  Ala Glu Asn Asn Leu  Asn Gly Gln Ser Lys  Leu Ala Glu
    7400                7405                7410

Ala Lys  Ser Asp Gly Asn Gln  Ser Ile Glu His Leu  Gln Gly Leu
    7415                7420                7425

Thr Gln  Ser Gln Lys Asp Lys  Gln His Asp Leu Ile  Asn Gln Ala
    7430                7435                7440

Gln Thr  Lys Gln Gln Val Asp  Asp Ile Val Asn Asn  Ser Lys Gln
    7445                7450                7455

Leu Asp  Asn Ser Met Asn Gln  Leu Gln Gln Ile Val  Asn Asn Asp
    7460                7465                7470

Asn Thr  Val Lys Gln Asn Ser  Asp Phe Ile Asn Glu  Asp Ser Ser
    7475                7480                7485

Gln Gln  Asp Ala Tyr Asn His  Ala Ile Gln Ala Ala  Lys Asp Leu
    7490                7495                7500

Ile Thr  Ala His Pro Thr Ile  Met Asp Lys Asn Gln  Ile Asp Gln
    7505                7510                7515

Ala Ile  Glu Asn Ile Lys Gln  Ala Leu Asn Asp Leu  His Gly Ser
    7520                7525                7530

Asn Lys  Leu Ser Glu Asp Lys  Lys Glu Ala Ser Glu  Gln Leu Gln
    7535                7540                7545

Asn Leu  Asn Ser Leu Thr Asn  Gly Gln Lys Asp Thr  Ile Leu Asn
    7550                7555                7560

His Ile  Phe Ser Ala Pro Thr  Arg Ser Gln Val Gly  Glu Lys Ile
    7565                7570                7575

Ala Ser  Ala Lys Gln Leu Asn  Asn Thr Met Lys Ala  Leu Arg Asp
    7580                7585                7590

Ser Ile  Ala Asp Asn Asn Glu  Ile Leu Gln Ser Ser  Lys Tyr Phe
    7595                7600                7605

Asn Glu  Asp Ser Glu Gln Gln  Asn Ala Tyr Asn Gln  Ala Val Asn
    7610                7615                7620

Lys Ala  Lys Asn Ile Ile Asn  Asp Gln Pro Thr Pro  Val Met Ala
    7625                7630                7635

Asn Asp  Glu Ile Gln Ser Val  Leu Asn Glu Val Lys  Gln Thr Lys
    7640                7645                7650

Asp Asn  Leu His Gly Asp Gln  Lys Leu Ala Asn Asp  Lys Thr Asp
    7655                7660                7665

Ala Gln  Ala Thr Leu Asn Ala  Leu Asn Tyr Leu Asn  Gln Ala Gln
    7670                7675                7680

Arg Gly  Asn Leu Glu Thr Lys  Val Gln Asn Ser Asn  Ser Arg Pro
    7685                7690                7695

Glu Val  Gln Lys Val Val Gln  Leu Ala Asn Gln Leu  Asn Asp Ala
    7700                7705                7710

Met Lys  Lys Leu Asp Asp Ala  Leu Thr Gly Asn Asp  Ala Ile Lys
    7715                7720                7725

Gln Thr  Ser Asn Tyr Ile Asn  Glu Asp Thr Ser Gln  Gln Val Asn
    7730                7735                7740
```

-continued

```
Phe Asp  Glu Tyr Thr Asp Arg  Gly Lys Asn Ile Val  Ala Glu Gln
    7745                 7750                 7755

Thr Asn  Pro Asn Met Ser Pro  Thr Asn Ile Asn Thr  Ile Ala Asp
    7760                 7765                 7770

Lys Ile  Thr Glu Ala Lys Asn  Asp Leu His Gly Val  Gln Lys Leu
    7775                 7780                 7785

Lys Gln  Ala Gln Gln Gln Ser  Ile Asn Thr Ile Asn  Gln Met Thr
    7790                 7795                 7800

Gly Leu  Asn Gln Ala Gln Lys  Glu Gln Leu Asn Gln  Glu Ile Gln
    7805                 7810                 7815

Gln Thr  Gln Thr Arg Ser Glu  Val His Gln Val Ile  Asn Lys Ala
    7820                 7825                 7830

Gln Ala  Leu Asn Asp Ser Met  Asn Thr Leu Arg Gln  Ser Ile Thr
    7835                 7840                 7845

Asp Glu  His Glu Val Lys Gln  Thr Ser Asn Tyr Ile  Asn Glu Thr
    7850                 7855                 7860

Val Gly  Asn Gln Thr Ala Tyr  Asn Asn Ala Val Asp  Arg Val Lys
    7865                 7870                 7875

Gln Ile  Ile Asn Gln Thr Ser  Asn Pro Thr Met Asn  Pro Leu Glu
    7880                 7885                 7890

Val Glu  Arg Ala Thr Ser Asn  Val Lys Ile Ser Lys  Asp Ala Leu
    7895                 7900                 7905

His Gly  Glu Arg Glu Leu Asn  Asp Asn Lys Asn Ser  Lys Thr Phe
    7910                 7915                 7920

Ala Val  Asn His Leu Asp Asn  Leu Asn Gln Ala Gln  Lys Glu Ala
    7925                 7930                 7935

Leu Thr  His Glu Ile Glu Gln  Ala Thr Ile Val Ser  Gln Val Asn
    7940                 7945                 7950

Asn Ile  Tyr Asn Lys Ala Lys  Ala Leu Asn Asn Asp  Met Lys Lys
    7955                 7960                 7965

Leu Lys  Asp Ile Val Ala Gln  Gln Asp Asn Val Arg  Gln Ser Asn
    7970                 7975                 7980

Asn Tyr  Ile Asn Glu Asp Ser  Thr Pro Gln Asn Met  Tyr Asn Asp
    7985                 7990                 7995

Thr Ile  Asn His Ala Gln Ser  Ile Ile Asp Gln Val  Ala Asn Pro
    8000                 8005                 8010

Thr Met  Ser His Asp Glu Ile  Glu Asn Ala Ile Asn  Asn Ile Lys
    8015                 8020                 8025

His Ala  Ile Asn Ala Leu Asp  Gly Glu His Lys Leu  Gln Gln Ala
    8030                 8035                 8040

Lys Glu  Asn Ala Asn Leu Leu  Ile Asn Ser Leu Asn  Asp Leu Asn
    8045                 8050                 8055

Ala Pro  Gln Arg Asp Ala Ile  Asn Arg Leu Val Asn  Glu Ala Gln
    8060                 8065                 8070

Thr Arg  Glu Lys Val Ala Glu  Gln Leu Gln Ser Ala  Gln Ala Leu
    8075                 8080                 8085

Asn Asp  Ala Met Lys His Leu  Arg Asn Ser Ile Gln  Asn Gln Ser
    8090                 8095                 8100

Ser Val  Arg Gln Glu Ser Lys  Tyr Ile Asn Ala Ser  Asp Ala Lys
    8105                 8110                 8115

Lys Glu  Gln Tyr Asn His Ala  Val Arg Glu Val Glu  Asn Ile Ile
    8120                 8125                 8130
```

-continued

```
Asn Glu  Gln His Pro Thr Leu  Asp Lys Glu Ile Ile  Lys Gln Leu
    8135                 8140                 8145

Thr Asp  Gly Val Asn Gln Ala  Asn Asn Asp Leu Asn  Gly Val Glu
    8150                 8155                 8160

Leu Leu  Asp Ala Asp Lys Gln  Asn Ala His Gln Ser  Ile Pro Thr
    8165                 8170                 8175

Leu Met  His Leu Asn Gln Ala  Gln Gln Asn Ala Leu  Asn Glu Lys
    8180                 8185                 8190

Ile Asn  Asn Ala Val Thr Arg  Thr Glu Val Ala Ala  Ile Ile Gly
    8195                 8200                 8205

Gln Ala  Lys Leu Leu Asp His  Ala Met Glu Asn Leu  Glu Glu Ser
    8210                 8215                 8220

Ile Lys  Asp Lys Glu Gln Val  Lys Gln Ser Ser Asn  Tyr Ile Asn
    8225                 8230                 8235

Glu Asp  Ser Asp Val Gln Glu  Thr Tyr Asp Asn Ala  Val Asp His
    8240                 8245                 8250

Val Thr  Glu Ile Leu Asn Gln  Thr Val Asn Pro Thr  Leu Ser Ile
    8255                 8260                 8265

Glu Asp  Ile Glu His Ala Ile  Asn Glu Val Asn Gln  Ala Lys Lys
    8270                 8275                 8280

Gln Leu  Arg Gly Lys Gln Lys  Leu Tyr Gln Thr Ile  Asp Leu Ala
    8285                 8290                 8295

Asp Lys  Glu Leu Ser Lys Leu  Asp Asp Leu Thr Ser  Gln Gln Ser
    8300                 8305                 8310

Ser Ser  Ile Ser Asn Gln Ile  Tyr Thr Ala Lys Thr  Arg Thr Glu
    8315                 8320                 8325

Val Ala  Gln Ala Ile Glu Lys  Ala Lys Ser Leu Asn  His Ala Met
    8330                 8335                 8340

Lys Ala  Leu Asn Lys Val Tyr  Lys Asn Ala Asp Lys  Val Leu Asp
    8345                 8350                 8355

Ser Ser  Arg Phe Ile Asn Glu  Asp Gln Pro Glu Lys  Lys Ala Tyr
    8360                 8365                 8370

Gln Gln  Ala Ile Asn His Val  Asp Ser Ile Ile His  Arg Gln Thr
    8375                 8380                 8385

Asn Pro  Glu Met Asp Pro Thr  Val Ile Asn Ser Ile  Thr His Glu
    8390                 8395                 8400

Leu Glu  Thr Ala Gln Asn Asn  Leu His Gly Asp Gln  Lys Leu Ala
    8405                 8410                 8415

His Ala  Gln Gln Asp Ala Ala  Asn Val Ile Asn Gly  Leu Ile His
    8420                 8425                 8430

Leu Asn  Val Ala Gln Arg Glu  Val Met Ile Asn Thr  Asn Thr Asn
    8435                 8440                 8445

Ala Thr  Thr Arg Glu Lys Val  Ala Lys Asn Leu Asp  Asn Ala Gln
    8450                 8455                 8460

Ala Leu  Asp Lys Ala Met Glu  Thr Leu Gln Gln Val  Val Ala His
    8465                 8470                 8475

Lys Asn  Asn Ile Leu Asn Asp  Ser Lys Tyr Leu Asn  Glu Asp Ser
    8480                 8485                 8490

Lys Tyr  Gln Gln Gln Tyr Asp  Arg Val Ile Ala Asp  Ala Glu Gln
    8495                 8500                 8505

Leu Leu  Asn Gln Thr Thr Asn  Pro Thr Leu Glu Pro  Tyr Lys Val
    8510                 8515                 8520

Asp Ile  Val Lys Asp Asn Val  Leu Ala Asn Glu Lys  Ile Leu Phe
```

-continued

```
    8525                8530                8535

Gly Ala Glu Lys Leu Ser Tyr Asp Lys Ser Asn Ala Asn Asp Glu
    8540                8545                8550

Ile Lys His Met Asn Tyr Leu Asn Asn Ala Gln Lys Gln Ser Ile
    8555                8560                8565

Lys Asp Met Ile Ser His Ala Ala Leu Arg Thr Glu Val Lys Gln
    8570                8575                8580

Leu Leu Gln Gln Ala Lys Ile Leu Asp Glu Ala Met Lys Ser Leu
    8585                8590                8595

Glu Asp Lys Thr Gln Val Val Ile Thr Asp Thr Thr Leu Pro Asn
    8600                8605                8610

Tyr Thr Glu Ala Ser Glu Asp Lys Lys Glu Lys Val Asp Gln Thr
    8615                8620                8625

Val Ser His Ala Gln Ala Ile Ile Asp Lys Ile Asn Gly Ser Asn
    8630                8635                8640

Val Ser Leu Asp Gln Val Arg Gln Ala Leu Glu Gln Leu Thr Gln
    8645                8650                8655

Ala Ser Glu Asn Leu Asp Gly Asp Gln Arg Val Glu Glu Ala Lys
    8660                8665                8670

Val His Ala Asn Gln Thr Ile Asp Gln Leu Thr His Leu Asn Ser
    8675                8680                8685

Leu Gln Gln Gln Thr Ala Lys Glu Ser Val Lys Asn Ala Thr Lys
    8690                8695                8700

Leu Glu Glu Ile Ala Thr Val Ser Asn Asn Ala Gln Ala Leu Asn
    8705                8710                8715

Lys Val Met Gly Lys Leu Glu Gln Phe Ile Asn His Ala Asp Ser
    8720                8725                8730

Val Glu Asn Ser Asp Asn Tyr Arg Gln Ala Asp Asp Asp Lys Ile
    8735                8740                8745

Ile Ala Tyr Asp Glu Ala Leu Glu His Gly Gln Asp Ile Gln Lys
    8750                8755                8760

Thr Asn Ala Thr Gln Asn Glu Thr Lys Gln Ala Leu Gln Gln Leu
    8765                8770                8775

Ile Tyr Ala Glu Thr Ser Leu Asn Gly Phe Glu Arg Leu Asn His
    8780                8785                8790

Ala Arg Pro Arg Ala Leu Glu Tyr Ile Lys Ser Leu Glu Lys Ile
    8795                8800                8805

Asn Asn Ala Gln Lys Ser Ala Leu Glu Asp Lys Val Thr Gln Ser
    8810                8815                8820

His Asp Leu Leu Glu Leu Glu His Ile Val Asn Glu Gly Thr Asn
    8825                8830                8835

Leu Asn Asp Ile Met Gly Glu Leu Ala Asn Ala Ile Val Asn Asn
    8840                8845                8850

Tyr Ala Pro Thr Lys Ala Ser Ile Asn Tyr Ile Asn Ala Asp Asn
    8855                8860                8865

Leu Arg Lys Asp Asn Phe Thr Gln Ala Ile Asn Asn Ala Arg Asp
    8870                8875                8880

Ala Leu Asn Lys Thr Gln Gly Gln Asn Leu Asp Phe Asn Ala Ile
    8885                8890                8895

Asp Thr Phe Lys Asp Asp Ile Phe Lys Thr Lys Asp Ala Leu Asn
    8900                8905                8910

Gly Ile Glu Arg Leu Thr Ala Ala Lys Ser Lys Ala Glu Lys Leu
    8915                8920                8925
```

-continued

```
Ile Asp Ser Leu Lys Phe Ile Asn Lys Ala Gln Phe Thr His Ala
    8930                8935                8940

Asn Asp Glu Ile Ile Asn Thr Asn Ser Ile Ala Gln Leu Ser Arg
    8945                8950                8955

Ile Val Asn Gln Ala Phe Asp Leu Asn Asp Ala Met Lys Ser Leu
    8960                8965                8970

Arg Asp Glu Leu Asn Asn Gln Ala Phe Pro Val Gln Ala Ser Ser
    8975                8980                8985

Asn Tyr Ile Asn Ser Asp Glu Asp Leu Lys Gln Gln Phe Asp His
    8990                8995                9000

Ala Leu Ser Asn Ala Arg Lys Val Leu Ala Lys Glu Asn Gly Lys
    9005                9010                9015

Asn Leu Asp Glu Lys Gln Ile Gln Gly Leu Lys Gln Val Ile Glu
    9020                9025                9030

Asp Thr Lys Asp Ala Leu Asn Gly Ile Gln Arg Leu Ser Lys Ala
    9035                9040                9045

Lys Ala Lys Ala Ile Gln Tyr Val Gln Ser Leu Ser Tyr Ile Asn
    9050                9055                9060

Asp Ala Gln Arg His Ile Ala Glu Asn Asn Ile His Asn Ser Asp
    9065                9070                9075

Asp Leu Ser Ser Leu Ala Asn Thr Leu Ser Lys Ala Ser Asp Leu
    9080                9085                9090

Asp Asn Ala Met Lys Asp Leu Arg Asp Thr Ile Glu Ser Asn Ser
    9095                9100                9105

Thr Ser Val Pro Asn Ser Val Asn Tyr Ile Asn Ala Asp Lys Asn
    9110                9115                9120

Leu Gln Ile Glu Phe Asp Glu Ala Leu Gln Gln Ala Ser Ala Thr
    9125                9130                9135

Ser Ser Lys Thr Ser Glu Asn Pro Ala Thr Ile Glu Glu Val Leu
    9140                9145                9150

Gly Leu Ser Gln Ala Ile Tyr Asp Thr Lys Asn Ala Leu Asn Gly
    9155                9160                9165

Glu Gln Arg Leu Ala Thr Glu Lys Ser Lys Asp Leu Lys Leu Ile
    9170                9175                9180

Lys Gly Leu Lys Asp Leu Asn Lys Ala Gln Leu Glu Asp Val Thr
    9185                9190                9195

Asn Lys Val Asn Ser Ala Asn Thr Leu Thr Glu Leu Ser Gln Leu
    9200                9205                9210

Thr Gln Ser Thr Leu Glu Leu Asn Asp Lys Met Lys Leu Leu Arg
    9215                9220                9225

Asp Lys Leu Lys Thr Leu Val Asn Pro Val Lys Ala Ser Leu Asn
    9230                9235                9240

Tyr Arg Asn Ala Asp Tyr Asn Leu Lys Arg Gln Phe Asn Lys Ala
    9245                9250                9255

Leu Lys Glu Ala Lys Gly Val Leu Asn Lys Asn Ser Gly Thr Asn
    9260                9265                9270

Val Asn Ile Asn Asp Ile Gln His Leu Leu Thr Gln Ile Asp Asn
    9275                9280                9285

Ala Lys Asp Gln Leu Asn Gly Glu Arg Arg Leu Lys Glu His Gln
    9290                9295                9300

Gln Lys Ser Glu Val Phe Ile Ile Lys Glu Leu Asp Ile Leu Asn
    9305                9310                9315
```

-continued

```
Asn Ala  Gln Lys Ala Ala Ile  Ile Asn Gln Ile Arg  Ala Ser Lys
    9320                 9325                 9330

Asp Ile  Lys Ile Ile Asn Gln  Ile Val Asp Asn Ala  Ile Glu Leu
    9335                 9340                 9345

Asn Asp  Ala Met Gln Gly Leu  Lys Glu His Val Ala  Gln Leu Thr
    9350                 9355                 9360

Ala Thr  Thr Lys Asp Asn Ile  Glu Tyr Leu Asn Ala  Asp Glu Asp
    9365                 9370                 9375

His Lys  Leu Gln Tyr Asp Tyr  Ala Ile Asn Leu Ala  Asn Asn Val
    9380                 9385                 9390

Leu Asp  Lys Glu Asn Gly Thr  Asn Lys Asp Ala Asn  Ile Ile Ile
    9395                 9400                 9405

Gly Met  Ile Gln Asn Met Asp  Asp Ala Arg Ala Leu  Leu Asn Gly
    9410                 9415                 9420

Ile Glu  Arg Leu Lys Asp Ala  Gln Thr Lys Ala His  Asn Asp Ile
    9425                 9430                 9435

Lys Asp  Thr Leu Lys Arg Gln  Leu Asp Glu Ile Glu  His Ala Asn
    9440                 9445                 9450

Ala Thr  Ser Asn Ser Lys Ala  Gln Ala Lys Gln Met  Val Asn Glu
    9455                 9460                 9465

Glu Ala  Arg Lys Ala Leu Ser  Asn Ile Asn Asp Ala  Thr Ser Asn
    9470                 9475                 9480

Asp Leu  Val Asn Gln Ala Lys  Asp Glu Gly Gln Ser  Ala Ile Glu
    9485                 9490                 9495

His Ile  His Ala Asp Glu Leu  Pro Lys Ala Lys Leu  Asp Ala Asn
    9500                 9505                 9510

Gln Met  Ile Asp Gln Lys Val  Glu Asp Ile Asn His  Leu Ile Ser
    9515                 9520                 9525

Gln Asn  Pro Asn Leu Ser Asn  Glu Glu Lys Asn Lys  Leu Ile Ser
    9530                 9535                 9540

Gln Ile  Asn Lys Leu Val Asn  Gly Ile Lys Asn Glu  Ile Gln Gln
    9545                 9550                 9555

Ala Ile  Asn Lys Gln Gln Ile  Glu Asn Ala Thr Thr  Lys Leu Asp
    9560                 9565                 9570

Glu Val  Ile Glu Thr Thr Lys  Lys Leu Ile Ile Ala  Lys Ala Glu
    9575                 9580                 9585

Ala Lys  Gln Met Ile Lys Glu  Leu Ser Gln Lys Lys  Arg Asp Ala
    9590                 9595                 9600

Ile Asn  Asn Asn Thr Asp Leu  Thr Pro Ser Gln Lys  Ala His Ala
    9605                 9610                 9615

Leu Ala  Asp Ile Asp Lys Thr  Glu Lys Asp Ala Leu  Gln His Ile
    9620                 9625                 9630

Glu Asn  Ser Asn Ser Ile Asp  Asp Ile Asn Asn Asn  Lys Glu His
    9635                 9640                 9645

Ala Phe  Asn Thr Leu Ala His  Ile Ile Ile Trp Asp  Thr Asp Gln
    9650                 9655                 9660

Gln Pro  Leu Val Phe Glu Leu  Pro Glu Leu Ser Leu  Gln Asn Ala
    9665                 9670                 9675

Leu Val  Thr Ser Glu Val Val  Val His Arg Asp Glu  Thr Ile Ser
    9680                 9685                 9690

Leu Glu  Ser Ile Ile Gly Ala  Met Thr Leu Thr Asp  Glu Leu Lys
    9695                 9700                 9705

Val Asn  Ile Val Ser Leu Pro  Asn Thr Asp Lys Val  Ala Asp His
```

-continued

```
    9710                9715                9720

Leu Thr  Ala Lys Val Lys Val  Ile Leu Ala Asp Gly  Ser Tyr Val
    9725                9730                9735

Thr Val  Asn Val Pro Val Lys  Val Val Glu Lys Glu  Leu Gln Ile
    9740                9745                9750

Ala Lys  Lys Asp Ala Ile Lys  Thr Ile Asp Val Leu  Val Lys Gln
    9755                9760                9765

Lys Ile  Lys Asp Ile Asp Ser  Asn Asn Glu Leu Thr  Ser Thr Gln
    9770                9775                9780

Arg Glu  Asp Ala Lys Ala Glu  Ile Glu Arg Leu Lys  Lys Gln Ala
    9785                9790                9795

Ile Asp  Lys Val Asn His Ser  Lys Ser Ile Lys Asp  Ile Glu Thr
    9800                9805                9810

Val Lys  Arg Thr Asp Phe Glu  Glu Ile Asp Gln Phe  Asp Pro Lys
    9815                9820                9825

Arg Phe  Thr Leu Asn Lys Ala  Lys Lys Asp Ile Ile  Thr Asp Val
    9830                9835                9840

Asn Thr  Gln Ile Gln Asn Gly  Phe Lys Glu Ile Glu  Thr Ile Lys
    9845                9850                9855

Gly Leu  Thr Ser Asn Glu Lys  Thr Gln Phe Asp Lys  Gln Leu Thr
    9860                9865                9870

Ala Leu  Gln Lys Glu Phe Leu  Glu Lys Val Glu His  Ala His Asn
    9875                9880                9885

Leu Val  Glu Leu Asn Gln Leu  Gln Gln Glu Phe Asn  Asn Arg Tyr
    9890                9895                9900

Lys His  Ile Leu Asn Gln Ala  His Leu Leu Gly Glu  Lys His Ile
    9905                9910                9915

Ala Glu  His Lys Leu Gly Tyr  Val Val Val Asn Lys  Thr Gln Gln
    9920                9925                9930

Ile Leu  Asn Asn Gln Ser Ala  Ser Tyr Phe Ile Lys  Gln Trp Ala
    9935                9940                9945

Leu Asp  Arg Ile Lys Gln Ile  Gln Leu Glu Thr Met  Asn Ser Ile
    9950                9955                9960

Arg Gly  Ala His Thr Val Gln  Asp Val His Lys Ala  Leu Leu Gln
    9965                9970                9975

Gly Ile  Glu Gln Ile Leu Lys  Val Asn Val Ser Ile  Ile Asn Gln
    9980                9985                9990

Ser Phe  Asn Asp Ser Leu His   Asn Phe Asn Tyr Leu   His Ser Lys
    9995                10000                10005

Phe Asp   Ala Arg Leu Arg Glu   Lys Asp Val Ala Asn   His Ile Val
    10010                10015                10020

Gln Thr   Glu Thr Phe Lys Glu   Val Leu Lys Gly Thr   Gly Val Glu
    10025                10030                10035

Pro Gly   Lys Ile Asn Lys Glu   Thr Gln Gln Pro Lys   Leu His Lys
    10040                10045                10050

Asn Asp   Asn Asp Ser Leu Phe   Lys His Leu Val Asp   Asn Phe Gly
    10055                10060                10065

Lys Thr   Val Gly Val Ile Thr   Leu Thr Gly Leu Leu   Ser Ser Phe
    10070                10075                10080

Trp Leu   Val Leu Ala Lys Arg   Arg Lys Lys Glu Glu   Glu Glu Lys
    10085                10090                10095

Gln Ser   Ile Lys Asn His His   Lys Asp Ile Arg Leu   Ser Asp Thr
    10100                10105                10110
```

```
Asp Lys   Ile Asp Pro Ile Val   Ile Thr Lys Arg Lys   Ile Asp Lys
    10115                10120                10125

Glu Glu   Gln Ile Gln Asn Asp   Asp Lys His Ser Ile   Pro Val Ala
    10130                10135                10140

Lys His   Lys Lys Ser Lys Glu   Lys Gln Leu Ser Glu   Glu Asp Ile
    10145                10150                10155

His Ser   Ile Pro Val Val Lys   Arg Lys Gln Asn Ser   Asp Asn Lys
    10160                10165                10170

Asp Thr   Lys Gln Lys Lys Val   Thr Ser Lys Lys Lys   Lys Thr Pro
    10175                10180                10185

Gln Ser   Thr Lys Lys Val Val   Lys Thr Lys Lys Arg   Ser Lys Lys
    10190                10195                10200


<210> SEQ ID NO 24
<211> LENGTH: 1973
<212> TYPE: PRT
<213> ORGANISM: Staphylococcus epidermidis

<400> SEQUENCE: 24

Met Lys Glu Asn Lys Arg Lys Asn Asn Leu Asp Lys Asn Asn Thr Arg
1               5                   10                  15

Phe Ser Ile Arg Lys Tyr Gln Gly Tyr Gly Ala Thr Ser Val Ala Ile
            20                  25                  30

Ile Gly Phe Ile Ile Ile Ser Cys Phe Ser Glu Ala Lys Ala Asp Ser
        35                  40                  45

Asp Lys His Glu Ile Lys Ser His Gln Gln Ser Met Thr Asn His Leu
    50                  55                  60

Thr Thr Leu Pro Ser Asp Asn Gln Glu Asn Thr Ser Asn Asn Glu Phe
65                  70                  75                  80

Asn Asn Arg Asn His Asp Ile Ser His Leu Ser Leu Asn Lys Ser Ile
                85                  90                  95

Gln Met Asp Glu Leu Lys Lys Leu Ile Lys Gln Tyr Lys Ala Ile Asn
            100                 105                 110

Leu Asn Asp Lys Thr Glu Glu Ser Ile Lys Leu Phe Gln Ser Asp Leu
        115                 120                 125

Val Gln Ala Glu Ser Leu Ile Asn Asn Pro Gln Ser Gln Gln His Val
    130                 135                 140

Asp Ala Phe Tyr His Lys Phe Leu Asn Ser Ala Gly Lys Leu Arg Lys
145                 150                 155                 160

Lys Glu Thr Val Ser Ile Lys His Glu Arg Ser Glu Ser Asn Thr Tyr
                165                 170                 175

Arg Leu Gly Asp Glu Val Arg Ser Gln Thr Phe Ser His Ile Arg His
            180                 185                 190

Lys Arg Asn Ala Val Ser Phe Arg Asn Ala Asp Gln Ser Asn Leu Ser
        195                 200                 205

Thr Asp Pro Leu Lys Ala Asn Glu Ile Asn Pro Glu Ile Gln Asn Gly
    210                 215                 220

Asn Phe Ser Gln Val Ser Gly Gly Pro Leu Pro Thr Ser Ser Lys Arg
225                 230                 235                 240

Leu Thr Val Val Thr Asn Val Asp Asn Trp His Ser Tyr Ser Thr Asp
                245                 250                 255

Pro Asn Pro Glu Tyr Pro Met Phe Tyr Thr Thr Thr Ala Val Asn Tyr
            260                 265                 270

Pro Asn Phe Met Ser Asn Gly Asn Ala Pro Tyr Gly Val Ile Leu Gly
```

```
        275                 280                 285

Arg Thr Thr Asp Gly Trp Asn Arg Asn Val Ile Asp Ser Lys Val Ala
    290                 295                 300

Gly Ile Tyr Gln Asp Ile Asp Val Val Pro Gly Ser Glu Leu Asn Val
305                 310                 315                 320

Asn Phe Ile Ser Thr Ser Pro Val Phe Ser Asp Gly Ala Ala Gly Ala
                325                 330                 335

Lys Leu Lys Ile Ser Asn Val Glu Gln Asn Arg Val Leu Phe Asp Ser
            340                 345                 350

Arg Leu Asn Gly Met Gly Pro Tyr Pro Thr Gly Lys Leu Ser Ala Met
        355                 360                 365

Val Asn Ile Pro Asn Asp Ile Asn Arg Val Arg Ile Ser Phe Leu Pro
    370                 375                 380

Val Ser Ser Thr Gly Arg Val Ser Val Gln Arg Ser Ser Arg Glu His
385                 390                 395                 400

Gly Phe Gly Asp Asn Ser Ser Tyr Tyr His Gly Gly Ser Val Ser Asp
                405                 410                 415

Val Arg Ile Asn Ser Gly Ser Tyr Val Val Ser Lys Val Thr Gln Arg
            420                 425                 430

Glu Tyr Thr Thr Arg Pro Asn Ser Ser Asn Asp Thr Phe Ala Arg Ala
        435                 440                 445

Thr Ile Asn Leu Ser Val Glu Asn Lys Gly His Asn Gln Ser Lys Asp
    450                 455                 460

Thr Tyr Tyr Glu Val Ile Leu Pro Gln Asn Ser Arg Leu Ile Ser Thr
465                 470                 475                 480

Arg Gly Gly Ser Gly Asn Tyr Asn Asn Ala Thr Asn Lys Leu Ser Ile
                485                 490                 495

Arg Leu Asp Asn Leu Asn Pro Gly Asp Arg Arg Asp Ile Ser Tyr Thr
            500                 505                 510

Val Asp Phe Glu Ser Ser Ser Pro Lys Leu Ile Asn Leu Asn Ala His
        515                 520                 525

Leu Leu Tyr Lys Thr Asn Ala Thr Phe Arg Gly Asn Asp Gly Gln Arg
    530                 535                 540

Thr Gly Asp Asn Ile Val Asp Leu Gln Ser Ile Ala Leu Leu Met Asn
545                 550                 555                 560

Lys Asp Val Leu Glu Thr Glu Leu Asn Glu Ile Asp Lys Phe Ile Arg
                565                 570                 575

Asp Leu Asn Glu Ala Asp Phe Thr Ile Asp Ser Trp Ser Ala Leu Gln
            580                 585                 590

Glu Lys Met Thr Glu Gly Gly Asn Ile Leu Asn Glu Gln Gln Asn Gln
        595                 600                 605

Val Ala Leu Glu Asn Gln Ala Ser Gln Glu Thr Ile Asn Asn Val Thr
    610                 615                 620

Gln Ser Leu Glu Ile Leu Lys Asn Asn Leu Lys Tyr Lys Thr Pro Ser
625                 630                 635                 640

Gln Pro Ile Ile Lys Ser Asn Asn Gln Ile Pro Asn Ile Thr Ile Ser
                645                 650                 655

Pro Ala Asp Lys Ala Asp Lys Leu Thr Ile Thr Tyr Gln Asn Thr Asp
            660                 665                 670

Asn Glu Ser Ala Ser Ile Ile Gly Asn Lys Leu Asn Asn Gln Trp Ser
        675                 680                 685

Leu Asn Asn Asn Ile Pro Gly Ile Glu Ile Asp Met Gln Thr Gly Leu
    690                 695                 700
```

-continued

```
Val Thr Ile Asp Tyr Lys Ala Val Tyr Pro Glu Ser Val Val Gly Ala
705                 710                 715                 720

Asn Asp Lys Thr Gly Asn Ser Asp Ala Ser Ala Glu Ser Arg Ile Thr
                725                 730                 735

Met Pro Arg Lys Glu Ala Thr Pro Leu Ser Pro Ile Val Glu Ala Asn
            740                 745                 750

Glu Glu Arg Val Asn Val Val Ile Ala Pro Asn Gly Glu Ala Thr Gln
        755                 760                 765

Ile Ala Ile Lys Tyr Arg Thr Pro Asp Gly Gln Glu Ala Thr Leu Val
    770                 775                 780

Ala Ser Lys Asn Gly Ser Ser Trp Thr Leu Asn Lys Gln Ile Asp Tyr
785                 790                 795                 800

Val Asn Ile Glu Glu Asn Ser Gly Lys Val Thr Ile Gly Tyr Gln Ala
                805                 810                 815

Val Gln Pro Glu Ser Glu Val Ile Ala Thr Glu Thr Lys Gly Asn Ser
            820                 825                 830

Asp Glu Ser Ala Glu Ser Arg Val Thr Met Pro Arg Lys Glu Ala Thr
        835                 840                 845

Pro His Ser Pro Ile Val Glu Ala Asn Glu Glu His Val Asn Val Thr
    850                 855                 860

Ile Ala Pro Asn Gly Glu Ala Thr Gln Ile Ala Ile Lys Tyr Arg Thr
865                 870                 875                 880

Pro Asp Gly Gln Glu Thr Thr Leu Ile Ala Ser Lys Asn Gly Ser Ser
                885                 890                 895

Trp Thr Leu Asn Lys Gln Ile Asp Tyr Val Asn Ile Glu Glu Asn Ser
            900                 905                 910

Gly Lys Val Thr Ile Gly Tyr Gln Ala Val Gln Leu Glu Ser Glu Val
        915                 920                 925

Ile Ala Thr Glu Thr Lys Gly Asn Ser Asp Ala Ser Ala Glu Ser Arg
    930                 935                 940

Ile Thr Met Leu Arg Lys Glu Ala Thr Pro His Ser Pro Ile Val Glu
945                 950                 955                 960

Ala Asn Glu Glu His Val Asn Val Thr Ile Ala Pro Asn Gly Glu Ala
                965                 970                 975

Thr Gln Ile Ala Ile Lys Tyr Arg Thr Pro Asp Gly Gln Glu Ala Thr
            980                 985                 990

Leu Val Ala Ser Lys Asn Glu Ser  Ser Trp Thr Leu Asn  Lys Gln Ile
        995                 1000                 1005

Asp His  Val Asn Ile Asp Glu  Asn Ser Gly Lys Val  Thr Ile Gly
    1010                 1015                 1020

Tyr Gln  Ala Val Gln Pro Glu  Ser Glu Ile Ile Ala  Thr Glu Thr
    1025                 1030                 1035

Lys Gly  Asn Ser Asp Ala Ser  Ala Glu Ser Arg Ile  Thr Met Pro
    1040                 1045                 1050

Arg Lys  Glu Ala Thr Pro Ile  Pro Pro Thr Leu Glu  Ala Ser Val
    1055                 1060                 1065

Gln Glu  Ala Ser Val Thr Val  Thr Pro Asn Glu Asn  Ala Thr Lys
    1070                 1075                 1080

Val Phe  Ile Lys Tyr Leu Asp  Ile Asn Asp Glu Ile  Ser Thr Ile
    1085                 1090                 1095

Ile Ala  Ser Lys Ile Asn Gln  Gln Trp Thr Leu Asn  Lys Asp Asn
    1100                 1105                 1110
```

-continued

```
Phe Gly  Ile Lys Ile Asn Pro  Leu Thr Gly Lys Val  Ile Ile Ser
    1115                 1120                 1125

Tyr Val  Ala Val Gln Pro Glu  Ser Asp Val Ile Ala  Ile Glu Ser
    1130                 1135                 1140

Gln Gly  Asn Ser Asp Leu Ser  Glu Glu Ser Arg Ile  Ile Met Pro
    1145                 1150                 1155

Thr Lys  Glu Glu Pro Pro Glu  Pro Pro Ile Leu Glu  Ser Asp Ser
    1160                 1165                 1170

Ile Glu  Ala Lys Val Asn Ile  Phe Pro Asn Asp Glu  Ala Thr Arg
    1175                 1180                 1185

Ile Val  Ile Met Tyr Thr Ser  Leu Glu Gly Gln Glu  Ala Thr Leu
    1190                 1195                 1200

Val Ala  Ser Lys Asn Glu Ser  Ser Trp Thr Leu Asn  Lys Gln Ile
    1205                 1210                 1215

Asp His  Val Asn Ile Asp Glu  Asn Ser Gly Lys Val  Thr Ile Gly
    1220                 1225                 1230

Tyr Gln  Ala Val Gln Pro Glu  Ser Glu Val Ile Ala  Thr Glu Thr
    1235                 1240                 1245

Lys Gly  Asn Ser Asp Ala Ser  Ala Glu Ser Arg Val  Thr Met Pro
    1250                 1255                 1260

Arg Lys  Glu Ala Thr Pro His  Ser Pro Ile Val Glu  Thr Asn Glu
    1265                 1270                 1275

Glu Arg  Val Asn Val Val Ile  Ala Pro Asn Gly Glu  Ala Thr Gln
    1280                 1285                 1290

Ile Ala  Ile Lys Tyr Arg Thr  Pro Asp Gly Gln Glu  Thr Thr Leu
    1295                 1300                 1305

Ile Ala  Ser Lys Asn Gly Ser  Ser Trp Thr Leu Asn  Lys Gln Ile
    1310                 1315                 1320

Asp His  Val Asn Ile Asp Glu  Asn Ser Gly Lys Val  Thr Ile Gly
    1325                 1330                 1335

Tyr Gln  Ala Val Gln Pro Glu  Ser Glu Ile Ile Ala  Thr Glu Thr
    1340                 1345                 1350

Lys Gly  Asn Ser Asp Ala Ser  Ala Glu Ser Arg Ile  Thr Met Pro
    1355                 1360                 1365

Arg Lys  Glu Ala Ile Pro His  Ser Pro Ile Val Glu  Ala Asn Glu
    1370                 1375                 1380

Glu His  Val Asn Val Thr Ile  Ala Pro Asn Gly Glu  Thr Thr Gln
    1385                 1390                 1395

Ile Ala  Val Lys Tyr Arg Thr  Pro Asp Gly Gln Glu  Ala Thr Leu
    1400                 1405                 1410

Ile Ala  Ser Lys Asn Glu Ser  Ser Trp Thr Leu Asn  Lys Gln Ile
    1415                 1420                 1425

Asp His  Val Asn Ile Asp Glu  Asn Ser Gly Lys Val  Thr Ile Gly
    1430                 1435                 1440

Tyr Gln  Ala Val Gln Pro Glu  Ser Glu Val Ile Ala  Thr Glu Thr
    1445                 1450                 1455

Lys Gly  Asn Ser Asp Ala Ser  Ala Glu Ser Arg Ile  Thr Met Pro
    1460                 1465                 1470

Val Lys  Glu Lys Thr Pro Ala  Pro Pro Ile Ser Ile  Ile Asn Glu
    1475                 1480                 1485

Ser Asn  Ala Ser Val Glu Ile  Ile Pro Gln Val Asn  Val Thr Gln
    1490                 1495                 1500

Leu Ser  Leu Gln Tyr Ile Asp  Ala Lys Gly Gln Gln  Gln Asn Leu
```

-continued

```
    1505                1510                1515

Ile Ala  Thr Leu Asn Gln Asn  Gln Trp Thr Leu Asn  Lys Asn Val
    1520                1525                1530

Ser His  Ile Thr Val Asp Lys  Asn Thr Gly Lys Val  Leu Ile Asn
    1535                1540                1545

Tyr Gln  Ala Val Tyr Pro Glu  Ser Glu Val Ile Ala  Arg Glu Ser
    1550                1555                1560

Lys Gly  Asn Ser Asp Ser Ser  Asn Val Ser Met Val  Ile Met Pro
    1565                1570                1575

Arg Lys  Thr Ala Thr Pro Lys  Pro Pro Ile Ile Lys  Val Asp Glu
    1580                1585                1590

Met Asn  Ala Ser Leu Ala Ile  Ile Pro Tyr Lys Asn  Asn Thr Ala
    1595                1600                1605

Ile Asn  Ile His Tyr Ile Asp  Lys Lys Gly Ile Lys  Ser Met Val
    1610                1615                1620

Thr Ala  Ile Lys Asn Asn Asp  Gln Trp Gln Leu Asp  Glu Lys Ile
    1625                1630                1635

Lys Tyr  Val Lys Ile Asp Ala  Lys Thr Gly Thr Val  Ile Ile Asn
    1640                1645                1650

Tyr Gln  Ile Val Gln Glu Asn  Ser Glu Ile Ile Ala  Thr Ala Ile
    1655                1660                1665

Asn Gly  Asn Ser Asp Lys Ser  Glu Glu Val Lys Val  Leu Met Pro
    1670                1675                1680

Ile Lys  Glu Phe Thr Pro Leu  Ala Pro Leu Leu Glu  Thr Asn Tyr
    1685                1690                1695

Lys Lys  Ala Thr Val Ser Ile  Leu Pro Gln Ser Asn  Ala Thr Lys
    1700                1705                1710

Leu Asp  Phe Lys Tyr Arg Asp  Lys Lys Gly Asp Ser  Lys Ile Ile
    1715                1720                1725

Ile Val  Lys Arg Phe Lys Asn  Ile Trp Lys Ala Asn  Glu Gln Ile
    1730                1735                1740

Ser Gly  Val Thr Ile Asn Pro  Glu Phe Gly Gln Val  Val Ile Asn
    1745                1750                1755

Tyr Gln  Ala Val Tyr Pro Glu  Ser Asp Ile Leu Ala  Ala Gln Tyr
    1760                1765                1770

Val Gly  Asn Ser Asp Ala Ser  Glu Trp Ala Lys Val  Lys Met Pro
    1775                1780                1785

Lys Lys  Glu Leu Ala Pro His  Ser Pro Ser Leu Ile  Tyr Asp Asn
    1790                1795                1800

Arg Asn  Asn Lys Ile Leu Ile  Ala Pro Asn Ser Asn  Ala Thr Glu
    1805                1810                1815

Met Glu  Leu Ser Tyr Val Asp  Lys Asn Asn Gln Ser  Leu Lys Val
    1820                1825                1830

Lys Ala  Leu Lys Ile Asn Asn  Arg Trp Lys Phe Asp  Ser Ser Val
    1835                1840                1845

Ser Asn  Ile Ser Ile Asn Pro  Asn Thr Gly Lys Ile  Val Leu Gln
    1850                1855                1860

Pro Gln  Phe Leu Leu Thr Asn  Ser Lys Ile Ile Val  Phe Ala Lys
    1865                1870                1875

Lys Gly  Asn Ser Asp Ala Ser  Ile Ser Val Ser Leu  Arg Val Pro
    1880                1885                1890

Ala Val  Lys Lys Ile Glu Leu  Glu Pro Met Phe Asn  Val Pro Val
    1895                1900                1905
```

```
Leu Val  Ser Leu Asn Lys Lys  Arg Ile Gln Phe Asp  Asp Cys Ser
    1910                 1915                 1920

Gly Val  Lys Asn Cys Leu Asn  Lys Gln Ile Ser Lys  Thr Gln Leu
    1925                 1930                 1935

Pro Asp  Thr Gly Tyr Ser Asp  Lys Ala Ser Lys Ser  Asn Ile Leu
    1940                 1945                 1950

Ser Val  Leu Leu Leu Gly Phe  Gly Phe Leu Ser Tyr  Ser Arg Lys
    1955                 1960                 1965

Arg Lys  Glu Lys Gln
    1970


<210> SEQ ID NO 25
<211> LENGTH: 10
<212> TYPE: PRT
<213> ORGANISM: Enterococcus faecalis
<220> FEATURE:
<221> NAME/KEY: misc_feature
<222> LOCATION: (3)..(3)
<223> OTHER INFORMATION: Xaa can be any naturally occurring amino acid

<400> SEQUENCE: 25

Leu Pro Xaa Thr Ser Ala Gly Ala Asn Ser
1               5                   10


<210> SEQ ID NO 26
<211> LENGTH: 30
<212> TYPE: DNA
<213> ORGANISM: Enterococcus faecalis

<400> SEQUENCE: 26

ccgcatgcca agagcaaaca gcaaaagaag                                      30


<210> SEQ ID NO 27
<211> LENGTH: 33
<212> TYPE: DNA
<213> ORGANISM: Enterococcus faecalis

<400> SEQUENCE: 27

ccgtcgactt aagtaccaga agtggtggtt ttc                                  33


<210> SEQ ID NO 28
<211> LENGTH: 30
<212> TYPE: DNA
<213> ORGANISM: Enterococcus faecalis

<400> SEQUENCE: 28

ccgcatgcca agagcaaaca gcaaaagaag                                      30


<210> SEQ ID NO 29
<211> LENGTH: 33
<212> TYPE: DNA
<213> ORGANISM: Enterococcus faecalis

<400> SEQUENCE: 29

gggtcgactt attgtttcaa ggttacttct gtc                                  33


<210> SEQ ID NO 30
<211> LENGTH: 33
<212> TYPE: DNA
<213> ORGANISM: Enterococcus faecalis

<400> SEQUENCE: 30
```

ccggatccgc agctaataaa gaagaatttt tag 33

<210> SEQ ID NO 31
<211> LENGTH: 33
<212> TYPE: DNA
<213> ORGANISM: Enterococcus faecalis

<400> SEQUENCE: 31
ccgtcgactt aagtaccaga agtggtggtt ttc 33

<210> SEQ ID NO 32
<211> LENGTH: 28
<212> TYPE: DNA
<213> ORGANISM: Enterococcus faecalis

<400> SEQUENCE: 32
ccgagctcga agaggttaac agcgatgg 28

<210> SEQ ID NO 33
<211> LENGTH: 31
<212> TYPE: DNA
<213> ORGANISM: Enterococcus faecalis

<400> SEQUENCE: 33
ccctgcagtt acccaccaaa tgtgataacc c 31

<210> SEQ ID NO 34
<211> LENGTH: 33
<212> TYPE: DNA
<213> ORGANISM: Enterococcus faecalis

<400> SEQUENCE: 34
ccggatccga agaaataact gatttatttt tac 33

<210> SEQ ID NO 35
<211> LENGTH: 36
<212> TYPE: DNA
<213> ORGANISM: Enterococcus faecalis

<400> SEQUENCE: 35
ccgagctctt attgttcctg aattaatttt tctaac 36

<210> SEQ ID NO 36
<211> LENGTH: 27
<212> TYPE: DNA
<213> ORGANISM: Enterococcus faecalis

<400> SEQUENCE: 36
ccgcatgctc gcaagcaagc gttcaag 27

<210> SEQ ID NO 37
<211> LENGTH: 33
<212> TYPE: DNA
<213> ORGANISM: Enterococcus faecalis

<400> SEQUENCE: 37
ccctgcagtt agaagcctga ctcttttact ttt 33

<210> SEQ ID NO 38
<211> LENGTH: 30
<212> TYPE: DNA
<213> ORGANISM: Enterococcus faecalis

<400> SEQUENCE: 38

```
ccggatccca agaagtaaca agtgatgctg                                        30


<210> SEQ ID NO 39
<211> LENGTH: 32
<212> TYPE: DNA
<213> ORGANISM: Enterococcus faecalis

<400> SEQUENCE: 39

ccgagctctt aagttacttg ttcgtccgca at                                     32


<210> SEQ ID NO 40
<211> LENGTH: 28
<212> TYPE: DNA
<213> ORGANISM: Enterococcus faecalis

<400> SEQUENCE: 40

ccggatccga aacaggatat gcgcaaac                                          28


<210> SEQ ID NO 41
<211> LENGTH: 32
<212> TYPE: DNA
<213> ORGANISM: Enterococcus faecalis

<400> SEQUENCE: 41

ccgagctctt attccttatt acgaatcgcc tg                                     32


<210> SEQ ID NO 42
<211> LENGTH: 29
<212> TYPE: DNA
<213> ORGANISM: Enterococcus faecalis

<400> SEQUENCE: 42

gcgggatccg aagaaaatgg ggagagcgc                                         29


<210> SEQ ID NO 43
<211> LENGTH: 33
<212> TYPE: DNA
<213> ORGANISM: Enterococcus faecalis

<400> SEQUENCE: 43

gcggagctct taggtacctt tgtgtttgtt tgg                                    33


<210> SEQ ID NO 44
<211> LENGTH: 22
<212> TYPE: DNA
<213> ORGANISM: Enterococcus faecalis

<400> SEQUENCE: 44

gaattgagca aaagttcaat cg                                                22


<210> SEQ ID NO 45
<211> LENGTH: 22
<212> TYPE: DNA
<213> ORGANISM: Enterococcus faecalis

<400> SEQUENCE: 45

caagtaaaaa agccggtaca gc                                                22


<210> SEQ ID NO 46
<211> LENGTH: 19
<212> TYPE: DNA
<213> ORGANISM: Enterococcus faecalis
```

-continued

<400> SEQUENCE: 46
tcgcaagcaa gcgttcaag 19

<210> SEQ ID NO 47
<211> LENGTH: 18
<212> TYPE: DNA
<213> ORGANISM: Enterococcus faecalis

<400> SEQUENCE: 47
gagagcgcac agctcgtg 18

<210> SEQ ID NO 48
<211> LENGTH: 34
<212> TYPE: DNA
<213> ORGANISM: Enterococcus faecalis

<400> SEQUENCE: 48
cgggatccca aaacagcggg aaagaaatga gcga 34

<210> SEQ ID NO 49
<211> LENGTH: 32
<212> TYPE: DNA
<213> ORGANISM: Enterococcus faecalis

<400> SEQUENCE: 49
cgggatccga aatggttcag attactttac ac 32

<210> SEQ ID NO 50
<211> LENGTH: 35
<212> TYPE: DNA
<213> ORGANISM: Enterococcus faecalis

<400> SEQUENCE: 50
cgggatccaa agcactgaac atcaagctaa atgcg 35

<210> SEQ ID NO 51
<211> LENGTH: 26
<212> TYPE: DNA
<213> ORGANISM: Enterococcus faecalis

<400> SEQUENCE: 51
gtctgtcttt tcacttgttt ctgttg 26

<210> SEQ ID NO 52
<211> LENGTH: 21
<212> TYPE: DNA
<213> ORGANISM: Enterococcus faecalis

<400> SEQUENCE: 52
aaaggaacct ttgcttggtt c 21

<210> SEQ ID NO 53
<211> LENGTH: 27
<212> TYPE: DNA
<213> ORGANISM: Enterococcus faecalis

<400> SEQUENCE: 53
aagcctgact cttttacttt tttattg 27

<210> SEQ ID NO 54
<211> LENGTH: 24
<212> TYPE: DNA
<213> ORGANISM: Enterococcus faecalis

```
<400> SEQUENCE: 54

ggtacctttg tgtttgtttg gtac                                24


<210> SEQ ID NO 55
<211> LENGTH: 33
<212> TYPE: DNA
<213> ORGANISM: Enterococcus faecalis

<400> SEQUENCE: 55

cccaagcttt catgtacctt tgtgtttatt tgg                      33


<210> SEQ ID NO 56
<211> LENGTH: 35
<212> TYPE: DNA
<213> ORGANISM: Enterococcus faecalis

<400> SEQUENCE: 56

tctgcagttc aattgactac tttcaatata ctgtc                    35


<210> SEQ ID NO 57
<211> LENGTH: 36
<212> TYPE: DNA
<213> ORGANISM: Enterococcus faecalis

<400> SEQUENCE: 57

cccaagcttt cagaatgctt gaccttgatt attgta                   36
```